United States Patent
Yin et al.

(10) Patent No.: US 8,188,245 B2
(45) Date of Patent: May 29, 2012

(54) **ENDURACIDIN BIOSYNTHETIC GENE CLUSTER FROM *STREPTOMYCES FUNGICIDICUS***

(75) Inventors: Xihou Yin, Corvallis, OR (US); T. Mark Zabriskie, Corvallis, OR (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 146 days.

(21) Appl. No.: 12/443,161

(22) PCT Filed: Oct. 1, 2007

(86) PCT No.: PCT/US2007/080126
§ 371 (c)(1),
(2), (4) Date: Mar. 26, 2009

(87) PCT Pub. No.: WO2008/054945
PCT Pub. Date: May 8, 2008

(65) Prior Publication Data
US 2010/0035256 A1    Feb. 11, 2010

Related U.S. Application Data

(60) Provisional application No. 60/827,666, filed on Sep. 29, 2006, provisional application No. 60/959,461, filed on Jul. 13, 2007.

(51) Int. Cl.
*C07H 21/02* (2006.01)
*C07C 49/04* (2006.01)
*C12P 19/62* (2006.01)

(52) U.S. Cl. .................... 536/23.1; 568/382; 435/76

(58) Field of Classification Search .................. None
See application file for complete search history.

(56) References Cited

OTHER PUBLICATIONS

Balibar et al., "Generation of D Amino Acid Residues in Assembly of Arthrofactin by Dual Condensation/Epimerization Domains", *Chemistry & Biology*, vol. 12, pp. 1189-1200, 2005.
Baltz et al., "Combinatorial biosynthesis of lipopeptide antibiotics in *Streptomyces roseosporus*", *J. Ind. Microbiol. Biotechnol.*, vol. 33, pp. 66-74, 2006.
Belshaw et al., "Aminoacyl-CoAs as Probes of Condensation Domain Selectivity in Nonribosomal Peptide Synthesis", *Science*, vol. 284, pp. 486-489, 1999.
Cane et al., "Harnessing the Biosynthetic Code: Combinations, Permutations, and Mutations", *Science*, vol. 282, pp. 63-68, 1998.
Challis et al., "Predictive, structure-based model of amino acid recognition by nonribosomal peptide synthetase adenylation domains", *Chemistry & Biology*, vol. 7, pp. 211-224, 2000.
Fang et al., "The mechanism of action of ramoplanin and enduracidin", *Molecular BioSystems*, vol. 2, pp. 69-76, 2006.
Higashide et al., "Enduracin, A New Antibiotic. I *Streptomyces fungicidicus* No. B5477, An Enduracidin Producing Organism", *Journal of Antibiotics*, vol. 21, pp. 126-137, 1968.
Iwasaki et al., "The complete genomic sequence of *Nocardia farcinica* IFM 10152", *Proc. Natl. Acad. Sci. U.S.A.*, vol. 101, 14925-14930, 2004.

(Continued)

*Primary Examiner* — Alexander Kim
(74) *Attorney, Agent, or Firm* — Klarquist Sparkman, LLP

(57) ABSTRACT

This disclosure describes the molecular cloning of an enduracidin biosynthetic gene cluster from *Streptomyces fungicidicus*, and characterization of individual genes in the gene cluster and the proteins encoded thereby. An enduracidin gene cluster is located within a 116 kilobases genetic locus and includes 25 open reading frames (ORFs). An additional 23 ORFs flank the disclosed enduracidin biosynthetic gene cluster. Enduracidin analogs and a method for producing them by manipulation of the enduracidin gene cluster and specific genes therein are also disclosed.

9 Claims, 15 Drawing Sheets enduracidin A ramoplanin-A2

OTHER PUBLICATIONS

Kohli et al., "The thioesterase domain from a nonribosomal peptide synthetase as a cyclization catalyst for integrin binding peptides", *Proc. Natl. Acad. Sci USA*, vol. 99, pp. 1247-1252, 2002.

Rausch et al., "Specificity prediction of adenylation domains in nonribosomal peptide synthetases (NRPS) using transductive support vector machines (TSVMs)", *Nucleic Acids Research*, vol. 33, No. 18, pp. 5799-5808, 2005.

Schneider et al., "Targeted alteration of the substrate specificity of peptide synthetases by rational module swapping", *Mol. Gen. Genet.*, vol. 257, pp. 308-318, 1998.

Stachelhaus et al., "The specificity-conferring code of adenylation domains in nonribosomal peptide synthetases", *Chemistry & Biology*, vol. 6, No. 8, pp. 493-505, 1999.

Stachelhaus et al., "Rational Design of Peptide Antibiotics by Targeted Replacement of Bacterial and Fungal Domains", *Science*, vol. 269, pp. 69-72, 1995.

Walker et al., "Chemistry and Biology of Ramoplanin: A Lipoglycodepsipeptide with Potent Antibiotic Activity", *Chemical Reviews*, vol. 105, No. 2, pp. 449-475, 2005.

Weist and Sussmuth "Mutational biosynthesis—a tool for the generation of structural diversity in the biosynthesis of antibiotics", *Appl. Microbiol. Biotechnol.*, vol. 68, pp. 141-150, 2005.

Yin and Zabriskie "The enduracidin biosynthetic gene cluster from *Streptomyces fungicidicus*", *Microbiology*, vol. 152, pp. 2969-2983, 2006.

Castiglione, et al., "Structure elucidation and 3D solution conformation of the antibiotic enduracidin determined by NMR spectroscopy and molecular dynamics", *Magnetic Resonance in Chemistry*, vol. 43, pp. 603-610, 2005.

Yin and Zabriskie, "The enduracidin biosynthetic gene cluster from *Streptomyces fungicidicus*", *Microbiology*, vol. 152, pp. 2969-2983, 2006.

International Search Report and Written Opinion for PCT/US2007/080129, dated Aug. 26, 2008.

Probe   sfPS18   aac(3)IV

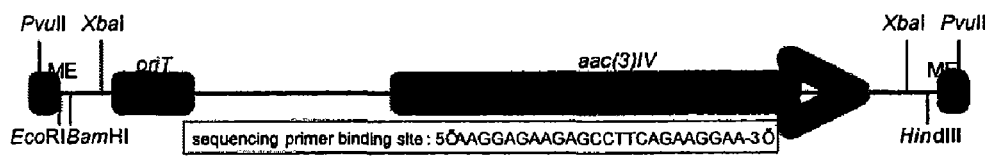
FIG. 8
FIG. 9A
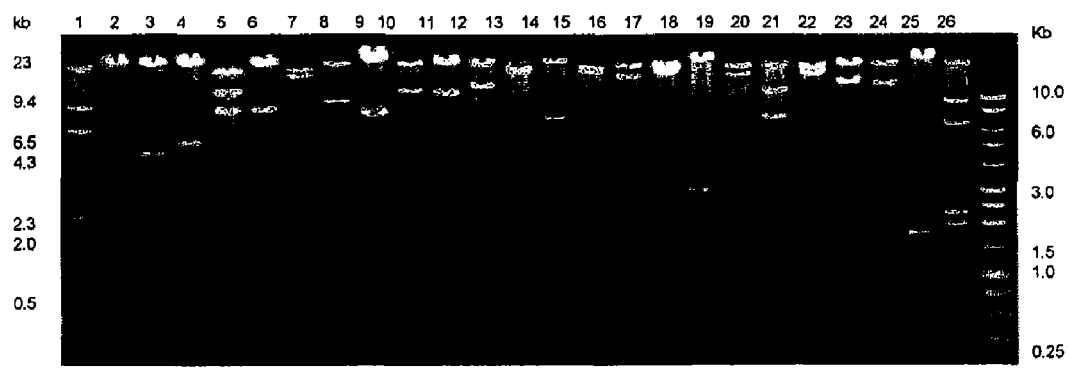
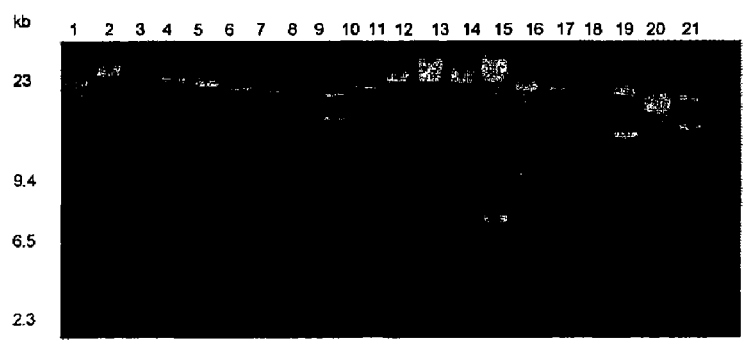
FIG. 9B
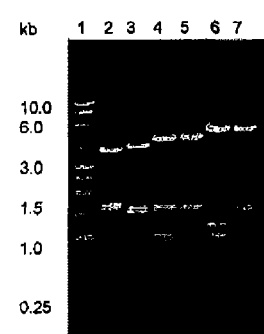
FIG. 9C

Tetrahydroenduracidin A: R =

Tetrahydroenduracidin B: R =

Deschloroenduracidin A =

Deschloroenduracidin B =

Deschlorotetrahydroenduracidin A: R=

Deschlorotetrahydroenduracidin B: R=

SEQUENCE LISTING

```
<160> NUMBER OF SEQ ID NOS: 103

<210> SEQ ID NO 1
<211> LENGTH: 409
<212> TYPE: PRT
<213> ORGANISM: Streptomyces fungicidicus

<400> SEQUENCE: 1

Ala Pro Gln Gly Met Phe Glu Asp Leu Gly Leu Lys Tyr Val Gly Pro
1               5                   10                  15

Met Asp Gly Arg Asp Ile Glu Ala Leu Glu Ser Ala Leu Thr Arg Ala
            20                  25                  30

Lys Arg Phe Gly Gly Pro Val Ile Val His Cys Leu Thr Glu Lys Gly
        35                  40                  45

Arg Gly Tyr Gln Pro Ala Leu Gln Asp Glu Ala Asp Arg Phe His Ala
    50                  55                  60

Val Gly Lys Ile His Pro Asp Thr Gly Leu Pro Ile Ala Ser Ser Gly
65                  70                  75                  80

Ala Asp Trp Thr Ser Val Phe Gly Glu Glu Met Val Lys Leu Gly Glu
                85                  90                  95

Glu Arg Asp Asp Val Val Ala Ile Thr Ala Ala Met Leu Gln Pro Val
            100                 105                 110
```

```
Gly Leu Asp Arg Phe Ala Lys Arg Phe Pro Asp Arg Val Tyr Asp Val
            115                 120                 125

Gly Ile Ala Glu Gln His Gly Ala Val Ser Ala Ala Gly Leu Ala His
            130                 135                 140

Ala Gly Val His Pro Val Phe Ala Val Tyr Ala Thr Phe Leu Asn Arg
145                 150                 155                 160

Ala Phe Asp Gln Val Leu Met Asp Val Ala Leu His Arg Cys Gly Val
                165                 170                 175

Thr Phe Val Leu Asp Arg Ala Gly Val Thr Gly Thr Asp Gly Ala Ser
            180                 185                 190

His Asn Gly Met Trp Asp Met Ser Ile Leu Gln Val Pro Gly Leu
            195                 200                 205

Arg Leu Ala Ala Pro Arg Asp Ala Asp Gln Val Arg Ala Gln Leu Arg
            210                 215                 220

Glu Ala Val Ala Val Glu Asp Ala Pro Thr Val Val Arg Phe Ser Lys
225                 230                 235                 240

Gly Ala Val Gly Pro Ala Val Pro Ala Val Gly Arg Val Gly Gly Met
                245                 250                 255

Asp Val Leu Arg Glu Pro Gly Thr Asp Thr Pro Asp Val Leu Leu Val
            260                 265                 270

Ser Val Gly Ala Leu Ala Pro Met Cys Leu Glu Ile Ala Gly Leu Leu
            275                 280                 285

Asp Arg Gln Gly Ile Ser Thr Thr Val Val Asp Pro Arg Trp Val Lys
            290                 295                 300

Pro Val Asp Glu Ala Met Ala Pro Leu Ala Glu Lys His Arg Val Val
305                 310                 315                 320

Val Thr Val Glu Asp Asn Ser Arg Val Gly Val Gly Ser Thr Ile
                325                 330                 335

Ala Gln Ala Leu Arg Asp Ala Gly Val Asp Val Pro Leu Arg Asp Phe
            340                 345                 350

Gly Ile Pro Pro Arg Phe Leu Asp His Ala Ser Arg Ala Glu Val Met
            355                 360                 365

Ala Glu Ile Gly Leu Thr Ala Pro Asp Ile Ala Arg Gln Val Thr Gly
            370                 375                 380

Leu Val Ala Lys Leu Asp Gly Arg Tyr Glu Arg Ser Ala Ala Asp Ala
385                 390                 395                 400

Ile Asp Ser Val Glu Pro Ala Arg Asp
                405

<210> SEQ ID NO 2
<211> LENGTH: 498
<212> TYPE: PRT
<213> ORGANISM: Streptomyces fungicidicus

<400> SEQUENCE: 2

Met Thr Ser Pro Leu Phe Arg Thr Lys Lys Val Glu Gln Ser Ile Arg
1               5                   10                  15

Asp Thr Glu Glu Pro Glu His Ala Leu Lys Lys Ser Leu Ser Ala Leu
            20                  25                  30

Asp Leu Thr Val Phe Gly Val Gly Val Ile Ile Gly Thr Gly Ile Phe
            35                  40                  45

Val Leu Thr Gly Thr Val Ala Lys Asp Asn Ala Gly Pro Ala Thr Ala
        50                  55                  60

Leu Ala Phe Val Val Ala Gly Val Val Cys Ala Leu Ala Ala Leu Cys
65                  70                  75                  80
```

```
Tyr Ala Glu Phe Ala Ser Thr Val Pro Val Ala Gly Ser Ala Tyr Thr
                    85                  90                  95

Phe Ser Tyr Ala Ser Leu Gly Glu Leu Pro Ala Trp Ile Ile Gly Trp
            100                 105                 110

Asp Leu Val Leu Glu Phe Ala Leu Gly Thr Ala Val Ala Val Val Gly
            115                 120                 125

Trp Ser Gly Tyr Ile Gln Ser Leu Leu Ser Asn Ala Gly Trp Glu Met
    130                 135                 140

Pro Ala Ala Leu Gly Ser Arg Glu Gly Ala Asp Val Phe Gly Phe Asp
145                 150                 155                 160

Ile Leu Ala Ala Ala Leu Val Leu Val Leu Thr Gly Ile Leu Val Leu
                165                 170                 175

Gly Met Lys Leu Ser Ala Arg Val Thr Ser Val Val Ala Ile Lys
                180                 185                 190

Val Thr Val Val Leu Val Val Ile Val Ala Gly Ala Phe Phe Ile Thr
                195                 200                 205

Ala Asp Asn Tyr Asp Pro Phe Ile Pro Lys Ser Glu Pro Val Pro Ala
210                 215                 220

Gly Asp Ser Leu Ala Ser Pro Leu Ile Gln Leu Met Phe Gly Trp Ala
225                 230                 235                 240

Pro Ala Asn Phe Gly Val Met Gly Ile Phe Thr Ala Ala Ser Val Val
                245                 250                 255

Phe Phe Ala Phe Ile Gly Phe Asp Ile Val Ala Thr Ala Ala Glu Glu
            260                 265                 270

Thr Lys Asn Pro Gln Arg Asp Met Pro Arg Gly Ile Leu Gly Ser Leu
    275                 280                 285

Leu Ile Cys Thr Val Leu Tyr Val Leu Val Ser Leu Val Thr Gly
            290                 295                 300

Met Gln His Tyr Ser Glu Leu Ser Val Asp Ala Pro Leu Ala Asp Ala
305                 310                 315                 320

Phe Lys Ala Thr Gly His Pro Trp Phe Ala Gly Phe Ile Ser Phe Gly
                325                 330                 335

Ala Ala Val Gly Leu Thr Thr Val Cys Met Ile Leu Leu Gly Gln
                340                 345                 350

Thr Arg Val Phe Phe Ala Met Ser Arg Asp Gly Leu Leu Pro Arg Phe
    355                 360                 365

Phe Ser Arg Val His Pro Arg Phe Arg Thr Pro Tyr Arg Pro Thr Ile
    370                 375                 380

Leu Leu Gly Val Ala Ile Ala Ile Leu Ala Gly Phe Thr Pro Leu Asn
385                 390                 395                 400

Glu Leu Ala Ala Leu Val Asn Ile Gly Thr Leu Phe Ala Phe Val Ile
                405                 410                 415

Val Ala Ile Ser Val Ile Ile Leu Arg Arg Thr Arg Pro Asp Leu Pro
                420                 425                 430

Arg Ala Phe Arg Thr Pro Trp Val Pro Val Leu Pro Ile Val Ser Val
            435                 440                 445

Ala Ala Ser Leu Trp Leu Met Leu Asn Leu Pro Ala Glu Thr Trp Val
            450                 455                 460

Arg Phe Gly Ile Trp Met Ala Val Gly Val Val Tyr Phe Leu Tyr
465                 470                 475                 480

Ser Arg Lys His Ser Arg Leu Ala Glu Glu Arg Gly Gly Glu Arg Thr
                485                 490                 495

Ser Ser
```

<210> SEQ ID NO 3
<211> LENGTH: 133
<212> TYPE: PRT
<213> ORGANISM: Streptomyces fungicidicus

<400> SEQUENCE: 3

Met Asp Asp Thr Gly Leu Leu Val Ile Val Asp Ala Ala Asn Val Val
1               5                   10                  15

Gly Ser Val Pro Asp Gly Trp Trp Arg Asp Arg Gly Ala Ala Glu
            20                  25                  30

Arg Leu Arg Asp Arg Leu Ala Ala Glu Gly Val Pro Gly His Pro Gly
        35                  40                  45

Pro Val Glu Ile Val Leu Val Thr Glu Gly Ala Ala Arg Gly Val Glu
    50                  55                  60

Ser Val Pro Gly Val Arg Val Asp Pro Ala Pro Gly Ser Gly Asp Asp
65                  70                  75                  80

Arg Met Val Asp Leu Val Ala Glu Ala Gly Asp Arg Pro Val Leu Val
                85                  90                  95

Val Thr Ala Asp Arg Glu Leu Arg Arg Val Thr Ser Leu Gly Ala
            100                 105                 110

Asp Val Thr Gly Pro Arg Ala Val Arg Pro Ala Gly Gly Ala Trp Ala
        115                 120                 125

Pro Arg Arg Asp Gly
    130

<210> SEQ ID NO 4
<211> LENGTH: 373
<212> TYPE: PRT
<213> ORGANISM: Streptomyces fungicidicus

<400> SEQUENCE: 4

Met Arg Arg Arg Ser Ala Gly Pro Val Gly Ala Ser Val Lys Asp Gly
1               5                   10                  15

Arg Ala Ala Gly Glu His Arg Glu Ala Ala Ser Gly Ala Ala His Gly
            20                  25                  30

Asp Trp Leu Thr Arg Gly Lys Asp Gly Arg Leu Thr Leu Tyr Val Pro
        35                  40                  45

Thr Asp Gly Gly Leu Leu Arg Trp Thr Glu Thr Ala Val Gly Gly Pro
    50                  55                  60

Gly Trp Ser Gly Pro His Phe Val Pro Val Ala Gly Leu Thr His Leu
65                  70                  75                  80

Ala Val Ala Gln Gly Ala Asn Gly Tyr Val His Phe Leu Gly Arg Arg
                85                  90                  95

Glu Arg Glu Gly Ala Asp Ser Thr Pro Gly Val Asp Ile Val His Ala
            100                 105                 110

Ile Gln Tyr Gln Thr Gly Leu Ala Phe Ser Asp Trp Arg Ser Leu Gly
        115                 120                 125

Asn Pro His Arg Val Pro Glu Glu Pro Gly Pro Leu Ala Val Pro Val
    130                 135                 140

Gly Ala Val Ala Arg Asp Gly Thr Val His Val Phe Val Arg Gly Ala
145                 150                 155                 160

His Gly Gly Leu Met Leu Arg Arg Glu Ala Pro Asn Gly Lys Trp Lys
                165                 170                 175

Ala Trp Glu Asp Leu Gly Gly Gly Ala Gly Ala Gln Pro Ala Ala
            180                 185                 190

```
Leu Ala Leu Thr Asp Gly Arg Ile Glu Val Cys Val Ala Ala Glu Thr
        195                 200                 205
Gly Val Leu Ala Trp Ser Gln Ser Lys Pro Gly Gly Asp Phe Thr Gly
    210                 215                 220
Pro Arg Gly Phe Ser Leu Arg Pro Val Pro Gly Thr Val Ala Ala Leu
225                 230                 235                 240
Glu Thr Gly Pro Gly Arg Ala Thr Phe Phe Trp Thr Asp Ala Glu Ser
            245                 250                 255
Gly Gly Ala Ala Ala Trp Arg Ala Gly Ala Trp Pro Val Ala Leu Gly
            260                 265                 270
Gly Thr Pro Ala Glu Arg Pro Cys Ala Val Leu Arg Thr Ser Leu Asp
            275                 280                 285
Gly Tyr Asp Cys Val Val Leu Ala Tyr Arg Asp Gln Asp Gly Thr Ala
            290                 295                 300
Val Leu Gly Met Gly Gly Thr Glu Asn Glu Ala Ala Gly Phe Trp Trp
305                 310                 315                 320
Tyr Ala Leu Thr Glu Ser Cys Gln Gly Ala Pro Ala Leu Ala Leu Asp
            325                 330                 335
Gly Arg Gly Arg Val Val Met Ala Leu Ile Gly Ala Asp Gly Arg Pro
            340                 345                 350
Arg Val Ala Arg Gln Glu Asp Gly Asp Gly Leu Ser Leu Thr Arg Trp
            355                 360                 365
Asp Val Leu Gly Gly
            370

<210> SEQ ID NO 5
<211> LENGTH: 360
<212> TYPE: PRT
<213> ORGANISM: Streptomyces fungicidicus

<400> SEQUENCE: 5

Met Thr His Ser Ala Thr Thr Glu Ser Arg Arg Ala Gln Pro Glu Ser
1               5                   10                  15
Gly Gly Gly Arg Arg Pro Lys Arg Arg Trp Gly Arg Ile Val
            20                  25                  30
Leu Leu Ser Leu Leu Ala Val Val Leu Ala Ala Gly Gly Thr Gly Tyr
            35                  40                  45
Trp Leu Tyr Ser Asp Leu Asn Gly Asn Ile Asp Gly Val Asp Leu Asp
    50                  55                  60
Glu Ala Leu Gly Glu Asp Arg Pro Glu Lys Leu Pro Thr Ser Gly Gln
65                  70                  75                  80
Asn Val Leu Val Leu Gly Ser Asp Ser Arg Ala Gly Asp Asn Ala Gly
                85                  90                  95
Leu Gly Thr Gly Lys Val Ala Gly Ala Arg Ser Asp Thr Ala Leu Val
            100                 105                 110
Met His Ile Pro Glu Gly Arg Arg Gln Ala Val Ala Val Ser Ile Pro
        115                 120                 125
Arg Asp Thr Leu Val Thr Arg Pro Glu Cys Thr Lys Ala Asp Gly Ser
130                 135                 140
Ala Leu Pro Gln Ala Glu Arg Val Met Phe Asn Ser Val Tyr Ser Thr
145                 150                 155                 160
Ala Gly Pro Ala Cys Val Val Lys Thr Val Glu Lys Met Ser Gly Val
                165                 170                 175
Arg Met Asp His Tyr Met Glu Ile Asp Phe Ala Gly Phe Lys Gly Leu
            180                 185                 190
```

```
Val Asp Ala Ile Gly Gly Val Thr Val Thr Val Asp Glu Pro Ile Lys
        195                 200                 205

Asp Ser Thr Ser Gly Leu Asp Leu Ser Ala Gly Thr His Lys Leu Asp
    210                 215                 220

Gly Thr Asp Ser Leu Ala Phe Val Arg Thr Arg His Gly Val Gly Asp
225                 230                 235                 240

Gly Ser Asp Leu Gly Arg Ile Gly Leu Gln Gln Gln Phe Met Ile Ala
            245                 250                 255

Leu Leu Ser Glu Val Lys Lys Gln Asp Leu Phe Gly Ser Pro Thr Lys
            260                 265                 270

Thr Tyr Lys Ile Ala Asp Thr Leu Thr Ser Ala Leu Thr Asp Ser
        275                 280                 285

Glu Leu Ala Ser Leu Thr Ser Leu Ala Asp Phe Ala Arg Ser Met Asn
290                 295                 300

Gly Val Asp Pro Ala Ser Met Glu Thr Val Met Leu Pro Val Ala Tyr
305                 310                 315                 320

Asp Lys Thr Asp Pro Asn Arg Val Val Ala Ala His Pro Gln Ala Asp
                325                 330                 335

Gln Leu Trp Lys Ala Ile Arg Ser Asp Ala Glu Ile Pro Glu Ser Ala
            340                 345                 350

Lys Lys Ser Pro Ala Thr Gly Gly
        355                 360

<210> SEQ ID NO 6
<211> LENGTH: 1290
<212> TYPE: PRT
<213> ORGANISM: Streptomyces fungicidicus

<400> SEQUENCE: 6

Met Val Gln Pro Arg Leu Ser Ile Val Val Pro Phe Gln Asp Val Glu
1               5                   10                  15

Val Tyr Leu Ala Glu Cys Leu Gly Ser Ile Ala Arg Gln Ser Phe Arg
            20                  25                  30

Asp Phe Glu Val Ile Leu Val Asp Asp Gly Ser Thr Asp Gly Ser Val
        35                  40                  45

Arg Ile Ala Ala Asp Phe Cys Ala Ala Asp Arg Arg Phe Arg Leu Val
50                  55                  60

Arg Gln His Ala His Gly Pro Gly His Ala Arg Asn Thr Gly Leu Arg
65                  70                  75                  80

Asn Thr His Pro Ala Ala Glu Phe Leu Ala Phe Val Asp Ser Gly Asp Asp
                85                  90                  95

Val Ile Pro Glu Tyr Ala Tyr Glu Leu Leu Val Arg Thr Leu Glu Glu
            100                 105                 110

Ser Glu Ser Asp Phe Val Ser Gly Asn Val Gln Met Met Asn Ser Thr
        115                 120                 125

Lys Lys Trp Gln Ser Pro Leu His Lys Gly Pro Met Gln Lys Asn Arg
    130                 135                 140

Arg Gly Thr His Ile Thr Lys Phe Asp Ala Leu Ile Tyr Asp Arg Thr
145                 150                 155                 160

Val Trp Asn Lys Leu Phe Arg Arg Ser Phe Trp Asn Gln Asn Ser Ile
                165                 170                 175

Arg Phe Pro Glu Gly Val Leu Tyr Glu Asp Ser Trp Val Asn Met Tyr
            180                 185                 190

Ala His Phe Arg Ala Ala Lys Val Asp Val Ile Thr Asp Val Val Tyr
        195                 200                 205
```

```
Phe Trp Arg Arg Arg Asp Gly Ala Ala Pro Ser Ile Thr Gln Arg
    210             215                 220

His Ser Glu Leu Ser Asn Leu Arg Asp Arg Val Ala Ala Val Gln Ser
225                 230                 235                 240

Val Ser Arg Phe Leu Gly Asp Arg Arg Ser Arg Glu Tyr Ala Asp Ser
                245                 250                 255

Lys Arg Lys Tyr Asp Leu Ala Cys Leu Lys Ser Asp Leu Leu Leu His
            260                 265                 270

Leu Lys Val Leu Pro Asp Ala Asp Glu Glu Tyr Gln His Ala Phe Met
        275                 280                 285

Lys Trp Ala Asn Glu Phe Leu Asp Glu Thr Asp Leu Thr Ile Ile Asp
290                 295                 300

Glu Leu Pro Ala Asp Ser Arg Val Lys Trp Leu Leu Val Arg Glu Glu
305                 310                 315                 320

Arg Leu Ala Glu Leu Leu Glu Val Ile Glu Phe Glu Arg Arg Gly Gly
                325                 330                 335

Pro Met Pro Val Gln Arg Arg Phe Arg Arg Tyr Leu Asn Tyr Pro Tyr
                340                 345                 350

Leu Gly Asp Arg Gly Val Gly Leu Asp Lys Lys Ala Tyr Arg Leu Asp
            355                 360                 365

Lys Glu Leu Ser Leu His Gly Ser Leu Ser Gly Ala Arg Trp Ser Thr
        370                 375                 380

Gly Ser Asp Leu Leu Thr Leu Thr Gly Thr Ala Tyr Val Arg Phe Ile
385                 390                 395                 400

Asn Val His Lys Lys His Met Ser Val Lys Ala Ile Ala Leu Arg Asn
                405                 410                 415

Lys Lys Gln Gly Arg Met Gln Ile Thr Thr Ala Lys Thr Val Tyr Ala
                420                 425                 430

Pro Gln Ala Thr Glu Asp Ser Lys Gln Asn Arg Tyr Cys Tyr Asp Trp
            435                 440                 445

Ala Gly Phe Glu Ala Arg Ile Asp Thr Thr Arg Leu Lys Arg Lys Gly
        450                 455                 460

Gln Trp Val Glu Gly Thr Trp Asp Val Ala Ala Gly Val Leu Ser Arg
465                 470                 475                 480

Gly Leu Phe Arg Tyr Arg Gly Ile Asp Arg Gly Gly Ala Gly Ser Ala
                485                 490                 495

Ala Asn Pro Pro Tyr Arg Tyr Val Asp Lys Asn Thr Arg Ile Leu Pro
                500                 505                 510

Val Phe Leu Gln Gly Lys Leu Lys Leu Arg Val Glu Ile Val Arg Cys
            515                 520                 525

Arg Ile Thr Lys His Arg Val Val Gly Asp Gln Leu Glu Leu Arg Gly
        530                 535                 540

Val Tyr Leu Gly Pro Lys Val Pro Glu Trp Gly Lys Leu Arg Val Thr
545                 550                 555                 560

Ser Met Ser Gly Ala Gly Arg His Asp Ala Arg Val His Phe Thr Pro
                565                 570                 575

Gly Gly Glu Gly Trp Cys Thr Phe Ser Ala Lys Leu Pro Leu Ser Arg
                580                 585                 590

Leu Val Pro Lys Ser Arg Val Gln Ala Gly Thr Asp Ala Asp Val Pro
            595                 600                 605

Gln Ser Trp Gly Met Gly Ser Asn Gly Trp Lys Thr Thr Phe His Val
        610                 615                 620

Glu Gly Arg Lys Ser Ala Ile Tyr Pro Val Met Ala Glu Glu Thr Pro
625                 630                 635                 640
```

```
Asp Gly His Tyr Ser Met Pro Ser Ser Leu Gln Thr Pro Glu Arg Asp
                645                 650                 655

Arg Glu Ile Val Val His Arg Asn Gly Ser Gly Tyr Leu Val Leu Phe
            660                 665                 670

Glu Arg Ala Thr Leu Pro Leu Ala Thr Arg Cys Asp Trp Gln Glu Asp
        675                 680                 685

Gly Ser Leu Trp Ile Gln Gly Arg Tyr Leu Ala Ala Asp Gln Leu Thr
    690                 695                 700

Pro Glu Gln Tyr Arg Ser Ala His Leu Val Val Arg Ser Arg Ala His
705                 710                 715                 720

Gly Ala Glu Arg Ser Val Pro Leu Thr Trp Asp Gly His Glu Phe Arg
                725                 730                 735

Cys Val Leu Ala Pro Ala Met Arg Thr Leu Ala Gly Asp Ile Pro
            740                 745                 750

Leu Ala Ala Gly Arg Trp Asp Phe Phe Leu Arg Arg Gln Asp Leu Ser
        755                 760                 765

Ala Val Ala Arg Glu Asp Arg Leu Glu Asp Leu Met Val Lys Ile Glu
    770                 775                 780

Gln Asp Leu Ile Glu Ala Phe Pro Gln Glu Tyr Glu Arg Asn Glu Arg
785                 790                 795                 800

Arg Tyr Glu Thr Gln Ala Glu Ala Tyr Asp Arg Leu Ser Leu Leu Val
                805                 810                 815

His Ser Ala Met Pro Asp His Ala Arg Gly Pro Tyr Arg Gln Lys Leu
            820                 825                 830

Leu Arg Thr Lys Ala Tyr Pro Asp Ala Arg Arg Arg Pro Val Arg Asp
        835                 840                 845

Ala Val Leu Phe Asp Ala Phe Lys Gly Thr Gln Tyr Ser Asp Ser Pro
    850                 855                 860

Arg Ala Leu His Glu Glu Leu Val Arg Arg Thr Gly Leu Glu His
865                 870                 875                 880

Leu Trp Val Val Arg Asp Asp Gln Val Gln Val Pro Pro Thr Ala Thr
                885                 890                 895

Pro Val Arg Met Trp Ser Pro Glu Trp Tyr Glu Ala Leu Ala Thr Ser
            900                 905                 910

Arg Tyr Val Val Ala Asn Asn His Leu Pro Asp Trp Phe Lys Lys Arg
        915                 920                 925

Asp Gly Gln Val Val Gln Thr Trp His Gly Thr Pro Leu Lys Lys
    930                 935                 940

Ile Gly His Asp Ile Glu Ser Ile His Phe Ala Asp Gln Arg Tyr Leu
945                 950                 955                 960

Glu Arg Val Glu Lys Glu Val Gln Asn Trp Asp Met Leu Val Ser Pro
                965                 970                 975

Asn Ser Phe Ser Thr Pro Ile Leu Lys Arg Ala Phe Gly Phe Pro Gly
            980                 985                 990

Glu Met Val Glu Ser Gly Tyr Pro Arg Asn Asp Ile Leu Arg Arg Pro
        995                 1000                1005

Asp Thr Gly Ala Arg Glu Gln Glu Ile Arg Arg Ser Ile Gly Leu
    1010                1015                1020

Pro Glu Gly Lys Arg Val Val Leu Tyr Ala Pro Thr Trp Arg Asp
    1025                1030                1035

Asp Gln Phe Tyr Ala Pro Gly Lys Tyr Lys Leu Asp Phe Arg Ile
    1040                1045                1050

Asp Leu Ala Ala Ala Arg Ala Gln Leu Gly Pro Asp His Val Leu
```

```
                1055                1060                1065
Met Val Arg Arg His Pro Asn Val Val Asp Pro Val Pro Gly Ala
        1070                1075                1080

Gly Asp Gly Phe Val Phe Asp Val Ser Asp Tyr Pro Asp Met Ala
        1085                1090                1095

Asp Leu Ser Leu Ile Thr Asp Val Met Ile Thr Asp Tyr Ser Ser
        1100                1105                1110

Leu Met Phe Asp Tyr Val Asn Thr Gly Arg Pro Ile Leu Phe Phe
        1115                1120                1125

Thr Tyr Asp Leu Asp His Tyr Arg Asp Thr Leu Arg Gly Phe Tyr
        1130                1135                1140

Phe Asp Phe Glu Gly Ser Ala Pro Gly Pro Leu Leu Tyr Thr Ser
        1145                1150                1155

Glu Glu Leu Val Ala Ala Ile Arg Asp Ile Asp Ala Ile Gln Asp
        1160                1165                1170

Leu Tyr Ala Glu Arg Tyr Arg Trp Phe Gln Arg Glu Phe Cys Asp
        1175                1180                1185

Leu Asp Asp Gly Tyr Ala Ala Ala Arg Leu Ala Asp Arg Met Leu
        1190                1195                1200

Val Ala Gly Gly Asp Leu Ala Pro Gly Gln Ala His Ala Pro Ala
        1205                1210                1215

Val Gly Ala Val Asp Thr Arg His Thr Gly Arg Pro Met Thr Pro
        1220                1225                1230

Leu Gln Trp Gly Asn Ser Glu Trp Phe Ala Gly Pro Arg Pro Pro
        1235                1240                1245

Ala Gly Leu Val Asp Ala Val Pro Ala Gln Pro Ala Pro Ala Tyr
        1250                1255                1260

Asp Ala Val Pro Gln His Gln Ala Gly Pro Phe Gly His Thr Pro
        1265                1270                1275

Pro Ala Gly Asp Arg Ser Tyr Glu Gly Val Ile Ala
        1280                1285                1290

<210> SEQ ID NO 7
<211> LENGTH: 305
<212> TYPE: PRT
<213> ORGANISM: Streptomyces fungicidicus

<400> SEQUENCE: 7

Met Leu Arg Asn Arg Thr Arg Ser Pro Arg Pro Arg Gly Arg Leu
1               5                   10                  15

Leu Ala Ala Val Thr Ala Ala Ala Leu Ala Gly Leu Ala Ala Val
                20                  25                  30

Val Thr His Glu Arg Ser Gly Asn Gly Ala Asp Arg Ser Ala Thr Gly
        35                  40                  45

Asp Arg Thr Leu Thr Val Ala Thr Trp Asn Met Cys Gly Val Arg Glu
50                  55                  60

Trp Asn Cys Glu Gly Thr Gly Gly Glu Asp Ala Lys Arg Gly Arg Thr
65                  70                  75                  80

Glu Arg Leu Ala Ala Glu Ser Gly Ala Arg Val Leu Phe Leu Gln Glu
                85                  90                  95

Thr Cys Ala Ala Asp Val Glu Val Arg Ala Ser Leu Gly Ala Ser
                100                 105                 110

Trp His Ala Glu Phe Arg Ala Tyr Thr Trp Arg Gly Arg Asp Gly Arg
        115                 120                 125

Arg Thr Ala Val Arg Cys Gly Ala Pro Gly Arg Gly Ser Ala Gly Tyr
```

```
                130                 135                 140
Ala Leu Leu Ser Ala Tyr Pro Leu Ser Ser Val Arg Ala Val Pro Ala
145                 150                 155                 160

Pro Gln Pro Ala Val Gly Val Gln Arg Gly Ile Leu Cys Ala Phe Val
            165                 170                 175

Ala Ala His Asp Leu Thr Val Cys Thr Ala His Leu Thr Pro Arg Gly
        180                 185                 190

Gly Asp Leu Ala His Pro Asp Arg Glu Phe Arg Ala Gly Gln Leu Lys
            195                 200                 205

Ala Leu Val Asp Ala Val Pro Glu Arg Arg Thr Val Tyr Gly Gly Asp
210                 215                 220

Leu Asn Val Asp Pro Pro Gly Glu Arg Asn Pro Leu Ser Arg Val Trp
225                 230                 235                 240

Pro Asp Gln Pro Tyr Gly Thr His Arg Glu Cys Asp Gly Thr Pro Gly
                245                 250                 255

Pro Leu Arg Pro Ala Arg Pro Thr His Val Ser His His Lys Leu Asp
            260                 265                 270

Tyr Leu Phe Thr Gly Leu Pro Val Leu Gly Cys Arg Val Ser Asp Thr
        275                 280                 285

Gly Val Ser Asp His Arg Ala Leu Leu Ile Arg Val Asp Thr Gly Thr
    290                 295                 300

Gly
305

<210> SEQ ID NO 8
<211> LENGTH: 481
<212> TYPE: PRT
<213> ORGANISM: Streptomyces fungicidicus

<400> SEQUENCE: 8

Met Ser Lys Ala Pro Ser Asn Gly Arg Gln Leu Leu Asn Gly Ile Glu
1               5                   10                  15

Ala Ser Gly Thr Phe Pro Val Glu Tyr Arg Phe Thr His Ala Lys Ser
            20                  25                  30

Gly Asn Arg His Leu Val Val Phe Ala Asn Phe Ser Ala Pro Glu
        35                  40                  45

Asp Tyr Gly Trp Ser Asn Gly Val Phe Asp Asn Val Arg Ala Asn Ile
    50                  55                  60

Leu Trp Ile Arg Asp Arg Phe Asp Gly Met Asn Ala Tyr Tyr Leu Cys
65                  70                  75                  80

Arg Asn Met Asp Phe Gly Leu Ala Asp Ser Val Gln Thr Leu Ile Ala
                85                  90                  95

Asn Val Thr Gly Ala Leu Gly Leu Thr Pro Asp Gln Val Thr Leu Trp
            100                 105                 110

Gly Gly Ser Lys Gly Gly Ser Ala Ala Leu Tyr Phe Gly Leu Arg Tyr
        115                 120                 125

Gly Tyr Arg Asn Ile Val Ala Ile Val Pro Gln Phe Leu Ile Gly Asp
    130                 135                 140

Ala Leu Glu Lys Arg His Pro Lys Val Ser Ala Tyr Met Leu Gly Glu
145                 150                 155                 160

Gly Ala Gln Ala His Asn Ala Arg Ile Leu Asp Ala Leu Leu Pro Asp
                165                 170                 175

Leu Val Arg Ala Lys Ala Asn Pro Gly Ala Asn Ile Tyr Val Leu Ser
            180                 185                 190

Ser Pro Gln Asp Glu His Tyr Ala Val Gln Val Glu Pro Phe Leu Gly
```

```
            195                 200                 205
Met Phe His Gly Tyr Glu Asn Phe Asn Phe Leu Tyr Ser Glu Ser Pro
210                 215                 220

Thr Ile Thr Gly His Ala Thr Thr Arg Arg Asn Val Pro Ala Leu
225                 230                 235                 240

Val Gly Leu Leu Asn Leu Leu Ala Asp Gly Tyr Ala Pro Arg Leu Gly
                245                 250                 255

Phe Thr Arg His Ala Ala Glu Asp Phe Asp His Asp Arg Ser Asp Ile
            260                 265                 270

Asn Ala Tyr Leu Ala Ser Thr Ser Lys Val Gln Gly Ala Asp Ala Phe
        275                 280                 285

Ala Pro Pro Val Val Thr Thr Pro Gly Phe Asn Ser Glu Val Pro Arg
290                 295                 300

Thr Gly Pro Trp Phe Thr Gly Thr Ala His Gly Ala Val Arg Val Ser
305                 310                 315                 320

Met Trp Arg Asn Gly Lys Phe Val Ala Ser Pro Gln Val Ala Asp Gly
                325                 330                 335

Thr Trp Ser Trp Gln Pro Thr Gly Pro Trp Glu Ala Gly Lys His Ile
            340                 345                 350

Val Lys Ile Phe Ala Val Asp Pro Ala Gly Phe His Ser Ala Arg Val
        355                 360                 365

Glu Ile Pro Phe Thr Val Val Asp Arg Asp Pro Pro Ala Pro Pro
370                 375                 380

Val Val Ser Ala Pro Val Ser Gly Gln Gln Thr Gly Ala Ala Val Gly
385                 390                 395                 400

Phe His Gly Ser Ala Pro Gly Ala Ser Gln Val Gly Phe Arg Glu Asn
                405                 410                 415

Gly Val Leu Leu Gly Ala Val Ala Val Ala Pro Asp Gly Thr Trp Gly
            420                 425                 430

Trp Asp Pro Gly Arg Pro Trp Pro Glu Gly Gln His Leu Val Glu Ile
        435                 440                 445

Val Ala Val Asp Ala Tyr Gly Met Glu Ser Ala Pro Ala Ala Ala Gly
450                 455                 460

Phe Thr Val Leu Gly His Ala Val Pro Ala Gly His Phe Thr Pro Arg
465                 470                 475                 480

Tyr

<210> SEQ ID NO 9
<211> LENGTH: 496
<212> TYPE: PRT
<213> ORGANISM: Streptomyces fungicidicus

<400> SEQUENCE: 9

Met Pro Lys Glu Ala Pro Thr Thr Arg Glu Leu Ile Thr Gly Ile Asp
1               5                   10                  15

Thr Ser Gly Ala Tyr Pro Val Glu Tyr Arg Phe Thr His Ala Lys Gly
                20                  25                  30

Gly Asn Arg His Leu Val Val Phe Ala Asn Phe Ala Val Lys Asp
            35                  40                  45

Asp Tyr Gly Trp Ser Asn Gly Val Leu Asn Pro Val Arg Ala Asn Ile
        50                  55                  60

Leu Trp Ile Arg Asp Arg Phe Arg Asp Met Asn Ser Tyr Tyr Leu Cys
65                  70                  75                  80

Glu Gly Met Asp Phe Ser Leu Glu Gln Ser Val Ile Gly Leu Ile Ser
                85                  90                  95
```

```
Lys Val Met Asn Ala Leu Glu Leu Thr Pro Glu Gln Val Thr Met Trp
             100                 105                 110
Gly Gly Ser Lys Gly Ser Ala Ala Leu Tyr Phe Gly Met Arg Tyr
         115                 120                 125
Gly Phe Gly Asn Ile Val Ser Ile Val Pro Gln Phe Leu Val Gly Thr
    130                 135                 140
Tyr Val Lys Arg Val His Pro Lys Val Ala Arg Phe Met Leu Gly Glu
145                 150                 155                 160
Ala Val Pro Glu Glu Asn Val Arg Ala Val Asp Ala Leu Ile Pro Asp
                165                 170                 175
Leu Ala Arg Ser Gly Val Ala Arg His Ser Asn Ile Tyr Leu Leu Ser
            180                 185                 190
Ser Pro Gln Asp Glu Gln Tyr Gln Glu Gln Val Glu Pro Phe Leu Gly
        195                 200                 205
Leu Phe Gln Gly Tyr Asp Asn Phe Asn Phe Val Phe Ser Glu Ser Pro
    210                 215                 220
His Ile Thr Arg His Ser Asp Val Thr Arg Arg Asn Val Pro Phe Leu
225                 230                 235                 240
Met Gly Leu Val Asn Met Leu Ala Asp Gly Met Ser Pro Arg Leu Gly
                245                 250                 255
Leu Val Arg Asn Gly Tyr Glu Glu Pro Asp Arg Asp Arg Ser Ala Ile
            260                 265                 270
Glu Gly Phe Leu Ala Ala Thr Ser Ala Glu Arg Pro Ser Ala Ile Pro
        275                 280                 285
Met Pro Val Val Thr His Pro Leu Pro His Met Glu Leu Pro Thr Asp
    290                 295                 300
Gly Val Tyr Phe Thr Gly Thr Ala Pro Gly Ala Val Arg Val Ser Leu
305                 310                 315                 320
Trp Glu His Gly Lys Phe Leu Gly Ser Pro Ser Val Ala Pro Asp Gly
                325                 330                 335
Thr Trp Ser Trp Lys Arg Asp Lys Pro Trp Ser Lys Gly Asp His Leu
            340                 345                 350
Val Lys Ala Val Gly Trp Asp Ala Glu Lys Arg Arg Thr Lys Gly Thr
        355                 360                 365
Val Val Pro Phe Thr Thr Val Ala Gly Ala Asn Ala Ala Pro Gly
    370                 375                 380
Ala Pro Ala Ala Pro Leu Ala Pro Gly Gln Pro Leu Pro Ala Pro
385                 390                 395                 400
Thr Val His Thr Pro Gly Ala Tyr Glu Gln Ile Thr Gly Thr Ala Val
                405                 410                 415
Arg Phe Ser Gly Phe Ala Pro Gly Ala Ala Gln Val Gly Phe Arg Ala
            420                 425                 430
Gly Gly Thr Leu Leu Gly Thr Ser Arg Val Ala Ala Asp Gly Thr Trp
        435                 440                 445
Ala Trp Asp Ser Gly Trp Pro Trp Gln Ala Gly Met His Thr Val Glu
    450                 455                 460
Val Phe Ala Val Asp Ala Ala Gly Ser Glu Ser Pro Val Ala Pro Val
465                 470                 475                 480
Pro Phe Asp Val Met His Ala Thr Ala Gly Ala Ser Pro Phe Ala Tyr
                485                 490                 495

<210> SEQ ID NO 10
<211> LENGTH: 709
<212> TYPE: PRT
```

<213> ORGANISM: Streptomyces fungicidicus

<400> SEQUENCE: 10

```
Met Ser Thr Thr Ala Glu Leu Leu Lys Gly Ala Ala Glu Leu Phe Pro
1               5                   10                  15

Gly Glu Val Val Thr Ser Ala His Val Arg His Phe Asp Leu Pro Leu
                20                  25                  30

Gly Ala Gly Arg Phe Ala Leu Ile Thr Leu Asp Asn Gly His Asp His
            35                  40                  45

Thr Lys Pro Thr Thr Leu Gly Pro Gln Ser Leu Ala Asn Ile Asp Ala
        50                  55                  60

Ala Ile Asp Arg Val Glu Lys Glu Ala Ala Asp Gly Glu Ile Val Gly
65                  70                  75                  80

Val Gly Val Thr Gly Lys Pro Phe Ile Phe Ala Val Gly Ala Asp Leu
                85                  90                  95

Lys Gly Val Glu Leu Leu Lys Arg His Glu Asp Ala Leu Ala Ile Gly
            100                 105                 110

Lys Gly Gly His Asp Val Phe Lys Arg Leu Ser Thr Leu Ala Val Pro
        115                 120                 125

Thr Phe Ala Tyr Tyr Asn Gly Ala Ala Met Gly Gly Gly Val Glu Val
130                 135                 140

Gly Leu His Cys Thr Tyr Arg Thr Val Ser Ala Ala Leu Pro Ala Phe
145                 150                 155                 160

Ser Leu Pro Glu Val Phe Leu Gly Leu Val Pro Gly Trp Gly Gly Cys
                165                 170                 175

Thr Leu Leu Pro Asn Leu Ile Gly Ala Glu Lys Ala Val Ser Val Ile
            180                 185                 190

Ile Glu Asn Ser Leu Asn Gln Asn Lys Gln Leu Lys Gly Ala Gln Val
        195                 200                 205

Phe Glu Leu Gly Ile Ala Asp Ala Ile Phe Glu Gly Ala Asp Phe Leu
210                 215                 220

Glu Gln Ser Leu Ile Trp Thr Ala Ala Val Leu Lys Asp Glu Ile Arg
225                 230                 235                 240

Ile Glu Arg Pro Val Ile Asp Arg Gly Glu Ala Trp Asp Gln Ala Val
                245                 250                 255

Ala Lys Gly Arg Phe Ile Ala Asp Ser Lys Val His Gly Ala Ala Pro
            260                 265                 270

Ala Ala Tyr Arg Ala Leu Asp Ile Ile Ala Ala Lys Asn Gly Asp
        275                 280                 285

Leu Gln Gln Gly Tyr Asp Ala Glu Asp Gln Ala Leu Ala Asp Leu Ile
290                 295                 300

Met Gly Gly Glu Leu Arg Ser Gly Ile Tyr Ala Phe Asn Leu Val Gln
305                 310                 315                 320

Lys Arg Gly Lys Arg Pro Ala Gly Ala Pro Asp Lys Ser Leu Ala Arg
                325                 330                 335

Pro Val Thr Lys Val Gly Val Val Gly Ala Gly Leu Met Ala Ser Gln
            340                 345                 350

Leu Ala Leu Leu Phe Leu Arg Arg Leu Glu Val Pro Val Val Leu Thr
        355                 360                 365

Asp Ile Asp Gln Ala Arg Ile Asp Lys Gly Val Gly Tyr Val His Ala
370                 375                 380

Glu Ile Asp Lys Leu Leu Gly Lys Gly Arg Ile Asn Gln Asp Lys Ala
385                 390                 395                 400

Asn Arg Leu Lys Ala Leu Val Thr Gly Val Leu Asp Lys Ala Glu Gly
```

```
                    405                 410                 415
Phe Ala Asp Ala Asp Phe Val Ile Glu Ala Val Phe Glu Glu Met Gly
                420                 425                 430

Val Lys Gln Gln Val Phe Ala Glu Val Glu Ala Val Ala Pro Ala His
            435                 440                 445

Ala Ile Leu Ala Thr Asn Ser Ser Leu Ser Val Ser Glu Met Ala
    450                 455                 460

Ser Lys Leu Lys His Pro Glu Arg Val Val Gly Phe His Phe Phe Asn
465                 470                 475                 480

Pro Val Ala Ile Leu Pro Leu Leu Glu Ile Val Arg Gly Glu Arg Thr
                485                 490                 495

Asp Asp Ala Ala Leu Ala Thr Ala Phe Gly Val Ala Lys Lys Leu Lys
            500                 505                 510

Lys Thr Ala Val Leu Val Lys Asp Ala Pro Ala Phe Val Val Asn Arg
        515                 520                 525

Ile Leu Thr Arg Phe Met Gly Glu Ile Gln Asn Val Ile Asp Glu Gly
    530                 535                 540

Thr Pro Val Glu Val Ala Glu Lys Ala Val Glu Pro Leu Gly Leu Pro
545                 550                 555                 560

Met Ser Pro Leu Val Leu Glu Leu Val Gly Pro Ala Ile Gly Leu
                565                 570                 575

His Val Ser Glu Thr Leu Asn Arg Ala Phe Pro Glu Arg Phe Thr Val
            580                 585                 590

Ser Pro Asn Leu Arg Ala Val Val Glu Ala Gly Lys Arg Gly Phe Tyr
        595                 600                 605

Leu Tyr Asp Ser Gly Lys Pro Glu Leu Asp Pro Glu Val Ala Ala Leu
    610                 615                 620

Leu Lys Gln Gly Asp Thr Val Leu Thr Glu Glu Gln Val Arg Ala Arg
625                 630                 635                 640

Val Leu Asp Ala Val Ala Gln Glu Ile Gly Leu Met Leu Asp Glu Gly
                645                 650                 655

Val Val Ala Glu Ala Gln Asp Ile Asp Leu Cys Leu Ile Thr Gly Ala
            660                 665                 670

Gly Trp Pro Phe His Leu Gly Gly Ile Thr Pro Tyr Leu Asp Arg Glu
        675                 680                 685

Gly Val Ser Glu Arg Val Asn Gly Lys Arg Phe Leu Glu Pro Gly Thr
    690                 695                 700

Ala Ser Val Pro Ala
705

<210> SEQ ID NO 11
<211> LENGTH: 405
<212> TYPE: PRT
<213> ORGANISM: Streptomyces fungicidicus

<400> SEQUENCE: 11

Met Pro Arg Thr Val Arg Asp Val Val Phe Val Asp Gly Val Arg Thr
1               5                   10                  15

Pro Phe Gly Lys Ala Gly Pro Lys Gly Ile Tyr His Glu Thr Arg Ala
                20                  25                  30

Asp Asp Leu Val Val Lys Ala Ile Arg Glu Leu Leu Arg Arg Asn Pro
            35                  40                  45

Gly Leu Asp Pro Lys Lys Ile Asp Glu Val Ala Val Ala Ala Thr Thr
        50                  55                  60

Gln Ile Gly Asp Gln Gly Leu Thr Ile Gly Arg Thr Ala Gly Ile Leu
```

```
                65                  70                  75                  80
        Ala Gly Leu Pro Thr Ser Val Pro Gly Tyr Ser Ile Asp Arg Met Cys
                        85                  90                  95

Ala Gly Ala Leu Thr Ala Val Thr Thr Val Ala Gly Ser Val Ala Phe
                    100                 105                 110

Gly Ala Tyr Asp Val Ala Ile Ala Gly Gly Val Glu His Met Gly Arg
                    115                 120                 125

His Pro Met Gly Glu Gly Val Asp Pro Asn Pro Arg Phe Val Ser Glu
                    130                 135                 140

Lys Leu Val Asp Glu Ser Ala Leu Phe Met Gly Met Thr Ala Glu Asn
        145                 150                 155                 160

Leu His Asp Arg Tyr Pro Ser Ile Thr Lys Gln Arg Ala Asp Glu Tyr
                        165                 170                 175

Ala Val Arg Ser Gln Glu Lys Ala Ala Lys Ala Tyr Ala Asn Gly Lys
                    180                 185                 190

Ile Gln Ala Asp Leu Val Pro Val Ser Val Arg Arg Thr Asn Glu Glu
                    195                 200                 205

Ala Gly Glu Thr Gly Trp Gly Leu Val Thr Ala Asp Glu Pro Met Arg
                    210                 215                 220

Pro Gly Thr Thr Leu Glu Asn Leu Ala Gly Leu Lys Thr Pro Phe Arg
        225                 230                 235                 240

Val His Gly Arg Val Thr Ala Gly Asn Ala Ala Gly Leu Asn Asp Gly
                        245                 250                 255

Ala Thr Ala Ser Val Ile Ala Ser Glu Asp Phe Ala Arg Glu Asn Gly
                    260                 265                 270

Leu Pro Val Lys Met Arg Leu Val Ser Tyr Ser Phe Ala Gly Val Glu
                    275                 280                 285

Pro Glu Val Met Gly Tyr Gly Pro Ile Pro Ala Thr Glu Lys Ala Leu
                    290                 295                 300

Ala Gln Ala Gly Leu Ser Ile Ser Asp Ile Gly Leu Phe Glu Ile Asn
        305                 310                 315                 320

Glu Ala Phe Ala Val Gln Val Leu Ala Phe Leu Glu His Tyr Gly Ile
                        325                 330                 335

Ala Asp Asp Asp Ala Arg Val Asn Gln Tyr Gly Gly Ala Ile Ala Phe
                    340                 345                 350

Gly His Pro Leu Ala Ser Ser Gly Val Arg Leu Met Thr Gln Leu Ala
                    355                 360                 365

Arg Gln Phe Glu Glu Gln Pro Gln Val Arg Tyr Gly Leu Thr Thr Met
                    370                 375                 380

Cys Val Gly Phe Gly Met Gly Ala Thr Val Ile Trp Glu Asn Pro His
        385                 390                 395                 400

Phe Glu Gly Asp Lys
                        405

<210> SEQ ID NO 12
<211> LENGTH: 345
<212> TYPE: PRT
<213> ORGANISM: Streptomyces fungicidicus

<400> SEQUENCE: 12

Met Thr Ala Thr Pro Thr Pro Arg Val Thr Ile Arg Asp Val Ala Ala
1               5                   10                  15

Arg Ala Gly Val Ser Lys Gly Ala Val Ser Leu Ala Phe Asn Arg Lys
            20                  25                  30

Pro Gly Leu Ser Glu Ala Thr Arg Asp Arg Ile Phe Arg Ala Ala Arg
```

```
                35                  40                  45
Glu Leu Gly Trp Ala Pro Ser Arg Thr Ala Arg Thr Leu Ala Gly Ser
 50                  55                  60

Arg Val Asp Val Val Gly Leu Ala Val Cys Arg Pro Ala Arg Leu Leu
 65                  70                  75                  80

Gly Leu Glu Pro Phe Tyr Met Glu Phe Ile Ser Gly Val Glu Ser Val
                 85                  90                  95

Leu Val Glu Arg Ser Cys Ser Leu Leu Arg Leu Val Arg Ser Pro
            100                 105                 110

Glu Glu Glu Val Gly Leu Met Glu Ser Trp Trp Arg Gly Arg Gln Ile
            115                 120                 125

Gly Gly Ser Ile Leu Val Asp Phe Arg Ala Gly Asp Pro Arg Pro Ala
130                 135                 140

Val Ala Glu Arg Leu Gly Leu Pro Ala Val Ala Val Gly His Pro Ala
145                 150                 155                 160

Leu Thr Gly Gly Leu Thr Ser Val Trp Thr Asp Asp Ala Thr Ala Val
                165                 170                 175

Thr Glu Ala Val Arg Tyr Leu Ala Ala Leu Gly His Arg Arg Ile Ala
            180                 185                 190

Arg Val Gly Gly Ala Ala Ala Leu Gly His Thr Ser Ile Arg Thr Ala
            195                 200                 205

Ala Phe Asp Glu Ala Val Arg Ala Leu Glu Pro Pro Ala Arg Ala Trp
210                 215                 220

Gln Thr Ala Thr Asp Phe Ser Gly Asp Ala Gly Ala Arg Ala Thr Arg
225                 230                 235                 240

Ser Leu Leu Ala Ala Pro Gly Glu Arg Pro Thr Ala Ile Val Tyr
                245                 250                 255

Asp Asn Asp Ile Met Ala Val Ala Gly Leu Ser Val Ala Ala Glu Met
            260                 265                 270

Gly Leu Arg Val Pro Asp Asp Val Ser Leu Leu Ala Trp Asp Asp Ser
            275                 280                 285

Gln Leu Cys Arg Leu Thr His Pro Thr Leu Ser Ala Met Ser His Asp
290                 295                 300

Val His Gly Phe Gly Ala Glu Val Ala Arg Thr Leu Phe Gly Val Ile
305                 310                 315                 320

Thr Gly Glu Glu Gln Pro Gly Ser His Pro Val Pro Thr Pro Val Leu
                325                 330                 335

Thr Pro Arg Gly Ser Thr Ala Pro Pro
            340                 345

<210> SEQ ID NO 13
<211> LENGTH: 793
<212> TYPE: PRT
<213> ORGANISM: Streptomyces fungicidicus

<400> SEQUENCE: 13

Met Arg Gln Val Thr Pro Leu Thr Glu Gly Trp Ile Leu Arg His Pro
1               5                  10                  15

Asp Gly Thr Gly Asp Ala Leu Pro Ala Ser Val Pro Gly Cys Val His
             20                  25                  30

Thr Asp Leu Leu Ala Ala Gly Leu Ile Pro Asp Pro Phe Leu Gly Arg
              35                  40                  45

Asn Glu Thr Glu Val Ala Trp Val Gly Arg Arg Glu Trp Thr Tyr Glu
 50                  55                  60

Thr Glu Leu Thr Ala Gly Thr Gly Pro His Glu Gln Thr Asp Leu Val
```

```
                65                  70                  75                  80
Phe Asp Gly Leu Asp Thr Val Ala Glu Ile Leu Leu Asp Gly Arg Pro
                    85                  90                  95
Leu Gly Arg Thr Arg Asn Met His Arg Ser Tyr Arg Phe Asp Val Thr
                    100                 105                 110
Gly Leu Ser Gly Arg Leu Thr Val Arg Phe Ala Ser Ala Tyr Ala Glu
                    115                 120                 125
Ala Glu Ala Val Arg Gly Arg Leu Gly Glu Arg Pro Gly Ala Tyr Ala
                    130                 135                 140
Glu Pro Tyr Gln Tyr Leu Arg Lys Met Ala Cys Ser Phe Gly Trp Asp
145                 150                 155                 160
Trp Gly Pro Thr Leu Val Thr Ala Gly Ile Trp Arg Pro Val Arg Leu
                    165                 170                 175
Glu Arg Trp Ser Thr Ala Arg Ile Ala Arg Val Arg Pro Leu Val Thr
                    180                 185                 190
Val Glu Asp Gly Val Gly Gln Ile Glu Leu Ala Val Asp Val Glu Arg
                    195                 200                 205
Ser Arg Val Glu Ala Pro Leu Thr Leu Glu Ala Ser Ala Gly Gly Val
210                 215                 220
Arg Ala Arg Ala Arg Val Asp Gly Thr Ala Gly Thr Val Arg Leu Arg
225                 230                 235                 240
Val Pro Asp Val Arg Leu Trp Trp Pro Arg Gly Tyr Gly Glu Gln Pro
                    245                 250                 255
Leu Tyr Asp Val Glu Leu Thr Leu Ser His Gly Asp Glu Ala Leu Asp
                    260                 265                 270
Ala Trp Arg Arg Arg Thr Gly Phe Arg Thr Val Glu Leu Asp Thr Ser
                    275                 280                 285
Ala Asp Ala His Gly Thr Gly Phe Thr Leu Val Val Asn Gly Glu Arg
                    290                 295                 300
Leu Phe Ala Arg Gly Val Asn Trp Ile Pro Asp Asp Val Phe Pro Ser
305                 310                 315                 320
Arg Ile Thr Arg Glu Arg Tyr Arg His Arg Leu Glu Gln Ala Ala Gly
                    325                 330                 335
Ala Gly Val Asp Leu Val Arg Val Trp Gly Gly Gly Ile Tyr Glu Asp
                    340                 345                 350
Glu Asp Phe Tyr Asp Ala Cys Asp Glu Leu Gly Leu Leu Val Trp Gln
                    355                 360                 365
Asp Phe Pro Phe Ala Cys Ala Ala Tyr Pro Glu Glu Gln Pro Leu Arg
                    370                 375                 380
Gly Glu Val Glu Ala Glu Ala Arg Glu Asn Val Val Arg Leu Met Pro
385                 390                 395                 400
His Pro Ser Leu Val Leu Trp Asn Gly Asn Asn Glu Asn Leu Trp Gly
                    405                 410                 415
Phe Arg Asp Trp Asp Trp Glu Gln Gly Leu Ala Gly Asp Ser Trp Gly
                    420                 425                 430
Glu Gly Tyr Tyr Leu Gly Val Leu Pro Arg Val Val Ala Glu Leu Asp
                    435                 440                 445
Pro Thr Arg Pro Tyr Thr Ala Gly Ser Pro Trp Ser Gly Ser Trp Arg
                    450                 455                 460
His His Pro Asn Asp Pro Ala His Gly Thr His Ser Trp Glu Val
465                 470                 475                 480
Trp Asn Arg Ala Asp Tyr Ala Asp Tyr Arg Arg Asp Val Pro Arg Phe
                    485                 490                 495
```

-continued

Val Ala Glu Phe Gly Trp Gln Ala Pro Pro Ala His Ala Thr Leu Arg
        500                 505                 510

Arg Ala Leu Pro Gly Glu Asp Pro Ala Pro Asp Ser Pro Gly Met Leu
        515                 520                 525

His His Gln Lys Ala Glu Asp Gly Asn Gly Lys Leu Glu Arg Gly Leu
    530                 535                 540

Ala Arg His Phe Ala Val Pro Glu Gly Asp Phe Asp Arg Trp His Tyr
545                 550                 555                 560

Leu Thr Gln Val Asn Gln Ala Arg Ala Val Ala Gly Val Glu His
                565                 570                 575

Trp Arg Ser His Trp Pro Val Cys Ala Gly Thr Val Val Trp Gln Leu
            580                 585                 590

Asn Asp Cys Trp Pro Val Thr Ser Trp Ala Ala Ile Asp Gly Asp Gly
        595                 600                 605

Arg Glu Lys Pro Leu Tyr His Glu Leu Arg Arg Leu Tyr Ala Asp Arg
    610                 615                 620

Leu Leu Thr Val Arg Ala Asp Gly Asp Gly Leu Val Ala Ala Val
625                 630                 635                 640

Asn Gln Ser Ala Glu Asp Trp Arg Gly Thr Leu Arg Leu Arg Arg Met
                645                 650                 655

Ser Val Asp Gly Ala Pro Ile Ala Glu Ala Ala Pro Ala Leu Asp Ala
            660                 665                 670

Gly Gly Arg Thr Val Ala Val Glu Val Pro Val Glu Leu Leu Pro
        675                 680                 685

Asp Gly Pro Gly Glu Phe Leu Val Ala Asp Ala Asp Gly Val Arg Ala
    690                 695                 700

Trp His Phe Pro Ala Pro Asp Arg Glu Ile Pro Tyr Pro Pro Glu
705                 710                 715                 720

Phe Glu Val Ala Leu Ala Pro Asp Gly Ile Thr Val Thr Ala Arg Thr
                725                 730                 735

Leu Val Arg Asp Leu Leu Leu Gln Ala Asp Arg Leu Asp Pro Gly Ala
            740                 745                 750

Arg Ala Asp Arg Gly Leu Val Thr Leu Leu Pro Gly Glu Gln Val Thr
        755                 760                 765

Ile Gly Val Arg Gly Trp Lys Thr Pro Asp Pro Asp Thr Ala Arg Ser
    770                 775                 780

Ala Leu Tyr Cys Val Glu Pro Thr Arg
785                 790

<210> SEQ ID NO 14
<211> LENGTH: 440
<212> TYPE: PRT
<213> ORGANISM: Streptomyces fungicidicus

<400> SEQUENCE: 14

Met His Leu Asn Arg Arg Thr Thr Leu Thr Gly Ser Leu Ala Leu Leu
1               5                   10                  15

Ala Leu Leu Ala Ser Ala Cys Thr Gly Thr Gly Gly Ser Ser Lys Gly
            20                  25                  30

Ala Asp Ala Lys Ala Pro Asp Asp Pro Ser Lys Val Lys Gly Ser Leu
        35                  40                  45

Thr Val Leu Thr His Arg Thr Asp Leu Val Gln Asp Gly Thr Met Lys
    50                  55                  60

Lys Tyr Ala Ala Glu Phe Asn Glu Thr Tyr Pro Gly Val Lys Val Glu
65                  70                  75                  80

```
Phe Asp Gly Leu Thr Asp Tyr Glu Gly Glu Val Lys Ile Arg Met Asn
                85                  90                  95

Thr Glu Asn Tyr Gly Asp Val Leu Met Ile Pro Ala Val Val Glu Lys
            100                 105                 110

Lys Asp Tyr Pro Lys Phe Phe Ala Ser Leu Gly Thr Lys Ala Glu Arg
        115                 120                 125

Ala Ala Lys Tyr Arg Phe Thr Asp Tyr Ser Thr Val Asp Gly Lys Val
    130                 135                 140

Tyr Gly Gln Ser Pro Val Gly Val Pro Gly Phe Ile Tyr Asn Lys
145                 150                 155                 160

Arg Val Trp Ser Glu Ala Gly Val Thr Asp Trp Pro Thr Pro Ala
                165                 170                 175

Glu Phe Leu Asp Asp Leu Lys Ala Ile Arg Ser Lys Thr Asp Ala Val
                180                 185                 190

Pro Tyr Tyr Thr Asn Phe Lys Asp Met Trp Pro Leu Thr Gln Trp Thr
        195                 200                 205

Asn Val Asn Gly Ser Val Gly Cys Asp Pro His Ala Thr Thr Lys Leu
    210                 215                 220

Ala Glu Gly Asp Pro Trp Ala Glu Gly Ala Asp Leu Arg Val Gly Asp
225                 230                 235                 240

Thr Leu Leu His Asp Ile Val Arg Gly Gly Leu Ala Glu Lys Asp Pro
                245                 250                 255

Thr Thr Thr Asn Trp Glu Gly Ser Lys Pro Lys Leu Ala Lys Gly Glu
            260                 265                 270

Ile Ala Thr Met Trp Leu Gly Ser Trp Ala Val Val Gln Met Arg Asp
        275                 280                 285

Ala Ala Lys Gln Ala Gly Ala Asp Pro Ala Asp Ile Gly Phe Met Pro
    290                 295                 300

Phe Pro Ala Gln Arg Asp Gly Thr Phe Cys Ala Val Thr Ser Pro Asp
305                 310                 315                 320

Tyr Gln Gln Ala Val Asn Val Asn Ser Asp Asn Lys Glu Ala Ala Arg
                325                 330                 335

Ala Trp Ile Asp Trp Phe Thr Asp Lys Ser Gly Tyr Ala Glu Ala Asn
            340                 345                 350

Leu Ala Leu Ser Pro Leu Lys Asp Ala Pro Leu Pro Ala Val Leu Glu
        355                 360                 365

Pro Tyr Glu Lys Ala Gly Val Lys Leu Leu Asp Leu Glu Asp Ser Lys
    370                 375                 380

Gly Ala Glu Val Lys Ser Leu Asp Asn Arg Ser Glu Val Gly Ile Tyr
385                 390                 395                 400

Lys Pro Asp Tyr Arg Gln Glu Leu Val Asp Leu Ala Arg Gly Ala Arg
                405                 410                 415

Lys Gly Gly Leu Asp Asp Tyr Leu Gly Gly Leu Gly Glu Arg Trp Ala
            420                 425                 430

Glu Ala Arg Ser Ala Leu Gly Ala
        435                 440

<210> SEQ ID NO 15
<211> LENGTH: 258
<212> TYPE: PRT
<213> ORGANISM: Streptomyces fungicidicus

<400> SEQUENCE: 15

Met Val Ala Tyr Ser Phe Thr Asp Trp Asp Gly Val Ser Pro Glu Leu
1               5                   10                  15
```

```
Asn Trp Thr Gly Thr Gly Asn Tyr Thr Glu Leu Leu Thr Arg Ser Glu
         20                  25                  30

Leu Phe Glu Val Phe Val Ser Gly Tyr Tyr Leu Val Ala Ser Ala
         35                  40                  45

Val Gln Ile Val Leu Ala Leu Tyr Phe Ala Thr Val Leu Ser Phe Asp
 50                  55                  60

Val Arg Phe Arg Asn Phe Phe Lys Gly Val Leu Phe Phe Pro Tyr Leu
 65                  70                  75                  80

Ile Asn Gly Val Ala Ile Gly Phe Val Phe Leu Tyr Phe Phe Gln Asp
                 85                  90                  95

Gly Gly Thr Leu Asp Ser Val Leu Gly Leu Leu Gly Val Glu Thr Asp
             100                 105                 110

His Ala Trp Leu Gly Thr Pro Phe Ser Ala Asn Thr Ser Leu Ala Gly
             115                 120                 125

Val Ser Val Trp Arg Tyr Leu Gly Leu Asn Phe Val Leu Phe Leu Gly
         130                 135                 140

Ala Ile Gln Ser Ile Pro Gly Glu Leu Tyr Glu Ala Ala Glu Ile Asp
145                 150                 155                 160

Gly Ala Asn Arg Trp Gln Gln Phe Arg His Ile Ile Ala Pro Gly Ile
                 165                 170                 175

Arg Pro Val Leu Ser Leu Ser Val Ile Leu Ser Val Ser Gly Ser Leu
             180                 185                 190

Ser Val Phe Glu Ile Pro Tyr Ile Met Thr Gly Gly Ala Thr Gly Thr
         195                 200                 205

Glu Thr Phe Val Ile Gln Thr Val Lys Leu Ala Phe Gln Phe Asn Lys
    210                 215                 220

Thr Gly Leu Ala Ser Ala Ala Val Val Leu Leu Ile Val Leu
225                 230                 235                 240

Ala Val Thr Trp Val Gln Arg Arg Ile Val Pro Asp Glu Lys Val Asp
                 245                 250                 255

Leu Val

<210> SEQ ID NO 16
<211> LENGTH: 276
<212> TYPE: PRT
<213> ORGANISM: Streptomyces fungicidicus

<400> SEQUENCE: 16

Met Thr Arg Arg Thr Ala Ala Arg Ala Leu Val Leu Thr Ser Leu Ile
 1               5                  10                  15

Leu Ala Thr Leu Val Val Leu Pro Leu Ala Val Val Phe Leu Thr
                 20                  25                  30

Ser Leu Lys Ser Ser Glu Glu Met Ala Asn Gly Ser Gly Ala Leu Thr
             35                  40                  45

Pro Pro Asp Asp Pro Leu Asn Phe Gly Asn Tyr Val Thr Ala Phe Arg
 50                  55                  60

Asp Gly Gln Met Leu Ser Ala Phe Gly Asn Thr Ala Val Ile Leu Val
 65                  70                  75                  80

Val Ala Val Gly Gly Thr Ile Leu Ile Gly Ser Met Thr Ala Tyr Ala
                 85                  90                  95

Ile Asp Arg Phe Arg Phe Arg Phe Lys Lys Leu Val Val Ala Leu Phe
                100                 105                 110

Leu Leu Ala Ala Leu Val Pro Gly Val Thr Thr Gln Val Ala Thr Phe
             115                 120                 125

Gln Ile Val Asn Ser Phe Gly Met Phe Asp Ser Leu Trp Ala Pro Ile
```

```
                130             135             140
Ala Leu Tyr Met Gly Thr Asp Ile Val Ser Ile Tyr Val Phe Leu Gln
145                 150                 155                 160

Phe Ile Arg Ser Ile Pro Val Ser Leu Asp Glu Ala Ala Arg Leu Asp
                165                 170                 175

Gly Ala Asn Ala Phe Thr Val Tyr Arg Lys Val Ile Phe Pro Leu Leu
            180                 185                 190

Lys Pro Ala Ile Ala Thr Val Val Ile Val Lys Gly Ile Asn Val Tyr
                195                 200                 205

Asn Asp Phe Tyr Ile Pro Phe Leu Tyr Met Pro Ser Glu Asp Leu Gly
210                 215                 220

Val Ile Ser Thr Ser Leu Phe Arg Phe Lys Gly Pro Phe Gly Ala His
225                 230                 235                 240

Trp Glu Thr Ile Ser Ala Gly Ala Val Leu Val Ile Leu Pro Thr Leu
                245                 250                 255

Ile Val Phe Leu Phe Leu Gln Arg Phe Ile Tyr Asn Gly Phe Met Arg
                260                 265                 270

Gly Ala Thr Lys
            275

<210> SEQ ID NO 17
<211> LENGTH: 430
<212> TYPE: PRT
<213> ORGANISM: Streptomyces fungicidicus

<400> SEQUENCE: 17

Met Thr Asp Ala His Asp Thr Ala Ala Asp Ser Ser Leu Arg Thr Thr
1               5                   10                  15

Gly Gly Ala Pro Pro Asp Gly Gly Ser Ser Val Thr Glu Ala Pro
                20                  25                  30

Thr Pro Leu Leu Glu Pro Arg Glu Gly Ile Pro Val Ile Ala Asp
                35                  40                  45

Glu Ala Ala Leu Ala Glu Ala Val Ala Ala Phe Ala Ala Gly Ser Gly
50                  55                  60

Pro Val Ala Val Asp Ala Glu Arg Ala Ser Gly Tyr Arg Tyr Gly Gln
65                  70                  75                  80

Arg Ala Tyr Leu Val Gln Leu Arg Arg Glu Gly Ala Gly Thr Ala Leu
                85                  90                  95

Ile Asp Pro Val Ala Cys Pro Asp Leu Ser Ala Leu Gly Glu Ala Leu
                100                 105                 110

Ser Gly Val Glu Trp Val Leu His Ala Ala Thr Gln Asp Leu Pro Cys
            115                 120                 125

Leu Arg Glu Ile Gly Met Val Pro Ser Arg Leu Phe Asp Thr Glu Leu
130                 135                 140

Ala Gly Arg Leu Ala Gly Phe Pro Arg Val Gly Leu Gly Ala Met Val
145                 150                 155                 160

Glu Asn Val Leu Gly Phe Val Leu Glu Lys Gly His Ser Ala Val Asp
                165                 170                 175

Trp Ser Thr Arg Pro Leu Pro Glu Pro Trp Leu Arg Tyr Ala Ala Leu
            180                 185                 190

Asp Val Glu Leu Leu Val Asp Leu Arg Asp Ala Leu Glu Lys Glu Leu
                195                 200                 205

Asp Arg Gln Gly Lys Leu Asp Trp Ala Arg Gln Glu Phe Asp Ala Ile
210                 215                 220

Ala Ser Ala Pro Pro Pro Glu Pro Arg Lys Asp Pro Trp Arg Arg Thr
```

```
                225                 230                 235                 240
Ser Gly Met His Lys Val Arg Arg Arg Gln Met Ala Val Val Arg
                    245                 250                 255

Glu Leu Trp Glu Thr Arg Asp Arg Ile Ala Arg Arg Asp Val Ser
                260                 265                 270

Pro Gly Lys Val Leu Ser Asp Ala Ala Ile Val Glu Ala Ala Leu Ala
            275                 280                 285

Leu Pro Ala Asn Leu His Ala Met Ala Ala Leu Asn Gly Phe Gly Gln
        290                 295                 300

Arg Val Gly Arg Arg Gln Leu Glu Gln Trp Gln Ala Ala Val Asp Arg
305                 310                 315                 320

Ala Lys Ala Leu Ser Glu Ala Gln Leu Pro Gln Pro Gly Gln Pro Val
                325                 330                 335

Thr Gly Pro Pro Pro Arg Ala Trp Ala Asp Lys Asp Pro Val Ala
                340                 345                 350

Ala Ala Arg Leu Ser Ala Ala Arg Ala Gly Val Ala Glu Leu Ala Glu
            355                 360                 365

Arg Leu Asn Met Pro Pro Glu Asn Leu Ile Thr Pro Asp Thr Val Arg
        370                 375                 380

Arg Val Cys Trp Glu Pro Pro Gly Pro Asp Glu Arg Ser Val Ala Ala
385                 390                 395                 400

Ala Leu Thr Ala His Gly Ala Arg Ala Trp Gln Val Asp Gln Val Thr
                405                 410                 415

Pro Val Leu Val Ala Ala Leu Ala Thr Ser Ser Pro Pro Ala
                420                 425                 430

<210> SEQ ID NO 18
<211> LENGTH: 220
<212> TYPE: PRT
<213> ORGANISM: Streptomyces fungicidicus

<400> SEQUENCE: 18

Met Ser Val Leu Leu Glu Gln Pro Ala Ser Leu Val Ala Tyr Arg Pro
1               5                   10                  15

Asn Lys Pro Thr Ala Met Val Val Ala Asp Pro Arg Val Arg Ser
                20                  25                  30

Thr Val Thr Arg His Leu Trp Ala Leu Gly Val Arg Asp Val Ile Glu
            35                  40                  45

Ala Ser Ser Val Ala Glu Ala Arg Pro Arg Ile Gly Asn Pro Arg Asp
        50                  55                  60

Ile Cys Val Ala Glu Val His Leu Pro Asp Gly Ser Gly Leu Thr Leu
65                  70                  75                  80

Leu Ser Glu Thr Arg Ala Ala Gly Trp Pro Asn Gly Leu Ala Leu Ser
                85                  90                  95

Ala Ala Asp Asp Ile Gly Ala Val Arg Asn Ala Leu Ala Gly Gly Val
            100                 105                 110

Lys Gly Tyr Val Val Thr Gly Thr Arg Thr Asn Leu Gly Leu Pro Thr
        115                 120                 125

Arg Pro Gly Ala Ala Pro Ile Gly Ala Ala Ala Arg Leu His Arg
        130                 135                 140

Arg Pro Pro Gly Ala Pro Ser His Pro Gly Gly Tyr Arg Glu Leu Ser
145                 150                 155                 160

Gly Arg Glu Val Glu Val Leu Arg Leu Val Ala Glu Gly Gln Ser Asn
                165                 170                 175

Lys Ala Ile Gly Val Ser Met Gly Leu Ser Ala Leu Thr Val Lys Ser
```

```
                    180                 185                 190
His Leu Ala Arg Ile Ala Arg Lys Leu Gly Thr Gly Asp Arg Ala Gly
                195                 200                 205

Met Val Ala Val Ala Leu Arg Thr Gly Ile Ile His
    210                 215                 220

<210> SEQ ID NO 19
<211> LENGTH: 224
<212> TYPE: PRT
<213> ORGANISM: Streptomyces fungicidicus

<400> SEQUENCE: 19

Met Ala Ala Ala Gln Gly Arg Leu Ser Asp Gly Ala Gly Gly Met Asp
1               5                   10                  15

Glu Pro Lys Glu Gly Gly Asp Pro Gly His Gly Gly Ala Pro Pro
            20                  25                  30

Pro Pro Phe Arg Ala Ala Val Glu Ala Leu Gln Ser Ala Arg Leu Arg
            35                  40                  45

Pro Gln Ile Glu Val Glu Thr Val Pro Ala Pro Lys Arg Leu Ala Pro
        50                  55                  60

Tyr Ala His Ala Leu Glu Ala Ala Val Val Asp Gly Glu Glu Asp Leu
65                  70                  75                  80

Ala Asp Gly Arg Leu Val Leu Leu Cys Asp Pro Ala Gly His Asp Ala
                85                  90                  95

Trp Arg Gly Thr Phe Arg Leu Val Thr Leu Val Arg Ala Glu Leu Glu
            100                 105                 110

Pro Glu Met Ala Ala Asp Pro Leu Leu Pro Asp Val Cys Trp Ser Trp
        115                 120                 125

Leu Thr Gly Ala Leu Ala Ala Arg Gly Leu Ser Tyr Gly Glu Pro Ser
    130                 135                 140

Gly Thr Val Thr Arg Ala Ser Ser His Tyr Phe Gly Gly Leu Ser Ala
145                 150                 155                 160

Arg Pro Ala Ala Ser Gln Ile Glu Ile Arg Ala Ser Trp Thr Pro Arg
                165                 170                 175

Glu Gly Leu Gly Gly Val Pro Asp Thr Ala Ala His Leu Val Ala Trp
            180                 185                 190

Ser Asp Leu Leu Ala Gln Val Ala Gly Leu Pro Pro Ala Ala Pro Gly
        195                 200                 205

Asp Ala Ser Val Val Thr Leu Pro Gln Arg Arg Gly Pro Gln Ser Arg
    210                 215                 220

<210> SEQ ID NO 20
<211> LENGTH: 364
<212> TYPE: PRT
<213> ORGANISM: Streptomyces fungicidicus

<400> SEQUENCE: 20

Met Ser Ala Asn Thr Ser Pro Lys Gly Gln Thr Pro Thr Ala Thr Pro
1               5                   10                  15

Asp Pro Val Lys Asn Asp Ala Val Arg Glu Ser Ala Phe Leu Lys Ala
            20                  25                  30

Cys Arg Arg Glu Pro Val Pro His Thr Pro Val Trp Phe Met Arg Gln
            35                  40                  45

Ala Gly Arg Ser Leu Pro Glu Tyr Arg Lys Val Arg Glu Gly Ile Gly
        50                  55                  60

Met Leu Asp Ser Cys Met Arg Pro Glu Leu Val Thr Glu Ile Thr Leu
65                  70                  75                  80
```

Gln Pro Val Arg Arg His His Val Asp Ala Ile Tyr Phe Ser Asp
                85                  90                  95

Ile Val Val Pro Leu Lys Ala Ile Gly Ile Asp Leu Asp Ile Lys Pro
            100                 105                 110

Gly Ile Gly Pro Val Val Glu Gln Pro Val Arg Thr Arg Ala Asp Leu
            115                 120                 125

Ala Arg Leu Arg Asp Leu Thr Pro Glu Asp Val Ser Tyr Val Thr Glu
130                 135                 140

Ala Ile Gly Met Leu Thr Arg Glu Leu Gly Ser Thr Pro Leu Ile Gly
145                 150                 155                 160

Phe Ala Gly Ala Pro Phe Thr Leu Ala Ser Tyr Leu Val Glu Gly Gly
                165                 170                 175

Pro Ser Arg Thr Tyr Glu Asn Ala Lys Ala Met Met Tyr Gly Asp Pro
            180                 185                 190

Glu Leu Trp Ala Asp Leu Leu Asp Arg Leu Ala Asp Ile Thr Ala Ala
            195                 200                 205

Phe Leu Asp Val Gln Ile Arg Ala Gly Ala Ser Ala Val Gln Leu Phe
210                 215                 220

Asp Ser Trp Ala Gly Ala Leu Ala Pro Ser Asp Tyr Arg Arg Ser Val
225                 230                 235                 240

Leu Pro Ala Ser Ala Lys Val Phe Arg Ala Val Ala Gly His Gly Val
                245                 250                 255

Pro Arg Ile His Phe Gly Val Gly Thr Gly Glu Leu Leu Gly Leu Met
            260                 265                 270

Gly Glu Ala Gly Ala Asp Ile Val Gly Val Asp Trp Arg Val Pro Met
            275                 280                 285

Asp Glu Ala Ala Arg Arg Val Gly Pro Gly Lys Ala Leu Gln Gly Asn
290                 295                 300

Leu Asp Pro Thr Val Leu Phe Ala Gly Arg Glu Ala Val Glu Thr Lys
305                 310                 315                 320

Ala Arg Glu Val Leu Asp Thr Ala Ala Gly Leu Glu Gly His Ile Phe
                325                 330                 335

Asn Leu Gly His Gly Val Met Pro Ser Thr Asp Pro Asp Ala Leu Thr
            340                 345                 350

Arg Leu Val Glu Tyr Val His Thr Gln Thr Ala Arg
            355                 360

<210> SEQ ID NO 21
<211> LENGTH: 664
<212> TYPE: PRT
<213> ORGANISM: Streptomyces fungicidicus

<400> SEQUENCE: 21

Met Phe Asp Pro Ala Pro Ile Gly Val Val Phe Thr Gln Gly Pro Glu
1               5                   10                  15

His Arg Leu Ala Tyr Thr Asn Ala Val Tyr Arg Glu Thr Phe Gly Asp
            20                  25                  30

Arg Pro Leu Gly Arg Thr Ile Arg Glu Ala Phe Pro Asp Leu Ala Gln
        35                  40                  45

Ser Gly Tyr Phe Asp Ile Phe Asp Arg Val Leu Thr Thr Gly Ala Ala
    50                  55                  60

Glu Val Val Thr Ala Val Pro Leu Asp Leu Ile Tyr Pro Gly Ser Thr
65                  70                  75                  80

Gly Glu Gly Arg Arg Tyr Phe Thr Phe Ser Ile Ser Arg Ala Thr Met
                85                  90                  95

```
Ser Asp Gly Arg Pro Gly Val Leu Gly Val Ile Val Glu Val Thr Ala
            100                 105                 110

Gln Val Thr Ala Ala Glu Arg Ile Arg Val Leu Ala Glu Glu Arg Arg
        115                 120                 125

Arg Ala Leu Gln Arg Tyr Arg Ser Leu Val Asn Ala Gly Thr Gln Met
    130                 135                 140

Val Trp Val Ala Asp Ala Lys Gly Arg Ile Thr Glu Pro Ser Pro Gly
145                 150                 155                 160

Trp Glu Arg Val Thr Gly Gln Thr Trp Glu Glu Phe Arg Gly Glu Gly
                165                 170                 175

Trp Met Asn Ala Val His Pro Asp Arg Ala Ala Ser Val Glu Ala
                180                 185                 190

Trp Arg Arg Ala Thr Thr Glu Gln Val Pro Arg Trp Ile His Thr Tyr
        195                 200                 205

Arg Leu Arg Leu Ala Ala Gly Gly Tyr Arg His Phe Val Val Asp Ala
    210                 215                 220

Ala Pro Val Arg Asp Gly Asn Thr Val Ile Glu Trp Val Gly Thr Cys
225                 230                 235                 240

Thr Asp Ile Glu Arg Glu Trp Gln Glu Gly Arg Arg Thr Glu Leu Leu
                245                 250                 255

Ala Arg Ala Ala Thr Ala Thr Ser Gly Ile Ala Arg Leu Asp Glu Met
        260                 265                 270

Leu Ala Ala Leu Ala Asp Val Ile Val Pro Asp Ile Ala Asp Asn Cys
    275                 280                 285

Thr Ile His Leu Leu Pro Gln Ala Leu His Arg Leu Pro Gly Thr Pro
290                 295                 300

Leu Thr Thr Glu Arg Val Ala Ala Val Thr Arg Pro Gly Leu Pro Asp
305                 310                 315                 320

Leu Pro Pro His His Glu Glu His Leu Arg Pro Gly Ser Pro Leu Ala
                325                 330                 335

Arg Ala Ala Asp Arg Arg Ser Pro Leu His Phe Val Phe Pro Pro Gly
        340                 345                 350

Glu Pro Pro Ala Asp Leu Ala Pro Leu Asp Gly Glu Pro Trp Met Ala
    355                 360                 365

Glu Asp Val Asn Ser Val Val Leu Leu Pro Val Val Val Asp Gly Thr
370                 375                 380

Thr Ala Ala Leu Val Ala Val Ser Thr Ser Gly Ala Arg Pro Pro Leu
385                 390                 395                 400

Gly Gln Ala Glu Ile Gly Leu Leu Gln Thr Leu Leu Glu Arg Ala His
                405                 410                 415

Thr Pro Leu Ser Asn Ala Leu Glu Tyr Gln Arg Thr Arg Gln Val Ala
        420                 425                 430

Leu Ala Leu Gln Asn Ser Leu Leu Thr Asp Pro Pro Asp Ala Pro Gly
    435                 440                 445

Leu Asp Ile Ala Val Arg Tyr Arg Pro Ser Thr Ala Ala Ala Glu Val
450                 455                 460

Gly Gly Asp Trp Tyr Asp Ala Phe Val Leu Arg Asp Gly Ala Thr Val
465                 470                 475                 480

Leu Thr Ile Gly Asp Val Ser Gly His Asp Leu Pro Ala Ala Val Thr
                485                 490                 495

Met Ser Gln Leu Arg Asn Met Leu Arg Gly Leu Thr Leu Asp Arg Gln
        500                 505                 510

Glu Pro Thr Gly Thr Ile Leu Arg Arg Leu Asp Ile Ala Val Gln Thr
```

```
                515                 520                 525
Leu Tyr Thr Glu Cys Thr Ala Thr Cys Val Leu Ala Arg Val Glu Arg
            530                 535                 540

Pro Asp Ser Gly Gly Val Arg Leu His Tyr Ser Val Ala Gly His Pro
545                 550                 555                 560

Pro Pro Leu Leu Val Glu Ala Asp Gly Ser Ala Arg Phe Leu Thr Gly
                565                 570                 575

Ala Arg Ser Pro Met Leu Gly Leu Val Pro Ala Pro Glu Tyr Ser Ser
            580                 585                 590

Ala Met Glu Pro Leu Pro Pro Gly Ser Thr Leu Leu Tyr Thr Asp
            595                 600                 605

Gly Leu Val Glu Arg Arg Asp Glu Asp Leu Thr Val Gly Leu Glu Arg
            610                 615                 620

Leu Arg His His Ala Ser Glu Ala Val Ser Arg Pro Leu Gln Asp Phe
625                 630                 635                 640

Cys Asp Thr Leu Leu Thr Gly Gln Leu Thr Val Asp Asn Asp Asp Asp
                645                 650                 655

Val Ala Met Leu Val Leu Arg Arg
            660

<210> SEQ ID NO 22
<211> LENGTH: 328
<212> TYPE: PRT
<213> ORGANISM: Streptomyces fungicidicus

<400> SEQUENCE: 22

Met Pro Thr Ala Gly Gln Gly Ala Val Arg Ala Ala Arg Val Val Arg
1               5                   10                  15

Glu Ser Pro Ala Glu Ser Glu Thr Val Thr Val Gln Ile Ala Ser Leu
            20                  25                  30

Leu Pro Gly Glu Ser Leu Arg Ser Lys Gly Ile Glu Gln Asn His Val
        35                  40                  45

Ala Ala Leu Ala Glu Val Asp Ala Pro Leu Pro Pro Ile Leu Val Asp
    50                  55                  60

Arg Lys Thr Met Arg Val Val Asp Gly Met His Arg Leu Leu Ala Ala
65                  70                  75                  80

Leu Leu Asn Gly Arg Gln Thr Ile Glu Ala Glu Leu Phe Asp Gly Thr
                85                  90                  95

Ala Asp Glu Gly Phe Leu Arg Ala Val Arg Glu Asn Val His Gly
            100                 105                 110

Leu Pro Leu Ser Gln Ala Asp Arg Ala Ala Ala Arg Ile Ile
        115                 120                 125

Val Ser His Pro His Leu Ser Asp Arg Ala Ile Ala Arg Ala Ser Gly
    130                 135                 140

Leu Gly Ala Lys Thr Val Ala Ala Val Arg Arg Ser Ser Thr Ala Val
145                 150                 155                 160

Val Pro Gln Leu Asn Thr Arg Val Gly Gln Asp Gly Arg Val Arg Pro
                165                 170                 175

Leu Asn Gly Gly Glu Gly Arg Arg Ala Met Ala Val Leu Ala Glu
            180                 185                 190

His Pro Asp Ala Ser Leu Arg Glu Val Ala Arg Leu Ser Gly Val Ser
        195                 200                 205

Pro Ala Thr Val Ser Asp Val Arg Arg Leu Ala Ala Gly Glu Ser
    210                 215                 220

Pro Leu Pro Ser Arg Arg Glu Pro Ala Glu Pro Arg Thr Gly Ala Asp
```

-continued

```
                225                 230                 235                 240
Ser His Arg Asn Gln Ser Phe Val Asp Pro Val Pro Val Leu Glu Lys
                    245                 250                 255

Leu Leu Arg Asp Pro Ser Leu Arg His Lys Glu Gly Gly Arg Gln Leu
                260                 265                 270

Leu Gln Leu Leu Arg Gln Asn Ala Val Gly Val Gln Asp Leu Met Glu
            275                 280                 285

Leu Ser Asp Ala Val Pro Ser His Cys Arg Ser Leu Val Ile His Leu
        290                 295                 300

Ala Gln Gln Tyr Arg Asp Ala Trp Gln Ser Phe Ala Glu Lys Leu Asp
305                 310                 315                 320

Glu Pro Ala Cys Ala Cys Pro Gly
                325

<210> SEQ ID NO 23
<211> LENGTH: 362
<212> TYPE: PRT
<213> ORGANISM: Streptomyces fungicidicus

<400> SEQUENCE: 23

Met Arg Thr Thr Thr Val Ile Gly Thr Gly Ala Ile Gly Thr Ser Val
1               5                   10                  15

Ala Leu Ala Leu Thr Arg Arg Gly Val Gly Val His Leu Glu Asp Val
                20                  25                  30

Asp Arg Asn Ala Ala Arg Thr Ala Glu Ala Met Gly Ala Gly Ser Leu
            35                  40                  45

Glu Arg Pro Asp Arg Gln Val Asp Leu Ala Val Leu Ala Val Pro Pro
        50                  55                  60

Ala Gln Val Gly Arg Val Leu Arg Ala Gln Glu Ser Gly Leu Ala
65                  70                  75                  80

Arg Ala Tyr Leu Asp Val Ala Ser Val Lys Lys Val Pro His Asp Asp
                85                  90                  95

Val Arg Ala Met Arg Ala Asp Pro Ala Ser Tyr Ile Gly Ser His Pro
            100                 105                 110

Leu Ala Gly Thr Glu Arg Ser Gly Pro Leu Ala Ala Arg Ala Asp Leu
        115                 120                 125

Phe Glu Gly Arg Pro Trp Val Leu Thr Pro Ser Glu Leu Thr Gly Gln
    130                 135                 140

Asp Val Leu Asn Thr Ala Leu Glu Met Val Ser Leu Cys Asp Gly Met
145                 150                 155                 160

Pro Val Val Met Asp Ala Gly Val His Asp His Ala Val Ala Leu Val
                165                 170                 175

Ser His Ala Pro His Arg Leu Ser Ser Leu Leu Ala Ala Arg Leu Glu
            180                 185                 190

His Ala Ala Glu Asp Ser Val Arg Leu Ala Gly Gln Gly Val Ala Asp
        195                 200                 205

Val Thr Arg Ile Ala Ala Gly Asp Ala Arg Leu Trp Gly Asp Ile Leu
    210                 215                 220

Arg Ser Asn Ala Thr Ala Val Ala Asp Val Leu Asp Ser Leu Ala Ala
225                 230                 235                 240

Gly Leu Gly Arg Ala Val Gly Ala Leu Arg Ala Val Ser Asp Ala Asp
                245                 250                 255

Pro Leu Val Arg Arg Ala Gln Glu Glu Leu Glu Glu Leu Leu Arg
            260                 265                 270

Glu Gly Asn Arg Gly Cys Ala Arg Ile Val Arg Lys Pro Gly Thr Arg
```

```
                275                 280                 285
Arg Thr Glu Leu Ala Thr Val Ser Val Thr Ile Ser Asp Lys Pro Gly
            290                 295                 300

Ala Leu Ala Glu Leu Phe Thr Ser Ile Gly Asp Leu Gly Val Asn Ile
305                 310                 315                 320

Glu Asp Val Arg Ile Glu His Gly Gln Asp Gln Thr Arg Gly Leu Val
                325                 330                 335

Glu Leu Val Val Arg Lys Asp Ser Ala Ala Glu Leu Ser Arg Trp Leu
            340                 345                 350

Glu Ser Gly Gly Thr Trp Ala Pro Ala Arg
            355                 360

<210> SEQ ID NO 24
<211> LENGTH: 311
<212> TYPE: PRT
<213> ORGANISM: Streptomyces fungicidicus

<400> SEQUENCE: 24

Met Glu Ile Ser Ser Leu Ser Thr Asp Gly Ser Pro Arg Ile Asp Gly
1               5                   10                  15

Glu Ser Pro Glu His Val Glu Met Leu Ala Ala Ala Asp Thr Ala Leu
            20                  25                  30

Pro Pro Ile Met Val His Arg Arg Thr Gly Arg Val Ile Asp Gly Met
        35                  40                  45

His Arg Leu Arg Ala Ala Met Leu Thr Gly Arg Thr Thr Ile Ala Val
    50                  55                  60

Arg Phe Phe Asp Gly Thr Glu Glu Asp Ala Phe Val Leu Ala Val Lys
65                  70                  75                  80

Ser Asn Ile Ala His Gly Leu Pro Leu Ser Ala Ala Asp Arg Arg Arg
                85                  90                  95

Ala Ala Gly Arg Ile Met Ala Thr His Pro Arg Trp Ser Asp Arg Met
            100                 105                 110

Ile Ala Ser Val Val Gly Thr Ser Ala Arg Thr Val Ala Glu Ile Arg
        115                 120                 125

Arg Asp Ala Gly Ala Ala Gly Ala Gly Glu Pro Thr Arg Ile Gly Arg
    130                 135                 140

Asp Gly Arg Val Arg Pro Val Asp Val Ser Glu Gly Arg Arg Leu Ala
145                 150                 155                 160

His Asp Met Ile Val Arg Asp Pro Gly Leu Ser Leu Arg Gln Val Ala
                165                 170                 175

Arg Ala Ala Gly Ile Ser Pro Glu Thr Val Arg Asp Val Arg His Arg
            180                 185                 190

Met Leu Arg Gly Glu Asp Pro Val Pro Ala Pro Arg Pro Arg Thr Leu
        195                 200                 205

Val Glu Arg Gly Ala Asp Arg Arg Ala Glu Pro Ala Gly Lys Ala Ala
    210                 215                 220

Ala Pro Cys Gly Thr Glu Pro Pro Ala Val Val Met Lys Arg Leu
225                 230                 235                 240

Arg Ala Asp Pro Ala Leu Arg Leu Asn Glu Asn Gly Arg Asp Leu Leu
                245                 250                 255

Arg Leu Leu Asp Ile His Thr Val Arg Leu Glu Asp Trp Asn Arg Ile
            260                 265                 270

Ile Glu Ser Val Pro Pro His Arg Leu Glu Thr Val Ala Gln Leu Ala
        275                 280                 285

Arg Ser Cys Ala Asp Lys Trp Ser Glu Ile Ala Ser Arg Ile Glu Ser
```

```
                290                 295                 300

Asn Ala Ser His Leu Ala Gly
305                 310

<210> SEQ ID NO 25
<211> LENGTH: 356
<212> TYPE: PRT
<213> ORGANISM: Streptomyces fungicidicus

<400> SEQUENCE: 25

Met Glu Ile Arg Ser Ile Asp His Val Glu Leu Phe Val Glu Asp Ala
1               5                   10                  15

Gln Asp Thr Ala Gly Arg Leu Cys Asp Ser Phe Gly Phe Val Arg Val
            20                  25                  30

Gly Arg Gly Ala Gly Thr Thr Gly Leu Arg Gly Cys Glu Ser Val Leu
        35                  40                  45

Leu Arg Gln Asn Asp Ile Ala Leu Leu Leu Thr Thr Ala Thr Asp Ala
    50                  55                  60

Asp His Arg Ala Ala Glu Tyr Val Lys Gln His Gly Asp Gly Val Ala
65                  70                  75                  80

Val Ile Gly Ile Gly Val Asp Asp Ala Arg Ala Ala Tyr Ala Glu Ala
                85                  90                  95

Val Arg Arg Gly Ala Val Pro Val Ala Ala Pro Glu Glu Phe Gly Pro
            100                 105                 110

Ala Gly Ala Arg Val Val Phe Ala Ser Val Ala Gly Phe Gly Asp Val
        115                 120                 125

Glu His Arg Phe Val Ser Arg Glu Asp Pro Gly Ala Pro Phe Ala Pro
    130                 135                 140

Phe Ile Glu Glu Thr Gly Ala His Gly Ser Gly Gly Met Leu Lys Arg
145                 150                 155                 160

Val Asp His Phe Ala Val Cys Val Pro Ala Gly Glu Leu Asp Gly Thr
                165                 170                 175

Val Arg Arg Tyr Gln Glu Val Phe Gly Leu Ser Gln Thr Phe Glu Glu
            180                 185                 190

Arg Ile Val Val Gly Ser Gln Ala Met Asp Ser Lys Val Val Gln Ser
        195                 200                 205

Asp Arg Gly Ala Val Thr Phe Thr Val Ile Glu Pro Asp Thr Thr Arg
    210                 215                 220

Ala Pro Gly Gln Ile Asp Ala Phe Val Ala Ser His Gly Gly Ala Gly
225                 230                 235                 240

Val Gln His Val Ala Phe Leu Thr Glu Asp Ile Thr Thr Ala Val Arg
                245                 250                 255

Thr Cys Thr Gly Arg Gly Val Arg Phe Leu Thr Thr Pro Pro Ser Tyr
            260                 265                 270

Tyr Glu Met Leu Pro Gly Arg Leu Gly Pro Val Gly Val Pro Val Glu
        275                 280                 285

Glu Leu Ser Ala Leu Asn Ile Leu Ala Asp Arg Asp Pro Ser Gly Ile
    290                 295                 300

Met Leu Gln Ile Phe Thr Glu Ser Thr His Pro Arg Arg Thr Leu Phe
305                 310                 315                 320

Trp Glu Leu Ile Asp Arg Arg Gly Ala Gln Thr Phe Gly Ser Asn Asn
                325                 330                 335

Ile Gln Ala Leu Tyr Glu Ala Val Glu Arg Gln Gln Ala Ala Glu Ala
            340                 345                 350

Ala Asp Gln Glu
```

-continued

<210> SEQ ID NO 26
<211> LENGTH: 279
<212> TYPE: PRT
<213> ORGANISM: Streptomyces fungicidicus

<400> SEQUENCE: 26

Met Thr Ala Thr Thr Gly His Thr His Pro Thr Asp Pro Asp Ala Ala
1               5                   10                  15

Gly Ala Ala Gly Pro Ile Gly Tyr Ser Leu Pro Leu Ser Pro Ser Gly
            20                  25                  30

Gln Ala Ser Met Leu Thr Pro Pro Trp His Phe Ser Gly Glu Ile
        35                  40                  45

Leu Met Val Asp Tyr Arg Val Asp Pro Asp Ala Ala Arg Arg Phe Leu
 50                  55                  60

Pro Pro Gly Leu Asp Ala Gly Asp Pro Gly Ala Ala Ala Val
65                  70                  75                  80

Phe Ala Thr Trp Gln Trp Cys Ser Glu Asp Gly Ala Glu Leu Ala Asp
                85                  90                  95

Pro Ala Val Cys Arg Phe Ser Glu Phe Leu Ile Leu Leu Gly Cys Ala
            100                 105                 110

Phe Glu Gly Arg Pro Met Ala Arg Cys Pro Phe Ala Trp Val Asp Gln
        115                 120                 125

Pro Val Pro Met Val Arg Gly Trp Val Gln Gly Met Pro Lys Gln Phe
    130                 135                 140

Gly Ala Ile His Gln Thr Arg Pro Val Thr Val Gly Arg Ala Gly Ser
145                 150                 155                 160

Arg Leu Ala Pro Gly Gly Arg Phe Asp Gly Ala Leu Ser Val His Gly
                165                 170                 175

Arg Leu Thr Ala Glu Ala Ser Val Thr Val Glu Arg Arg Ser Glu Arg
            180                 185                 190

Pro Pro Ala Leu His Asp Val Pro Leu Ala His Ser Leu Val Leu Pro
        195                 200                 205

Arg Trp Val Pro Ser Asp Ala Pro Pro Arg Pro Arg Leu Val Ala Ser
    210                 215                 220

Glu Val Ser Gly Val Glu Phe Ser Pro Val Trp Ser Pro Gly Arg
225                 230                 235                 240

Leu Ala Leu Ser Gly Arg Pro Gly Thr Asp Leu Ala Leu Leu Ala Pro
                245                 250                 255

Val Glu Val Gly Ala Gly His Val Phe Ala Tyr Gly Glu Thr Leu His
            260                 265                 270

Gly Gly Arg Leu Leu Gly Ala
        275

<210> SEQ ID NO 27
<211> LENGTH: 419
<212> TYPE: PRT
<213> ORGANISM: Streptomyces fungicidicus

<400> SEQUENCE: 27

Met Thr Ala Ala Gly Glu Gly Thr Leu Pro Tyr Gly Thr Ala Arg Pro
1               5                   10                  15

Leu Ser His Thr Arg Arg Trp Arg Arg Gly Val Val Gln Glu Val Ala
            20                  25                  30

Pro Ala Gly Val Leu Asp Leu Gly Pro Gly Tyr Leu Glu Pro Ala Leu
        35                  40                  45

Leu Pro Val Gly Leu Val Arg Asp Ala Tyr Ala Arg Ala Leu Glu Glu
            50                  55                  60

Tyr Gly Ala Ala Ala Leu Gly Tyr Gly His Asp Pro Gly Ala Leu Pro
65                  70                  75                  80

Leu Arg Ala Glu Leu Ala Ala Arg Ala Thr Val Arg Gly Arg Ser Pro
                85                  90                  95

Cys Gly Pro Glu His Val Val Thr Ala Gly Thr Ser Gln Ala Leu
            100                 105                 110

His Leu Leu Ala Thr Thr Leu Ala Arg Pro Gly Asp Thr Val Leu Val
            115                 120                 125

Glu Gly Leu Gly Tyr Asp Leu Gly Gln Arg Ile Leu Gly Asp Cys Ala
        130                 135                 140

Leu Arg Leu Arg Arg Val Ala Leu Asp Ala Ser Gly Met Val Pro Glu
145                 150                 155                 160

Ala Leu Arg Arg Ala Leu Ala Gly Thr Ala Arg Gly Glu Gly Gly
                165                 170                 175

Thr Gly Arg Thr Ala Phe Val Tyr Leu Thr Pro Thr His His Asn Pro
            180                 185                 190

Thr Gly Ala Thr Met Pro Leu Glu Arg Arg Leu Arg Leu Leu Glu Ala
        195                 200                 205

Ala Ala Glu His Gly Val Leu Val Glu Asp Ala Tyr Gly Glu
        210                 215                 220

Leu Gly Leu Thr Asp Gly Pro Pro Ala Pro Pro Leu Ala Ala Leu
225                 230                 235                 240

Ala Gly His Arg Gly Val Val Arg Leu Gly Ser Phe Ser Lys Thr Leu
                245                 250                 255

Gly Pro Gly Leu Arg Leu Gly Trp Leu Val Thr Glu Pro Ala Leu Ala
            260                 265                 270

Glu Arg Ile Ala Ser His Gly Leu Phe Arg Ser Gly Ser Leu Asn
        275                 280                 285

His Ile Thr Ser Leu Ala Val Ala Gly Leu Leu Ser Asp Gly Gly Tyr
        290                 295                 300

Asp Arg His Leu Glu Met Leu Arg Ala Gly Leu Arg Ala Arg Arg Asp
305                 310                 315                 320

Ala Leu Leu Asp Ala Leu Arg Glu Ala Ala Asp Leu Pro Val Arg Ile
                325                 330                 335

Ser Arg Pro Glu Gly Gly Phe Phe Leu Trp Leu Arg Cys Gly Thr Gly
            340                 345                 350

Leu Gly Glu Asp Glu Leu Leu Ala Arg Ala Glu Arg Ala Gly Val Arg
        355                 360                 365

Val Thr Ala Gly Ser Arg Phe Gly Gly Thr Arg Glu Pro Ser Val Arg
        370                 375                 380

Leu Ala Tyr Ser Phe Asn Pro Pro Leu Leu Glu Arg Ala Ala Arg
385                 390                 395                 400

Arg Leu Thr Gln Ala Trp Ser Gly Gly Pro Pro Asp Arg Gln Ile Gly
                405                 410                 415

Gly Asn Pro

<210> SEQ ID NO 28
<211> LENGTH: 293
<212> TYPE: PRT
<213> ORGANISM: Streptomyces fungicidicus

<400> SEQUENCE: 28

```
Met Leu Ser Cys Tyr Ser Ser Val Ala Met Glu Ile Leu Ser Arg
1               5                  10                  15

Ala Leu Ala Ser Val Thr Asp Ser Val Ala Leu Val His Pro Thr Phe
            20                  25                  30

Asp Asn Ile Ala Asp Leu Leu Arg Gly Asn Arg Leu Gly Leu Val Pro
            35                  40                  45

Leu Glu Glu Asp Pro Leu His Ala Asp Asp Leu Pro Ala Glu Leu Leu
    50                  55                  60

Glu Ser Val Gly Cys Val Phe Val Thr Thr Pro Asn Asn Pro Thr Gly
65                  70                  75                  80

Arg Val Val Ser Ala Glu Arg Leu Arg Arg Leu Ala Gly Gln Cys Ala
                85                  90                  95

Arg His Gly Val Ile Leu Ala Leu Asp Thr Ser Phe Arg Gly Phe Asp
            100                 105                 110

Thr Arg Ala Gln Tyr Asp His Tyr Glu Ile Leu Asp Ala Ser Asp Val
            115                 120                 125

Arg Trp Val Val Ile Glu Asp Thr Gly Lys Leu Trp Pro Thr Leu Asp
    130                 135                 140

Leu Lys Val Gly Met Leu Val His Ser Glu Asn Leu Gly Leu Pro Val
145                 150                 155                 160

Glu Lys Ile Tyr Ser Asp Ile Leu Leu Gly Val Ser Pro Leu Ile Leu
                165                 170                 175

Gly Met Val Arg Arg Phe Ser Glu Asp Ala Ala Ala Gly Gly Leu Thr
            180                 185                 190

Glu Leu His Glu Phe Ile Ala Ala Gln Arg Ser Val Val Arg Ala Gly
            195                 200                 205

Leu Ala Asp Leu Ser Thr Thr Gly Val Pro Asp Pro Asp Ser Arg Ala
    210                 215                 220

Ser Val Glu Arg Val Leu Ile Arg His Leu Thr Gly Thr Glu Val Trp
225                 230                 235                 240

Glu Ala Leu Arg Glu His His Val Tyr Ala Leu Pro Cys Arg Ala Phe
                245                 250                 255

Tyr Trp Ala Asp Pro Ala Arg Gly Asp Arg Thr Leu Arg Leu Ala Leu
            260                 265                 270

Ala Arg Ala Ser Ala Pro Leu Ala Gln Cys Val Arg Ala Leu Arg His
            275                 280                 285

Val Leu Thr Pro Arg
        290

<210> SEQ ID NO 29
<211> LENGTH: 808
<212> TYPE: PRT
<213> ORGANISM: Streptomyces fungicidicus

<400> SEQUENCE: 29

Met Glu Leu Ser Leu Asp Glu Phe Ala Ser Leu Ala Arg Glu Arg Leu
1               5                   10                  15

Asp Pro Ala Val Trp Asp Phe Ile Glu Gly Gly Ala Gly Glu Glu Arg
            20                  25                  30

Thr Leu Ala Ala Asn Thr Ala Ala Phe Asp Arg Val Pro Leu Arg Pro
            35                  40                  45

Ser Val Leu Arg Gly Ala Gly Ser Pro His Thr Gly Thr Thr Ile Leu
    50                  55                  60

Gly Arg Thr Trp Asp Ala Pro Leu Ala Val Ala Pro Val Ala Tyr His
65                  70                  75                  80
```

```
Thr Leu Ala Asp Pro Ala Gly Glu Val Ala Thr Val Arg Gly Thr Ala
             85                   90                  95
Ala Ala Ala Gly Leu Pro Val Val Ser Thr Phe Ala Gly Arg Thr
        100                 105                 110
Phe Glu Asp Ile Ala Ala Glu Ala Thr Val Pro Leu Trp Leu Gln Val
            115                 120                 125
Tyr Cys Leu Arg Asp Arg Ser Leu Thr Arg Gly Leu Ile Glu Arg Ala
        130                 135                 140
Glu Asn Ala Gly Phe Glu Ala Leu Val Leu Thr Val Asp Ala Pro His
145                 150                 155                 160
Leu Gly Arg Arg Leu Arg Asp Leu Arg Asn Gly Phe Arg Leu Pro Ala
                165                 170                 175
Gly Thr Val Pro Ala Asn Leu Pro Val Asp Gly Phe Ala Asp Pro Ala
            180                 185                 190
Ala His Ser Arg Ala Asp Phe Asp Pro Gly Leu Asp Trp Ser Val Val
        195                 200                 205
Glu Trp Leu Arg Ser Val Ser Glu Leu Pro Leu Leu Val Lys Gly Ile
    210                 215                 220
Leu Thr Gly Ala Asp Ala Val Arg Ala Ala Glu Ala Gly Val Asp Gly
225                 230                 235                 240
Val Met Val Ser Asn His Gly Gly Arg Gln Leu Asp Gly Val Pro Ala
                245                 250                 255
Thr Leu Asp Val Leu Pro Glu Val Ala Glu Ala Val Gly Gly Arg Leu
            260                 265                 270
Pro Val Leu Leu Asp Gly Gly Val Arg Arg Gly Arg Asp Ile Leu Ala
        275                 280                 285
Ala Leu Ala Leu Gly Ala Asp Ala Ala Leu Val Gly Arg Pro Val Leu
    290                 295                 300
His Gly Leu Ala Ala Gly Gly Ala Gly Val Thr Gly Val Leu Ser
305                 310                 315                 320
Val Leu Leu Glu Glu Leu Thr Asp Ala Met Ser Leu Ala Gly Leu Arg
                325                 330                 335
Thr Leu Ala Asp Ile Gly Pro Ser Leu Val Gly Arg Ala Pro Asp His
            340                 345                 350
Pro Arg Arg Ser Thr Val Asp Ala Gly Lys Gly Ala Gly Ser Asp Arg
        355                 360                 365
Arg Thr Ala Ala Gly Gly Ala Gly Leu Arg Leu Ala Asp Leu His
    370                 375                 380
Pro Ser Val Ala Asp Pro Val Met Asp Thr Met Asn Phe Leu Asn Glu
385                 390                 395                 400
Val Thr Leu Arg Tyr Pro Glu Ala Val Ser Phe Ala Pro Gly Arg Pro
                405                 410                 415
Tyr Ala Glu Phe Phe Glu Thr Glu Gln Val Phe Arg His Leu Arg Arg
            420                 425                 430
Tyr Leu Asp His Leu Ala Glu Gln Gly Arg Ser Pro Ala Gln Val Arg
        435                 440                 445
Asp Ala Leu Phe Gln Tyr Gly Pro Ser Ala Gly Val Ile Arg Glu Leu
    450                 455                 460
Ile Ala His Ser Leu Arg Val Asp Glu Gly Ile Asp Val Ser Pro Glu
465                 470                 475                 480
Ser Ile Val Val Thr Val Gly Cys Gln Glu Ala Met Phe Leu Thr Leu
                485                 490                 495
Arg Ala Leu Met Ser Gly Pro Asp Asp Val Leu Leu Val Ser Ser Pro
            500                 505                 510
```

```
Cys Tyr Val Gly Ile Thr Gly Ala Ala Arg Leu Leu Asp Val Ala Val
            515                 520                 525

Thr Ala Val Glu Glu Gly Asp Gly Leu Ser Cys Asp Ala Leu Glu
    530                 535                 540

Ala Ala Val Ser Ala Glu Arg Ala Arg Gly Arg Pro Arg Ala Val
545                 550                 555                 560

Tyr Val Val Pro Asp His Ser Asn Pro Ser Gly Ala Thr Met Pro Leu
            565                 570                 575

Glu Ala Arg Lys Ser Leu Leu Glu Leu Ala Gln Arg Leu Asp Val Leu
            580                 585                 590

Val Leu Glu Asp Ser Pro Tyr Arg His Val Ser Pro Gly Thr Gln Val
        595                 600                 605

Ala Ser Leu Lys Ala Leu Asp Arg Thr Arg Arg Val Ile His Leu Gly
        610                 615                 620

Ser Tyr Ala Lys Thr Val Phe Pro Gly Ala Arg Leu Gly Phe Ala Val
625                 630                 635                 640

Ala Asp Gln Pro Val Leu Ala Pro Asp Gly Gly Thr Ser Leu Leu Ala
            645                 650                 655

Asp Glu Leu Ala Lys Ile Lys Ser Met Val Thr Val Asn Thr Ser Pro
            660                 665                 670

Leu Ser Gln Ala Ala Val Ala Gly Ala Leu Leu Glu Ser Gly Gly Arg
        675                 680                 685

Val Ser Glu Leu Asn Ala Arg Asn Ala Ala His Tyr Gly Glu Ala Met
690                 695                 700

Arg Phe Thr Leu Gln Cys Leu Glu Arg Glu Phe Pro Ala Ala Arg Arg
705                 710                 715                 720

Thr Arg Leu Gly Val Arg Trp Asn Ala Pro Ser Gly Gly Phe Phe Leu
                725                 730                 735

Thr Leu Gln Val Pro Phe Arg Ala Asp Asn Ser Ala Leu Ala Arg Ser
            740                 745                 750

Ala Gln Asp Phe Gly Val Ile Trp Thr Pro Met Ser Tyr Phe Tyr Pro
            755                 760                 765

Gln Gly Gly Gly Leu His Thr Leu Arg Leu Ser Thr Ser Tyr Leu Thr
        770                 775                 780

His Ala Asp Ile Glu Lys Gly Ile Ser Arg Leu Ala Gly Phe Ile Glu
785                 790                 795                 800

Phe Glu Cys Gly Asp Pro Val Ala
            805

<210> SEQ ID NO 30
<211> LENGTH: 504
<212> TYPE: PRT
<213> ORGANISM: Streptomyces fungicidicus

<400> SEQUENCE: 30

Met Pro Gly Gly Arg Met Ser Thr Gly Gln His Glu Glu Phe Asp Val
1               5                   10                  15

Val Val Val Gly Gly Gly Pro Ser Gly Ser Thr Leu Ser Thr Leu Val
                20                  25                  30

Ala Met Gln Gly His Ser Val Leu Leu Leu Glu Lys Glu Thr Phe Pro
            35                  40                  45

Arg Tyr Gln Ile Gly Glu Ser Leu Leu Pro Ser Thr Ile His Gly Ile
        50                  55                  60

Cys His Leu Leu Gly Val Thr Asp Glu Leu Ala Ala Ala Gly Phe Pro
65                  70                  75                  80
```

```
His Lys Arg Gly Gly Thr Phe Arg Trp Gly Ala Ser Pro Lys Pro Trp
                85                  90                  95
Asn Phe Ser Phe Ser Val Ser Ser Lys Val Ser Gly Pro Thr Ser Phe
            100                 105                 110
Ala Tyr Gln Val Glu Arg Ser Lys Phe Asp Lys Ile Leu Leu Asp Asn
        115                 120                 125
Ala Ala Arg Lys Gly Val Val Arg Gln Asp Arg Thr Val Thr Asp
    130                 135                 140
Val Val Asp Asp Ala Asp Gly Arg Ala Arg Gly Leu Arg Tyr Thr Asp
145                 150                 155                 160
Pro Asp Gly Thr Glu His Glu Val Ser Ala Arg Tyr Val Asp Ala
                165                 170                 175
Ser Gly Asn Thr Ser Arg Ile His Lys Arg Val Gly Gly Ser Arg Thr
            180                 185                 190
Tyr Ser Asp Phe Phe Lys Ser Leu Ala Leu Phe Gly Tyr Phe Glu Asn
        195                 200                 205
Gly Lys Arg Met Pro Ala Pro Tyr Ala Gly Asn Ile Leu Cys Val Ala
    210                 215                 220
Phe Gly Ser Gly Trp Phe Trp Tyr Ile Pro Leu Ser Ser Thr Leu Thr
225                 230                 235                 240
Ser Val Gly Ala Val Arg Arg Glu Asp Ala Ala Lys Val Gln Gly
                245                 250                 255
Asp Pro Glu Ser Ala Leu Arg Gly Leu Ile Asp Glu Cys Pro Met Ile
            260                 265                 270
Lys Glu Tyr Leu Ala Asp Ala Thr Arg Val Thr Thr Gly Gln Tyr Gly
        275                 280                 285
Gln Leu Arg Val Arg Lys Asp Tyr Ser Tyr His His Thr Thr Phe Trp
    290                 295                 300
Arg Pro Gly Met Val Leu Val Gly Asp Ala Ala Cys Phe Val Asp Pro
305                 310                 315                 320
Val Phe Ser Ser Gly Val His Leu Ala Thr Tyr Ser Ala Leu Leu Ala
                325                 330                 335
Ala Arg Ser Leu Asn Ser Val Leu Ala Gly Arg Ile Asp Glu Arg Arg
            340                 345                 350
Ala Phe Asp Glu Phe Glu Ala Arg Tyr Arg Arg Glu Tyr Gly Val Phe
        355                 360                 365
Tyr Glu Phe Leu Thr Ser Phe Tyr Asp Met His Val Asp Glu Asp Ser
    370                 375                 380
Tyr Phe Trp Thr Ala Lys Lys Val Thr Arg Ser Ser His Ala Glu Leu
385                 390                 395                 400
Glu Ser Phe Val Glu Leu Val Ala Gly Met Ser Ser Thr Asp Phe Asp
                405                 410                 415
Leu Ser Asp Ala Glu Ser Ser Val Leu Arg Leu Lys Gln Gln Ser Ala
            420                 425                 430
Glu Phe Ala Asp Ala Val Asp Asp Met Ala Gly Arg Gln Glu Glu Asn
        435                 440                 445
Met Ala Pro Leu Phe Arg Ser Ser Ala Val Ser Arg Ala Met Gln Glu
    450                 455                 460
Gly Ser Gln Val Gln Thr Arg Ala Gln Leu Gly Glu Tyr Ala Gly Glu
465                 470                 475                 480
Asp Val Pro Leu Phe Asp Gly Gly Leu Val Ala Ser Ser Asp Ser Met
                485                 490                 495
Phe Trp Glu Glu Pro His Pro Ser
```

-continued

<210> SEQ ID NO 31
<211> LENGTH: 341
<212> TYPE: PRT
<213> ORGANISM: Streptomyces fungicidicus

<400> SEQUENCE: 31

Met Met Trp Leu Ser Trp Arg Gln Phe Arg Val Gln Ala Leu Phe Gly
1               5                   10                  15

Ala Gly Ala Leu Ala Val Ile Ala Val Tyr Leu Leu Tyr Leu Gly Gly
            20                  25                  30

Asp Ile Arg Asp Ala His Asp Val Tyr Gln Ala Asn Cys Asp Asn Ser
        35                  40                  45

Ala Asn Cys Ala Gln Ala Arg Ser Gln Phe Arg Ser Thr Phe Gln Asn
    50                  55                  60

Thr Leu Leu Phe Leu Ala Thr Gly Leu Ala Leu Ile Pro Ala Leu Ile
65                  70                  75                  80

Gly Thr Phe Trp Gly Ala Pro Leu Ile Ala Arg Glu Leu Glu Asn Gly
                85                  90                  95

Thr His Arg Leu Val Trp Asn Gln Ser Val Thr Arg Pro Arg Trp Leu
            100                 105                 110

Leu Ser Lys Ile Leu Leu Ile Gly Ala Ala Ser Val Ile Val Thr Gly
        115                 120                 125

Ala Ala Ala Ala Leu Leu Thr Trp Ala Ala Arg Pro Phe Asp Asp Val
    130                 135                 140

Val Lys Glu Gln Phe Asp Thr Phe Val Phe Gly Ala Arg Asn Ile Ala
145                 150                 155                 160

Pro Ile Gly Tyr Ala Ala Leu Ala Phe Thr Phe Gly Thr Val Val Gly
                165                 170                 175

Leu Leu Leu Arg Arg Thr Leu Pro Ala Met Ala Val Thr Leu Val Val
            180                 185                 190

Phe Ile Ala Phe Gln Phe Phe Phe Pro Asn Val Val Arg Pro Ser Leu
        195                 200                 205

Met Pro Pro Asp Arg Thr Thr Leu Ala Met Thr Ala Glu Ala Ile Asn
    210                 215                 220

Ser Ala Gln Asn Leu Gly Ser Ile Gly Gly Gly Ser Val Ile Gly Gly
225                 230                 235                 240

Val Arg Ile Pro Asp Ala Pro Asp Ala Trp Ile Ala Glu Thr Ser Pro
                245                 250                 255

Leu Arg Thr Ala Asp Gly Arg Thr Leu Ala Ser Ser Glu Phe Asn Gly
            260                 265                 270

Cys Leu Asp Asp Pro Pro Lys Thr Gly Ala Gly Gly Thr Phe Gly Asp
        275                 280                 285

Thr Ala Val Cys Leu Ala Glu His Asp Leu His Val Asp Val Leu Tyr
    290                 295                 300

His Pro Ser Ser Arg Tyr Trp Ala Phe Gln Trp Leu Glu Thr Ala Ile
305                 310                 315                 320

Tyr Val Ala Leu Ser Gly Ile Leu Thr Val Phe Gly Val Trp Arg Ile
                325                 330                 335

Arg Arg Arg Val Ser
            340

<210> SEQ ID NO 32
<211> LENGTH: 307
<212> TYPE: PRT

<213> ORGANISM: Streptomyces fungicidicus

<400> SEQUENCE: 32

| | | | | | | | | | | | | | | |
|---|---|---|---|---|---|---|---|---|---|---|---|---|---|---|
| Met | Pro | His | Ala | Asp | Ser | Pro | Val | Leu | His | Ala | Glu | Gly | Leu | Thr |
| 1 | | | | 5 | | | | | 10 | | | | | 15 |
| Lys | Lys | Tyr | Gly | Arg | Arg | Gly | Lys | Leu | Ala | Leu | Ser | Asp | Val | His | Leu |
| | | | 20 | | | | | 25 | | | | | 30 | | |
| Ser | Val | Pro | Ala | Gly | Arg | Val | Ile | Gly | Leu | Val | Gly | Pro | Asn | Gly | Ala |
| | | | 35 | | | | | 40 | | | | | 45 | | |
| Gly | Lys | Ser | Thr | Leu | Leu | His | Leu | Ala | Cys | Gly | Leu | Thr | Glu | Pro | Thr |
| | 50 | | | | | 55 | | | | | 60 | | | | |
| Ser | Gly | Ser | Leu | Ser | Val | Leu | Gly | Ser | Arg | Pro | Ala | Ala | Asn | Ala | Ser |
| 65 | | | | | 70 | | | | | 75 | | | | | 80 |
| His | Leu | Ala | Arg | Val | Gly | Phe | Val | Ala | Gln | Asn | Thr | Pro | Val | Tyr | Gly |
| | | | | 85 | | | | | 90 | | | | | 95 | |
| Ala | Phe | Thr | Val | Ala | Glu | His | Leu | Lys | Phe | Gly | Ala | Lys | Met | Asn | Pro |
| | | | 100 | | | | | 105 | | | | | 110 | | |
| Gly | Trp | Asp | Pro | Val | Leu | Ala | Glu | Arg | Arg | Ile | Ser | Gln | Val | Gly | Leu |
| | | 115 | | | | | 120 | | | | | 125 | | | |
| Ser | Ala | Gly | Gln | Lys | Ala | Gly | Gln | Leu | Ser | Gly | Gly | Gln | Arg | Ala | Gln |
| | 130 | | | | | 135 | | | | | 140 | | | | |
| Leu | Ala | Leu | Thr | Ile | Ala | Ala | Lys | Arg | Pro | Glu | Leu | Leu | Ile | Phe |
| 145 | | | | | 150 | | | | | 155 | | | | | 160 |
| Asp | Glu | Pro | Ala | Ala | Ala | Leu | Asp | Pro | Leu | Ala | Arg | Arg | Gly | Phe | Leu |
| | | | | 165 | | | | | 170 | | | | | 175 | |
| Gln | Asn | Leu | Met | Glu | Phe | Val | Leu | Glu | Leu | Gly | Ala | Ser | Ala | Val | Leu |
| | | | 180 | | | | | 185 | | | | | 190 | | |
| Ser | Ser | His | Leu | Leu | Gly | Asp | Val | Glu | Gln | Val | Cys | Asp | Tyr | Leu | Ile |
| | | 195 | | | | | 200 | | | | | 205 | | | |
| Val | Leu | Cys | Asp | Ala | Arg | Val | Gln | Val | Ala | Gly | Asp | Thr | Arg | Glu | Leu |
| | 210 | | | | | 215 | | | | | 220 | | | | |
| Leu | Ala | Gly | His | Ala | Arg | Leu | Val | Ala | Ala | Arg | Gly | Glu | Phe | Asp | Gln |
| 225 | | | | | 230 | | | | | 235 | | | | | 240 |
| Pro | Pro | Ala | Gly | Ile | Glu | Val | Ile | Ser | Val | Glu | His | Ser | Gly | Lys | His |
| | | | | 245 | | | | | 250 | | | | | 255 | |
| Ser | Ser | Ala | Val | Val | Arg | Thr | Gly | Ala | Ala | Thr | Glu | Ala | Leu | Pro | Tyr |
| | | | 260 | | | | | 265 | | | | | 270 | | |
| Arg | Ser | Glu | Pro | Val | Thr | Leu | Glu | Glu | Leu | Val | Leu | Ala | Tyr | Met | Thr |
| | | 275 | | | | | 280 | | | | | 285 | | | |
| Arg | Ala | Ala | Ala | Val | Pro | Ala | Ala | Arg | Thr | Glu | Ala | Ala | Ala | Trp | Gly |
| | 290 | | | | | 295 | | | | | 300 | | | | |
| Ala | Thr | Arg |
| 305 | | |

<210> SEQ ID NO 33
<211> LENGTH: 651
<212> TYPE: PRT
<213> ORGANISM: Streptomyces fungicidicus

<400> SEQUENCE: 33

| | | | | | | | | | | | | | | |
|---|---|---|---|---|---|---|---|---|---|---|---|---|---|---|
| Met | Thr | Val | Gly | His | Asp | Pro | Thr | Met | Gly | Thr | Ile | Gly | Leu | Arg | Val |
| 1 | | | | 5 | | | | | 10 | | | | | 15 | |
| Glu | Gly | Leu | Val | Asp | Pro | Gln | Pro | Val | Arg | Ser | Gly | Thr | Phe | Lys | Arg |
| | | | 20 | | | | | 25 | | | | | 30 | | |
| Ile | Ile | Pro | Tyr | Ala | Met | Arg | Tyr | Arg | Arg | Ala | Met | Ala | Met | Val | Met |
| | | | 35 | | | | | 40 | | | | | 45 | | |

```
Val Ala Thr Ile Val Asp Ser Leu Ile Thr Val Ser Ile Pro Leu Thr
 50                  55                  60
Leu Lys Met Ile Ile Asp Asp Gly Ile Ile Pro Gly Lys Thr Ser Val
 65                      70                  75                  80
Val Phe Gly Leu Ala Gly Leu Val Ala Gly Leu Ala Leu Leu Asn Val
                 85                  90                  95
Val Ala Val Tyr Thr Gln Thr Trp Phe Ser Gly Arg Val Gly Gln Gly
                100                 105                 110
Leu Ile Phe Asp Leu Arg Thr Ala Val Phe Ser His Ile Gln Arg Gln
            115                 120                 125
Pro Val Ala Phe Phe Thr Arg Thr Gln Thr Gly Ser Leu Val Ser Arg
            130                 135                 140
Ile Asn Thr Asp Ile Val Gly Ala Gln Gln Ala Leu Thr Ser Leu Leu
145                 150                 155                 160
Ser Gln Ser Leu Ser Thr Leu Leu Thr Leu Val Leu Val Leu Ala Ala
                165                 170                 175
Met Leu Tyr Leu Ser Trp Pro Ile Thr Val Ala Ala Leu Ile Met Ile
            180                 185                 190
Pro Leu Phe Phe Ile Pro Gly Lys Ile Ile Ala Gln Arg Leu Glu Lys
            195                 200                 205
Leu Ala Arg Ala Gly Met Gln Asn Asp Ala Lys Leu Gly Ser Met Met
210                 215                 220
Thr Glu Arg Phe Asn Ile Ser Gly Ala Met Leu Val Lys Leu Tyr Gly
225                 230                 235                 240
Arg Pro Glu Asp Glu Ser Ala Glu Phe Ser Lys Lys Ala Gly Leu Val
                245                 250                 255
Arg Asp Ile Ala Ile Ser Met Asp Val His Ala Arg Leu Leu Phe Ile
            260                 265                 270
Leu Val Thr Leu Leu Thr Thr Val Thr Ala Met Val Tyr Gly Phe
            275                 280                 285
Gly Gly Trp Phe Val Ile Asp Gly Ser Leu Gln Ile Gly Thr Leu Val
290                 295                 300
Ala Met Val Ala Leu Leu Leu Met Leu Tyr Gly Pro Val Asn Gln Leu
305                 310                 315                 320
Thr Asn Ile Gln Ser Asp Val Met Thr Ala Leu Val Ser Phe Asp Arg
                325                 330                 335
Val Phe Glu Val Leu Asp Leu Lys Pro Leu Ile Thr Glu Arg Pro Gly
            340                 345                 350
Ala Arg Pro Leu Pro Ala Arg Ala Ser Ala Asn Gly Asp Gly Thr Ala
            355                 360                 365
Pro Pro Val Glu Phe Asp Gln Val Ala Phe Arg Tyr Pro Ser Ala Glu
            370                 375                 380
Glu Val Ser Leu Pro Ser Leu Glu Leu Met Pro Gln Arg Lys Ser Glu
385                 390                 395                 400
Gln Gly Pro Gly Ala Leu Val Leu Asn Asp Val Ser Phe His Ala Pro
                405                 410                 415
Ala Gly Arg Leu Thr Ala Leu Val Gly Pro Ser Gly Ala Gly Lys Thr
            420                 425                 430
Thr Ile Thr His Leu Val Pro Arg Leu Tyr Asp Ala Thr Ser Gly Thr
            435                 440                 445
Val Arg Ile Gly Gly His Asp Val Arg Asp Leu Thr Leu Gly Ser Leu
450                 455                 460
Gln Asn Thr Val Gly Val Val Thr Gln Asp Ala His Leu Phe His Asp
```

```
                465                 470                 475                 480
Thr Ile Arg Ala Asn Leu Leu Tyr Ala Arg Pro Asp Ala Ser Glu Pro
                    485                 490                 495
Glu Ile Val Gln Ala Cys Glu Ala Ala Arg Ile Trp Pro Thr Ile Ser
                500                 505                 510
Gln Leu Pro Asp Gly Leu Asp Thr Val Val Gly Asp Arg Gly Tyr Arg
            515                 520                 525
Leu Ser Gly Gly Glu Lys Gln Arg Leu Ala Ile Ala Arg Leu Leu Leu
        530                 535                 540
Lys Ser Pro Pro Ile Val Val Leu Asp Glu Ala Thr Ala His Leu Asp
545                 550                 555                 560
Ser Glu Ser Glu Leu Ala Ile Gln Arg Ala Leu Lys Thr Ala Leu Thr
                565                 570                 575
Gly Arg Thr Ser Leu Val Ile Ala His Arg Leu Ser Thr Ile Gln Asp
            580                 585                 590
Ala Asp Gln Ile Leu Val Ile Asp Asp Gly Arg Ile Gln Glu Arg Gly
        595                 600                 605
Thr His Asp Gln Leu Leu Ala Gly Gly Leu Tyr Ser Glu Leu Tyr
    610                 615                 620
Arg Thr Gln Phe Ala His Gln Gln Gly Arg Gly Arg Pro Ala Glu Ser
625                 630                 635                 640
Thr Ala Ala Gly Asn Gly Asn Arg Ala Leu Asp
                645                 650

<210> SEQ ID NO 34
<211> LENGTH: 275
<212> TYPE: PRT
<213> ORGANISM: Streptomyces fungicidicus

<400> SEQUENCE: 34

Met Asp His Thr Ala Gly Arg Arg Ala Pro His Phe Val Thr Val Gly
1               5                   10                  15
Gly Val Arg Ile Ala Tyr Gln Arg Ala Gly Arg Gly Glu Pro Val Leu
                20                  25                  30
Met Ile Met Gly Ser Gly Ser Ala Gly His Ala Trp Thr Leu His Gln
            35                  40                  45
Thr Pro Ala Leu His Thr Ala Gly Tyr Ser Thr Val Val Phe Asp His
        50                  55                  60
Arg Gly Val Pro Pro Ser Asp Ala Pro Pro Gly Arg Tyr Ser Leu Leu
65                  70                  75                  80
Asp Met Thr Ala Asp Ala Lys Gly Leu Ile Glu Ala Leu Asp Leu Ala
                85                  90                  95
Pro Cys Arg Ile Val Gly Thr Ser Leu Gly Ala Met Ile Ala Gln Glu
                100                 105                 110
Leu Ala Ile Gly His Pro Glu Leu Val Arg Cys Ala Val Leu Ile Ala
            115                 120                 125
Thr Arg Ala Arg Ala Asp Ala Ala Arg Ala Gln Thr Arg Ala Glu
        130                 135                 140
Thr Ala Leu Val Glu Ser Gly Val Arg Leu Pro Ala Ala Tyr Asp Ala
145                 150                 155                 160
Ala Ser Thr Val Phe Arg Met Phe Ser Pro Ala Thr Leu Asn Asp Asp
                165                 170                 175
Gln Ala Val Thr Ala Trp Leu Asp Val Phe Glu Leu Ser Gly Gly Gly
            180                 185                 190
Glu Ala Gln Ala Arg His Ala Trp Ala Asp Ile Met Asp Asp Arg Arg
```

```
            195                 200                 205
Pro Ala Leu Arg Arg Val Ala Ala Pro Cys Arg Val Val Thr Phe Ala
210                 215                 220

Asp Asp Leu Ile Thr Pro Pro His Leu Gly Val Glu Val Ala Glu Ala
225                 230                 235                 240

Val Pro Asp Cys Asp Leu Val Glu Ile Pro Asp Cys Gly His Leu Gly
                245                 250                 255

Tyr Phe Glu Arg Pro Asp Ala Val Asn Ala Ala Ile Val Glu Phe Leu
            260                 265                 270

Asp Lys His
        275

<210> SEQ ID NO 35
<211> LENGTH: 90
<212> TYPE: PRT
<213> ORGANISM: Streptomyces fungicidicus

<400> SEQUENCE: 35

Met Ser Ala Ser Asp Leu Pro Ala Thr Arg Leu Thr Pro Glu Lys Ile
1               5                   10                  15

Arg Ser Trp Leu Val Asp Arg Val Ala Tyr Tyr Ala Arg Leu Pro Ala
                20                  25                  30

Glu Glu Ile Gly Ala Asp Val Pro Leu Ala His Tyr Gly Leu Asp Ser
            35                  40                  45

Val Tyr Ala Phe Ala Leu Cys Gly Asp Ile Glu Asp Gly Leu Gly Leu
        50                  55                  60

Val Val Glu Pro Val Leu Leu Trp Asp Val Asp Thr Ile Thr Glu Leu
65                  70                  75                  80

Thr Asp His Leu Ala Glu Leu Thr Ala Asp
                85                  90

<210> SEQ ID NO 36
<211> LENGTH: 2101
<212> TYPE: PRT
<213> ORGANISM: Streptomyces fungicidicus

<400> SEQUENCE: 36

Met Arg Arg Lys Asp Leu Glu Arg Leu Thr Ser Gly Gln Leu Gly Val
1               5                   10                  15

Trp Tyr Ala Gln Gln Leu Glu Pro Leu Ser Pro Val Tyr Asn Ile Ala
                20                  25                  30

Glu Tyr Val Glu Ile Arg Gly Asp Val Asp Val Gly Leu Leu Val Ser
            35                  40                  45

Ala Leu Arg Ser Ala Leu Asp Glu Ala Gln Thr Tyr Arg Leu Arg Phe
        50                  55                  60

Arg Gln Glu Asp Ala Gly Pro Gly Gln Tyr Val Asp Asp Ser Leu Glu
65                  70                  75                  80

Leu Pro Val His Val Ala Asp Leu Gly Ser Ala Gly Asp Pro Arg Ala
                85                  90                  95

Ala Ala Val Glu Trp Met Thr Ala Asp Leu Asp Arg Pro Ala Asp Pro
            100                 105                 110

Leu Thr Gly Pro Leu Ala Ala His Ala Val Phe Arg Leu Gly Pro Gly
        115                 120                 125

His Val Leu Trp Tyr Gln Arg Ala His His Leu Val Leu Asp Gly Thr
130                 135                 140

Ser Leu Ser Val Phe Ala Ala Arg Val Ala Asp Leu Tyr Thr Ala Ser
145                 150                 155                 160
```

```
Ala Ser Gly Arg Pro Ala Gly Ala Pro Gly Pro Leu Ser Val
            165                 170                 175

Leu Leu Asp Ala Asp Arg Ser Tyr Leu Arg Ser Glu Glu Tyr Ala Arg
            180                 185                 190

Asp Arg Arg Phe Trp Arg Glu Tyr Leu Ala Asp Leu Pro Gly Gln Gly
            195                 200                 205

Ala Ala Arg Gly Asp Arg Thr Arg Ser Leu Pro Gly Arg Pro Leu Leu
210                 215                 220

His Thr His Pro Asn Asp Ala Ser Ala Ala Thr Glu Leu Arg Glu Ala
225                 230                 235                 240

Ala Arg Arg Leu Arg Thr Ser Pro Ala Val Leu Ser Leu Thr Ala Ala
            245                 250                 255

Ala Leu Tyr Arg His Arg Thr Thr Gly Thr Arg Asp Val Val Leu Gly
            260                 265                 270

Val Pro Val Thr Gly Arg Thr Thr Gly Arg Glu Leu Gly Ile Pro Gly
            275                 280                 285

Met Thr Ser Asn Val Val Pro Leu Arg Leu Ser Leu Asp Arg Gly Val
            290                 295                 300

Thr Val Ala Glu Leu Leu Arg Arg Thr Ser Arg Thr Leu Arg Asp Cys
305                 310                 315                 320

Leu Arg His Gln Arg Tyr Pro Tyr Gly Asp Ile Leu Ala Asp Gln Gly
            325                 330                 335

Leu Val Gly Arg Gly Ala Leu Arg Asp Leu Ser Val Asn Leu Met Phe
            340                 345                 350

Leu Asn Arg Pro Leu Arg Phe Gly Asp Ala Val Ala Thr Arg Thr Gly
            355                 360                 365

Leu Ser Ser Gly Pro Ile Asp Asp Val Ala Ile Gly Val Tyr Asp Arg
            370                 375                 380

Gly Asp Asp Gly Phe Arg Thr Val Val Gln Thr Asn Pro Gly Leu His
385                 390                 395                 400

Asp Pro Gly Ala Gly Ala Glu Ile Ser Arg Ala Phe Arg Thr Val Leu
            405                 410                 415

Gly Arg Leu Ala Ala Ala Pro Ala Asp Ala Phe Ala Asp Arg Ile Asp
            420                 425                 430

Ala Leu Asp Glu Asp Gln Arg Arg Arg Val Leu Val Thr Trp Asn Arg
            435                 440                 445

Thr Val Thr Ser Gly Val Ala Pro Ser Val Leu Ser Arg Phe Glu Glu
            450                 455                 460

His Ala Ala Arg Thr Pro Asp Ala Val Ala Val Val Cys Gly Ala Ser
465                 470                 475                 480

Glu Thr Thr Tyr Arg Glu Leu Asp Glu Arg Ala Glu Arg Leu Ala Gly
            485                 490                 495

Val Leu Arg Gly His Gly Val Gly Pro Glu Ala Val Val Ala Val Cys
            500                 505                 510

Leu Pro Pro Gly Pro Ala Leu Leu Thr Ala Phe Leu Ala Ala Trp Lys
            515                 520                 525

Ala Gly Ala Ala Tyr Leu Pro Met Asp Pro Gly His Pro Ala Glu Arg
            530                 535                 540

Ala Arg Leu Thr Leu Ala Glu Ser Arg Ala Thr Ala Leu Ile Ala Thr
545                 550                 555                 560

Gly Glu Pro Leu Arg Asp Leu Ala Gly Ser Gly Ile Ala Ala Leu Asp
            565                 570                 575

Pro Asp Asp Leu Pro Val Thr Ala Pro Ala Ala Pro Ala Ala Pro Ala
```

```
                580                 585                 590
Pro Leu Pro Ala Gln Leu Ala Tyr Leu Ile Phe Thr Ser Gly Ser Thr
            595                 600                 605
Gly Val Pro Lys Gly Val Ala Val Thr His Gly Ala Leu Ala Asn Tyr
            610                 615                 620
Thr Val Trp Ala Ala Glu Phe Phe Arg Met Arg Pro Gly Asp His Ser
625                 630                 635                 640
Pro Met His Ser Ser Thr Ala Phe Asp Leu Ala Val Thr Gly Val Leu
                645                 650                 655
Val Pro Leu Val Cys Gly Gly Ala Val Asp Ile Ser Pro Glu Gly Gly
            660                 665                 670
Ala Ala Gly Leu Ala Ala Leu Thr Arg Ala Arg Ala Gly Glu Pro Phe
            675                 680                 685
Gly Leu Val Lys Val Val Pro Gly His Leu Pro Leu Leu Thr Glu Thr
            690                 695                 700
Leu Thr Val Pro Glu Arg Ala Ser Ala Thr Arg Arg Leu Val Val Gly
705                 710                 715                 720
Gly Glu Ala Leu Pro Gly Ala His Val Arg Ala Trp Leu Arg Asp Ala
                725                 730                 735
Pro Asp Thr Val Val Asn His Tyr Gly Pro Thr Glu Thr Thr Val
            740                 745                 750
Gly Cys Cys Val Phe Glu Val Pro Ser Gly Arg Pro Val Gly Asp Arg
            755                 760                 765
Val Pro Ile Gly Arg Pro Ile Ala Asn Thr Arg Leu Tyr Ala Leu Asp
            770                 775                 780
Asp Ala Leu Asn Pro Val Pro Val Gly Ala Leu Gly Glu Leu Tyr Val
785                 790                 795                 800
Ala Gly Ala Gly Leu Ala Arg Gly Tyr Ala Arg Arg Ala Gly Pro Thr
                805                 810                 815
Ala Glu Arg Phe Val Ala Cys Pro Phe Gly Pro Pro Gly Gln Arg Met
                820                 825                 830
Tyr Arg Thr Gly Asp Leu Val Arg Trp Thr Ala Gly Gly Gln Leu Glu
            835                 840                 845
Phe Ala Gly Arg Ala Asp Asp Gln Ile Lys Ile Asn Gly Tyr Arg Val
850                 855                 860
Glu Pro Ala Glu Ile Glu Ala Val Leu Ser Arg His Pro Ala Val Ala
865                 870                 875                 880
Arg Ala Val Val Val Pro Arg Thr Thr Asp Arg Asp Gly Pro Pro Gln
                885                 890                 895
Leu Val Ala Tyr Val Val Pro Ala Gly Gly Lys Glu Ala Asp Thr Arg
            900                 905                 910
Glu Val Arg Arg Phe Ala Ala His Ala Leu Pro Ala His Met Val Pro
            915                 920                 925
Ala Thr Val Val Ala Leu Asp Thr Leu Pro Leu Thr Ala Asn Gly Lys
            930                 935                 940
Ala Asp Arg Ser Ala Leu Pro Ala Pro Asp Pro Gly Thr Ser Asp Arg
945                 950                 955                 960
Ala Pro Arg Ser Pro Arg Gln Thr Ile Leu Cys Glu Leu Phe Ala Glu
                965                 970                 975
Val Leu Gly Leu Pro Arg Val Gly Thr Asp Asp Phe Phe Ala Leu
            980                 985                 990
Gly Gly His Ser Leu Pro Ala Thr  Arg Leu Ile Ala Arg  Ile Arg Ala
            995                 1000                1005
```

-continued

```
Gly Leu Gly Val Glu Val Pro Met Lys Ala Leu Phe Ala Ala Pro
    1010                1015                1020

Thr Val Ala Ala Leu Asp Thr Trp Leu Asp Asp Gly Pro Thr
    1025                1030                1035

Arg Pro Pro Val Arg Pro Ala Pro Arg Pro Asp Pro Leu Pro Leu
    1040                1045                1050

Ser Pro Ala Gln His Arg Leu Trp Phe Leu His Arg Met Arg Gly
    1055                1060                1065

Gln Ser Ala Thr Tyr Asn Val Pro Leu Gly Leu Arg Leu Thr Gly
    1070                1075                1080

Pro Leu Asp Arg Glu Ala Leu Gln Ala Ala Leu Cys Asp Leu Val
    1085                1090                1095

Glu Arg His Gln Thr Leu Arg Thr Val Tyr Pro Asp Thr Asp Gly
    1100                1105                1110

Val Pro Arg Gln Arg Ile Leu Ala Pro Glu Glu Ala Arg Pro Arg
    1115                1120                1125

Leu Glu Thr Ser Glu Trp Asp Gly Pro Gly Gly Leu Glu Arg Ala
    1130                1135                1140

Ala Arg Tyr Ala Phe Asp Leu Arg His Glu Leu Pro Leu Arg Ala
    1145                1150                1155

Glu Leu Leu Thr Val Gly Pro Arg Glu His Val Leu Leu Leu Ile
    1160                1165                1170

Val His His Ile Ala Ala Asp Ala Trp Ser Met Ser Pro Leu Ala
    1175                1180                1185

Arg Asp Leu Ala Thr Ala Tyr Ala Ala Arg Ser Arg Gly Arg Ala
    1190                1195                1200

Pro Asp Trp Pro Arg Leu Pro Ala Gln Tyr Ala Asp Tyr Thr Leu
    1205                1210                1215

Trp Gln Arg Gln Leu Leu Gly Ala Ala Asp Asp Pro Gly Ser Leu
    1220                1225                1230

Leu Gly Ser Gln Ile Arg Tyr Trp Arg Glu Gln Leu Asp Gly Leu
    1235                1240                1245

Pro Ala Arg Leu Glu Leu Pro Ala Asp Arg Pro Arg Pro Ala Val
    1250                1255                1260

Ala Ser His Arg Gly Ala Arg Leu Pro Ile Arg Leu Glu Gln Asp
    1265                1270                1275

Leu His Gln Ala Leu Thr Arg Leu Ala Arg Gln Gln Gly Ala Thr
    1280                1285                1290

Leu Phe Met Val Leu His Ala Ala Val Ala Ala Leu Leu Thr Arg
    1295                1300                1305

Leu Gly Ala Gly Thr Asp Ile Pro Leu Gly Ala Pro Ile Ala Gly
    1310                1315                1320

Arg Thr Asp Glu Ala Leu Asp Asp Leu Ala Gly Cys Phe Val Asn
    1325                1330                1335

Thr Leu Val Leu Arg Ala Asp Thr Ser Gly Asn Pro Ala Phe Asp
    1340                1345                1350

Asp Leu Leu Gln Gln Val Arg Asn Thr Asp Leu Ala Ala Tyr Glu
    1355                1360                1365

His Gln Asp Val Pro Phe Glu His Leu Val Glu Val Leu Asn Pro
    1370                1375                1380

Glu Arg Ser Gln Ala His His Pro Leu Phe Gln Val Gly Leu Gly
    1385                1390                1395

Leu Gln Asn Val Ser Pro Pro Thr Leu Gly Leu Pro Gly Leu Asp
    1400                1405                1410
```

```
Thr Arg Pro Glu Pro Val Asp Thr Gly Thr Ala Arg Phe Asp Leu
    1415            1420                1425
Met Leu Asn Leu Thr Asp Thr His Thr Asp Asp Ala Thr Pro Ala
    1430            1435                1440
Gly Val Thr Gly Thr Val Glu Tyr Ala Thr Asp Leu Phe Asp Ala
    1445            1450                1455
Gly Thr Val Arg Thr Leu Val Asp Arg Leu Val Arg Leu Leu Glu
    1460            1465                1470
Gln Val Ala Asp Asp Pro Arg Arg Arg Leu Gly Asp Leu Asp Leu
    1475            1480                1485
Leu Thr Ala Glu Glu Arg Arg Gly Leu Val Ala Glu Thr Thr Ala
    1490            1495                1500
Ala Glu Gly Ser Glu Ala Thr Leu Pro Glu Leu Phe Ala Val Gln
    1505            1510                1515
Ala Ala Arg Thr Pro Asp Ala Thr Ala Val Thr Ala Gly Gly Val
    1520            1525                1530
Glu Leu Ser Tyr Ala Glu Leu Asp Ala Arg Ala Glu Gly Leu Ala
    1535            1540                1545
Arg Gly Leu Val Gly Arg Gly Val Gly Pro Glu Ser Val Val Gly
    1550            1555                1560
Val Leu Leu Gly Arg Ser Ala Asp Val Val Val Ala Val Leu Ala
    1565            1570                1575
Val Ala Lys Ala Gly Gly Ala Tyr Leu Pro Val Asp Pro Asp Tyr
    1580            1585                1590
Pro Ala Asp Arg Val Ala Phe Val Leu Ser Asp Ala Gly Ala Glu
    1595            1600                1605
Trp Val Val Thr Ser Ala Glu Phe Ala Pro Val Leu Pro Ala Gly
    1610            1615                1620
Val Ala Ala Val Thr Val Asp Gly Ala Gly Ser Gly Pro Val Phe
    1625            1630                1635
Asp Ser Val Pro Leu Pro Thr Val Arg Pro Asp His Pro Ala Tyr
    1640            1645                1650
Val Ile Tyr Thr Ser Gly Ser Thr Gly Arg Pro Lys Gly Val Val
    1655            1660                1665
Val Pro His Arg Ser Val Val Ala Leu Phe Ala Ala Thr Arg Gly
    1670            1675                1680
Val Phe Glu Phe Gly Ala Gly Asp Val Trp Ser Trp Phe His Ser
    1685            1690                1695
Leu Ala Phe Asp Phe Ser Val Trp Glu Val Trp Gly Ala Leu Leu
    1700            1705                1710
His Gly Gly Arg Val Val Val Val Pro Phe Asp Val Ser Arg Ser
    1715            1720                1725
Pro Arg Glu Phe Val Glu Leu Leu Glu Arg Glu Arg Val Thr Val
    1730            1735                1740
Leu Ser Gln Thr Pro Ser Ala Phe Tyr Gln Leu Met Gly Val Gly
    1745            1750                1755
Gly Gly Leu Pro Ala Leu Arg Thr Val Val Phe Gly Gly Glu Ala
    1760            1765                1770
Leu Glu Pro Gly Arg Leu Asp Gly Trp Trp Glu Arg Phe Gly Glu
    1775            1780                1785
Ala Gly Pro Arg Leu Val Asn Met Tyr Gly Ile Thr Glu Thr Thr
    1790            1795                1800
Val His Val Thr His Gln Asp Leu Arg Pro Asp Thr Ala Ala Asp
```

```
              1805                1810                1815

Gly Ser Val Ile Gly Arg Gly Leu Pro Gly Leu Ser Val Phe Leu
    1820                1825                1830

Leu Asp Glu Trp Leu Arg Pro Val Pro Val Gly Ala Val Gly Glu
    1835                1840                1845

Met Tyr Val Ala Gly Ala Gln Val Ala Arg Gly Tyr Arg Gly Arg
    1850                1855                1860

Ala Gly Leu Thr Gly Glu Arg Phe Val Ala Cys Pro Phe Gly Ala
    1865                1870                1875

Ala Gly Gly Arg Met Tyr Arg Thr Gly Asp Arg Ala Arg Trp Ser
    1880                1885                1890

Arg Asp Gly Arg Leu Val Phe Ala Gly Arg Ala Asp Glu Gln Val
    1895                1900                1905

Lys Ile Arg Gly Phe Arg Ile Glu Pro Gly Glu Val Glu Ala Val
    1910                1915                1920

Val Ala Gly His Arg Asp Val Ala Gln Val Ala Val Val Ala Arg
    1925                1930                1935

Glu Gly Gly Pro Gly Gly Leu Arg Leu Val Ala Tyr Ile Val Ala
    1940                1945                1950

Ala Glu Gly Thr Asp Gly Leu Ala Asp Arg Val Arg Val Phe Ala
    1955                1960                1965

Gly Glu Arg Leu Pro Ser Tyr Met Val Pro Ser Ala Phe Val Val
    1970                1975                1980

Leu Gly Gly Leu Pro Leu Thr Val Asn Gly Lys Leu Asp Arg Thr
    1985                1990                1995

Ala Leu Pro Glu Pro Thr Tyr Thr Ala Gly Gly Arg Ala Ala
    2000                2005                2010

Ala Thr Ala Glu Glu Glu Leu Leu Cys Gln Ala Phe Ala Glu Val
    2015                2020                2025

Leu Gly Leu Pro Thr Val Gly Val Asp Asp Phe Ala Leu
    2030                2035                2040

Gly Gly His Ser Leu Leu Ala Thr Arg Leu Ile Ala Arg Val Arg
    2045                2050                2055

Ala Ser Leu Arg Glu Glu Leu Pro Ile Glu Glu Leu Phe Ala Thr
    2060                2065                2070

Pro Thr Pro Ala Ala Leu Ala Ala Trp Leu Ala Glu His Gly Gly
    2075                2080                2085

Gly Thr Arg Ser Thr Arg Pro Ala Leu Arg Pro Met Arg
    2090                2095                2100

<210> SEQ ID NO 37
<211> LENGTH: 6943
<212> TYPE: PRT
<213> ORGANISM: Streptomyces fungicidicus

<400> SEQUENCE: 37

Met Ile Pro Ala Ser Phe Ala Gln Arg Arg Leu Trp Leu Gln Trp Arg
1               5                   10                  15

Ile Glu Gly Pro Ser Ala Thr Tyr Asn Ser Pro Thr Ile Leu Arg Leu
            20                  25                  30

Thr Gly Arg Leu Asp Arg Gln Ala Leu Ala Ser Ala Leu Arg Asp Val
        35                  40                  45

Ile Thr Arg His Glu Ala Leu Arg Thr Val Phe Arg Glu Ala Asp Gly
    50                  55                  60

Glu Pro His Gln Arg Ile Val Pro Leu Ala Glu Leu Asp Trp Ala Leu
```

-continued

```
               65                  70                  75                  80
His Val Val Glu Val Ile Gly Gly Ala His Leu Pro Ser His Gln Arg
                        85                  90                  95

Leu Tyr Thr His Glu Glu Leu Arg Trp Asp Glu Pro Val Leu Asp Leu
                        100                 105                 110

Pro Thr Val Glu Pro Ala Ser Asp Leu Pro Ala Glu Arg Ile Asp Ala
                        115                 120                 125

Ala Gln Leu Thr Gly Ala Val Ala Arg Val Ala Ala His Thr Phe Asp
                        130                 135                 140

Leu Ser Thr Glu Ile Pro Ile Arg Ala Trp Leu Phe Ala Met Ala Pro
145                     150                 155                 160

Asp Glu His Val Leu Val Thr Val Val His Ile Ala Thr Asp Gly
                        165                 170                 175

Trp Ser Ala Gly Pro Phe Thr Arg Asp Leu Ser Thr Ala Tyr Thr Ala
                        180                 185                 190

Arg Asn His Gly Arg Ala Pro Gln Trp Ser Pro Leu Pro Val Gln Tyr
                        195                 200                 205

Gly Asp Tyr Thr Leu Trp Gln Arg Glu Leu Leu Gly Asp Arg Asp Asp
210                     215                 220

Pro Gly Ser Val Leu Ser Arg Gln Ile Ala Tyr Trp Arg Glu Asn Leu
225                     230                 235                 240

Glu Gly Ala Pro Glu Glu Leu Thr Leu Pro Phe Asp Arg Pro Arg Pro
                        245                 250                 255

Val Glu Pro Ser His Arg Gly His Ala Val Thr Ile Gly Leu Pro Ala
                        260                 265                 270

Gln Thr His Ala Ala Leu Ala Ala Val Ala Arg Arg His Arg Ala Thr
                        275                 280                 285

Leu Pro Met Leu Phe Gln Ala Gly Leu Ala Val Thr Leu Ser Arg Leu
        290                 295                 300

Gly Ala Gly His Asp Ile Pro Leu Gly Thr Pro Thr Ala Gly Arg Ser
305                     310                 315                 320

Asp Glu Ala Leu Asp Asp Leu Ile Gly Phe Phe Val Asn Thr Leu Val
                        325                 330                 335

Ile Arg Ala Asp Leu Ala Gly Asp Pro Thr Leu Ala Glu Val Ile Asp
                        340                 345                 350

Arg Val Arg Thr Thr Ala Val Arg Ala Phe Gly His Gln Asp Val Pro
                        355                 360                 365

Phe Glu Arg Leu Val Glu Glu Phe Ala Pro Thr Arg Ser Leu Ala Arg
        370                 375                 380

His Pro Leu Phe Gln Val Val Leu Ala Pro Leu Asp Asp Gly Ala Arg
385                     390                 395                 400

Leu Asp Ile Pro Gly Leu Arg Gly Glu Val Leu Ser Ile Gly Arg Ser
                        405                 410                 415

Thr Ala Lys Phe Asp Leu Glu Ala Thr Leu Gly Glu Ala Phe Asp Asp
                        420                 425                 430

Asp Gly Glu Ala Ala Gly Ile Arg Gly Val Val Thr Gly Ser Ala Asp
                        435                 440                 445

Leu Phe Asp Gln Ser Thr Val Glu Arg Ile Ala Gly Cys Leu Val Arg
        450                 455                 460

Val Leu Thr Ala Phe Ala Ala Asp Pro Glu Gln His Val Gly Ser Val
465                     470                 475                 480

Asp Ile Leu Gly Ala Asp Glu Arg Ser Arg Leu Val Glu Gly Phe Asn
                        485                 490                 495
```

```
Ala Thr Ala Val Pro Val Arg Asp Ala Ser Leu Pro Glu Met Phe Ala
            500                 505                 510

Arg Gln Leu Ala Ala Cys Pro Asp Ala Pro Ala Val Cys Gly Ala
        515                 520                 525

Thr Glu Leu Ser Tyr Ala Glu Leu Asp Thr Arg Ser Asp Arg Leu Ala
        530                 535                 540

Arg Ala Leu Val Ala Glu Gly Val Gly Gln Glu Ser Ala Val Ala Val
545                 550                 555                 560

Leu Met Glu Arg Ser Ile Asp Leu Val Val Ala Leu Ala Val Val
            565                 570                 575

Lys Ala Gly Gly Ala Phe Val Pro Leu Asp Thr Gly Trp Pro Glu Ala
            580                 585                 590

Arg Lys Arg Ala Val Ile Glu Asp Ala Gly Ala Ser Val Met Val Val
        595                 600                 605

Asp Asp Lys Ala Ala Gly His Glu Gln Phe Gly Ala Ser Leu Val Ala
        610                 615                 620

Val Gly Ser Gly Ala Asp Ser Asp Val Val Leu Pro Ala Ser Val Ala
625                 630                 635                 640

Pro Gly Ala Ala Ala Tyr Val Met Tyr Thr Ser Gly Ser Thr Gly Val
                645                 650                 655

Pro Lys Gly Val Val Ala Thr His Arg Asp Val Val Arg Leu Ala Lys
            660                 665                 670

Asp Arg Cys Trp Gly Ala Pro Ala Arg Val Leu Phe His Ala Pro His
        675                 680                 685

Ala Phe Asp Ala Ser Ser Tyr Glu Leu Trp Val Pro Leu Leu Ser Gly
        690                 695                 700

Gly Thr Val Val Ala Pro Asp Glu Ala Met Asp Gly Ala Val Leu
705                 710                 715                 720

Arg Arg Leu Val Ser Asp His Gly Val Ser His Val His Val Thr Ala
                725                 730                 735

Gly Leu Leu Arg Val Leu Ala Asp Gln Asp Pro Gly Ser Phe Ser Gly
            740                 745                 750

Val Arg Glu Val Leu Thr Gly Gly Asp Val Val Pro Ala Glu Ser Val
        755                 760                 765

Arg Arg Val Leu Asp Ala Asn Pro Gly Val Thr Val Arg Gln Leu Tyr
770                 775                 780

Gly Pro Thr Glu Val Thr Leu Cys Ala Thr Gln Tyr Glu Val Ala Asp
785                 790                 795                 800

Ala Ala Glu Val Asp Gly Val Leu Pro Ile Gly Arg Pro Leu Asp Asn
                805                 810                 815

Thr Arg Val Tyr Val Leu Asp Gly Ala Leu Ser Pro Val Pro Val Gly
            820                 825                 830

Val Ala Gly Glu Leu Tyr Val Ala Gly Ala Gly Val Ala Arg Gly Tyr
        835                 840                 845

Leu Gly Arg Pro Val Leu Thr Gly Glu Arg Phe Val Ala Cys Pro Phe
850                 855                 860

Gly Ala Thr Gly Glu Arg Met Tyr Arg Thr Gly Asp Leu Val Arg Trp
865                 870                 875                 880

Asp Ala Glu Gly Arg Leu Val Phe Met Gly Arg Ala Asp Asp Gln Val
                885                 890                 895

Lys Ile Arg Gly Phe Arg Val Glu Pro Gly Glu Val Glu Thr Val Val
            900                 905                 910

Ala Ala His Pro Ala Val Gly Gln Ala Ala Val Val Val Arg Glu Asp
        915                 920                 925
```

-continued

Thr Pro Gly Asp Lys Arg Leu Val Ala Tyr Leu Val Pro Ala Gly Thr
    930             935                 940

Glu Thr Ser Leu Ala Asp Ala Val Arg Ala His Thr Ala Glu Arg Leu
945             950                 955                 960

Pro Glu Tyr Leu Val Pro Ser Ala Phe Val Leu Glu Asn Leu Pro
        965                 970                 975

Leu Thr Pro Ser Gly Lys Leu Asp Arg Lys Val Leu Pro Ala Pro Leu
        980                 985                 990

Tyr Ala Ser Gly Ala Gly Arg Glu Pro Ala Thr Val Arg Glu Glu Leu
        995             1000                1005

Val Cys Arg Ala Phe Ala Glu Val Leu Gly Leu Ala Ser Val Gly
    1010                1015                1020

Val Glu Asp Asp Phe Phe Ala Leu Gly Gly His Ser Leu Leu Ala
    1025                1030                1035

Val Ser Leu Val Glu Trp Leu Arg Arg Arg Gly Val Ser Val Ser
    1040                1045                1050

Val Arg Ala Leu Phe Val Thr Pro Thr Pro Ala Ala Leu Ala Ala
    1055                1060                1065

Val Ala Gly Pro Glu Leu Val Glu Val Pro Pro Asn Leu Ile Pro
    1070                1075                1080

Glu Gly Ala Ser Glu Leu Arg Pro Glu Met Leu Pro Leu Val Glu
    1085                1090                1095

Leu Ser Glu Ala Glu Val Ala Arg Val Val Ala Ala Val Pro Gly
    1100                1105                1110

Gly Ala Ala Asn Val Gln Asp Val Tyr Pro Leu Ala Pro Leu Gln
    1115                1120                1125

Glu Gly Ile Phe Phe His His Leu Met Ala Glu Arg Asp Gly Glu
    1130                1135                1140

Asp Val Tyr Ala Met Pro Phe Thr Leu Arg Phe Ala Glu Arg Ser
    1145                1150                1155

Gly Leu Asp Ala Phe Leu Gly Ala Leu Gln Arg Val Val Asp Arg
    1160                1165                1170

His Asp Val Tyr Arg Thr Ser Ile Val Trp Glu Gly Leu Arg Glu
    1175                1180                1185

Pro Val Gln Val Val Trp Arg Arg Ala Glu Leu Pro Val Thr Glu
    1190                1195                1200

Val Val Pro Asp Ala Ser Gly Glu Ser Asp Ala Ala Gly Arg Pro
    1205                1210                1215

Ala Thr Leu Met Thr Ala Val Gly Gly Arg Met Glu Leu Asp Arg
    1220                1225                1230

Ala Pro Leu Leu Thr Val His Ile Ala Ala Glu Pro Asp Gly Asp
    1235                1240                1245

Gly Trp Gln Ala Leu Val Arg Met His His Leu Val Gln Asp His
    1250                1255                1260

Thr Ala Leu Glu Val Val Leu Asp Glu Val Arg Ala Ile Leu Ala
    1265                1270                1275

Gly Arg Ala Asp Glu Leu Pro Ala Pro Val Pro Phe Arg Asp Phe
    1280                1285                1290

Val Ala Gln Ala Arg Leu Gly Val Ser Glu Glu Ala His Arg Glu
    1295                1300                1305

Tyr Phe Thr Arg Leu Leu Gly Asp Val Thr Glu Thr Thr Ala Pro
    1310                1315                1320

Tyr Gly Leu Leu Asp Val His Gly Asp Gly Thr Gly Ile Ala Gln

-continued

```
           1325                1330                1335

Gly Arg Leu Thr Val Glu Ser Gly Leu Ala Ala Arg Val Arg Arg
    1340                1345                1350

Ala Ala Gln Ser Leu Ala Val Ser Pro Ala Thr Val Phe His Val
    1355                1360                1365

Ala Trp Gly Arg Val Leu Ala Ala Val Ser Gly Arg Asp Asp Val
    1370                1375                1380

Val Phe Gly Thr Val Leu Leu Gly Arg Ala Thr Val Gly Ala Asp
    1385                1390                1395

Arg Val Pro Gly Leu Phe Met Asn Thr Leu Pro Val Arg Val Arg
    1400                1405                1410

Thr Ala Gly Arg Thr Val Arg Asp Ala Leu Asp Asp Met Arg Glu
    1415                1420                1425

Gln Leu Ala Glu Leu Gln Val His Glu His Ala Pro Leu Thr Leu
    1430                1435                1440

Ala Gln Glu Ala Ala Asp Leu Pro Thr Gly Ser Pro Leu Phe Thr
    1445                1450                1455

Ser Ile Phe Asn Tyr Arg His Leu Gln Ala Asp Val Pro Arg Ser
    1460                1465                1470

Gly Thr Gly Ile Glu Gly Val Asp Ala Thr Ala Thr Arg Asp Ala
    1475                1480                1485

Thr Asn Tyr Pro Leu Asp Leu Ser Val Asn Gln Ser Gly Ser Gly
    1490                1495                1500

Phe Glu Leu Val Val Glu Ala Thr Ala Pro Val Asp Pro Ala Ala
    1505                1510                1515

Val Cys Gly Leu Leu His Ala Ser Val Ala Asn Leu Val Thr Ala
    1520                1525                1530

Leu Glu Asp Thr Pro Asp Leu Ile Leu Gly Ala Leu Asp Val Leu
    1535                1540                1545

Asp Ala Glu Tyr Thr Ala Leu Leu Arg Gln Val Asn Asp Thr Ala
    1550                1555                1560

Ala Pro Ala Pro Ala Gly Leu Val Pro Ala Leu Phe Thr Ala Gln
    1565                1570                1575

Ala Ala Arg Leu Pro Glu Ala Val Ala Leu Val Gly Ala Gly Val
    1580                1585                1590

Glu Leu Ser Tyr Gly Glu Val Glu Ala Arg Ser Asn Gln Trp Ala
    1595                1600                1605

Arg His Leu Ile Ala Ala Gly Val Gly Pro Glu Ser Val Val Ala
    1610                1615                1620

Leu Val Leu Glu Arg Ser Pro Asp Leu Leu Val Ala Ile Leu Ala
    1625                1630                1635

Val Leu Lys Ala Gly Gly Ala Tyr Leu Pro Ile Asp Pro Asp Gln
    1640                1645                1650

Pro Ala Glu Arg Val Ala Phe Met Ile Glu Asp Ala Ala Pro Val
    1655                1660                1665

Leu Val Leu Asp Glu Ser Ala Leu Gln Ala Gly Ala Gly Asp Arg
    1670                1675                1680

Ala Asp Ser Ala Val Ser Asp Ala Asp Arg Leu Ala Pro Leu Leu
    1685                1690                1695

Pro Thr His Pro Ala Tyr Val Ile Tyr Thr Ser Gly Ser Thr Gly
    1700                1705                1710

Arg Pro Lys Gly Val Val Val Thr His Glu Gly Phe Ala Asn Leu
    1715                1720                1725
```

```
Ser Leu Ser His Arg Arg Phe Glu Val Gly Pro Gly Ser Arg Val
    1730                1735                1740

Ala Gln Phe Ala Ser Ala Gly Phe Asp Met Phe Cys Glu Glu Trp
    1745                1750                1755

Leu Leu Ala Leu Leu Ser Gly Ala Ala Leu Val Thr Val Pro Ala
    1760                1765                1770

Asp Arg Arg Leu Gly Ala Asp Phe Ala Glu Phe Leu Ala Glu Ser
    1775                1780                1785

Gly Val Thr His Ala Thr Leu Pro Pro Ala Ala Val Ala Thr Leu
    1790                1795                1800

Pro Glu Gly Ala Leu Asp Asp Gly Phe Val Leu Asp Val Gly Gly
    1805                1810                1815

Glu Ala Leu Pro Ala Glu Thr Val Ser Arg Trp Ala Ala Gly Arg
    1820                1825                1830

Lys Met Phe Asn Ser Tyr Gly Pro Thr Glu Thr Thr Val Asn Ala
    1835                1840                1845

Ala Val Trp Arg Cys Arg Ser Gly Leu Ala Ala Gly Ala Glu Val
    1850                1855                1860

Pro Ile Gly Arg Pro Ile Val Asn Thr Arg Val His Val Leu Asp
    1865                1870                1875

Asp Ala Leu Arg Pro Val Pro Ala Gly Val Leu Gly Glu Leu Tyr
    1880                1885                1890

Val Thr Gly Thr Gly Leu Ala Arg Gly Tyr Leu Gly Arg Ala Gly
    1895                1900                1905

Leu Thr Ala Glu Arg Phe Val Ala Cys Pro Phe Glu Pro Gly Gln
    1910                1915                1920

Arg Met Tyr Arg Thr Gly Asp Arg Val Lys Trp Asn Ala Asp Gly
    1925                1930                1935

Asp Leu Val Phe Ala Gly Arg Ala Asp Asp Gln Val Lys Ile Arg
    1940                1945                1950

Gly Phe Arg Ile Glu Pro Gly Glu Val Glu Ala Val Leu Ala Ala
    1955                1960                1965

His Pro Trp Val Asp Arg Ala Ala Val Val Val Arg Glu Asp Thr
    1970                1975                1980

Pro Gly Asp Pro Arg Leu Val Gly Tyr Val Ile Pro Ala Glu Asp
    1985                1990                1995

Ile Asp Thr His Glu Leu Pro Ser Leu Leu Thr Glu Phe Ala Ala
    2000                2005                2010

Gln Arg Leu Pro Ala His Met Val Pro Ser Ala Val Thr Thr Leu
    2015                2020                2025

Asp Ala Phe Pro Leu Thr Pro Asn Ala Lys Leu Asp Arg Lys Ala
    2030                2035                2040

Leu Pro Arg Pro Arg Tyr Thr Ala Ala Ala Gly Ala Gly Arg Ala
    2045                2050                2055

Pro Ala Asp Val Arg Glu Glu Thr Ile Cys Ala Ala Phe Ala Glu
    2060                2065                2070

Val Leu Gly Leu Asp Arg Val Gly Val Asp Asp Asp Phe Phe Ala
    2075                2080                2085

Leu Gly Gly His Ser Leu Leu Val Val Ser Leu Val Glu Arg Leu
    2090                2095                2100

Arg Arg Arg Gly Val Ser Val Ser Val Arg Ala Leu Phe Thr Thr
    2105                2110                2115

Pro Thr Pro Ala Gly Leu Ala Ala Ala Ala Gly Pro Glu Ala Val
    2120                2125                2130
```

```
Asp Val Pro Pro Asn Leu Ile Pro His Ala Ala Asn Glu Ile Thr
    2135            2140            2145

Pro Glu Met Leu Pro Leu Val Pro Leu Thr Thr Ala Glu Ile Glu
    2150            2155            2160

Arg Val Thr Ala Ala Val Pro Gly Gly Ala Pro Asn Ile Gln Asp
    2165            2170            2175

Val Tyr Pro Leu Ala Pro Leu Gln Glu Gly Ile Phe Phe His His
    2180            2185            2190

Leu Thr Ala Asp Arg Asp Gly Thr Asp Val Tyr Val Thr Pro Ser
    2195            2200            2205

Thr Leu Arg Phe Asp Ser Arg Ser Arg Leu Asp Ser Phe Leu Ala
    2210            2215            2220

Ala Leu Gln Lys Val Val Asp Arg Asn Asp Val Tyr Arg Thr Ala
    2225            2230            2235

Ile Leu Trp Glu Gly Leu Arg Glu Pro Val Gln Val Val Val Arg
    2240            2245            2250

His Ala Glu Leu Pro Val Thr Glu Glu Pro Ala Glu Arg Leu Leu
    2255            2260            2265

Ala Ala Gly Gly Gly Trp Met Asp Ile Gly Arg Ala Pro Leu Leu
    2270            2275            2280

Asp Val Arg Thr Ala Ala Glu Pro Asp Thr Gly Arg Trp Leu Ala
    2285            2290            2295

Leu Val Arg Val His His Leu Val Gln Asp His Thr Ala Ser Asp
    2300            2305            2310

Val Leu Leu Asp Glu Val Arg Ala Phe Met Ala Gly Gln Ala Asp
    2315            2320            2325

Arg Leu Gln Pro Ala Val Pro Phe Arg Glu Phe Val Ala Gln Ala
    2330            2335            2340

Arg Leu Gly Met Pro Arg Glu Glu His Glu Arg Tyr Phe Thr Gly
    2345            2350            2355

Leu Leu Gly Asp Ile Thr Glu Pro Thr Ala Pro Tyr Gly Leu Met
    2360            2365            2370

Asp Val Leu Gly Asp Gly Gly Ala Ala Arg Thr Gly Arg Leu Pro
    2375            2380            2385

Val Glu Pro Gly Leu Ala Arg Arg Val Arg Glu Val Ala Arg Ala
    2390            2395            2400

Arg Gly Val Ser Pro Ala Thr Val Leu His Leu Ala Trp Ala Arg
    2405            2410            2415

Val Leu Ala Ala Val Ala Gly Arg Gln Asp Val Val Phe Gly Thr
    2420            2425            2430

Val Met Phe Gly Arg Met His Ser Gly Glu Ser Ala Asp Arg Val
    2435            2440            2445

Ala Gly Leu Leu Ile Asn Thr Leu Pro Val Arg Val Asn Thr Ala
    2450            2455            2460

Gly Ala Gly Val Gly Glu Ala Leu Thr Gly Leu Arg Asp Gln Leu
    2465            2470            2475

Ala Asp Leu Leu Val His Glu His Ala Ser Leu Ala Leu Ala Gln
    2480            2485            2490

Ser Ala Ser Gly Leu Pro Gly Gly Pro Leu Phe Thr Ser Leu
    2495            2500            2505

Phe Asn Tyr Arg His Leu Gln Gly Thr Asp Ala Gly Gly Thr Glu
    2510            2515            2520

Leu Asp Gly Ile Glu Val Leu Ser Val His Asp His Thr Asn Tyr
```

-continued

```
            2525                2530                2535

Pro Leu Thr Val Ser Val Asp Gln Ser Ala Thr Gly Leu Glu Leu
    2540                2545                2550

Val Val Glu Ser Val Ala Gln Val Asp Ala Thr Glu Val Cys Gly
    2555                2560                2565

Leu Leu His Thr Cys Leu Ala Asn Leu Val Thr Ala Leu Thr Asp
    2570                2575                2580

Ser Pro Asp Val Pro Leu Gly Ala Ile Asp Val Leu Asp Ala Ala
    2585                2590                2595

Tyr Ala Ala Arg Leu Cys Arg Ser Asp Glu Asp Thr Ala Gly Pro
    2600                2605                2610

Val Pro Gly Ala Ser Val Pro Glu Leu Phe Ala Ala Arg Ala Arg
    2615                2620                2625

Leu Ser Pro Asp Ala Val Ala Leu Val Gly Gly Gly Val Gln Leu
    2630                2635                2640

Ser Tyr Gly Glu Val Glu Glu Arg Ala Asn Arg Leu Ala Arg Lys
    2645                2650                2655

Leu Ile Ala Arg Gly Val Gly Pro Glu Ser Val Val Ala Leu Val
    2660                2665                2670

Leu Glu Arg Ser Pro Glu Val Val Ile Ala Ala Leu Ala Val Leu
    2675                2680                2685

Lys Ala Gly Gly Ala Tyr Leu Pro Val Asp Pro Gly Gln Pro Ala
    2690                2695                2700

Glu Arg Ile Arg Ser Val Ile Glu Asp Ala Ala Pro Val Leu Val
    2705                2710                2715

Leu Asp His Pro Asp Phe Leu Ala Glu Thr Ala Asp Tyr Asp Ala
    2720                2725                2730

Ala Pro Val Thr Asp Ala Asp Arg Val Ser Pro Leu Leu Pro Ser
    2735                2740                2745

His Pro Ala Tyr Val Ile Tyr Thr Ser Gly Ser Thr Gly Arg Pro
    2750                2755                2760

Lys Gly Val Val Val Ser His Arg Ser Val Val Ala Leu Phe Val
    2765                2770                2775

Ala Ala Gly Gly Val Phe Glu Phe Gly Ala Gly Asp Val Trp Ser
    2780                2785                2790

Trp Phe His Ser Leu Ala Phe Asp Phe Ser Val Trp Glu Val Trp
    2795                2800                2805

Gly Ala Leu Leu His Gly Gly Arg Val Val Val Pro Phe Asp
    2810                2815                2820

Val Ser Arg Ser Pro Arg Glu Phe Val Glu Leu Leu Glu Arg Glu
    2825                2830                2835

Arg Val Thr Val Leu Ser Gln Thr Pro Ser Ala Phe Tyr Gln Leu
    2840                2845                2850

Met Gly Val Gly Gly Leu Pro Ala Leu Arg Thr Val Val Phe
    2855                2860                2865

Gly Gly Glu Ala Leu Glu Pro Gly Arg Leu Asp Gly Trp Trp Glu
    2870                2875                2880

Arg Phe Gly Glu Ala Gly Pro Arg Leu Val Asn Met Tyr Gly Ile
    2885                2890                2895

Thr Glu Thr Thr Val His Val Thr His Gln Asp Leu Arg Pro Asp
    2900                2905                2910

Thr Ala Ala Asp Gly Ser Val Ile Gly Arg Gly Leu Pro Gly Leu
    2915                2920                2925
```

-continued

```
Ser Val Phe Leu Leu Asp Glu Trp Leu Arg Pro Val Pro Val Gly
    2930                2935                2940

Ala Val Gly Glu Met Tyr Val Ala Gly Ala Gln Val Ala Arg Gly
    2945                2950                2955

Tyr Arg Gly Arg Ala Gly Leu Thr Gly Glu Arg Phe Val Ala Cys
    2960                2965                2970

Pro Phe Gly Val Ala Gly Gly Arg Met Tyr Arg Thr Gly Asp Arg
    2975                2980                2985

Ala Arg Trp Ser Arg Glu Gly Arg Leu Val Phe Ala Gly Arg Ala
    2990                2995                3000

Asp Glu Gln Val Lys Ile Arg Gly Phe Arg Ile Glu Pro Gly Glu
    3005                3010                3015

Val Glu Ala Val Val Ala Gly His Pro Asp Val Ala Gln Val Ala
    3020                3025                3030

Val Val Ala Arg Glu Gly Gly Pro Gly Gly Leu Arg Leu Val Ala
    3035                3040                3045

Tyr Ile Val Pro Glu Pro Ala Glu Gln Ala Glu Gly Phe Ser Glu
    3050                3055                3060

Arg Val Arg Val Tyr Ala Gly Glu Arg Leu Pro Ser Tyr Met Val
    3065                3070                3075

Pro Ser Ala Phe Val Val Leu Asp Gly Leu Pro Leu Thr Val Asn
    3080                3085                3090

Gly Lys Leu Asp Arg Thr Ala Leu Pro Glu Pro Asp Asn Ala Val
    3095                3100                3105

Val Ser Ala Gly Arg Ala Pro Val Thr Ala Gln Glu Glu Leu Leu
    3110                3115                3120

Cys Ala Ala Phe Ala Glu Val Leu Gly Leu Asp Gln Val Gly Val
    3125                3130                3135

Asp Asp Asp Phe Phe Ala Leu Gly Gly His Ser Leu Leu Ala Val
    3140                3145                3150

Ser Leu Val Glu Trp Leu Arg Gln Arg Gly Val Ser Val Ser Val
    3155                3160                3165

Arg Ala Leu Phe Ala Ser Ala Thr Pro Ala Arg Leu Ala Glu Val
    3170                3175                3180

Ala Gly Pro Asp Arg Ile Glu Val Pro Pro Arg Arg Ile Pro Asp
    3185                3190                3195

Gly Ala Thr Arg Ile Thr Pro Asp Met Leu Pro Leu Ala Glu Leu
    3200                3205                3210

Thr Glu Glu Glu Leu Ala Arg Val Glu Ala Ala Val Pro Gly Gly
    3215                3220                3225

Ala Ser Asn Ile Gln Asp Val Tyr Pro Leu Ala Pro Leu Gln Glu
    3230                3235                3240

Gly Leu Phe Phe His His Leu Met Ala Asp Arg Asp Gly Thr Asp
    3245                3250                3255

Val Tyr Ala Thr Pro Met Val Leu Thr Ile Ala Thr Arg Glu Arg
    3260                3265                3270

Leu Glu Asp Phe Leu Thr Ala Leu Arg Arg Met Val Val Arg Asn
    3275                3280                3285

Asp Ile Tyr Arg Thr Ala Ile Val Trp Glu Gly Leu Arg Glu Pro
    3290                3295                3300

Val Gln Val Val Val Arg His Ala Glu Leu Pro Val Glu Glu Ile
    3305                3310                3315

Ala Pro Ala Pro Asp Gly Ser Asp Ala Val Asp Arg Leu Leu Ser
    3320                3325                3330
```

```
Thr Gly Glu Ser Ala Met Asp Leu Thr Arg Ala Pro Leu Leu Arg
    3335            3340            3345

Val Arg Val Met Glu Ala Pro Asp Gly Gly Trp Thr Val Leu Leu
    3350            3355            3360

Arg Ile His His Leu Val Gln Asp His Thr Phe Asp Val Val
    3365            3370            3375

Leu Asp Glu Leu Arg Ala Phe Met Asn Gly Arg Gly Gly Thr Leu
    3380            3385            3390

Pro Ala Pro Val Pro Phe Arg Glu Phe Val Ala Arg Ala Arg Phe
    3395            3400            3405

Gly Val Ser Arg Glu Glu His Glu Arg Tyr Phe Thr Asp Leu Leu
    3410            3415            3420

Gly Asp Val Thr Asp Thr Thr Ala Pro Tyr Gly Leu Thr Asp Val
    3425            3430            3435

Tyr Gly Asp Gly Thr Glu Ala Thr Gln Val Arg Leu Thr Val Asp
    3440            3445            3450

Asp Thr Leu Thr Gly Arg Val Arg Ser Leu Ala Arg Ser His Gly
    3455            3460            3465

Val Ser Pro Ala Thr Leu Phe His Val Ala Trp Ala Arg Val Leu
    3470            3475            3480

Gly Thr Leu Ser Gly Arg Asp Asp Val Val Phe Gly Thr Ile Leu
    3485            3490            3495

Phe Gly Arg Met Asn Ala Gly Ala Gly Ala Asp Arg Ala Pro Gly
    3500            3505            3510

Leu Phe Ile Asn Thr Leu Pro Val Arg Met Arg Pro Ala Gly Arg
    3515            3520            3525

Ser Val Ala Glu Ala Leu Thr Asp Met Arg Gly Gln Leu Ala Gln
    3530            3535            3540

Leu Met Val His Glu His Ala Ser Leu Thr Leu Ala Gln Arg Ala
    3545            3550            3555

Gly Gly Val Pro Ala Ser Ser Pro Leu Phe Thr Ser Val Phe Asn
    3560            3565            3570

Tyr Arg His Asn Leu Pro Thr Glu Arg His Pro Gly Ala Asp Leu
    3575            3580            3585

Asp Gly Val Asp Leu Leu Leu His Arg Asp Tyr Ser Asn Tyr Pro
    3590            3595            3600

Met Val Val Ser Val Asp Asp Gly Thr Gly Phe Glu Val Glu
    3605            3610            3615

Ile Glu Ala Val Ala Pro Val Asp Pro Glu Gly Ala Gly Gly Leu
    3620            3625            3630

Leu Leu Thr Cys Leu Glu Gly Leu Ala Ala Ala Leu Glu Asp Ala
    3635            3640            3645

Pro Ala Thr Pro Leu Thr Gly Ile Asp Val Leu Gly Ser Thr Glu
    3650            3655            3660

Arg Thr Arg Ile Leu Thr Gly Trp Asn Asp Thr Thr Ala Pro Val
    3665            3670            3675

Ser Gly Val Ser Val Pro Arg Ala Phe Ala Ala Arg Val Ala Ala
    3680            3685            3690

His Pro Asp Ala Val Ala Val Val Ser Asp Gly Val Arg Leu Thr
    3695            3700            3705

Tyr Arg Glu Leu Asp Leu Arg Ser Asp Arg Leu Ala Arg Ala Leu
    3710            3715            3720

Ile Arg Ser Asp Ala Gly Pro Glu Pro Val Phe Ala Val Leu Met
```

```
                     3725                3730                3735

Glu Arg Ser Ala Asp Leu Val Ala Leu Leu Ala Val Leu Lys
         3740                3745                3750

Ala Gly Gly Ala Phe Leu Pro Leu Asp Ala Thr Trp Pro Gln Ala
         3755                3760                3765

Arg Met Arg Ser Val Ile Glu Asp Ala Ala Cys Leu Val Val
         3770                3775                3780

Val Ser Glu Thr Trp Ala Gly His Asp Leu Gly Ile Thr Glu Val
         3785                3790                3795

Ala Val Asp Ala Gly Ser Asp Glu Gly His Leu Pro Val Val Pro
         3800                3805                3810

Glu Ala Ala Thr Ala Tyr Val Met Tyr Thr Ser Gly Ser Ala Gly
         3815                3820                3825

Val Pro Lys Gly Val Val Ala Ala His Arg Asp Val Val Ala Leu
         3830                3835                3840

Ala Gly Asp Arg Cys Trp Gly Ala Pro Ala Arg Val Leu Phe His
         3845                3850                3855

Ala Pro His Ala Phe Asp Ala Ser Ser Tyr Glu Leu Trp Val Pro
         3860                3865                3870

Leu Leu Ser Gly Gly Thr Val Val Val Ala Pro Asp Gly Arg Met
         3875                3880                3885

Asp Thr Thr Val Leu Arg Arg Leu Val Leu Asp His Asp Val Ser
         3890                3895                3900

His Val His Val Thr Ala Gly Leu Leu Arg Val Leu Ala Asp Gln
         3905                3910                3915

Asp Pro Gly Cys Phe Ala Gly Val Arg Glu Val Leu Thr Gly Gly
         3920                3925                3930

Asp Val Val Pro Ala Glu Ser Val Arg Arg Val Leu Asp Ala Asn
         3935                3940                3945

Pro Asp Val Arg Val Arg Gln Leu Tyr Gly Pro Thr Glu Val Thr
         3950                3955                3960

Leu Cys Ala Thr Gln Tyr Glu Val Ala Asp Ala Ala Glu Val Asp
         3965                3970                3975

Gly Val Leu Pro Ile Gly Arg Pro Leu Asp Asn Thr Arg Val Tyr
         3980                3985                3990

Val Leu Asp Gly Ala Leu Asn Pro Val Pro Val Gly Val Ala Gly
         3995                4000                4005

Glu Leu Tyr Val Ala Gly Ala Gly Val Ala Arg Gly Tyr Leu Gly
         4010                4015                4020

Arg Pro Val Leu Thr Gly Glu Arg Phe Val Ala Cys Pro Phe Gly
         4025                4030                4035

Gly Ala Gly Glu Arg Met Tyr Arg Thr Gly Asp Leu Val Arg Trp
         4040                4045                4050

Asp Ala Glu Gly Arg Leu Val Phe Val Gly Arg Ala Asp Glu Gln
         4055                4060                4065

Val Lys Ile Arg Gly Phe Arg Val Glu Pro Ala Glu Val Glu Ala
         4070                4075                4080

Val Leu Gly Ala His Pro Ala Val Gly Gln Ala Ala Val Val Ala
         4085                4090                4095

Arg Glu Asp Thr Pro Gly Asp Lys Arg Leu Ile Ala Tyr Leu Val
         4100                4105                4110

Pro Gln Asn Glu Gly Glu Thr Leu Asp Gly Pro Val Arg Glu Tyr
         4115                4120                4125
```

-continued

```
Ala Ala Glu Arg Leu Pro Glu Tyr Met Leu Pro Ala Ala Phe Val
4130                4135                4140

Glu Leu Asp Thr Leu Pro Leu Thr Val Asn Gly Lys Leu Asp Arg
4145                4150                4155

Lys Ala Leu Pro Ala Pro Arg Tyr Ser Pro Asp Thr Gly Arg Ala
4160                4165                4170

Pro Ala Thr Ala Arg Glu Glu Leu Leu Cys His Leu Phe Ala Asp
4175                4180                4185

Thr Leu Gly Leu Pro Arg Val Gly Val Asp Asp Asp Phe Phe Leu
4190                4195                4200

Leu Gly Gly His Ser Leu Leu Ala Met Arg Leu Val Ser Arg Val
4205                4210                4215

Arg Glu Val Leu Gly Val Glu Met Pro Leu Arg Ala Leu Phe Glu
4220                4225                4230

Ala Arg Thr Pro Ala Gly Ala Ala Ala Arg Ser Val Arg Ala Thr
4235                4240                4245

Pro Gly Arg Thr Ala Leu Lys Ala Gly Ala Arg Pro Glu Arg Ile
4250                4255                4260

Pro Leu Ser Tyr Ala Gln Arg Arg Leu Trp Phe Leu Gly Gln Leu
4265                4270                4275

Glu Gly Pro Ser Pro Ala Tyr Asn Ile Pro Leu Ala Leu Arg Leu
4280                4285                4290

Thr Gly Thr Leu Asp Arg Asp Ala Phe Ala Ala Ala Leu Arg Asp
4295                4300                4305

Val Val Glu Arg His Glu Val Val Arg Thr Val Ile Arg Thr Ala
4310                4315                4320

Asp Gly Glu Pro Phe Gln Arg Val Leu Ser Pro Glu Glu Ala Ala
4325                4330                4335

Phe Glu Leu Glu Ile Val Glu Val Ala Thr Gly Glu Leu Ala Gly
4340                4345                4350

Arg Val Ala Gly Ala Ala Arg Tyr Ala Phe Asp Leu Ala Ala Glu
4355                4360                4365

Pro Pro Leu Arg Ala Thr Leu Phe Thr Ala Ala Pro Asp Glu His
4370                4375                4380

Val Leu Val Leu Val Leu His His Ile Ala Gly Asp Ala Trp Ser
4385                4390                4395

Met Glu Pro Leu Ala Arg Asp Val Ser Ala Ala Tyr Thr Ala Arg
4400                4405                4410

Leu Ala Gly Asp Ala Pro Val Trp Glu Pro Leu Pro Val Gln Tyr
4415                4420                4425

Ala Asp Tyr Ala Leu Trp Gln Arg Glu Leu Leu Gly Asp Glu Ala
4430                4435                4440

Asp Pro Arg Ser Leu Leu Ser Arg Gln Val Ala His Trp Arg Glu
4445                4450                4455

Thr Leu Ala Gly Ile Pro Glu Glu Leu Asn Leu Pro Thr Asp Arg
4460                4465                4470

Pro Arg Pro Ala Glu Ile Ser Leu Leu Gly Arg Arg Ala Arg Val
4475                4480                4485

Glu Ile Pro Ala Glu Leu His Gly Gly Leu Leu Glu Val Ala Arg
4490                4495                4500

Ala Glu Gly Val Thr Val Phe Met Ala Leu Gln Ala Ala Leu Ala
4505                4510                4515

Val Thr Leu Ser Arg Leu Gly Ala Gly Thr Asp Ile Pro Val Gly
4520                4525                4530
```

```
Val Ala Val Ala Gly Arg Thr Asp Gly Ala Val Glu Asp Leu Val
    4535                4540                4545
Gly Phe Phe Val Asn Thr Leu Val Leu Arg Thr Asp Leu Ser Gly
    4550                4555                4560
Asp Pro Thr Leu Thr Glu Val Leu Arg Arg Val Arg Glu Thr Ser
    4565                4570                4575
Leu Ser Ala Leu Thr His Gln Asp Val Pro Phe Glu Lys Leu Val
    4580                4585                4590
Glu Glu Leu Ala Pro Ala Arg Ser Leu Ala Arg His Pro Leu Phe
    4595                4600                4605
Gln Val Met Met Thr Leu Gln Asn Thr Gly Asn Pro Ala Asp Ala
    4610                4615                4620
Ala Leu Pro Gly Leu Thr Ala Thr Pro Leu Ala Thr Asp Gly Thr
    4625                4630                4635
Ala Leu Arg Phe Asp Leu Asp Leu Asn Leu Gly Glu Ala Phe Asp
    4640                4645                4650
Glu Ala Gly Asp Pro Ala Gly Ile Asn Gly Ser Leu Ile Ala Ser
    4655                4660                4665
Ala Asp Leu Phe Asp Gln Ser Thr Val Glu Arg Leu Thr Glu Gln
    4670                4675                4680
Leu Leu Arg Val Leu Arg Thr Met Thr Ala His Pro Ala Thr Arg
    4685                4690                4695
Ile Ala Asp Val Asp Val Leu Gly Pro Gln Asp Arg Arg Arg Val
    4700                4705                4710
Leu Thr Glu Trp Asn Gly Thr Ala Val Ala Val Ala Asp Val Ser
    4715                4720                4725
Val Pro Glu Ala Phe Ala Arg Ser Ala Ala Ala Asp Pro Gly Ala
    4730                4735                4740
Leu Ala Val Gln Cys Asp Asp Phe Arg Leu Gln Tyr Asp Glu Val
    4745                4750                4755
Asp Ala Arg Ser Asp Glu Leu Ala Arg Arg Leu Met Ala Ala Gly
    4760                4765                4770
Val Arg Pro Glu Ser Val Val Ala Val Ala Met Glu Arg Ser Ala
    4775                4780                4785
Asp Leu Val Val Val Phe Leu Ala Val Leu Lys Ala Gly Gly Thr
    4790                4795                4800
Tyr Leu Pro Leu Asp Leu Gly Trp Pro Thr Ala Arg Met Arg Ala
    4805                4810                4815
Val Ala Glu Asp Ala Asp Ala Arg Cys Ile Val Thr His Gln Ala
    4820                4825                4830
Thr Ala Gly His Glu Phe Val Arg Thr Thr Ala Leu Ser Glu Val
    4835                4840                4845
Arg Val Asp Val Ile Ala Gly Pro Ala Ala Glu Val Thr Leu Pro
    4850                4855                4860
Leu Val Asp Pro Gly Ala Ala Ala Tyr Val Met Tyr Thr Ser Gly
    4865                4870                4875
Ser Thr Gly Val Pro Lys Gly Val Val Ala Thr His Arg Asp Val
    4880                4885                4890
Val Arg Leu Ala Lys Asp Arg Cys Trp Gly Asp Pro Ala Arg Val
    4895                4900                4905
Leu Phe His Ala Pro His Ala Phe Asp Ala Ser Thr Tyr Glu Leu
    4910                4915                4920
Trp Val Pro Leu Leu Ser Gly Gly Thr Val Val Val Ala Pro Gly
```

-continued

```
                    4925                4930                4935

Glu Ala Ile Asp Gly Ala Val Leu Arg Arg Leu Val Ser Val His
        4940                4945                4950

Gly Leu Ser His Val His Val Thr Ala Gly Leu Leu Arg Val Leu
        4955                4960                4965

Ala Asp Gln Asp Pro Gly Cys Phe Ala Gly Val Arg Glu Val Leu
        4970                4975                4980

Thr Gly Gly Asp Val Val Ala Ala Glu Ser Val Arg Arg Val Leu
        4985                4990                4995

Glu Ala Asn Pro Gly Val Gly Val Arg Gln Leu Tyr Gly Pro Thr
        5000                5005                5010

Glu Val Thr Leu Cys Ala Thr Gln Tyr Glu Val Ala Asp Ala Ala
        5015                5020                5025

Glu Val Asp Gly Val Leu Pro Ile Gly Arg Pro Leu Asp Asn Thr
        5030                5035                5040

Arg Val Tyr Val Leu Asp Gly Ser Leu Ser Pro Val Pro Val Gly
        5045                5050                5055

Val Ala Gly Glu Leu Tyr Val Ala Gly Ala Gly Val Ala Arg Gly
        5060                5065                5070

Tyr Leu Gly Arg Pro Val Leu Thr Gly Glu Arg Phe Val Ala Cys
        5075                5080                5085

Pro Phe Ala Gly Ala Gly Glu Arg Met Tyr Arg Thr Gly Asp Leu
        5090                5095                5100

Val Arg Trp Asp Val Glu Gly Arg Leu Val Phe Leu Gly Arg Ala
        5105                5110                5115

Asp Glu Gln Val Lys Ile Arg Gly Phe Arg Val Glu Pro Gly Glu
        5120                5125                5130

Val Glu Thr Val Val Ala Ala His Pro Ala Val Ala Gln Ala Thr
        5135                5140                5145

Val Leu Val Arg Glu Asp Val Pro Gly Asp Lys Arg Leu Val Ala
        5150                5155                5160

Tyr Leu Val Leu Ala Gly Ala Glu Thr Ala Ala Val Asp Ala Val
        5165                5170                5175

His Thr His Val Ala Glu Gln Leu Pro Ser Tyr Leu Val Pro Ser
        5180                5185                5190

Ala Phe Val Glu Leu Glu Thr Leu Pro Leu Thr Pro Thr Gly Lys
        5195                5200                5205

Val Asp Arg Ala Ala Leu Pro Ala Pro Arg Tyr Thr Ala Gly Thr
        5210                5215                5220

Gly Arg Ala Pro Ala Asp Ala Arg Glu Glu Leu Val Cys Arg Ala
        5225                5230                5235

Phe Ala Glu Val Leu Gly Leu Ala Ala Val Gly Val Glu Asp Asp
        5240                5245                5250

Phe Phe Ala Leu Gly Gly His Ser Leu Leu Ala Val Ser Leu Val
        5255                5260                5265

Glu Trp Leu Arg Arg Arg Gly Val Ser Val Ser Val Arg Ala Leu
        5270                5275                5280

Phe Val Thr Pro Thr Pro Ala Ala Leu Ala Ala Val Ala Gly Pro
        5285                5290                5295

Glu Leu Val Glu Val Pro Pro Asn Leu Ile Pro Pro Gly Ala Asp
        5300                5305                5310

Glu Ile Thr Pro Glu Met Leu Pro Leu Val Pro Leu Thr Thr Ala
        5315                5320                5325
```

-continued

| | | | | | | | | | | | |
|---|---|---|---|---|---|---|---|---|---|---|---|
|Glu|Ile|Glu|Arg|Val|Thr|Ala|Ala|Val|Pro|Gly|Gly|Ala|Pro|Asn|
| |5330| | | |5335| | | |5340| | | | | |
|Ile|Gln|Asp|Val|Tyr|Pro|Leu|Ala|Pro|Leu|Gln|Glu|Gly|Ile|Phe|
| |5345| | | |5350| | | |5355| | | | | |
|Phe|His|His|Leu|Met|Ala|Glu|Arg|Asp|Gly|Glu|Asp|Val|Tyr|Ala|
| |5360| | | |5365| | | |5370| | | | | |
|Met|Pro|Phe|Thr|Leu|Arg|Phe|Ala|Asp|Arg|Ser|Gly|Leu|Asp|Ala|
| |5375| | | |5380| | | |5385| | | | | |
|Phe|Leu|Gly|Ala|Leu|Gln|Arg|Val|Val|Asp|Arg|His|Asp|Val|Tyr|
| |5390| | | |5395| | | |5400| | | | | |
|Arg|Thr|Ser|Ile|Val|Trp|Glu|Glu|Leu|Pro|Gln|Pro|Val|Gln|Val|
| |5405| | | |5410| | | |5415| | | | | |
|Val|Trp|Arg|Asp|Ala|Glu|Leu|Pro|Val|Thr|Glu|Ile|Ile|Leu|Asp|
| |5420| | | |5425| | | |5430| | | | | |
|Pro|Glu|Gly|Gly|Glu|Asp|Ala|Val|Arg|Gln|Leu|Leu|Ala|Ala|Ala|
| |5435| | | |5440| | | |5445| | | | | |
|Gly|Ser|Trp|Met|Glu|Val|His|Arg|Ala|Pro|Leu|Leu|Thr|Val|His|
| |5450| | | |5455| | | |5460| | | | | |
|Thr|Ala|Ala|Glu|Pro|Asp|Gly|Asp|Gly|Trp|Leu|Ala|Leu|Val|Arg|
| |5465| | | |5470| | | |5475| | | | | |
|Met|His|His|Leu|Val|Gln|Asp|His|Thr|Ala|Leu|Asp|Ile|Val|Leu|
| |5480| | | |5485| | | |5490| | | | | |
|Asp|Glu|Ile|Lys|Ala|Ile|Leu|Ala|Gly|Arg|Ala|Asp|Glu|Leu|Pro|
| |5495| | | |5500| | | |5505| | | | | |
|Ala|Pro|Val|Pro|Phe|Arg|Asp|Phe|Val|Ala|Gln|Ala|Arg|Leu|Gly|
| |5510| | | |5515| | | |5520| | | | | |
|Val|Ser|Glu|Glu|Ala|His|Arg|Glu|Tyr|Phe|Thr|Arg|Leu|Leu|Gly|
| |5525| | | |5530| | | |5535| | | | | |
|Asp|Ile|Thr|Glu|Thr|Thr|Ala|Pro|Tyr|Gly|Leu|Leu|Asp|Val|Arg|
| |5540| | | |5545| | | |5550| | | | | |
|Gly|Asp|Gly|Thr|Asp|Leu|Ala|Gln|Ala|Arg|Arg|Arg|Val|Asp|Glu|
| |5555| | | |5560| | | |5565| | | | | |
|Ala|Leu|Thr|Arg|Arg|Val|Gln|Ala|Leu|Ala|Arg|Ser|Arg|Gly|Val|
| |5570| | | |5575| | | |5580| | | | | |
|Ser|Pro|Ala|Thr|Val|Phe|His|Leu|Ala|Trp|Ala|Arg|Met|Leu|Ser|
| |5585| | | |5590| | | |5595| | | | | |
|Ala|Val|Ser|Ala|Arg|Asp|Asp|Ile|Val|Phe|Gly|Thr|Val|Leu|Leu|
| |5600| | | |5605| | | |5610| | | | | |
|Gly|Arg|Ala|Thr|Val|Gly|Ala|Asp|Arg|Val|Pro|Gly|Leu|Phe|Met|
| |5615| | | |5620| | | |5625| | | | | |
|Asn|Thr|Leu|Pro|Val|Arg|Val|Asp|Pro|Ala|Gly|Arg|Thr|Val|Gly|
| |5630| | | |5635| | | |5640| | | | | |
|Gln|Ala|Leu|Ala|Gly|Leu|Arg|Asp|Gln|Leu|Ala|Glu|Leu|Leu|Ala|
| |5645| | | |5650| | | |5655| | | | | |
|His|Glu|His|Ala|Pro|Leu|Thr|Leu|Ala|Gln|Ala|Ala|Ala|Gly|Leu|
| |5660| | | |5665| | | |5670| | | | | |
|Pro|Ala|Gly|Ser|Pro|Leu|Phe|Thr|Ala|Leu|Phe|Asn|Tyr|Arg|His|
| |5675| | | |5680| | | |5685| | | | | |
|Ser|Lys|Pro|Pro|Val|His|Glu|Pro|Asp|Gly|Val|Leu|Ala|Asp|Val|
| |5690| | | |5695| | | |5700| | | | | |
|Thr|Thr|Leu|Phe|Thr|Gln|Glu|Arg|Asn|Asn|Tyr|Pro|Leu|Gly|Val|
| |5705| | | |5710| | | |5715| | | | | |
|Ser|Val|Asp|Asp|Asp|Gly|Gln|Ser|Phe|Gly|Ile|Thr|Val|Asp|Val|
| |5720| | | |5725| | | |5730| | | | | |

-continued

```
Ala Tyr Pro Val Asp Ala Gly Lys Val Ala Ala Leu Leu Glu Thr
    5735            5740                5745
Thr Leu Ala His Leu Thr Thr Ala Leu Glu Asp Thr Pro Asp Leu
    5750            5755                5760
Pro Leu Leu Ser Val Asp Val Pro Gly Ala Ala Arg Pro Ala Thr
    5765            5770                5775
Pro Asp Gly Asn Arg Ala Gly Arg Arg Ala Val Leu Val Pro Glu
    5780            5785                5790
Ala Gly Asn Arg Thr Thr Gly Gly Ser Gly Arg Ala Pro Ala Thr
    5795            5800                5805
Ala Gln Glu Glu Leu Leu Cys Gln Ala Phe Ala His Val Leu Asp
    5810            5815                5820
Val Arg Gln Val Gly Pro Asp Asp Asp Phe Phe Ala Leu Gly Gly
    5825            5830                5835
Asn Ser Leu Val Ala Thr Arg Leu Val Ser Arg Leu Arg Thr Val
    5840            5845                5850
Leu Gly Arg Glu Val Ser Ile Arg Ala Leu Phe Glu Ala Leu Thr
    5855            5860                5865
Pro Ala Arg Leu Ala Glu Arg Leu Ser Pro Val Ala Pro Asp Arg
    5870            5875                5880
Pro Ala Leu Thr Pro Arg Lys Arg Pro Glu Arg Val Pro Leu Ser
    5885            5890                5895
Phe Ala Gln Arg Arg Leu Trp Phe Ile Gly Gln Leu Glu Gly Ser
    5900            5905                5910
Ser Ala Ser Tyr Ser Asn Thr Thr Ala Leu Arg Leu Arg Gly Thr
    5915            5920                5925
Leu Asp Arg Glu Ala Met Asp Ala Ala Leu Arg Asp Val Ile Gly
    5930            5935                5940
Arg His Glu Val Leu Arg Thr Val Leu Pro Ala Glu Asp Gly Glu
    5945            5950                5955
Pro His Gln Arg Ile Leu Glu Val Glu Glu Thr Ala Phe Gly Leu
    5960            5965                5970
Thr Val Val Asp Thr Ala Ala Ala Glu Val Ala Ala Thr Ile Asp
    5975            5980                5985
Arg Leu Ala Gly His Asp Phe Asp Leu Ala Thr Glu Ile Pro Leu
    5990            5995                6000
Arg Ala Trp Leu Leu Ala Leu Ser Pro Asp Glu His Val Leu Val
    6005            6010                6015
Leu Ala Val His His Ile Ala Thr Asp Gly Trp Ser Thr Ala Ala
    6020            6025                6030
Leu Ala His Asp Met Ser Thr Ala Tyr Ala Ala Arg Leu Glu Gly
    6035            6040                6045
Arg Ala Pro Asp Trp Ala Pro Leu Pro Val Gln Tyr Ala Asp Tyr
    6050            6055                6060
Ala Leu Trp Gln His Glu Leu Leu Gly Asp Ala Asp Asp Pro Asp
    6065            6070                6075
Ser Val Arg Ser Arg Gln Leu Ala Phe Trp Arg Glu Thr Leu Ala
    6080            6085                6090
Gly Ala Pro Asp Glu Thr Ala Leu Pro Thr Asp Arg Pro Arg Pro
    6095            6100                6105
Pro Val Ala Thr His Arg Gly Asp Glu Ile Ala Val Glu Leu Pro
    6110            6115                6120
Ala Glu Leu His Arg Arg Ile Ala Glu Leu Ala Ala Thr Glu Gln
```

```
                    6125                6130                6135

Val Thr Val Phe Met Val Leu Gln Ala Gly Leu Ala  Ala Leu Leu
    6140                6145                6150

Ser Arg Leu Gly Ala Gly Thr Asp Ile Pro Ile Gly  Thr Ala Leu
    6155                6160                6165

Ala Gly Arg Thr Asp Asp Ala Met Asp Asp Leu Ile  Gly Phe Phe
    6170                6175                6180

Val Asn Met Leu Val Leu Arg Thr Asp Val Ser Gly  Asp Pro Thr
    6185                6190                6195

Phe Ala Glu Leu Leu Arg Arg Val Arg Glu Thr Asp  Leu Ala Ala
    6200                6205                6210

Tyr Ala His Gln Asp Leu Pro Phe Asp Gln Val Val  Glu Glu Leu
    6215                6220                6225

Val Pro Asp Arg Ser Leu Ala Arg Gln Pro Leu Phe  Gln Val Ala
    6230                6235                6240

Leu Asp Val Gln Asn Val Pro Glu Gly Ala Leu Arg  Leu Pro Gly
    6245                6250                6255

Leu Asp Val Ala Gly Glu Pro Phe Ala His Gly Thr  Ala Arg Tyr
    6260                6265                6270

Asp Leu Ala Leu Ser Leu Ser Glu Arg His Asp Asp  Gln Gly Ala
    6275                6280                6285

Pro Asp Gly Met Tyr Gly Thr Leu Thr Thr Ala Ala  Asp Leu Phe
    6290                6295                6300

Glu Arg Ala Thr Ala Glu Arg Ile Ala Gly Tyr Leu  Val Arg Val
    6305                6310                6315

Leu Thr Ala Ala Val Ala Glu Pro Glu Ala Pro Leu  Ala Ala Leu
    6320                6325                6330

Glu Leu Leu Thr Gly Asp Glu His Arg Arg Ile Val  Glu Asp Trp
    6335                6340                6345

Asn Asp Thr Ala Gly Pro Val Pro Asp Gly Leu Val  Pro Glu Leu
    6350                6355                6360

Phe Ala Ala Gln Ala Arg Leu Ser Pro Glu Thr Val  Ala Leu Ala
    6365                6370                6375

Gly Ala Gly Val Glu Leu Ser Tyr Arg Glu Val Glu  Glu Arg Ala
    6380                6385                6390

Asn Arg Leu Ala Arg Lys Leu Ile Ala Arg Asp Val  Gly Pro Glu
    6395                6400                6405

Ser Val Val Ala Leu Val Leu Glu Arg Ser Pro Glu  Leu Val Ile
    6410                6415                6420

Ala Val Leu Ala Val Leu Lys Ala Gly Gly Ala Tyr  Leu Pro Ile
    6425                6430                6435

Asp Pro Gly Gln Pro Ala Glu Arg Ile Arg Ser Val  Ile Glu Asp
    6440                6445                6450

Ala Ala Pro Val Leu Val Ile Asp Asp Pro Asp Phe  Leu Ala Glu
    6455                6460                6465

Thr Ala Asp His Thr Ala Ala Pro Val Thr Asp Ala  Asp Arg Val
    6470                6475                6480

Ser Pro Leu Leu Pro Ser His Pro Ala Tyr Val Ile  Tyr Thr Ser
    6485                6490                6495

Gly Ser Thr Gly Arg Pro Lys Gly Val Val Val Thr  His Glu Gly
    6500                6505                6510

Cys Ala Asn Leu Ser Ala Ser His Asp Trp Tyr Gly  Val Ala Ala
    6515                6520                6525
```

```
Gly Ser Arg Val Ala Gln Phe Ala Ser Val Gly Phe Asp Met Phe
6530                6535                6540

Cys Glu Glu Trp Leu Leu Ala Leu Leu Arg Gly Ala Thr Leu Val
6545                6550                6555

Thr Val Pro Ala Asp Arg Arg Leu Gly Pro Asp Leu Gly His Phe
6560                6565                6570

Leu Val Asp Gln Gly Val Thr His Ala Ala Leu Pro Pro Ala Val
6575                6580                6585

Ala Ala Thr Ile Pro Asp Gly Leu Leu Asp Pro Ser Phe Val Leu
6590                6595                6600

Asp Val Gly Gly Glu Ala Cys Pro Pro Glu Leu Val Glu Arg Trp
6605                6610                6615

Thr Ala Asp Gly Arg Thr Met Phe Asn Ala Tyr Gly Pro Thr Glu
6620                6625                6630

Ala Thr Val Asp Ala Thr Val Trp Arg Cys Ala Pro Gly Leu Asp
6635                6640                6645

Ala Gly Ala Ala Val Pro Ile Gly Arg Pro Val Leu Asn Thr Arg
6650                6655                6660

Ala Tyr Val Leu Asp Asp Ala Leu Arg Pro Val Pro Val Gly Val
6665                6670                6675

Val Gly Glu Leu His Leu Ala Gly Ser Gly Leu Ala Arg Gly Tyr
6680                6685                6690

Leu Gly Arg Thr Gly Leu Thr Ala Glu Arg Phe Val Ala Cys Pro
6695                6700                6705

Phe Gln Pro Gly Arg Arg Met Tyr Arg Thr Gly Asp Arg Val Lys
6710                6715                6720

Trp Asp Ala Asp Gly Gln Leu Val Phe Ala Gly Arg Ala Asp Asp
6725                6730                6735

Gln Val Lys Ile Arg Gly Phe Arg Ile Glu Pro Gly Glu Val Glu
6740                6745                6750

Ala Val Leu Ala Ser His Pro Asp Val Ala Arg Ala Ala Val Thr
6755                6760                6765

Val Arg Glu Asp Ser Pro Gly Asp Leu Arg Leu Val Gly Tyr Val
6770                6775                6780

Val Pro Ala Glu Asp Val Asp Ala Gly Glu Leu Pro Arg Thr Val
6785                6790                6795

Arg Gly Phe Ala Gly Glu Arg Leu Pro Ser Tyr Met Val Pro Ser
6800                6805                6810

Ala Val Val Pro Leu Asp Ala Leu Pro Leu Thr Pro Asn Gly Lys
6815                6820                6825

Leu Asp Arg Arg Ala Leu Pro Ala Pro Asp Tyr Gly Ala Ala Ala
6830                6835                6840

Thr Gly Arg Ala Pro Ala Thr Pro Gln Glu Glu Leu Val Cys Arg
6845                6850                6855

Ala Phe Ala Asp Ile Leu Gly Leu Pro Ala Val Gly Ala Asp Asp
6860                6865                6870

His Phe Phe Ala Leu Gly Gly His Ser Leu Leu Ala Thr Arg Leu
6875                6880                6885

Leu Ser Arg Val Arg Thr Ala Ala Gly Val Asp Val Pro Leu Arg
6890                6895                6900

Val Leu Phe Ala Asn Pro Thr Pro Ala Gly Val Ala Glu Trp Leu
6905                6910                6915

Thr Ala His Thr Gly Thr Pro Lys Lys Thr Arg Pro Thr Leu Arg
6920                6925                6930
```

```
Pro Met Arg Thr Gln Lys Lys Glu Phe Ser
    6935                6940

<210> SEQ ID NO 38
<211> LENGTH: 8986
<212> TYPE: PRT
<213> ORGANISM: Streptomyces fungicidicus

<400> SEQUENCE: 38

Met Ile Pro Leu Ser Phe Ala Gln Arg Arg Leu Trp Phe Leu Trp Lys
1               5                   10                  15

Leu Glu Gly Ala Ala Thr Thr Phe Asn Ile Pro Leu Thr Leu Arg Leu
            20                  25                  30

Arg Gly Thr Leu Asp Arg Glu Ala Met Asp Ala Ala Leu Arg Asp Val
        35                  40                  45

Ile Gly Arg His Glu Val Leu Arg Thr Val Leu Pro Ala Val Asp Gly
    50                  55                  60

Glu Pro Tyr Gln Arg Ile Leu Pro Leu Arg Glu Thr Gly Phe Glu Leu
65                  70                  75                  80

Gly Val Val Gln Val Pro Pro Glu Asp Ala Glu Ala Val Arg Arg
            85                  90                  95

Ala Ser Thr Tyr Ala Phe Asp Leu Ala Glu Glu Ile Pro Val Arg Ala
            100                 105                 110

Asp Leu Phe Glu Val Gly Pro Asp Glu His Val Leu Ala Leu Val Val
        115                 120                 125

His His Ile Ala Ala Asp Gly Trp Ser Ile Gly Pro Leu Met Arg Asp
    130                 135                 140

Leu Ser Thr Ala Tyr Thr Ala Arg Leu Ala Gly Arg Ala Pro Arg Trp
145                 150                 155                 160

Glu Pro Leu Pro Val Gln Tyr Ala Asp Tyr Ala Leu Trp Gln Arg Glu
                165                 170                 175

Leu Leu Gly Thr Gly Asp Asp Pro Glu Ser Thr Leu Ser Glu Gln Val
            180                 185                 190

Ala Tyr Trp Arg Arg Thr Leu Ala Gly Ala Pro Glu Glu Leu Glu Leu
        195                 200                 205

Pro Thr Asp Arg Pro Arg Pro Ala Gln Thr Thr Pro Arg Gly His Thr
    210                 215                 220

Ala Glu Leu Glu Leu Pro Ala Asp Thr His Arg Arg Leu Arg Glu Leu
225                 230                 235                 240

Ala Gly Asp His Gly Ala Ser Leu Leu Met Val Ala Gln Ser Ala Leu
                245                 250                 255

Ala Val Leu Leu Ser Arg Thr Gly Ala Gly Glu Asp Leu Pro Met Gly
            260                 265                 270

Thr Leu Val Ala Gly Arg Asn Asp Glu Gly Leu Asn Asp Leu Val Gly
        275                 280                 285

Phe Phe Val Asn Asn Leu Val Ile Arg Ala Asp Leu Ser Gly Asp Pro
    290                 295                 300

Thr Phe Thr Glu Val Leu Glu Arg Val Arg Glu Ala Ser Leu Asp Ala
305                 310                 315                 320

Tyr Glu Tyr Gln Asp Val Pro Phe Glu Lys Leu Val Glu Glu Leu Ser
                325                 330                 335

Pro Thr Arg Ser Leu Ala Arg His Pro Leu Phe Gln Val Met Ala Ala
            340                 345                 350

Val Glu Thr Gly Asp Pro Met Ser Thr Gly Pro Gly Gly Gly Pro Ala
        355                 360                 365
```

```
Leu Glu Leu Pro Gly Leu Arg Val Glu Met Leu Ser Asp Asp Gln Gln
    370                 375                 380

Ala Arg Asp Leu Asp Leu Asp Leu Val Leu Arg Glu Thr His Asp Gly
385                 390                 395                 400

Asp Gly Arg Pro Ala Gly Leu Arg Gly Ala Leu Ile Gly Ala Ala Asp
                405                 410                 415

Leu Phe Asp Ala Gly Thr Val Gln Arg Ile Ala Asp Met Leu Ala Arg
        420                 425                 430

Val Leu Glu Gln Val Ala Thr Thr Pro Thr Ala His Val Arg Ser Leu
        435                 440                 445

Asp Val Leu Asp Pro Glu Glu Gln Arg Arg Leu Leu Gly Val Gly Ser
        450                 455                 460

Gly Ala Val Val Glu Val Pro Gly Gly Ser Leu Pro Glu Leu Phe Ala
465                 470                 475                 480

Ala Gln Ala Arg Leu Ser Pro Asp Ala Val Ala Leu Val Gly Ser Gly
                485                 490                 495

Val Glu Leu Ser Tyr Arg Glu Val Asp Ala Arg Ala Asn Arg Leu Ala
            500                 505                 510

Arg Lys Leu Ile Gly Arg Gly Val Gly Pro Glu Ser Val Val Ala Leu
        515                 520                 525

Val Leu Glu Arg Ser Pro Glu Leu Val Ile Ala Val Leu Ala Val Leu
        530                 535                 540

Lys Ala Gly Gly Ala Tyr Val Ala Val Asp Pro Gly Gln Pro Ala Asp
545                 550                 555                 560

Arg Ile Arg Phe Val Ile Glu Asp Ala Ser Pro Val Leu Val Ile Asp
                565                 570                 575

Asp Leu Asn Phe Leu Ala Glu Thr Glu Asp Phe Asp Asp Phe Pro Val
            580                 585                 590

Thr Asp Ala Asp Arg Ile Ser Pro Leu Leu Pro Ser His Pro Ala Tyr
        595                 600                 605

Val Ile Tyr Thr Ser Gly Ser Thr Gly Arg Pro Lys Gly Val Leu Ile
        610                 615                 620

Ser His Ala Ala Cys Val Ser Tyr Val Ala Ser His Val Arg Tyr Gly
625                 630                 635                 640

Val Ser Glu Ser Ser Arg Val Ala Gln Phe Ala Ser Ala Gly Phe Asp
                645                 650                 655

Ala Phe Cys Glu Glu Trp Trp Leu Ala Leu Leu Gly Gly Gly Ala Leu
            660                 665                 670

Val Val Val Pro Ser Glu Arg Arg Leu Gly Glu Glu Leu Val Arg Phe
        675                 680                 685

Leu Leu Glu Glu Arg Val Thr His Ala Thr Leu Pro Pro Ala Val Ala
        690                 695                 700

Val Leu Met Arg Glu Glu Ala Leu Ala Pro Gly Phe Val Leu Asp Val
705                 710                 715                 720

Gly Gly Glu Val Cys Pro Pro Asp Leu Val Asp Arg Trp Val Ala Ala
                725                 730                 735

Gly Arg Thr Leu Phe Asn Ser Tyr Gly Pro Ser Glu Ala Thr Val Asn
            740                 745                 750

Val Thr Val Trp Gln Ala Val Asp Gly Ser Leu Gly Ala Gly Val Pro
        755                 760                 765

Ile Gly Arg Pro Val Gly Asn Thr Arg Leu Tyr Val Leu Asp Asp Gly
        770                 775                 780

Leu Arg Pro Val Pro Val Gly Val Leu Gly Glu Leu Tyr Val Ser Gly
```

```
                785                 790                 795                 800
Val Gln Leu Gly Arg Gly Tyr Leu Gly Arg Ala Gly Leu Thr Ala Glu
                805                 810                 815

Arg Phe Val Ala Cys Pro Tyr Ala Ser Gly Glu Arg Met Tyr Arg Thr
            820                 825                 830

Gly Asp Arg Val Lys Trp Asn Ala Glu Gly Glu Leu Val Phe Ala Gly
            835                 840                 845

Arg Ala Asp Asp Gln Val Lys Val Arg Gly Phe Arg Ile Glu Pro Gly
            850                 855                 860

Glu Val Glu Thr Val Leu Ala Ala His Pro Ala Val Ala His Ala Ala
865                 870                 875                 880

Val Val Val Arg Glu Asp Thr Pro Gly Asp Lys Arg Leu Thr Ala Tyr
                885                 890                 895

Val Val Pro Arg Thr Pro Gly Thr Gly Val Gly Ala Ala Ala Val Ala
            900                 905                 910

Arg Val Ala Glu Arg Leu Pro Ala Tyr Met Val Pro Ser Ala Val Val
            915                 920                 925

Glu Leu Asp Ala Leu Pro Leu Thr Ala Asn Gly Lys Leu Asp Arg Glu
            930                 935                 940

Ala Leu Pro Val Pro Glu Tyr Gln Gly Ala Gly Gly Arg Ala Pro
945                 950                 955                 960

Glu Asn Ala Gln Glu Glu Leu Val Cys Gln Ala Phe Ala Glu Val Phe
                965                 970                 975

Gly Val Asp Arg Ala Ala Val Gly Val Glu Asp Phe Phe Ala Leu
            980                 985                 990

Gly Gly His Ser Leu Leu Ala Val  Ser Leu Val Glu Trp  Leu Arg Arg
            995                 1000                1005

Arg Gly Val Ser Val Ser Val  Arg Ala Leu Phe Val  Ser Ala Thr
    1010                1015                1020

Pro Ala  Ala Leu Ala Ala Ala  Ala Gly Pro Glu Pro  Val Thr Val
    1025                1030                1035

Pro Pro Asn Leu Ile Pro Asp  Gly Ala Thr Glu Ile  Thr Pro Asp
    1040                1045                1050

Met Leu Thr Leu Val Glu Leu  Thr Glu Glu Ile  Ala Arg Val
    1055                1060                1065

Ala Ala Ala Val Pro Gly Gly  Ala Ala Asn Ile Ala  Asp Ile Tyr
    1070                1075                1080

Pro Leu Ala Pro Leu Gln Glu  Gly Leu Leu Phe His  His Leu Met
    1085                1090                1095

Thr Asp Gly Asp Gly Thr Asp  Val Tyr Ile Thr Pro  Ala Val Val
    1100                1105                1110

Glu Phe Asp Ser Arg Asp Arg  Leu Asp Asp Phe Phe  Ala Ala Leu
    1115                1120                1125

Arg Trp Met Val Asp Arg His  Asp Ile Tyr Arg Thr  Ala Val Val
    1130                1135                1140

Ser Asp Gly Leu Arg Glu Pro  Val Gln Val Val  Arg His Ala
    1145                1150                1155

Glu Leu Thr Val Glu Glu Thr  Val Leu Asp Ala Asp  Gly Pro Asp
    1160                1165                1170

Pro Val Glu Gln Met Leu Ala  Leu Gly Gly Arg Arg  Met Glu Leu
    1175                1180                1185

Asn Arg Val Pro Leu Met Ser  Ala His Ile Ala Ala  Asp Pro Gly
    1190                1195                1200
```

-continued

Gly Asp Arg Trp Leu Ala Leu Leu Arg Ile His His Leu Leu Gln
1205                1210                1215

Asp His Thr Thr Gln Asp Val Leu Phe Asp Leu Trp Ala Phe
1220                1225                1230

Leu Ala Gly Arg Ala Asp Ala Leu Pro Pro Leu Pro Phe Arg
1235                1240                1245

Asp Phe Val Ala Gln Ser Arg Leu Gly Thr Pro Arg Glu Glu His
1250                1255                1260

Glu Arg Tyr Phe Ala Glu Leu Leu Gly Asp Val Thr Glu Thr Thr
1265                1270                1275

Ala Pro Tyr Gly Leu Thr Asp Val His Gly Asp Gly Ser Gly Ser
1280                1285                1290

Glu Gln Ala Arg Leu Arg Leu Asp Asp Ala Leu Ala Ala Arg Val
1295                1300                1305

Arg Arg Ala Ala Arg Thr Leu Gly Ala Ser Pro Ala Thr Leu Phe
1310                1315                1320

His Leu Ala Trp Ala Arg Val Leu Gly Ala Val Ser Gly Arg Asp
1325                1330                1335

Asp Val Val Phe Gly Thr Val Leu Phe Gly Arg Met Asn Ala Gly
1340                1345                1350

Glu Gly Ala Asp Arg Val Pro Gly Leu Phe Ile Asn Thr Leu Pro
1355                1360                1365

Val Arg Val Arg Leu Asp Arg Gln Ser Val Ala Glu Ala Leu Thr
1370                1375                1380

Gly Leu Arg Arg Asp Leu Ala Asp Leu Leu Val His Glu His Ala
1385                1390                1395

Pro Leu Thr Leu Ala Gln Ala Ala Cys Gly Leu Pro Gly Gly Ser
1400                1405                1410

Pro Leu Phe Thr Ser Ile Leu Asn Tyr Arg His Asn Thr Asn Gly
1415                1420                1425

Pro His Glu Ser Arg Ala Glu Leu Asp Gly Met Gln Val Leu Ser
1430                1435                1440

Ala Arg Asp Leu Thr Asn Tyr Pro Leu Ala Val Ala Val Asp Ala
1445                1450                1455

Asp Thr Ala Gly Phe Thr Val Thr Val Asp Ala Val Thr Pro Ala
1460                1465                1470

Asp Pro Ala Arg Val Gly Ala Leu Leu Thr Thr Cys Leu Glu Ser
1475                1480                1485

Leu Thr Ser Ala Ile Gln Asp Glu Pro Ala Thr Pro Leu Arg Met
1490                1495                1500

Val Glu Val Leu Asp Gly Ala Glu Leu Thr Ala Leu Leu Asp Gly
1505                1510                1515

Trp Asn Asp Thr Ala Val Pro Ala Pro Asp Ala Ser Leu Pro Glu
1520                1525                1530

Ala Phe Ala Ala Thr Val Ala Ala Ala Pro Asp Ala Val Ala Leu
1535                1540                1545

Val Cys Gly Asp Asp Arg Ile Thr Tyr Ala Glu Leu Asp Ala Arg
1550                1555                1560

Ala Asp Arg Leu Ala Arg Thr Leu Val Ala Ser Gly Val Arg Pro
1565                1570                1575

Glu Ser Ala Val Ala Val Ala Met Glu Arg Ser Ala Asp Leu Val
1580                1585                1590

Val Ala Leu Leu Ala Val Ser Lys Ala Gly Gly Val Phe Val Pro
1595                1600                1605

-continued

Leu Asp Ala Gly Trp Pro Ala Ala Arg Thr Arg Ala Val Ile Glu
1610            1615            1620

Asp Ala Asp Ala Cys Leu Val Leu Val Asp Gly Thr Thr Ala Gly
1625            1630            1635

Leu Glu Ala Gly Val Ala Leu Leu Arg Val Asp Ala Thr Thr Asp
1640            1645            1650

Thr Val Val Asp Leu Pro Gly Pro Val Pro Pro Asp Gly Ala Ala
1655            1660            1665

Tyr Val Met Tyr Thr Ser Gly Ser Thr Gly Val Pro Lys Gly Val
1670            1675            1680

Val Thr Thr His Lys Asp Leu Val Arg Leu Ala Thr Asp Arg Cys
1685            1690            1695

Trp Gly Thr Thr Pro Arg Val Leu Phe His Ala Pro His Ala Phe
1700            1705            1710

Asp Ala Ser Cys Tyr Glu Leu Trp Val Pro Leu Leu Ser Gly Gly
1715            1720            1725

Thr Val Val Ile Ala Pro Arg Glu Arg Val Asp Ala Ala Leu Met
1730            1735            1740

Arg Arg Leu Thr Thr Ala His Arg Leu Thr His Val His Val Thr
1745            1750            1755

Ala Gly Leu Leu Arg Val Leu Ala Asp Asp Pro Gly Cys Phe
1760            1765            1770

Asp Gly Val Arg Glu Val Leu Thr Gly Gly Asp Val Val Pro Ala
1775            1780            1785

Asp Ala Val Arg Arg Ile Leu Asp Ala Asn Pro Arg Ala Val Val
1790            1795            1800

Arg His Met Tyr Gly Pro Thr Glu Val Thr Leu Cys Ala Thr Gln
1805            1810            1815

His Glu Val Ala Asp Ala Ala Glu Val Asp Gly Val Leu Pro Ile
1820            1825            1830

Gly Arg Pro Leu Asp Asn Thr Arg Val Tyr Val Leu Asp Asp Gly
1835            1840            1845

Leu Asn Val Val Pro Val Gly Val Thr Gly Glu Leu Tyr Val Ala
1850            1855            1860

Gly Ser Gly Leu Ala Arg Gly Tyr Ala Asn Arg Ala Glu Ser Thr
1865            1870            1875

Ala Glu Arg Phe Val Ala Cys Pro Phe Gly Pro Gly Glu Arg Met
1880            1885            1890

Tyr Arg Thr Gly Asp Leu Ala Arg Trp Thr Pro Asp Gly Arg Leu
1895            1900            1905

Val Phe Ala Gly Arg Ala Asp Asp Gln Val Lys Ile Arg Gly Phe
1910            1915            1920

Arg Val Glu Pro Gly Glu Val Glu Ala Val Leu Ala Ala His Pro
1925            1930            1935

Ala Val Ala Gln Ala Thr Val Ala Val Arg Glu Asp Thr Pro Gly
1940            1945            1950

Asp Lys Arg Leu Ile Gly Tyr Leu Val Pro Val Glu Gln Gly Ser
1955            1960            1965

Ala Leu Thr Ala Ala Val Arg Ala Tyr Ala Ala Glu Arg Leu Pro
1970            1975            1980

Glu Tyr Leu Val Pro Ala Ala Phe Val Glu Leu Asp Ala Phe Pro
1985            1990            1995

Leu Thr Val Asn Gly Lys Val Asp Arg Ala Ala Leu Pro Ala Pro

```
                    2000                2005                2010

Arg Tyr Leu Thr Gly Ala Gly Arg Leu Pro Ala Asp Ala Arg Glu
    2015                2020                2025

Glu Leu Leu Cys Gln Val Phe Ala Glu Val Leu Gly Leu Pro Ala
    2030                2035                2040

Val Gly Val Asp Asp Phe Phe Thr Leu Gly Gly His Ser Leu
    2045                2050                2055

Leu Val Thr Arg Leu Val Ser Arg Val Arg Ala Thr Leu Asp Val
    2060                2065                2070

Glu Leu Gln Ile Arg Thr Val Phe Glu Ala Pro Thr Pro Gly Arg
    2075                2080                2085

Leu Ala Ala Arg Leu Thr Glu Thr Ala Val Pro Gly Arg Lys Ala
    2090                2095                2100

Leu Val Ala Arg Thr Arg Pro Gln Arg Thr Pro Leu Ser Phe Ala
    2105                2110                2115

Gln Gln Arg Leu Trp Phe Leu Ala Gln Leu Glu Gly Pro Ser Pro
    2120                2125                2130

Thr Tyr Asn Leu Pro Leu Ala Leu Arg Leu Thr Gly Thr Leu Asp
    2135                2140                2145

Arg Glu Ala Phe Leu Ala Ala Leu Gly Asp Thr Val Ala Arg His
    2150                2155                2160

Glu Val Leu Arg Thr Val Phe Glu Val Ala Asp Asp Gly Thr Pro
    2165                2170                2175

Tyr Gln Arg Val Leu Pro Ala Asp Ala Thr Gly Phe Ala Pro Glu
    2180                2185                2190

Val Val Glu Val Pro Ser Asp Gly Leu Ala Asp Ala Leu Ala Arg
    2195                2200                2205

Ala Ala Ala Tyr Ala Phe Asp Leu Ala Val Glu Thr Pro Leu Arg
    2210                2215                2220

Ala Thr Leu Phe Ala Val Ala Pro Asp Glu His Val Leu Val Leu
    2225                2230                2235

Val Val His His Ile Ala Gly Asp Ala Trp Ser Met Glu Pro Leu
    2240                2245                2250

Ala Arg Asp Val Ser Thr Ala Tyr Ala Ala Arg Leu Val Gly Asp
    2255                2260                2265

Ala Pro Arg Trp Glu Pro Leu Pro Val Gln Tyr Ala Asp Tyr Thr
    2270                2275                2280

Leu Trp Gln Arg Glu Leu Leu Gly Asp Glu Asp Pro Asp Ser
    2285                2290                2295

Leu Leu Ser Arg Gln Val Ser His Trp Arg Asp Ala Leu Ser Gly
    2300                2305                2310

Ala Pro Glu Glu Leu Asp Leu Pro Ala Asp Arg Pro Arg Pro Ala
    2315                2320                2325

Glu Phe Ser His Arg Gly Arg Thr Ala Gly Leu Glu Phe Pro Ala
    2330                2335                2340

Glu Leu His Arg Arg Leu Arg Glu Val Ala Arg Ala Glu Gly Val
    2345                2350                2355

Thr Val Phe Met Val Leu Gln Ala Ala Leu Ala Val Thr Leu Ser
    2360                2365                2370

Arg Leu Gly Gly Gly Thr Asp Ile Pro Ile Gly Thr Ala Val Ala
    2375                2380                2385

Gly Arg Thr Asp Gln Ala Leu Asp Glu Leu Ala Gly Phe Phe Val
    2390                2395                2400
```

```
Asn Thr Leu Val Leu Arg Thr Asp Leu Ser Gly Asn Pro Thr Phe
2405                    2410                2415

Ala Glu Thr Leu His Arg Val Arg Asp Asp Leu Leu Thr Ala Leu
2420                    2425                2430

Ala His Gln Asp Val Pro Phe Glu Arg Leu Val Glu Glu Leu Ala
2435                    2440                2445

Pro Val Arg Ser Leu Thr Arg His Pro Leu Phe Gln Val Met Leu
2450                    2455                2460

Thr Leu Gln Asn Thr Ala Arg Ala Gly Gly Gly Ala Ser Ala Ala
2465                    2470                2475

Leu Pro Gly Leu Glu Thr Ala Val Leu Pro Thr Gly Ala Thr Ala
2480                    2485                2490

Ala Lys Phe Asp Leu Asp Leu Ala Leu Ala Glu Thr Phe Asp Pro
2495                    2500                2505

Glu Gly Ala Pro Thr Gly Met His Gly Thr Leu Val Ala Ala Ala
2510                    2515                2520

Asp Leu Phe Asp Gln Glu Thr Ala Asp Arg Leu Val Ala Cys Phe
2525                    2530                2535

Thr Arg Ala Leu Glu Ala Leu Thr His Arg Thr Asp Leu Arg Leu
2540                    2545                2550

Gly Glu Val Asp Leu Leu Asp Glu Ala Glu Leu Ser Thr Leu Val
2555                    2560                2565

Glu Asp Trp Asn Gly Pro Ala Leu Pro Thr Ser Glu Ala Thr Leu
2570                    2575                2580

Pro Glu Leu Phe Ala Val Gln Ala Ala Arg Thr Pro Asp Ala Thr
2585                    2590                2595

Ala Val Thr Ala Gly Gly Val Glu Leu Ser Tyr Ala Glu Leu Asp
2600                    2605                2610

Ala Arg Ala Asp Arg Leu Ala Arg Gly Leu Val Gly Arg Gly Val
2615                    2620                2625

Gly Pro Glu Ser Val Val Gly Val Leu Leu Gly Arg Ser Ala Asp
2630                    2635                2640

Val Val Val Ala Val Leu Ala Val Ala Lys Ala Gly Gly Ala Tyr
2645                    2650                2655

Leu Pro Val Asp Pro Asp Tyr Pro Ala Asp Arg Val Ala Phe Val
2660                    2665                2670

Leu Ser Asp Ala Gly Ala Glu Trp Val Val Thr Ser Ala Glu Phe
2675                    2680                2685

Ala Pro Val Leu Pro Ala Gly Val Ala Ala Val Pro Val Asp Gly
2690                    2695                2700

Ala Gly Ser Gly Pro Val Phe Asp Ser Val Pro Leu Pro Thr Val
2705                    2710                2715

Arg Pro Asp His Pro Ala Tyr Val Ile Tyr Thr Ser Gly Ser Thr
2720                    2725                2730

Gly Arg Pro Lys Gly Val Val Pro His Arg Ser Val Val Ala
2735                    2740                2745

Leu Phe Ala Ala Ala Arg Glu Met Phe Ala Phe Gly Ala Asp Asp
2750                    2755                2760

Val Trp Ser Gly Phe His Ser Phe Ala Phe Asp Val Ser Val Trp
2765                    2770                2775

Glu Met Trp Gly Ala Leu Leu His Gly Gly Arg Leu Val Val Val
2780                    2785                2790

Pro Phe Asp Val Ser Arg Ser Pro Arg Glu Phe Val Glu Leu Leu
2795                    2800                2805
```

```
Glu Arg Glu Arg Val Thr Val Leu Ser Gln Thr Pro Ser Ala Phe
    2810            2815            2820

Tyr Gln Leu Met Gly Ala Gly Ala Leu Pro Asp Leu His Thr
    2825            2830            2835

Val Val Phe Ala Gly Glu Ala Leu Glu Pro Ala Arg Leu Asp Gly
    2840            2845            2850

Trp Trp Glu Arg His Gly Gly Thr Gly Pro Arg Leu Val Asn Met
    2855            2860            2865

Tyr Gly Ile Thr Glu Thr Thr Val His Val Thr His His Asp Leu
    2870            2875            2880

Arg Pro Asp Thr Ala Ala Asp Gly Ser Val Ile Gly Arg Gly Leu
    2885            2890            2895

Pro Gly Leu Ser Val Phe Leu Leu Asp Glu Trp Leu Arg Pro Val
    2900            2905            2910

Pro Val Gly Val Thr Gly Glu Leu Tyr Val Ala Gly Ala Gln Ala
    2915            2920            2925

Ala Arg Gly Tyr Leu Gly Arg Ala Gly Leu Thr Gly Glu Arg Phe
    2930            2935            2940

Val Ala Cys Pro Phe Gly Glu Ala Gly Gly Arg Met Tyr Arg Ser
    2945            2950            2955

Gly Asp Arg Ala Arg Trp Ser Arg Asp Gly Arg Leu Val Phe Ala
    2960            2965            2970

Gly Arg Ala Asp Glu Gln Val Lys Ile Arg Gly Phe Arg Ile Glu
    2975            2980            2985

Pro Gly Glu Val Glu Ala Val Leu Ala Gly His Pro Asp Val Ala
    2990            2995            3000

Gln Ala Ala Val Leu Val Gly Asp Asp Thr Leu Gly Gly Arg Arg
    3005            3010            3015

Leu Ile Gly Tyr Val Thr Pro Gly Gly Thr Thr Glu Asp Ala Asp
    3020            3025            3030

Gly Leu Ala Asp Ala Val Arg Val Tyr Ala Gly Glu Arg Leu Pro
    3035            3040            3045

Ser Tyr Met Val Pro Ser Ala Phe Val Val Leu Asp Gly Leu Pro
    3050            3055            3060

Leu Thr Val Asn Gly Lys Leu Asp Arg Arg Ala Leu Pro Ala Pro
    3065            3070            3075

Ala His Thr Ala Gly Gly Arg Ala Ala Thr Val Glu Glu
    3080            3085            3090

Glu Leu Leu Cys Gln Gly Phe Ala Glu Val Leu Gly Leu Pro Ala
    3095            3100            3105

Val Gly Val Asp Asp Asp Phe Phe Ala Leu Gly Gly His Ser Leu
    3110            3115            3120

Leu Ala Val Ser Leu Val Glu Trp Leu Arg Gln Arg Gly Val Ser
    3125            3130            3135

Val Ser Val Arg Ala Leu Phe Val Thr Pro Thr Pro Ala Gly Leu
    3140            3145            3150

Ala Ala Val Ala Ala Ala Pro Ala Val Val Pro Pro Pro Gly
    3155            3160            3165

Met Ile Pro Glu Gly Ala Thr Glu Ile Thr Pro Glu Met Leu Pro
    3170            3175            3180

Leu Val Asp Leu Thr Glu Asp Glu Ile Ala Arg Val Thr Glu Thr
    3185            3190            3195

Val Pro Gly Gly Ala Ala Asn Val Gln Asp Val Tyr Pro Leu Ala
```

```
                      3200               3205                  3210

Pro Leu Gln Glu Gly Ile Phe Phe His His Leu Val Ala Asp Arg
3215                3220                  3225

Asp Gly Thr Asp Val Tyr Val Thr Pro Thr Val Leu Asp Phe Asp
3230                3235                  3240

Thr Arg Glu Arg Leu Asp Asp Phe Leu Ala Gly Leu Gln Trp Val
3245                3250                  3255

Met Asp Arg His Asp Ile Tyr Arg Thr Ala Ile Val Trp Glu Gly
3260                3265                  3270

Leu Arg Glu Pro Val Gln Val Val Trp Arg Arg Ala Gly Leu Pro
3275                3280                  3285

Val Gln Glu Arg Glu Leu Asp Pro Ala Gly Pro Glu Ala Val Glu
3290                3295                  3300

Gln Leu Arg Thr Ala Ala Gly Gly Arg Ile Glu Leu Asp Gly Ala
3305                3310                  3315

Pro Leu Leu Arg Val Asp Val Ala Ala Ala Pro Glu Gly Gly Trp
3320                3325                  3330

Leu Met Leu Leu Arg Ile His His Leu Val Gln Asp His Thr Ser
3335                3340                  3345

Val Glu Val Leu Leu Asp Asp Leu Arg Ala Phe Leu Asp Gly Asp
3350                3355                  3360

Ala Asp Arg Leu Pro Ala Pro Val Pro Phe Arg Asp Phe Val Ala
3365                3370                  3375

Gln Ala Arg Leu Gly Thr Pro Arg Glu Glu His Glu Arg Tyr Phe
3380                3385                  3390

Ala Glu Leu Leu Gly Asp Val Thr Glu Pro Thr Ala Pro Tyr Gly
3395                3400                  3405

Leu Thr Asp Val Arg Gly Asp Gly Glu Gly Ser Arg His Ala Arg
3410                3415                  3420

Leu Arg Val Asp Asp Ala Leu Thr Gly Arg Met Arg Glu Val Ala
3425                3430                  3435

Arg Ser Leu Gly Val Ser Pro Ala Ser Leu Phe His Leu Ala Trp
3440                3445                  3450

Ala Arg Val Leu Gly Ala Val Ser Gly Arg Asp Asp Val Val Phe
3455                3460                  3465

Gly Thr Leu Leu Phe Gly Arg Met Asn Ala Gly Ala Gly Ala Asp
3470                3475                  3480

Arg Ala Pro Gly Leu Phe Leu Asn Thr Leu Pro Val Arg Val Arg
3485                3490                  3495

Met Ala Gly Lys Ser Val Thr Glu Ala Leu Thr Glu Leu Arg His
3500                3505                  3510

Gln Leu Ala Asp Leu Met Val His Glu His Ala Pro Leu Thr Leu
3515                3520                  3525

Ala Gln Ser Ala Thr Gly Leu Thr Gly Gly Gly Pro Leu Phe Thr
3530                3535                  3540

Ala Leu Phe Asn Tyr Arg His Asn Arg Glu Ala Pro Glu Pro Gly
3545                3550                  3555

Glu Gly Ile Glu Gly Val Arg Thr Val Tyr Thr Arg Glu His Thr
3560                3565                  3570

Asn Tyr Pro Leu His Val Ala Val Asp Asn Asp Gly Ser Ser Phe
3575                3580                  3585

Asp Ile Thr Val Asn Ala Val Ala Pro Ala Asp Pro Asp Glu Val
3590                3595                  3600
```

-continued

| | | | | | | | | | | | |
|---|---|---|---|---|---|---|---|---|---|---|---|
|Cys|Ala|Leu|Leu|His|Thr|Gly|Leu|Ala|Asn|Leu|Val|Thr|Ala|Leu|
| |3605| | | |3610| | | |3615| | | | | |

Cys Ala Leu Leu His Thr Gly Leu Ala Asn Leu Val Thr Ala Leu
3605            3610           3615

Ala Glu Ala Pro Gly Thr Pro Leu Ala Gly Leu Gly Val Leu Asp
3620            3625           3630

Glu Arg Thr Arg Thr Arg Met Arg Thr Glu Trp Asn Asp Thr Ala
3635            3640           3645

Val Asp Val Pro Asp Val Thr Val Pro Ala Ala Phe Ser Ala Gln
3650            3655           3660

Ala Ala Arg Val Pro Gln Ala Thr Ala Leu Val Cys Gly Asp Val
3665            3670           3675

Glu Ile Gly Tyr Ala Glu Leu Asp Ala Arg Ala Asp Arg Leu Ala
3680            3685           3690

Arg Val Leu Val Glu Ala Gly Val Ala Ala Glu Ser Thr Val Ala
3695            3700           3705

Val Val Met Glu Arg Ser Val Asp Leu Val Val Thr Leu Leu Ala
3710            3715           3720

Val Leu Lys Ala Gly Ala Val Tyr Val Pro Leu Asp Ala Gly Trp
3725            3730           3735

Pro Val Ala Arg Met Arg Thr Val Val Glu Asp Ser Gly Ala Arg
3740            3745           3750

Trp Val Val His Glu Pro Thr Ser Gly His Glu Phe Leu Arg
3755            3760           3765

Gly Leu Gly Ile Pro Thr Leu Ser Ala Asp Thr Asp Ala Asp Ala
3770            3775           3780

Glu Glu Cys Val Leu Pro Gln Arg Trp Ser Pro Arg Gln Ala Ala
3785            3790           3795

Tyr Val Met Tyr Thr Ser Gly Ser Thr Gly Val Pro Lys Gly Val
3800            3805           3810

Val Ala Thr His Gly Asp Val Val Arg Leu Ala Thr Asp Arg Cys
3815            3820           3825

Trp Gly Ala Thr Pro Arg Val Leu Phe His Ala Pro His Ala Phe
3830            3835           3840

Asp Ala Ser Thr Tyr Glu Leu Trp Ala Pro Leu Leu Ser Gly Gly
3845            3850           3855

Thr Val Val Ile Ala Pro Asn Glu Arg Val Asp Pro Val Val Leu
3860            3865           3870

Arg Arg Leu Val Thr Gly His Gly Leu Thr His Val His Ala Thr
3875            3880           3885

Ala Gly Leu Leu Arg Val Leu Ala Asp Gln Asp Pro Gly Cys Phe
3890            3895           3900

Thr Gly Val Arg Glu Val Leu Thr Gly Gly Asp Val Val Pro Ala
3905            3910           3915

Glu Ser Val Arg Arg Val Leu Asp Ala Asn Pro Gly Val Val Val
3920            3925           3930

Arg Gln Leu Tyr Gly Pro Thr Glu Val Thr Leu Cys Ala Thr Gln
3935            3940           3945

Tyr Glu Val Ala Asp Ala Ala Glu Val Asp Gly Val Leu Pro Ile
3950            3955           3960

Gly Arg Pro Leu Asp Asn Thr Arg Val Tyr Val Leu Asp Gly Ala
3965            3970           3975

Leu Asn Pro Val Pro Val Gly Val Ala Gly Glu Leu Tyr Val Ala
3980            3985           3990

Gly Ala Gly Val Ala Arg Gly Tyr Leu Gly Arg Pro Val Leu Thr
3995            4000           4005

```
Gly Glu Arg Phe Val Ala Cys Pro Phe Glu Thr Ser Gly Glu Arg
    4010                4015                4020

Arg Tyr Arg Thr Gly Asp Leu Val Arg Trp Asp Thr Glu Gly Arg
    4025                4030                4035

Leu Val Phe Leu Gly Arg Ala Asp Glu Gln Val Lys Ile Arg Gly
    4040                4045                4050

Phe Arg Val Glu Pro Gly Glu Val Glu Thr Val Val Thr Ala His
    4055                4060                4065

Pro Ala Val Ala Gln Ala Thr Val Leu Val Arg Glu Asp Val Pro
    4070                4075                4080

Gly Asp Lys Arg Leu Val Ala Tyr Leu Val Pro Ala Asp Pro Gly
    4085                4090                4095

Ala Ala Val Gly Leu Thr Val Arg Ala Tyr Ala Ala Glu Arg Leu
    4100                4105                4110

Pro Glu Tyr Met Leu Pro Ser Ala Met Val Glu Leu Asp Ala Leu
    4115                4120                4125

Pro Leu Thr Pro Asn Gly Lys Val Asp Arg Ala Ala Leu Pro Ala
    4130                4135                4140

Pro Asp Tyr Ala Ala Gly Ala Gly Arg Val Pro Ala Asp Ala Arg
    4145                4150                4155

Glu Glu Leu Leu Cys Gln Ala Phe Ala Ala Val Leu Gly Leu Pro
    4160                4165                4170

Ala Phe Gly Val Asp Asp Asp Phe Phe Ala Lys Gly Gly His Ser
    4175                4180                4185

Leu Leu Ala Thr Val Leu Val Gly Arg Ile Arg Ala Thr Phe His
    4190                4195                4200

Val Glu Met Thr Ile Val Ala Leu Phe Asp Ala Pro Thr Pro Ala
    4205                4210                4215

Ser Leu Ala Arg Trp Leu Val Gln Ala Arg Pro Gly Arg Ile Glu
    4220                4225                4230

Leu Ala Ala Arg Glu Arg Pro Glu Arg Val Pro Leu Ser Phe Ala
    4235                4240                4245

Gln Arg Arg Leu Trp Phe Leu Gly Gln Leu Glu Gly Pro Gly Ala
    4250                4255                4260

Thr Tyr Asn Ile Pro Leu Leu Thr Arg Ile Thr Gly Pro Leu Asp
    4265                4270                4275

Arg Thr Ala Val Asp Ala Ala Leu Arg Asp Val Leu Asp Arg His
    4280                4285                4290

Glu Val Leu Arg Thr Val Tyr Ala Val His Gly Gly Glu Pro His
    4295                4300                4305

Gln Arg Ser Arg Pro Val Asp Thr Ser Gly Phe Ala Leu Pro Val
    4310                4315                4320

Val Asp Val Ala Pro Gly Gly Leu Thr Asp Ala Leu Glu Arg Ala
    4325                4330                4335

Ala Gly His Glu Phe Asp Leu Ser Thr Asp Ile Pro Val Arg Ala
    4340                4345                4350

Trp Leu Phe Ala Thr Ala Pro Glu Glu His Val Leu Ala Leu Val
    4355                4360                4365

Val His His Ile Ala Ala Asp Ala Trp Ser Met Ala Pro Leu Thr
    4370                4375                4380

Arg Asp Phe Ala Ala Ala Tyr Ala Ala Arg Arg Ala Gly Glu Glu
    4385                4390                4395

Pro Asp Trp Thr Pro Leu Pro Val Gln Tyr Ala Asp Tyr Ala Leu
```

-continued

```
              4400                4405                4410

Trp Gln Arg Asp Leu Leu Gly Asp Glu Gly Asp Pro Asp Ser Leu
    4415                4420                4425

Ile Ser Gln Gln Val Ala Tyr Trp Arg Asp Thr Leu Asp Gly Ala
    4430                4435                4440

Pro Glu Glu Leu Arg Leu Pro Ala Asp Arg Pro Arg Pro Ala Thr
    4445                4450                4455

Val Ser Tyr Arg Gly His Leu Ala Pro Val Glu Ile Pro Ala Asp
    4460                4465                4470

Val His Gly Arg Leu Gln Gln Val Ala Arg Glu His Gly Val Thr
    4475                4480                4485

Leu Phe Met Thr Val Gln Thr Ala Leu Ala Val Thr Leu Ser Arg
    4490                4495                4500

Leu Gly Ala Gly Thr Asp Ile Pro Ile Gly Thr Thr Val Ala Gly
    4505                4510                4515

Arg Thr Asp Gln Ala Leu Asp Asp Leu Ile Gly Phe Phe Val Asn
    4520                4525                4530

Thr Leu Val Leu Arg Thr Arg Leu Gly Gly Asp Pro Thr Val Thr
    4535                4540                4545

Asp Val Leu Arg Arg Val Arg Glu Thr Ser Leu Ala Ala Phe Thr
    4550                4555                4560

His Gln Asp Val Pro Phe Glu Lys Leu Val Glu Glu Leu Ala Pro
    4565                4570                4575

Ser Arg Ser Leu Ala Arg His Pro Leu Phe Gln Val Met Leu Thr
    4580                4585                4590

Leu Gln Asn Ala Gly Thr Pro Gly Gly Gly Pro Ser Ala Val Leu
    4595                4600                4605

Pro Gly Leu Arg Thr Glu Ser Leu Pro Thr Asp Asp Val Ala Ala
    4610                4615                4620

Lys Phe Asp Leu Asp Ile Thr Met Gly Glu Thr Phe Asp Ala Val
    4625                4630                4635

Gly Ala Pro Ala Gly Ile Gln Gly Met Leu Val Ala Ala Ala Asp
    4640                4645                4650

Leu Phe Asp Pro Ala Thr Ala Glu Arg Ile Ala Asp Ser Leu Val
    4655                4660                4665

Arg Val Leu Lys Leu Ile Ala Glu Asp Thr Gly Thr Arg Leu Ser
    4670                4675                4680

Ala Val Asp Leu Leu Asp Ala Gly Glu Arg Arg Arg Val Val Glu
    4685                4690                4695

Glu Trp Asn Asp Thr Asp Ala Pro Pro Pro Ala Leu Ser Val Pro
    4700                4705                4710

Ala Ala Phe Glu Ala Gln Ala Ala Leu Thr Pro Asp Ala Val Ala
    4715                4720                4725

Val Leu Gly Gly Asp Thr Arg Leu Thr Tyr Ala Glu Leu Asn Ala
    4730                4735                4740

Arg Ala Asn Arg Leu Ala Arg Leu Leu Val Arg His Gly Val Gly
    4745                4750                4755

Pro Glu Ser Ser Val Ala Val Cys Leu Arg Arg Ser Ala Glu Leu
    4760                4765                4770

Pro Val Ala Leu Leu Ala Val Leu Lys Ala Gly Gly Ala Tyr Leu
    4775                4780                4785

Pro Val Asp Pro Gly His Pro Ala Glu Arg Val Gly His Val Leu
    4790                4795                4800
```

```
Asp Asp Ala Arg Pro Ala Leu Leu Leu Thr Asp Arg Ala Thr Ala
4805                4810                4815

Ala Asp Leu Pro Gly Pro Glu His Leu Val Val Asp Asp Pro Arg
4820                4825                4830

Thr Ala Ala Glu Leu Gln Ala Leu Asp Thr His Asp Leu Thr Ala
4835                4840                4845

Arg Glu Arg Leu Gly Ala Leu Leu Pro Gly His Pro Ala Tyr Val
4850                4855                4860

Ile His Thr Ser Gly Ser Thr Gly Arg Pro Lys Gly Val Val Val
4865                4870                4875

Pro His Gly Ala Met Ala Asn Phe Val Ala Met Arg Glu Arg
4880                4885                4890

Phe Pro Met Ser Ser Ala Asp Arg Leu Leu Ala Val Thr Thr Val
4895                4900                4905

Ser Phe Asp Ile His Val Leu Glu Leu Tyr Val Pro Leu Leu Ala
4910                4915                4920

Gly Ala Gly Val Val Val Ala Glu Asp Ala Asp Val Arg Asp Pro
4925                4930                4935

Ala Ala Val Ala Ala Leu Ile Glu Arg Phe Gly Val Thr Val Met
4940                4945                4950

Gln Ala Thr Pro Ala Leu Trp Gln Ala Leu Leu Thr Glu His Ala
4955                4960                4965

Gly Ser Ala Ser Gly Leu Arg Leu Leu Val Gly Gly Glu Ala Leu
4970                4975                4980

Pro Ala Ala Leu Ala Ala Arg Met Ala Ala Val Gly Asp Thr Val
4985                4990                4995

Thr Asn Leu Tyr Gly Pro Thr Glu Val Thr Val Trp Ala Thr Ala
5000                5005                5010

Ala Gly Leu Thr Ala Asp Asp Pro Asp Ser Arg Val Pro Ile Gly
5015                5020                5025

Arg Pro Leu Pro Asn Thr Arg Ala Tyr Val Leu Asp Asp Ala Leu
5030                5035                5040

Arg Pro Val Pro Pro Gly Ser Pro Gly Glu Leu Tyr Leu Ala Gly
5045                5050                5055

Val Gln Leu Ala Arg Gly Tyr Leu Gly Arg Pro Ala Leu Ser Ala
5060                5065                5070

Glu Arg Phe Thr Ala Cys Pro Phe Ala Ser Gly Glu Arg Met Tyr
5075                5080                5085

Arg Thr Gly Asp Leu Val Arg Trp Arg Thr Asp Gly Ala Leu Glu
5090                5095                5100

Phe Leu Glu Arg Ala Asp Asp Gln Val Lys Ile Arg Gly Phe Arg
5105                5110                5115

Ile Glu Leu Gly Glu Val Glu Ala Val Leu Gly Ala His Pro Ala
5120                5125                5130

Val Gln Arg Ala Ala Ala Val Arg Glu Asp Thr Pro Gly Asp
5135                5140                5145

Arg Arg Leu Val Gly Tyr Ala Val Ala Asp Thr Pro Asp Pro Arg
5150                5155                5160

Ala Leu Ala Glu Ala Val Arg Ala His Ala Ala Glu Arg Leu Pro
5165                5170                5175

Ser Tyr Met Val Pro Ser Ala Val Val Val Leu Asp Ala Leu Pro
5180                5185                5190

Leu Thr Ala Asn Gly Lys Leu Asp Arg Lys Ala Leu Pro Ala Pro
5195                5200                5205
```

```
Asp Phe Glu Ala Ala Ala Gly Ser Gly Arg Ala Pro Ala Gly Pro
    5210                5215                5220

Arg Glu Glu Leu Leu Cys Ala Ala Phe Glu Arg Val Leu Gly Leu
    5225                5230                5235

Glu Arg Val Gly Val Asp Asp Phe Ala Leu Gly Gly His
    5240                5245                5250

Ser Leu Leu Ala Val Ser Leu Val Glu His Leu Arg Glu Arg Gly
    5255                5260                5265

Val Ser Val Ser Val Arg Ala Leu Phe Gln Ser Ala Thr Pro Ala
    5270                5275                5280

Gly Leu Ala Ala Ala Ser Gly Ala Ala Asp Gln Val Thr Val Pro
    5285                5290                5295

Pro Asn Leu Ile Pro Pro Gly Ala Thr Val Ile Thr Pro Asp Met
    5300                5305                5310

Leu Thr Leu Ala Asp Leu Thr Glu Ala Glu Ile Ala Arg Val Val
    5315                5320                5325

Asp Thr Val Pro Gly Gly Ala Ala Asn Ile Ala Asp Val Tyr Pro
    5330                5335                5340

Leu Ala Pro Leu Gln Glu Gly Met Phe Phe His His Leu Met Ala
    5345                5350                5355

Gly Gly Asp Asp Gly Asp Val Tyr Val Leu Pro Thr Val Leu Gly
    5360                5365                5370

Phe Asp Ser Arg Asp Arg Leu Asp Ala Phe Leu Ser Ala Leu Gln
    5375                5380                5385

Gln Val Val Asp Arg His Asp Thr Tyr Arg Thr Ala Phe Val Trp
    5390                5395                5400

Glu Gly Leu Arg Glu Pro Val Gln Val Val Trp Arg Asn Ala Ala
    5405                5410                5415

Leu Pro Val Asp Glu Val Leu Asp Thr Ala Glu Asp Pro Ala
    5420                5425                5430

Gly Gln Leu Leu Ser Gly Ala Gly Ala Trp Arg Thr Leu Asn Arg
    5435                5440                5445

Ala Pro Leu Met Arg Val Arg Ile Ala Ala Glu Pro Gly Thr Gly
    5450                5455                5460

Arg Trp Val Ala Leu Leu Leu Ile His His Leu Val Gln Asp His
    5465                5470                5475

Thr Ala Leu Asp Val Leu Leu His Glu Val Ser Ala Phe Leu Ser
    5480                5485                5490

Gly Asp Ala Ala Asp Leu Pro Glu Pro Val Pro Phe Arg Gly Tyr
    5495                5500                5505

Val Ala Gln Ala Arg Leu Gly Thr Ala Arg Glu Glu His Glu Ala
    5510                5515                5520

Tyr Phe Ser Gly Leu Leu Gly Asp Val Thr Glu Pro Thr Ala Pro
    5525                5530                5535

Tyr Gly Leu Leu Asp Val His Gly Asp Gly Gly Pro Glu Thr Arg
    5540                5545                5550

Ala Gln His Trp Val Asp Asp Ala Leu Ala Ala Arg Val Arg Gly
    5555                5560                5565

Leu Ala Arg Ser Lys Gly Val Ser Ala Ala Thr Val Phe His Leu
    5570                5575                5580

Ala Trp Ala Arg Val Leu Gly Ala Leu Ala Gly Arg Asp Asp Val
    5585                5590                5595

Val Phe Gly Thr Ile Val Phe Gly Arg Met Asn Ser Gly Thr Gly
```

```
                      5600              5605            5610

Ser Ala Arg Val Pro Gly Leu Phe Met Asn Thr Leu Pro Val Arg
    5615              5620            5625

Val Arg Leu Gly Ala Gly Ala Ala Asp Ala Ala Leu Thr Asp Met
    5630              5635            5640

Arg Asp Gln Leu Ala Glu Leu Met Ala His Glu His Ala Pro Leu
    5645              5650            5655

Thr Leu Ala Gln Ser Val Ser Gly Val Gln Gly Gly Thr Pro Leu
    5660              5665            5670

Phe Thr Ser Leu Phe Asn Tyr Arg Phe Thr Ala Ala Pro Asp Thr
    5675              5680            5685

Glu Pro Ala Ala Gly Glu Ala Gly Pro Leu Asp Gly Ile Gly Leu
    5690              5695            5700

Leu Ala Tyr Arg Glu Gln Ser Glu Tyr Pro Leu Thr Met Ser Val
    5705              5710            5715

Asp Asp Ala Gly Glu Arg Phe Leu Leu Thr Ala Asp Ala His Ala
    5720              5725            5730

Pro Ala Asp Pro Asp Gln Ala Cys Arg Leu Leu His Thr Cys Leu
    5735              5740            5745

Glu Ser Leu Val Thr Thr Leu Glu Gly Ala Pro His Thr Gly Leu
    5750              5755            5760

Ala Ala Val Asp Val Leu Asp Pro Asp Glu His Arg Arg Leu Leu
    5765              5770            5775

Gly Val Gly Ser Gly Ala Val Val Glu Val Pro Gly Val Ser Phe
    5780              5785            5790

Pro Glu Leu Phe Ala Ala Gln Ala Arg Leu Ser Pro Asp Ala Val
    5795              5800            5805

Ala Leu Val Gly Ser Gly Val Glu Leu Ser Tyr Ala Glu Val Glu
    5810              5815            5820

Ala Arg Ala Asn Arg Leu Ala Arg Lys Leu Ile Gly Leu Gly Val
    5825              5830            5835

Gly Pro Glu Ser Val Val Ala Leu Val Leu Glu Arg Ser Pro Glu
    5840              5845            5850

Leu Val Ile Ala Val Leu Ala Val Leu Lys Ala Gly Gly Ala Tyr
    5855              5860            5865

Val Ala Val Asp Pro Gly Gln Pro Ala Asp Arg Ile Arg Phe Val
    5870              5875            5880

Val Glu Asp Ala Ser Pro Val Leu Val Ile Asp Asp Val Asp Phe
    5885              5890            5895

Leu Thr Glu Thr Ala Asp Phe Asp Ala Ala Pro Val Ser Asp Ala
    5900              5905            5910

Asp Arg Leu Ser Pro Leu Leu Pro Ser His Pro Ala Tyr Val Ile
    5915              5920            5925

Tyr Thr Ser Gly Ser Thr Gly Arg Pro Lys Gly Val Leu Ile Ser
    5930              5935            5940

His Ala Ala Cys Val Ser Tyr Val Ala Ser His Val Arg Tyr Gly
    5945              5950            5955

Val Gly Glu Gly Ser Arg Val Ala Gln Phe Ala Ser Ala Gly Phe
    5960              5965            5970

Asp Ala Phe Cys Glu Glu Trp Trp Leu Ala Leu Leu Gly Gly Gly
    5975              5980            5985

Ala Leu Val Val Val Pro Ser Glu Arg Arg Leu Gly Glu Glu Leu
    5990              5995            6000
```

-continued

```
Val Arg Phe Leu Glu Glu Arg Val Thr His Ala Thr Leu Pro
6005                6010                6015

Pro Ala Val Ala Val Leu Met Arg Glu Glu Ala Leu Ala Pro Gly
6020                6025                6030

Phe Val Leu Asp Val Gly Gly Glu Val Cys Pro Asp Leu Val
6035                6040                6045

Asp Arg Trp Val Ala Gly Gly Arg Thr Leu Phe Asn Ser Tyr Gly
6050                6055                6060

Pro Ser Glu Ala Thr Val Asn Val Thr Val Trp Gln Ala Val Asp
6065                6070                6075

Gly Ser Val Gly Ala Gly Val Pro Ile Gly Arg Pro Val Gly Asn
6080                6085                6090

Thr Arg Val Phe Val Leu Asp Asp Gly Leu Arg Pro Val Pro Val
6095                6100                6105

Gly Val Leu Gly Glu Leu Tyr Val Ser Gly Val Gln Leu Gly Arg
6110                6115                6120

Gly Tyr Leu Gly Arg Pro Gly Leu Thr Ala Glu Arg Phe Val Ala
6125                6130                6135

Cys Pro Phe Asp Pro Gly Gln Arg Met Tyr Arg Thr Gly Asp Arg
6140                6145                6150

Val Lys Trp Ser Ala Asp Gly Glu Leu Val Phe Ala Gly Arg Ala
6155                6160                6165

Asp Asp Gln Val Lys Ile Arg Gly Phe Arg Ile Glu Pro Gly Glu
6170                6175                6180

Val Glu Thr Val Leu Ala Ala His Pro Ala Val Ala His Ala Ala
6185                6190                6195

Val Val Val Arg Glu Asp Thr Pro Gly Asp Lys Arg Leu Thr Ala
6200                6205                6210

Tyr Val Val Pro Ala His Asp Thr Asp Phe Ala Asp Val Pro Glu
6215                6220                6225

Thr Leu Arg Ala Tyr Ala Ala Glu Gln Leu Pro Ala Tyr Met Leu
6230                6235                6240

Pro Ser Ala Ile Val Glu Leu Asp Val Leu Pro Leu Thr Thr Asn
6245                6250                6255

Gly Lys Leu Asp Arg Lys Ala Leu Pro Ala Pro Glu Tyr Ala Ala
6260                6265                6270

Gly Ala Gly Arg Ala Ala Ala Asp Ala Arg Glu Glu Leu Leu Cys
6275                6280                6285

Gly Ala Phe Ala Gln Val Leu Gly Leu Glu Arg Val Gly Val Asp
6290                6295                6300

Asp Asp Phe Phe Ala Leu Gly Gly His Ser Leu Leu Ala Thr Arg
6305                6310                6315

Leu Val Ser Arg Val Arg Ala Val Leu Asp Val Glu Leu Pro Ile
6320                6325                6330

Arg Ala Leu Phe Glu Thr Pro Thr Pro Ala Ala Leu Ala Arg Gly
6335                6340                6345

Leu Ala His Ala Ala Pro Gly Arg Ala Ala Leu Glu Pro Arg Glu
6350                6355                6360

Arg Pro Ala Arg Ala Pro Leu Ser Phe Ala Gln Arg Arg Leu Trp
6365                6370                6375

Phe Leu Gly Arg Leu Asp Gly Pro Asn Ala Thr Tyr Asn Ile Pro
6380                6385                6390

Leu Ala Leu Arg Leu Thr Gly Glu Leu Asp Arg Glu Ala Leu Ala
6395                6400                6405
```

```
Gly Ala Phe Arg Asp Val Met Glu Arg His Glu Val Leu Arg Thr
    6410            6415            6420

Val Phe Ala Thr Ala Asp Gly Glu Pro Tyr Gln Gln Val Leu Pro
    6425            6430            6435

Val Asp Ala Ala Gly Phe Ala Leu Arg Val Ala Asp Val Asp Val
    6440            6445            6450

Asp Gly Leu Asp Gly Ala Val Thr Glu Ala Ala Gly His Ala Phe
    6455            6460            6465

Asp Leu Ser Ala Glu Ile Pro Leu Arg Ala Trp Leu Phe Ala Thr
    6470            6475            6480

Ala Pro Glu Glu His Val Leu Leu Met Val Val His His Ile Ala
    6485            6490            6495

Gly Asp Ala Trp Ser Met Glu Pro Leu Ala Arg Asp Met Ala Ala
    6500            6505            6510

Ala Tyr Ala Ala Arg Arg Glu Gly Arg Glu Pro Gly Trp Ala Pro
    6515            6520            6525

Leu Pro Val Gln Tyr Val Asp Tyr Ala Leu Trp Gln Arg Asp Val
    6530            6535            6540

Leu Asp His Glu Gly Asp Ser Gly Ser Val Leu Ser Arg Gln Val
    6545            6550            6555

Ala Tyr Trp Arg Asp Ala Leu Ala Gly Ala Pro Glu Glu Leu Glu
    6560            6565            6570

Leu Pro Ala Asp Arg Pro Arg Pro Ala Glu Val Ser Thr Arg Gly
    6575            6580            6585

His Gln Ala Pro Val Leu Val Pro Ala Glu Val His Glu Arg Leu
    6590            6595            6600

Leu Glu Val Ala Arg Gly Gly Val Thr Val Phe Met Val Leu
    6605            6610            6615

Gln Ala Ala Phe Ala Thr Leu Leu His Arg Leu Gly Ala Gly Asp
    6620            6625            6630

Asp Val Pro Val Gly Ala Ser Val Ala Gly Arg Thr Asp Glu Gly
    6635            6640            6645

Leu Asn Asp Leu Val Gly Phe Phe Val Asn Thr Leu Val Ile Arg
    6650            6655            6660

Thr Asp Leu Ser Gly Asp Pro Thr Phe Arg Glu Leu Leu Gly Arg
    6665            6670            6675

Val Arg Ala Val Ser Leu Ser Ala Tyr Glu Asn Gln Asp Val Pro
    6680            6685            6690

Phe Glu Arg Leu Val Glu Glu Leu Ala Pro Ala Arg Ser Leu Ala
    6695            6700            6705

Arg His Pro Leu Phe Gln Val Met Leu Thr Leu Gln Asn Thr Gly
    6710            6715            6720

Gly Pro Gly Gly Gly Pro Ala Val Asp Leu Pro Gly Leu Arg Thr
    6725            6730            6735

Asp Ser Leu Ser Ala Gly Ser Val Ala Ala Lys Phe Asp Leu Asp
    6740            6745            6750

Leu Ser Val Gly Glu Thr Leu Asp Ala Thr Gly Ala Pro Ala Gly
    6755            6760            6765

Ile Glu Gly Val Leu Val Ala Ala Ala Asp Leu Phe Asp Pro Ala
    6770            6775            6780

Thr Val Glu Arg Ile Ala Gly Arg Leu Val Arg Leu Leu Glu Leu
    6785            6790            6795

Val Ala Gly Asp Thr Asp Met Pro Leu Ser Ala Val Asp Val Leu
```

-continued

```
              6800                6805                6810

Asp Ala Asp Glu Arg Arg Gln Val Val Glu Glu Trp Asn Gly Thr
    6815                6820                6825

Asp Ala Pro Leu Pro Ala Arg Ser Val Ser Asp Met Phe Arg Ala
    6830                6835                6840

Gln Ala Ala Val Thr Pro Asp Ala Val Ala Val Leu Cys Gly Asp
    6845                6850                6855

Asp Arg Leu Thr Tyr Ala Glu Leu Asp Ala Arg Val Asn Arg Leu
    6860                6865                6870

Ala Arg Leu Leu Ile Arg Arg Gly Val Gly Pro Glu Ala Arg Val
    6875                6880                6885

Ala Val Cys Met Glu Arg Ser Ala Asp Leu Leu Val Ala Leu Leu
    6890                6895                6900

Ala Val Leu Arg Thr Gly Ala Ala Tyr Leu Pro Val Asp Pro Gly
    6905                6910                6915

His Pro Ala Glu Arg Val Ala Phe Met Leu Asp Glu Ala Arg Pro
    6920                6925                6930

Ala Leu Leu Leu Thr Gly Arg Gly Thr Ala Val Glu Ala Phe Gly
    6935                6940                6945

Pro Glu Arg Val Val Val Asp Asp Pro Arg Thr Val Ala Glu Leu
    6950                6955                6960

Ala Asp Leu Asp Ala Gly Ala Val Thr Asp Ala Glu Arg Val Thr
    6965                6970                6975

Pro Pro Leu Pro Asp His Pro Ala Tyr Val Ile Tyr Thr Ser Gly
    6980                6985                6990

Ser Thr Gly Arg Pro Lys Gly Val Val Val Thr His Gly Ala Met
    6995                7000                7005

Ala Asn Leu Val Ala Thr Met Gly Arg Arg Phe Pro Met Asp Thr
    7010                7015                7020

Glu Asp Arg Leu Leu Ala Val Thr Thr Val Thr Phe Asp Ile His
    7025                7030                7035

Val Phe Glu Leu Tyr Val Pro Leu Leu Ala Gly Ala Ala Val Val
    7040                7045                7050

Ile Ala Val Asp Gly Asp Val Arg Asp Pro Ala Ala Val Ala Gly
    7055                7060                7065

Leu Val Glu Arg Phe Gly Ala Ser Leu Met Gln Gly Thr Pro Ala
    7070                7075                7080

Leu Trp His Gly Leu Leu Thr Ala His Ala Glu Ala Ala Arg Gly
    7085                7090                7095

Leu Arg Leu Leu Val Ala Gly Glu Ala Leu Ser Gly Ser Leu Ala
    7100                7105                7110

Ala Arg Met Ala Ala Val Gly Ser Thr Val Thr Asn Leu Tyr Gly
    7115                7120                7125

Pro Thr Glu Ala Thr Val Tyr Ala Thr Ala Ala Gly Val Glu Ala
    7130                7135                7140

Gly Thr Thr Ala Ser Gln Val Pro Ile Gly Arg Pro Ile Asp Asn
    7145                7150                7155

Thr Arg Ala Tyr Val Leu Asp Gly Arg Leu Gln Pro Val Pro Pro
    7160                7165                7170

Gly Val Ser Gly Glu Leu Tyr Leu Ala Gly Ala Gln Leu Ala Arg
    7175                7180                7185

Gly Tyr Leu Glu Arg Pro Gly Leu Ser Ala Glu Arg Phe Val Ala
    7190                7195                7200
```

```
Cys Pro Phe Gly Ala Ala Gly Glu Arg Met Tyr Arg Thr Gly Asp
    7205            7210                7215

Val Val Arg Arg Arg Thr Asp Gly Gln Leu Glu Phe Arg Gly Arg
    7220            7225                7230

Ala Asp Asp Gln Val Lys Ile Arg Gly Phe Arg Ile Glu Pro Gly
    7235            7240                7245

Glu Val Glu Ala Val Leu Gly Ala His Pro Ala Val Gly Arg Ala
    7250            7255                7260

Ala Ala Val Val Arg Glu Asp Val Pro Gly Asp Lys Arg Leu Val
    7265            7270                7275

Ala Tyr Val Val Ala Ala Gly Pro Asp Asp Gly Pro Asp Pro Asp
    7280            7285                7290

Gly Gly Pro Asp Asp Gly Gly Leu Ala Ala Val Ala His Asp His
    7295            7300                7305

Ala Ala Glu His Leu Pro Ser Tyr Met Val Pro Ser Ala Val Val
    7310            7315                7320

Val Val Asp Ala Leu Pro Leu Thr Ser Thr Gly Lys Leu Asp Arg
    7325            7330                7335

Arg Ala Leu Pro Ala Pro Ala Tyr Thr Ala Gly Gly Arg Ala
    7340            7345                7350

Ala Ala Thr Val Glu Glu Glu Leu Leu Cys Gln Gly Phe Ala Glu
    7355            7360                7365

Val Leu Gly Leu Pro Ala Val Gly Val Asp Asp Asp Phe Phe Ala
    7370            7375                7380

Leu Gly Gly His Ser Leu Leu Ala Val Ser Leu Val Glu Trp Leu
    7385            7390                7395

Arg Gln Arg Gly Leu Pro Val Ser Val Arg Ala Leu Phe Thr Thr
    7400            7405                7410

Pro Thr Pro Ala Gly Leu Ala Ala Ala Gly Pro Glu Thr Val
    7415            7420                7425

Val Val Pro Pro Asn Leu Ile Pro Asp Asp Ala Thr Glu Ile Thr
    7430            7435                7440

Pro Glu Ile Leu Thr Leu Val Asp Leu Thr Glu Asp Glu Ile Ala
    7445            7450                7455

Arg Val Thr Glu Thr Val Pro Gly Gly Ala Ala Asn Ile Gln Asp
    7460            7465                7470

Val Tyr Pro Leu Ala Pro Leu Gln Glu Gly Ile Leu Phe His His
    7475            7480                7485

Leu Met Leu Asp Arg Asp Ala Thr Asp Val Tyr Val Thr Pro Thr
    7490            7495                7500

Val Ile Gly Phe Asp Ser Arg Arg Arg Leu Asp Gly Phe Leu Glu
    7505            7510                7515

Ala Met Arg Trp Val Leu Glu Arg His Asp Val Tyr Arg Thr Ala
    7520            7525                7530

Phe Val Ser Asp Gly Leu Pro Glu Pro Val Gln Val Val Leu Arg
    7535            7540                7545

His Ala Gly Leu Pro Val Glu Val Val Leu Asp Pro Ala Gly
    7550            7555                7560

Pro Asp Ala Glu Gln Gln Leu Ala Ala Ala Val Arg Gly Arg Leu
    7565            7570                7575

Asp Leu His Arg Ala Pro Leu Ile Thr Thr His Val Ala Ala Asp
    7580            7585                7590

Pro Arg Thr Gly Gly Arg Trp Leu Cys Leu Leu Arg Val His His
    7595            7600                7605
```

```
Leu Leu Gln Asp His Thr Gly Leu Gln Ile Met Leu Asp Glu Leu
    7610            7615                7620
Arg Ala His Leu Ala Gly Arg Thr Glu His Leu Pro Glu Pro Leu
    7625            7630                7635
Pro Phe Arg Asp Phe Val Ala Gln Ala Arg Leu Gly Val Pro Arg
    7640            7645                7650
Glu Gln His Arg Arg His Phe Thr Gly Leu Leu Gly Asp Val Thr
    7655            7660                7665
Glu Pro Thr Ala Pro Tyr Gly Leu Val Glu Val His Gly Asp Gly
    7670            7675                7680
Thr Ala Val Ala Gln Ala Arg Leu Arg Val Asp Gly Glu Leu Thr
    7685            7690                7695
Val Arg Leu Lys Gly Val Ala Arg Ser Leu Gly Val Ser Pro Ala
    7700            7705                7710
Thr Leu Phe His Leu Ala Trp Ala Arg Val Leu Gly Ala Val Ser
    7715            7720                7725
Gly Arg Asp Asp Val Val Phe Gly Thr Ile Val Phe Gly Arg Met
    7730            7735                7740
Asn Ser Gly Ala Gly Ala Asp Arg Val Pro Gly Leu Phe Ile Asn
    7745            7750                7755
Thr Leu Pro Val Arg Val Arg Leu Ala Gly Ala Ser Val Gly Glu
    7760            7765                7770
Ala Leu Thr Gly Leu Arg His Gln Leu Ala Asp Leu Met Val His
    7775            7780                7785
Glu His Ala Pro Leu Ala Leu Ala Gln Ala Ala Ser Gly Met Pro
    7790            7795                7800
Gly Gly Pro Leu Phe Thr Ser Leu Phe Asn Tyr Arg His Asn Gln
    7805            7810                7815
Asp Val Pro Gln Glu Thr Ala Gly Ala Met Asp Gly Met Gly Leu
    7820            7825                7830
Leu Ser Asp Arg Asp Ile Thr Asp Tyr Pro Leu Ala Val Ala Ile
    7835            7840                7845
Asp Val Gly Gly Gly Gly Phe Thr Ile Ala Val Asp Ala Val Ala
    7850            7855                7860
Pro Ala Asp Pro Asp Gln Val Cys Thr Leu Leu Arg Thr Cys Leu
    7865            7870                7875
Asp Asn Leu Val Thr Ala Leu Glu Glu Ala Pro Asp Thr Pro Leu
    7880            7885                7890
Arg Ser Leu Asp Val Leu Gly Gly Ala Glu Leu Ser Glu Leu Val
    7895            7900                7905
Glu Gly His Asn Ala Thr Ser Val Ala Arg Ala Asp Val Ser Val
    7910            7915                7920
Pro Glu Ala Phe Ala Arg Arg Thr Ala Ala Asp Arg Asp Ala Val
    7925            7930                7935
Ala Leu Val Ser Asp Ser Gly Glu Val Thr Tyr Gly Glu Leu Asp
    7940            7945                7950
Ala Arg Ala Asp Glu Leu Ala Arg Ala Leu Val Ala Ser Gly Val
    7955            7960                7965
Gly Pro Glu Ser Val Val Ala Val Leu Met Glu Arg Ser Ala Asp
    7970            7975                7980
Leu Val Val Ala Leu Leu Ala Val Leu Lys Ala Gly Gly Ala Tyr
    7985            7990                7995
Leu Pro Leu Asp Val Arg Trp Pro Val Ala Arg Met Arg Ala Val
```

```
                    8000                    8005                    8010

Ile Glu Asp Ala Gly Ala Thr Ser Val Val His Asp Ala Thr
    8015                    8020                    8025

Ala Gly His Asp Leu Gly Arg Thr Thr Gly Leu Asp Val Ile Pro
    8030                    8035                    8040

Val Ala Ala Gly Ala Asp Ser Ala Val Val Leu Pro Ala Ala Val
    8045                    8050                    8055

Ala Pro Gly Ala Ala Ala Tyr Val Met Tyr Thr Ser Gly Ser Thr
    8060                    8065                    8070

Gly Val Pro Lys Gly Val Val Ala Thr His Arg Asp Val Val Ala
    8075                    8080                    8085

Leu Ala Gly Asp Arg Cys Trp Gly Ala Thr Pro Arg Val Leu Phe
    8090                    8095                    8100

His Ala Pro His Ala Phe Asp Ala Ser Thr Tyr Glu Leu Trp Val
    8105                    8110                    8115

Pro Leu Leu Ser Gly Gly Thr Val Val Leu Ala Pro Asp Glu Ala
    8120                    8125                    8130

Val Asp Gly Ser Val Leu Arg Thr Leu Val Thr Gly His Asp Leu
    8135                    8140                    8145

Ser His Val His Val Thr Ala Gly Leu Leu Arg Val Leu Ala Asp
    8150                    8155                    8160

Gln Asp Pro Gly Cys Phe Thr Gly Val Arg Glu Val Leu Thr Gly
    8165                    8170                    8175

Gly Asp Val Val Pro Ala Glu Ser Val Arg Arg Val Leu Asp Ala
    8180                    8185                    8190

Asn Pro Gly Val Val Arg Gln Leu Tyr Gly Pro Thr Glu Val
    8195                    8200                    8205

Thr Leu Cys Ala Thr Gln Tyr Glu Val Ala Asp Ala Ala Glu Val
    8210                    8215                    8220

Asp Ser Val Leu Pro Ile Gly Arg Pro Leu Asp Asn Thr Arg Val
    8225                    8230                    8235

Tyr Val Leu Asp Gly Ser Leu Asn Pro Val Pro Val Gly Val Ala
    8240                    8245                    8250

Gly Glu Leu Tyr Val Ala Gly Ala Gly Val Ala Arg Gly Tyr Leu
    8255                    8260                    8265

Gly Arg Pro Val Leu Thr Ser Glu Arg Phe Val Ala Cys Pro Phe
    8270                    8275                    8280

Gly Val Thr Gly Glu Arg Met Tyr Arg Thr Gly Asp Leu Val Arg
    8285                    8290                    8295

Trp Asp Ala Glu Gly Arg Leu Val Phe Met Gly Arg Ala Asp Asp
    8300                    8305                    8310

Gln Val Lys Ile Arg Gly Phe Arg Val Glu Pro Gly Glu Val Glu
    8315                    8320                    8325

Thr Val Val Ala Ala His Pro Ala Val Gly Gln Ala Ala Val Val
    8330                    8335                    8340

Val Arg Glu Asp Thr Pro Gly Asp Lys Arg Leu Val Ala Tyr Leu
    8345                    8350                    8355

Val Pro Ala Gly Thr Glu Thr Ser Phe Ala Asp Ala Val Arg Ala
    8360                    8365                    8370

His Thr Ala Asp Arg Leu Pro Glu Tyr Leu Val Pro Ser Ala Phe
    8375                    8380                    8385

Val Glu Leu Glu Asn Leu Pro Leu Thr Val Asn Gly Lys Leu Asp
    8390                    8395                    8400
```

```
Arg Glu Ala Leu Pro Ala Pro Gly Phe Pro His Gly Ala Gly Asp
8405                 8410                8415

Thr Val Ala His Gly Pro Val Ala Ala Leu Glu Gln Ala Met Cys
8420                 8425                8430

Glu Ala Phe Ala Glu Val Leu Gly Leu Pro Ser Val Gly Val Asp
8435                 8440                8445

Asp Asp Phe Phe Ala Leu Gly Gly His Ser Leu Leu Ala Val Arg
8450                 8455                8460

Leu Val His Arg Leu Arg Asp Arg Gly Val Thr Thr Ser Val Arg
8465                 8470                8475

Asp Leu Met Ala Ala Pro Thr Val Thr Ala Leu Arg Gly Thr Leu
8480                 8485                8490

Gly Leu Ser Ser Val Arg Asp Ser Leu Gly Val Leu Leu Thr Ile
8495                 8500                8505

Arg Gly Asp Gly Gly Arg Pro Pro Leu Phe Cys Val His Pro Ala
8510                 8515                8520

Gly Gly Leu Ser Trp Cys Tyr Thr Pro Phe Ala Gln His Ala Pro
8525                 8530                8535

Asp Asp Gln Pro Val Tyr Gly Leu Gln Ala Arg Gly Val Asp Gly
8540                 8545                8550

Gly Ala Pro Phe Ala Gly Ser Leu Ala Glu Met Ala Ala Asp Tyr
8555                 8560                8565

Ile Glu Gln Leu Arg Gln Val Gln Pro Ala Gly Pro Tyr His Leu
8570                 8575                8580

Val Gly Tyr Ser Phe Gly Ala Ala Pro Ala His Glu Ile Ala Val
8585                 8590                8595

Gln Leu Arg Glu Gln Gly Glu Glu Val Ala Ala Leu Val Ile Met
8600                 8605                8610

Asp Ser Phe Pro Leu Asp Arg Glu Ile Ala Ala Thr Gly Ala Glu
8615                 8620                8625

Asp Gly Ala Ala Pro Gly Gly Asp Leu Ser Trp Glu Gly Ala Ile
8630                 8635                8640

Arg Ala Glu Phe Gly His Leu Leu Gly Gly Phe Thr Asp Glu Glu
8645                 8650                8655

Ile Ala Val Val Ala Arg Thr Phe Glu Asn Asn Thr Arg Ile Arg
8660                 8665                8670

Ala Ala His Thr Thr Gly Arg Phe Asp Gly Asp Ala Leu Ile Leu
8675                 8680                8685

Thr Ser Ala Asp Ser Thr Thr Glu Asp Gly Pro Leu Thr Ala Lys
8690                 8695                8700

Trp Ala Pro His Val Leu Gly Glu Leu Thr Glu Val Ser Ile Pro
8705                 8710                8715

Cys Gly His Val Asp Met Val Arg Pro Asp Met Met Gly Leu Ala
8720                 8725                8730

Trp Gln Ala Ile Ser Ala Trp Leu Lys Ser Pro Leu Thr Arg Gly
8735                 8740                8745

Thr Glu Arg Thr Asp Met Arg Arg Thr Ser Leu Leu Cys Val Pro
8750                 8755                8760

Phe Ala Gly Ala Gly Ala Ser Phe Phe His Pro Trp Ala Ala Leu
8765                 8770                8775

Thr Asp Gly Asn Pro Arg Ile Val Ala Leu Gln Leu Pro Gly Arg
8780                 8785                8790

Glu Trp Arg Leu Ser Glu Glu Pro Tyr Arg Asp Val Ala Arg Ala
8795                 8800                8805
```

```
Ala Ala Glu Leu Leu Pro Val Val Thr Glu Ile Gly Pro Asp
        8810                8815                8820

Asp Arg Val Val Ile Phe Gly His Ser Leu Gly Ala Val Leu Ala
    8825                8830                8835

Tyr Glu Leu Ala His Leu Leu Val Asp Arg Thr Gly Val Asp Val
    8840                8845                8850

Ala Arg Leu Phe Ala Ser Gly Ser Pro Gly Pro Trp Thr Arg Arg
    8855                8860                8865

Thr Arg Arg Ala Thr Gly Leu Pro Asp Glu Glu Phe Leu Leu Arg
    8870                8875                8880

Val Lys Glu Phe Ala Gly Tyr Asp His Glu Ala Leu Ser His Pro
    8885                8890                8895

Asp Met Arg Glu Leu Ile Leu Pro Thr Leu Arg Ala Asp Val Glu
    8900                8905                8910

Met His Glu Asn Tyr Val Pro Ala Gly Asp Arg Pro Leu Pro Val
    8915                8920                8925

Pro Val Thr Ala Val Arg Gly Thr Arg Asp Asp Leu Val Thr Ala
    8930                8935                8940

Glu Gln Thr Gly Glu Trp Ala Arg Ala Thr Ser Ala Gly Phe Thr
    8945                8950                8955

Arg Ala Glu Val Glu Gly Gly His Met Tyr Ile Ala Glu Asp Pro
    8960                8965                8970

Gly Ser Leu Leu Arg Leu Val Asp Asp Ala Leu Ala Arg
    8975                8980                8985

<210> SEQ ID NO 39
<211> LENGTH: 274
<212> TYPE: PRT
<213> ORGANISM: Streptomyces fungicidicus

<400> SEQUENCE: 39

Met Gln Leu Ala Gly Lys Thr Ala Ile Val Thr Gly Ala Ala Arg Gly
1               5                   10                  15

Leu Gly Arg Ala Cys Ala Val Ala Phe Ala Arg Glu Gly Ala Asp Leu
            20                  25                  30

Val Leu Leu Asp Leu Cys Ala Asp Leu Pro Gly Val Pro Tyr Pro Leu
        35                  40                  45

Gly Gly Pro Gly Gln Leu Ala His Thr Ala Asp Leu Cys Arg Gly His
    50                  55                  60

Gly Ala Ala Val Leu Val Arg Gln Ala Asp Val Arg Asp Leu Gly Ala
65                  70                  75                  80

Leu Arg His Ala Val Asp Asp Ala His Gly Arg Phe Gly Arg Ile Asp
                85                  90                  95

Val Leu Leu Asn Asn Ala Gly Ile Ala Ala Pro Ser Gly Lys Pro Val
            100                 105                 110

Asp Glu Ile Asp Glu Asp Glu Trp Gln Leu Met Ile Asp Val Asp Leu
        115                 120                 125

Ser Gly Ala Trp Arg Ala Thr Lys Ala Val Gly Lys Ile Met Thr Ala
    130                 135                 140

Gln Arg Ala Gly Ser Ile Ile Asn Val Ala Ser Thr Ala Gly Gln Val
145                 150                 155                 160

Gly Tyr Arg Asn Phe Ala Gly Tyr Val Ala Ala Lys His Gly Val Ile
                165                 170                 175

Gly Leu Thr Arg Ala Thr Ala Leu Asp Phe Ala Pro Met Arg Val Arg
            180                 185                 190
```

```
Ala Asn Ala Leu Cys Pro Gly Ser Val Arg Asp Asp Pro Ala Val Glu
            195                 200                 205

Gly Arg Met Leu Ser Glu Ile Ala Arg Ser Leu Gln Val Pro Val Ala
            210                 215                 220

Glu His Glu Glu Ala Phe Val Gln Ser Gln Pro Met Asn Ala Leu Ile
225                 230                 235                 240

Glu Pro Asp Asp Val Ala Ser Ala Ala Val Trp Leu Ala Ser Asp Gly
            245                 250                 255

Ser Arg Gln Val Thr Gly Ser Val Ile Thr Val Asp Gly Gly Phe Thr
            260                 265                 270

Thr Arg

<210> SEQ ID NO 40
<211> LENGTH: 859
<212> TYPE: PRT
<213> ORGANISM: Streptomyces fungicidicus

<400> SEQUENCE: 40

Met Val Thr Val Gln Ser Ala Glu Asp Ala Arg His Cys His Ala Leu
1               5                   10                  15

Arg Val Arg Leu Gly Ala Ser Asp Arg Val Asp Ala Pro Trp Val Glu
            20                  25                  30

Arg Val Pro Phe Ala Ser Asp Glu Pro Gly Ala Ala Arg His Arg Ala
            35                  40                  45

Arg Glu Leu Ala Arg Pro Val Asp Ala Gly Arg Gly Ser Arg Ala Val
        50                  55                  60

Leu Leu Val Tyr Thr Asp Gly Arg Ala Asp Leu Val Val Val Ala His
65                  70                  75                  80

Arg Ser Ala Tyr Gly Gln Arg Ala Leu Arg Arg Leu Ala Ala Ala Leu
                85                  90                  95

Leu Asp Pro Ala Arg Pro Ala Pro Ala Arg Gly Gln Gly Ala Val Pro
            100                 105                 110

Ser Gly Ser Gly His Thr Pro Asp Trp Gly Leu Gly Gly Pro Ala Gln
            115                 120                 125

Gly Asp Ala Arg Asp Gly His Arg Val Ala Leu Pro Glu Gly Thr Ser
    130                 135                 140

Arg Glu Pro Glu Gly Trp Leu Ala Ala Leu Ala Gln Val Leu Ser Arg
145                 150                 155                 160

Tyr Glu Pro Glu Arg Thr Pro Glu Ala Thr Ala Leu Asp Ala Gly Asp
                165                 170                 175

Arg Ala Ala Ser Pro Pro Ala Thr Pro Val Ser Ala Gly Leu Val Phe
            180                 185                 190

Asp Leu Gly Gly Glu Gly Glu Tyr Val Pro Cys Leu Ala Pro Val Phe
            195                 200                 205

Pro Leu Thr Val Thr Val Gly Glu Asp Gly Leu Arg Cys Asp His Arg
            210                 215                 220

Leu Gly Asp Val Ser Thr Pro Ile Ala Glu Gln Phe Val Arg His Leu
225                 230                 235                 240

Val Glu Ala His Arg Arg Leu Thr Gly Pro Pro Gly Ile Leu Asp Pro
                245                 250                 255

Ala Glu His Glu Arg Ile Leu Arg Leu Gly Arg Ala Ala Gln Pro Leu
            260                 265                 270

Lys Ser Thr Pro Arg Arg Ile Pro Asp Val Phe Ala Glu Arg Ala Ala
            275                 280                 285
```

```
Glu Arg Pro Asp Ala Leu Ala Leu Val Asp Gly Asp Arg Thr Val Thr
    290                 295                 300
Tyr Arg Arg Leu Asp Glu Trp Ser Asp Arg Leu Ala His Gly Leu Arg
305                 310                 315                 320
Ala Ala Gly Ala Gly Asp Gly Thr Leu Val Gly Val Cys Leu Glu Arg
                325                 330                 335
Ser Ala Gln Leu Val Ala Val Leu Leu Ala Val Leu Lys Ala Gly Ala
                340                 345                 350
Val Tyr Val Pro Leu Asp Pro Ala Tyr Pro Ala Asp Arg Leu Ala Tyr
                355                 360                 365
Thr Val Glu Asp Ser Gly Thr Asp Val Val Thr Glu Ser Ala Gly
    370                 375                 380
Phe Pro Gly Ser Pro Gly Val Arg Val Leu Thr Pro Ala Gln Val Leu
385                 390                 395                 400
Glu Ser Gly Gly Ala Ala Pro Asp Gly Pro Pro Ala Thr Gly Ala Gly
                405                 410                 415
Pro Gln Glu Ala Ala Tyr Val Ile Tyr Thr Ser Gly Ser Thr Gly Arg
                420                 425                 430
Pro Lys Gly Val Leu Val Pro His Ala His Val Val Ala Leu Met Asp
                435                 440                 445
Ala Thr Arg Asp Asp Phe Thr Leu Gly Ala Ala Asp Val Trp Thr Phe
    450                 455                 460
Phe His Ser Val Ala Phe Asp Phe Ser Val Trp Glu Ile Trp Gly Cys
465                 470                 475                 480
Leu Leu Thr Gly Gly Arg Leu Val Val Val Pro Tyr Trp Val Ser Arg
                485                 490                 495
Ser Pro Glu Gln Phe His Gly Leu Val Ala Ala Arg Gly Val Thr Val
                500                 505                 510
Leu Ser Gln Thr Pro Ser Ala Phe Thr Gln Phe Ala Ala Ala Asp Arg
                515                 520                 525
Asp Thr Ala Glu Pro Leu Ala Val Arg Leu Val Val Phe Gly Gly Glu
    530                 535                 540
Pro Leu Asp Thr Arg Ser Leu Leu Pro Trp Leu Asp Arg His Pro Gly
545                 550                 555                 560
Asp Arg Cys Arg Leu Val Asn Met Tyr Gly Ile Thr Glu Thr Thr Val
                565                 570                 575
His Val Thr Ala Glu Thr Val Thr Arg Arg Leu Ala Leu Ala Gly Ser
                580                 585                 590
Arg Ser Val Gly Arg Ala Leu Pro Gly Trp Arg Val Tyr Val Leu Asp
                595                 600                 605
Ala Arg Gly Arg Leu Ala Pro Pro Gly Val Ala Gly Glu Ile His Val
    610                 615                 620
Gly Gly Ala Gly Val Ala Leu Gly Tyr Leu Arg Arg Pro Asp Leu Thr
625                 630                 635                 640
Arg Glu Arg Phe Arg Pro Asp Pro Phe Gly Gly Arg Met Tyr Arg
                645                 650                 655
Thr Gly Asp Arg Gly Arg Leu Arg Pro Asp Gly Ala Leu Glu His Leu
                660                 665                 670
Gly Arg Leu Asp Asn Gln Val Lys Leu Arg Gly Phe Arg Ile Glu Leu
                675                 680                 685
Asp Glu Ile Arg Thr Val Leu Ala Glu Cys Pro Gly Val Thr Ala Ala
    690                 695                 700
Ala Val Thr Phe Arg Gln Thr Asp Pro Gly Asp Ala Ala Thr Gly Arg
705                 710                 715                 720
```

```
Leu Asp Ala Tyr Val Val Leu Ser Glu Gly Ser Thr Ala Asp Val Arg
                725                 730                 735

Glu Arg Ala Ala Arg Val Leu Pro Ala His Met Leu Pro Ser Thr Leu
            740                 745                 750

Thr Ala Leu Pro Ala Leu Pro Val Thr Ala Asn Gly Lys Thr Asp Leu
        755                 760                 765

Ala Ala Leu Pro Glu Pro Ala Val Ala Ala Ser Gly Gly Gly Ala Val
    770                 775                 780

Pro Ala Gly Gly Glu Asp Gly Leu Ser Gly Glu Leu Leu Ser Val Trp
785                 790                 795                 800

Arg Gln Leu Phe Gly Phe Thr Val Gly Leu Ser Asp Ser Phe Trp Glu
                805                 810                 815

Leu Gly Gly Asn Ser Leu Leu Ala Val Arg Met Ala Ser Leu Met Arg
            820                 825                 830

Glu Arg Gly Leu Pro Ser Leu His Pro Arg Leu Leu Tyr Leu Asn Pro
        835                 840                 845

Thr Val Arg Gln Leu Ala Val Ala Leu Lys Gly
    850                 855

<210> SEQ ID NO 41
<211> LENGTH: 223
<212> TYPE: PRT
<213> ORGANISM: Streptomyces fungicidicus

<400> SEQUENCE: 41

Met Thr Ile Lys Val Leu Leu Ala Asp Asp Gln Ala Met Ile Arg Arg
1               5                   10                  15

Gly Pro Cys Gly Ser Ser Trp Arg Thr Ser Arg Asp Ile Thr Val Val
            20                  25                  30

Gly Glu Ala Glu Asp Gly Ala Glu Ala Ile Ala Met Ala Arg Arg Leu
        35                  40                  45

Arg Pro Asp Val Cys Leu Val Asp Ile Arg Met Pro Lys Leu Asp Gly
    50                  55                  60

Ile Glu Val Thr Arg Ala Leu Ala Gly Pro Lys Ala Ala Asp Pro Met
65                  70                  75                  80

Arg Val Ile Val Val Thr Thr Phe Asp Leu Asp Glu Tyr Val Tyr Gly
                85                  90                  95

Ala Leu Arg Gly Gly Ala Ala Gly Phe Val Leu Lys Asp Ala Gly Pro
            100                 105                 110

Ala Leu Leu Ile Glu Ala Val Arg Ala Ala Tyr Asn Gly Glu Ala Leu
        115                 120                 125

Val Ser Pro Ser Val Thr Leu Arg Leu Leu Lys His Leu Asn Glu Ser
    130                 135                 140

Gln Ala Met Pro Arg Gly Gly Ala Ala Arg Ser Ser Glu Leu Ser Gly
145                 150                 155                 160

Arg Ala Leu Glu Val Val Arg Ala Ile Ala Arg Gly Arg Thr Asn Gln
                165                 170                 175

Glu Ile Ala Ala Glu Leu Phe Ile Ser Leu Ser Thr Val Lys Ser His
            180                 185                 190

Leu Ser Gly Ile Gln Thr Lys Leu Gly Val Arg Asn Arg Thr Glu Ile
        195                 200                 205

Ala Val Trp Ala Trp Glu Asn Arg Val Val Glu Ser Thr Ser Glu
    210                 215                 220

<210> SEQ ID NO 42
```

```
<211> LENGTH: 370
<212> TYPE: PRT
<213> ORGANISM: Streptomyces fungicidicus

<400> SEQUENCE: 42

Met Ser Val Phe Ser Thr Val Gly Leu Ala Val Ala Phe Leu Thr Ala
1               5                   10                  15

Ile Ala Val Gln Ala Val Ala Leu Ala Gln Thr Trp Gly Ala Ala Ser
            20                  25                  30

Trp Val Pro Gly Ala Ala Ser Val Val Cys Gly Leu Ala Leu
        35                  40                  45

Leu Arg His Arg Glu Arg Thr Trp Thr Ser Val Gly Leu Val Val
    50                  55                  60

Ala Ala Leu Ser Val Leu Val Pro Leu Leu Pro Gly Thr Arg Leu Pro
65                  70                  75                  80

Ala Gly Leu Gly Pro Ser Thr Ala Leu Gly Leu Ala Val Leu Ile Gly
                85                  90                  95

Ser Ala Val Arg Ala Leu Pro Pro Val Arg Ala Gly Thr Ile Ala Gly
                100                 105                 110

Ala Gly Leu Leu Leu Val Ala Ala Gln Phe Ala Thr Arg Pro Val Thr
            115                 120                 125

Ala Val Pro Ala Ile Ala Ala Val Ala Trp Leu Ala Ala Val Gly Val
130                 135                 140

Gly Leu Ser Leu Arg Arg Leu Asp Glu His Ala Lys Ala Thr Ala Gln
145                 150                 155                 160

Gln Val Arg Arg Thr Glu Arg Leu Glu Leu Ala Arg Glu Leu His Asp
                165                 170                 175

Ile Val Ala His His Ile Thr Gly Met Leu Ile Gln Ala Gln Ala Ala
            180                 185                 190

Gln Val Val Ala Arg Arg Asn Pro Glu Asp Val Ser Asp Ser Leu Thr
        195                 200                 205

Glu Ile Glu Thr Ala Gly Phe Glu Ala Met Ala Ala Met Arg Arg Val
210                 215                 220

Val Gly Leu Leu Arg Asp Thr Asp Asp Ala Ala Pro Ala Ser Pro Gly
225                 230                 235                 240

Pro Glu Gly Leu Gly Ala Leu Val Glu Arg Phe Ser Arg Gln Gly Pro
                245                 250                 255

Lys Val Arg Leu Ser Val Pro Asp Asp Asp Thr Arg Trp Pro Pro Glu
            260                 265                 270

Val Thr Ser Thr Val Tyr Arg Ile Val Gln Glu Ser Leu Thr Asn Val
        275                 280                 285

Leu Arg His Ala Arg His Ala His Ser Ile Asp Val Thr Val Gly Arg
290                 295                 300

Asp Ala Asp Ala Val Thr Val Glu Val Arg Asp Ala Pro Pro Asn
305                 310                 315                 320

Ser Ala Arg Ser His His Arg Gly Gly Tyr Gly Leu Val Gly Met Arg
                325                 330                 335

Glu Arg Val Glu Thr Leu Gly Gly Ser Leu His Ala Gly Pro Arg Pro
            340                 345                 350

Gly Ala Gly Trp Ser Val Arg Ala Thr Leu Pro Val Pro Thr Arg Glu
        355                 360                 365

Pro Gly
    370

<210> SEQ ID NO 43
```

```
<211> LENGTH: 181
<212> TYPE: PRT
<213> ORGANISM: Streptomyces fungicidicus

<400> SEQUENCE: 43
```

Met Asn Thr Ala Glu Gly Pro Thr Arg Pro Gly Arg Met Phe Asp
1               5                   10                  15

Val Gly Leu Ala Val Val Leu Ala Leu Gly Ile Val Phe Thr Ala Phe
            20                  25                  30

Met Phe Met Thr Ser Trp Gly Thr Ala Trp Leu Phe Gly Thr Ala
        35                  40                  45

Val Ser Val Val Val Ser Ala Val Ala Leu Phe Arg Ala Arg Phe Lys
    50                  55                  60

Ala Leu Thr Ala Val Ala Gly Leu Val Leu Thr Ala Gly Ala Val Thr
65                  70                  75                  80

Val Ser Arg Ile Ala Gly Asp Asp Leu Pro Gln Glu Pro Ala Pro Ala
                85                  90                  95

Thr Ala Leu Ala Leu Ser Val Leu Val Gly Ser Ala Ile Arg Thr Leu
            100                 105                 110

Pro Ala Gly Gly Ala Ala Ile Ala Val Gly Val Ala Val Thr
            115                 120                 125

Val Ala Phe Trp Leu Glu Gly Leu Ser Gly Val Ala Ser Ala Ala Thr
    130                 135                 140

Leu Ala Met Thr Ala Ala Leu Val Leu Gly Pro Val Leu Arg Leu Leu
145                 150                 155                 160

Asp Arg Arg Ala Leu Ala Thr Pro Arg Glu Pro Gln Glu Ser Trp Ala
                165                 170                 175

His Pro Pro His Ser
            180

```
<210> SEQ ID NO 44
<211> LENGTH: 624
<212> TYPE: PRT
<213> ORGANISM: Streptomyces fungicidicus

<400> SEQUENCE: 44
```

Met Gly Glu Gly Gly Ala Ala Arg Pro Ala Gly Gln Ala Arg Asp Asp
1               5                   10                  15

Ala Ala Asp Thr Gly Ala Val Gly Gly Pro Gly Gly Arg Arg Ala Arg
            20                  25                  30

Arg Thr Ala Gly Gly Ala Arg Gly Ala Gly Gly Ala Gly Arg Gly Pro
        35                  40                  45

Gly Asp Pro Val Arg Cys Ala Ala Asp Arg Leu Pro Gly Arg Pro Leu
    50                  55                  60

Met Gly Ala Ala Glu Leu Asp Val Leu Leu Gly Asp Pro Trp Asp Asp
65                  70                  75                  80

Arg Asn Pro Val Gly His Ala Ala Val Leu Ala Ala Asp Glu Arg Gln
                85                  90                  95

Glu Met Pro Ala Glu Gly Glu Arg Val Leu Asp Glu Tyr Arg Leu Asn
            100                 105                 110

Ala Glu Phe Val Pro Val Val His Gly Gly Arg Leu Glu Arg Ala Asp
        115                 120                 125

Arg Leu Ala Glu Val Leu Arg Thr Val Trp Arg Arg Asp Pro Cys Leu
    130                 135                 140

Gly Leu Gly Tyr Gly Phe Ser Ser Leu Ile Ala Ser Val Asn Val Trp
145                 150                 155                 160

-continued

Thr Thr Gly Asp Glu Glu Gln Arg Arg Val Ala Asp Leu Leu Leu
              165                 170                 175

Ala Asn Gly Arg Val Ala Ala Phe His Glu Leu Ala His Gly Asn
            180                 185                 190

Asp Phe Ala His Ala Glu Cys Ala Ala Arg Pro Asp Gly Ala Gly Trp
            195                 200                 205

Arg Leu Thr Gly Arg Lys Glu Ile Val Thr Asn Val Arg Arg Ala Gln
            210                 215                 220

Ala Met Val Leu Phe Ala Arg Thr Gly Thr Gly Ala Gly Ser Arg Gly
225                 230                 235                 240

His Ser Gln Phe Leu Leu Thr Arg Asp Asp Leu Pro Ala Ala Ala Val
                245                 250                 255

Arg Asp Leu Pro Arg Phe His Ser Ser Gly Met Arg Gly Ile Glu Leu
                260                 265                 270

Gly Gly Val Glu Phe Ala Asp Cys Pro Val Pro Ala Asp Ala Leu Ile
                275                 280                 285

Gly Ser Pro Gly Gln Gly Ile Glu Val Ala Leu Arg Ser Tyr Gln Ile
        290                 295                 300

Thr Arg Ser Val Gly Pro Ala Val Leu Val Gly Pro Leu Glu Thr Ala
305                 310                 315                 320

Leu Arg Leu Ala Met Arg Cys Ser Leu Glu Arg Arg Leu Tyr Gly Gly
                325                 330                 335

Thr Val Ala Asp Leu Pro Tyr Val Arg Ala Val Ile Ala Arg Ser Tyr
                340                 345                 350

Ala Asp Leu Leu Ala Met Asp Ala Phe Ser Ala Val Val Leu Arg Ala
                355                 360                 365

Leu His Leu Arg Pro Glu Ala Met Ala Val Tyr Ala Pro Ala Ala Lys
        370                 375                 380

Tyr Leu Thr Ala Arg Met Leu Leu Asp Ala Phe Glu Asp Leu Arg Ala
385                 390                 395                 400

Val Leu Gly Ser Arg Ser Tyr Leu Arg Arg Gly Pro Tyr Ala Thr Phe
                405                 410                 415

Gln Lys Leu Ala Gly Glu Val Ala Pro Ala Thr Phe Ala His Val Ser
                420                 425                 430

Leu Thr Ala Ala Leu Val Thr Leu Leu Pro Gln Leu Pro Arg Leu Ala
        435                 440                 445

Arg Arg Ser Trp Leu Ala Asp Pro Ser Ala Pro Ala Ser Leu Phe Asp
450                 455                 460

Pro Gly Gly Glu Leu Pro Ala Leu Ala Pro Asp Arg Leu Ser Thr Gly
465                 470                 475                 480

Met Pro Arg His Asp Gly Val Val Gly Ala Leu Thr Glu Leu Ala Asp
                485                 490                 495

Gly Val Pro Ala Asp Asp Arg Asp Pro Val Arg Arg Phe Ala Ala Arg
            500                 505                 510

Leu Arg Asp Glu Leu Arg Thr Leu Arg Asp Gly Cys Ala Ala Leu Gly
        515                 520                 525

Pro Gly Asp Ile Thr Ile Asp Ala Pro Ala Ala Phe Ala Leu Ala
        530                 535                 540

Asp Arg Tyr Thr Val Val Leu Ala Ala Ser Val Leu Ala Val Trp
545                 550                 555                 560

Arg Arg Cys Ala Gly Arg Tyr Pro Asp Ala Ala Leu Leu Gly Ala Leu
                565                 570                 575

Asp Arg Leu Thr Gly Arg Leu Gly Gly Pro Pro Val Leu Thr Ala Ala
        580                 585                 590

```
Glu Arg Lys Asp Val Glu Arg Glu Leu Phe Gly Leu Ala Val Ala Arg
            595                 600                 605

Cys His Asp Gly Arg Leu Leu Asp Leu Ser Ala Arg His Val Pro Gly
            610                 615                 620

<210> SEQ ID NO 45
<211> LENGTH: 1177
<212> TYPE: PRT
<213> ORGANISM: Streptomyces fungicidicus

<400> SEQUENCE: 45

Met Thr Val Asp Leu Ser Gly Tyr Pro Ser Leu Gly Ala Ala Phe Ala
1               5                   10                  15

Ala Arg Ala Asp Ala His Pro Gly Arg Thr Ala Leu Thr Leu Trp His
            20                  25                  30

Gly Ser Thr Gly Ala Asp Pro Glu Ser Val Thr Tyr Gly Glu Leu Ala
            35                  40                  45

Arg Arg Ser Arg Val Arg Ala Arg Glu Leu Ala Arg Arg Leu Ala Pro
50                  55                  60

Gly Glu Arg Val Leu Val Ala Leu Pro Thr Gly Ile Glu Phe Ala Glu
65                  70                  75                  80

Val Tyr Leu Ala Cys Leu Thr Ala Gly Leu Val Ala Val Pro Ser Pro
                85                  90                  95

Met Pro Gly Gly Ser Ala Ser Ala Gly Glu Arg Ile Ala Ala Ile Ala
            100                 105                 110

Ala Asp Cys Ser Pro Gly Leu Val Leu Thr Thr Asp Ala Ala Arg Ala
            115                 120                 125

Glu Val Ala Glu His Leu Arg Gly His Gly Pro Glu Gly Leu Ala Val
130                 135                 140

Glu Ala Val Leu Pro Val Gly Gly Arg Ser Ala Pro Gly Glu Gly Ala
145                 150                 155                 160

Asp Gly Arg Asp Val Ala Ala Ala Arg Thr Arg Ser Cys Ser Thr Ala
                165                 170                 175

Pro Val His Arg Val Ala Glu Gly Val Ile Leu Thr His Gly Ala Val
            180                 185                 190

Leu Ala Asn Val Ser Ala Val Cys Thr Tyr Val Gly Leu Val Pro Glu
            195                 200                 205

Asp Arg Phe Gly Ser Trp Leu Pro Leu His His Asp Met Gly Leu Phe
210                 215                 220

Thr Gln Leu Thr Ala Ala Leu Leu Cys Gly Ala His Leu Thr Leu Met
225                 230                 235                 240

Thr Pro Ala Gln Phe Ile Arg Arg Pro Ala Glu Trp Phe Arg Met Leu
                245                 250                 255

Asp Arg Phe Arg Ile Thr Tyr Thr Val Ala Pro Asn Phe Ala Tyr Glu
            260                 265                 270

Leu Cys Thr Arg Val Ile Thr Asp Glu Met Thr Arg Gly Leu Asp Leu
            275                 280                 285

Ser Ala Leu Arg Tyr Leu Gly Asn Gly Ala Glu Pro Ile His Ala Pro
290                 295                 300

Thr Val Arg Ala Phe Met Glu Arg Phe Ala His Leu Gly Leu Arg Ser
305                 310                 315                 320

His Val His Ser Ser Gly Tyr Gly Leu Ala Glu Ser Thr Ala Tyr Val
                325                 330                 335

Thr Cys Val Pro Glu Glu Thr Ser Pro Thr Val Leu Thr Val Asp Pro
            340                 345                 350
```

```
Leu Arg Leu Glu Ser Gly Glu Arg Pro Glu Leu Arg Pro Val Ala Glu
            355                 360                 365

Gly Ala Gly Arg Pro Val Met Gly Leu Gly Arg Pro His Ala Phe Asp
            370                 375                 380

Leu Arg Ile Val Asp Pro Glu Arg Val Pro Leu Pro Glu Gly Arg
385                 390                 395                 400

Ile Gly Glu Ile Trp Leu Arg Gly Glu Ser Ile Gly Arg Gly Tyr Trp
                405                 410                 415

Gly Arg Pro Glu Leu Ser Ala Glu Val Phe Asp Ala Arg Leu Ala Asp
            420                 425                 430

Ser Ala Glu Gly Pro Gly Trp Leu Arg Thr Gly Asp Leu Gly Ala Leu
            435                 440                 445

Val Asp Gly Glu Leu Phe Val Thr Gly Arg Leu Lys Glu Leu Leu Ile
450                 455                 460

Val His Gly Arg Asn Ile Phe Pro Gln Asp Val Glu His Glu Ala Arg
465                 470                 475                 480

Ala Ala His Gln Ala Leu Gly Gly Gln Leu Gly Ala Ala Phe Gly Val
            485                 490                 495

Gly Ser Pro Asp Glu Arg Val Val Leu Val His Glu Val His Pro Arg
            500                 505                 510

Thr Pro Arg Thr Glu Leu Pro Glu Val Val Thr Ala Val Thr Arg Arg
            515                 520                 525

Leu Asn Arg Phe Val Arg Ser Pro Pro Ala Gln Arg Arg Ala Gly Ala
530                 535                 540

Ala Arg His Arg Thr Pro His His Gln Arg Glu Asp Pro Ala His Arg
545                 550                 555                 560

His Ala Gly Thr Val Pro Arg Gly Arg His Asp Arg Ala Ala Arg Arg
                565                 570                 575

Ala Gly Ala Arg Ala Ala Arg Thr Gly Gly Gly Ala Ala Val Arg Ala
            580                 585                 590

Pro Val His Thr Gly Thr Gly Ala Gly Arg Glu Ala Ala Leu Asp Ala
            595                 600                 605

Phe Leu Thr Asp Ala Gly Pro Asp Gly Ala Gly Asp Val Ala Arg
            610                 615                 620

Arg Val Ala Gly Glu Asp Ala Ala Glu Glu Phe Pro Ala Thr Leu Val
625                 630                 635                 640

Ala Arg Leu Asp Ala Phe Gly Leu Pro Ala Tyr Tyr Val Pro Ala Glu
                645                 650                 655

Trp Gly Gly Ala Gly Ala Asp His Glu Val Leu Leu Arg Leu Trp Arg
            660                 665                 670

Thr Val Ala Arg Arg Asp Leu Ser Ala Ala Val Ala His Gly Lys Thr
            675                 680                 685

Tyr Leu Gly Ala Ala Ser Val Trp Cys Ala Gly Asp Ala Ala Gln Ala
            690                 695                 700

Thr Ala Thr Ala Asp Ala Val Leu Ala Gly Glu Pro Val Ala Trp Ala
705                 710                 715                 720

Leu Ser Glu Pro Asp His Gly Ala Asp Leu Leu Asn Gly Glu Leu Thr
                725                 730                 735

Ala Thr Ala Gln Asp Gly Gly Arg Leu Asp Gly Val Lys Trp Pro
            740                 745                 750

Val Asn Asn Ala Thr Arg Ala Arg Leu Leu Thr Val Leu Ala Arg Thr
            755                 760                 765

Gly Ala Ala Gly Ser Gly Arg Gly Gln Ser Leu Phe Leu Val Asp Lys
```

```
                770              775              780
Ser Ala Leu Ala Pro Gly Ser Trp His Val Leu Pro Lys Glu Pro Thr
785              790              795              800

His Gly Ile Arg Gly Ile Asp Ile Ser Gly Ile Ala Phe Glu Gly Ala
            805              810              815

Val Pro Ala Pro Gly Ala Leu Phe Gly Arg Glu Gly Gly Gly Ala Glu
            820              825              830

Thr Val Leu Arg Ala Leu Gln Leu Thr Arg Thr Met Cys Ala Ala Leu
            835              840              845

Ser Leu Gly Ala Gly Glu His Ala Leu Arg Ile Thr Ala Ala Phe Ala
        850              855              860

Ala Glu Arg Ile Ile Gln Arg Pro Leu Leu Asp Arg Ala His Pro
865              870              875              880

Arg Ala Ile Leu Gly Arg Cys Ala Ala Leu Thr Ala Ala Glu Ser
                885              890              895

Ala Ala Leu Val Gly Ser Arg Ala Ile His Thr Leu Thr Gly Glu Met
            900              905              910

Ser Val Val Ser Ala Val Val Lys Ser Val Ala Pro Ala Leu Thr Asp
        915              920              925

Ala Val Ile Ala Glu Leu Ala Glu Leu Leu Gly Ala Arg Ser Phe Leu
        930              935              940

Thr Gly Val Tyr Ala His Gly Ala Phe Gln Lys Ile Trp Arg Asp His
945              950              955              960

Gln Ile Val Ser Val Phe Asp Gly Ser Thr Pro Val Asn Arg Ala Ala
            965              970              975

Leu Val Gln Gln Phe Pro Arg Leu Val Arg Glu Tyr Arg Ala Gly Thr
            980              985              990

Val Asp Glu Lys Gly Leu Ala Gly Ala Ala Ala Val Gly Glu Pro Ala
        995              1000             1005

Gly Pro Leu Asp Arg Gly Ala Leu Thr Leu Leu Ser Arg Arg Gly
    1010             1015             1020

Cys Ser Val Val Gln Ser Leu Pro Ala Leu Ser Arg Ala Leu Ala
    1025             1030             1035

Gly Glu Ala Ala Pro Glu Gly Leu Val Ala His Ala Val Ala Val
    1040             1045             1050

Ala Ala Ala Ala Gly Glu Val His Ala Arg Met Ala Ala Val Ala
    1055             1060             1065

Pro Ala Ala His Pro Pro Met Ser Ala Tyr Glu Thr Ala Ala Ala
    1070             1075             1080

Tyr Glu Leu Cys Tyr Ala Ala Ala Ala Cys Leu His Thr Trp Ser
    1085             1090             1095

Ala Gly Arg His Ser Arg Arg Gly Glu Pro Leu Trp Glu Asp Gly
    1100             1105             1110

Leu Trp Ala Arg Ala Ala Leu Arg Ala Leu Arg Ala Arg Leu Ala
    1115             1120             1125

Thr Thr Leu Arg Thr Pro Ala Pro Ser Ala Ala Pro Gly Asp Asp
    1130             1135             1140

Gly Leu Asp Gly Leu Leu Ala Glu His Val Ala Arg Ala Ala Arg
    1145             1150             1155

Asp Gly Ala Pro Val Thr Pro Phe Gly Ala Pro Leu Thr Gly Ser
    1160             1165             1170

Gln Asp Gly Arg
    1175
```

<210> SEQ ID NO 46
<211> LENGTH: 71
<212> TYPE: PRT
<213> ORGANISM: Streptomyces fungicidicus

<400> SEQUENCE: 46

Met Pro Asn Pro Phe Glu Asp Pro Asp Ala Ser Tyr Leu Val Leu Val
1               5                   10                  15

Asn Asp Glu Gly Gln His Ser Leu Trp Pro Val Phe Ala Lys Val Pro
            20                  25                  30

Asp Gly Trp Thr Ser Val Phe Gly Glu Ala Gly Arg Gln Asp Cys Leu
        35                  40                  45

Asp Tyr Ile Glu Lys Asn Trp Thr Asp Met Arg Pro Lys Ser Leu Ile
    50                  55                  60

Glu Ala Met Glu Asn Gln Arg
65                  70

<210> SEQ ID NO 47
<211> LENGTH: 245
<212> TYPE: PRT
<213> ORGANISM: Streptomyces fungicidicus

<400> SEQUENCE: 47

Met Val Met Pro Val His Asp Val Asn Pro Thr Arg Arg Thr Pro Trp
1               5                   10                  15

Val Thr Tyr Ala Leu Leu Ala Ala Asn Phe Val Val Phe Leu Ala Phe
            20                  25                  30

Thr Pro Gly Val Ile Gly Ser Leu Thr Gly Gly Ser Ser Leu Ala Asp
        35                  40                  45

Leu Cys His Leu Gln Ala Phe Leu Asp Arg Tyr Ala Val Val Pro Gln
    50                  55                  60

Glu Leu Ile His His Arg Met Pro Asn Leu Val Pro Thr Gly Ala Thr
65                  70                  75                  80

Gly Val Gly Pro Gln Gly Pro Gly Cys Val Val Asp Arg Pro Gly Tyr
                85                  90                  95

Glu Lys Ser Pro Glu Leu Ser Val Leu Thr Ala Met Phe Leu His Gly
            100                 105                 110

Gly Trp Leu His Leu Leu Gly Asn Met Leu Phe Leu Trp Ile Phe Gly
        115                 120                 125

Asn Asn Val Ala Asp Arg Met Gly His Val Arg Phe Leu Leu Phe Tyr
130                 135                 140

Leu Val Cys Gly Tyr Ala Ala Ala Tyr Gly Phe Ala Val Leu Asn Ala
145                 150                 155                 160

Gly Ser Gly Glu Pro Leu Ile Gly Ala Ser Gly Ala Val Ala Gly Val
                165                 170                 175

Leu Gly Ala Tyr Leu Val Leu Tyr Pro Arg Ala Arg Val Trp Val Leu
            180                 185                 190

Val Pro Phe Leu Ile Phe Leu Pro Leu Arg Leu Pro Ala Trp Ile Val
        195                 200                 205

Leu Gly Met Trp Phe Val Leu Gln Ala Val Tyr Ser Ser Gly Gln Gly
    210                 215                 220

Val Thr Asp Ala Gly Thr Val Ala Tyr Leu Gly Ala Arg Val Arg Leu
225                 230                 235                 240

Arg Gly Gly Ala Cys
                245

```
<210> SEQ ID NO 48
<211> LENGTH: 118
<212> TYPE: PRT
<213> ORGANISM: Streptomyces fungicidicus

<400> SEQUENCE: 48

Met Arg Arg Ala Pro Arg Gly Pro Gln Pro Met Ala His Arg Leu Leu
1               5                   10                  15

Gln Arg His Arg Pro Pro His Leu Gly Gly Glu Pro Pro Arg Leu Leu
            20                  25                  30

Ala Glu Pro Gly Asp Val Leu Pro Gly Glu Ala His His Glu Arg Glu
        35                  40                  45

Leu Gly Leu Ala Val Gly Gln Arg Val His Arg Gly Gly His Ser Val
    50                  55                  60

Val His Arg Leu Phe Leu Thr Ser Asp Pro Ala Ala Pro Phe Pro Ala
65                  70                  75                  80

Pro Arg Ala Val Ala Glu Ser Tyr Ala Arg Pro Tyr Gly Gly Val Gln
                85                  90                  95

Arg Arg Arg Gly Phe Thr Ala Gly Arg Pro Gly Thr Ser Gly Thr Trp
            100                 105                 110

Ser Cys Pro Ser Met Thr
        115

<210> SEQ ID NO 49
<211> LENGTH: 116000
<212> TYPE: DNA
<213> ORGANISM: Streptomyces fungicidicus

<400> SEQUENCE: 49
gccccgcagg gcatgttcga ggacctcggc ctgaagtacg tcggcccgat ggacggccgc      60
gacatcgagg ccctggagtc cgccctgacc cgcgccaagc ggttcggcgg cccggtcatc     120
gtgcactgcc tcaccgagaa gggccgcggc taccagcccg ccctccagga cgaggccgac     180
cgcttccacg cggtcggcaa gatccatccc gacacgggcc tgccgatcgc cagctccggc     240
gccgactgga cctccgtctt cggcgaggag atggtgaagc tcggcgagga gcgcgacgac     300
gtcgtcgcca tcaccgccgc catgctccag ccggtcggcc tcgacaggtt cgccaagcgc     360
ttcccggacc gggtctacga cgtcggcatc gccgagcagc acggcgccgt ctccgccgcc     420
ggcctggcgc acgccggggt gcaccccgtc ttcgccgtct acgccacctt cctgaaccgc     480
gccttcgacc aggtgctgat ggacgtggcc ctgcacaggt gcggcgtgac gttcgtgctc     540
gaccgggccg gggtcaccgg caccgacggc gcctcccaca acggcatgtg ggacatgtcg     600
atcctccagg tcgtccccgg actgcggctc gccgcccccgc gcgacgccga ccaggtgcgc     660
gcccagctcc gggaggccgt cgccgtcgag gacgcgccca ccgtggtgcg cttctccaag     720
ggcgccgtcg gccccgccgt acccgccgtg ggccgcgtcg gcggcatgga cgtgctgcgc     780
gagcccggca ccgacacccc ggacgtgctg ctggtctccg tgggcgcgct cgccccgatg     840
tgcctggaga tcgccgggct gctcgaccgg cagggcatct ccaccaccgt cgtcgacccc     900
cgctgggtca gcccgtcga cgaggcgatg gccccgctcg ccgagaagca ccgggtcgtc     960
gtcaccgtcg aggacaactc ccgcgtcggc ggcgtcggct ccacgatcgc ccaggcgctg    1020
cgcgacgccg cgtcgacgt gccgctgcgc gacttcggca tcccgccgcg cttcctcgac    1080
cacgcctcgc gcgccgaggt catggcggag atcgggctga ccgcccccga catcgcccgc    1140
caggtcaccg gcctggtcgc caagctcgac ggacggtacg agcggtccgc cgccgacgcc    1200
atcgactcgg tggagccggc ccgcgactga cgccgtcgac gacgcgtcgc ccggatgggc    1260
```

```
cgcgcgcacc accccttcgcg gtggcgcgcg cggcccgttt gcgtgaaggc gcccacgccg   1320
gggcatacga gctacgcccc ctctcgatca tgtcgaggac gacaagcgtg ggaggaaacc   1380
gtgacaagcc ccctcttccg gacgaagaag gtcgaacagt ccatccgtga cacggaggaa   1440
cccgagcacg cgctcaagaa atccctctcc gcgctggacc tgaccgtctt cggcgtcggt   1500
gtcatcatcg gcaccggcat cttcgtcctc accggcacgg tcgccaagga caacgccggg   1560
cccgccacgg cgctggcgtt cgtggtggcc ggcgtcgtct gcgcgctcgc cgcgctctgc   1620
tacgccgagt tcgcctccac cgtcccggtg gcgggctccg cgtacacgtt ctcctacgcc   1680
tccctgggcg agctgccggc ctggatcatc ggctgggacc tggtcctgga gttcgccctg   1740
ggcacggcgg tggtggccgt cggctggtcg ggctacatcc agtcgctcct gtccaacgcg   1800
ggctgggaga tgcccgccgc gctgggcagc cgcgagggcg ccgacgtctt cgggttcgac   1860
atcctcgccg ccgccctggt gctggtgctc acgggcatcc tcgtcctcgg catgaagctg   1920
tccgcccgcg tcacctcggt cgtcgtcgcc atcaaggtga ccgtggtcct cgtggtgatc   1980
gtcgcgggag ccttcttcat caccgccgac aactacgacc cgttcatccc gaagtccgag   2040
cccgtccccg cgggcgacag cctcgcctcc ccgctcatcc agctgatgtt cggctgggcc   2100
ccggccaact tcggcgtgat gggcatcttc accgccgcct cggtggtgtt cttcgccttc   2160
atcggcttcg acatcgtcgc cacggccgcg gaggagacca agaacccgca gcgcgacatg   2220
ccgcgcggca tcctcggctc cctgctgatc tgcaccgtgc tgtacgtcct ggtgtcgctc   2280
gtcgtcaccg gtatgcagca ctactccgag ctgagcgtgg acgccccgct cgcggacgcc   2340
ttcaaggcca ccggacatcc ctggttcgcg ggcttcatca gcttcggcgc cgccgtcggc   2400
ctgaccacgg tctgcatgat cctgctgctc ggccagaccc gggtcttctt cgcgatgagc   2460
cgcgacgggc tgctgccccg gttcttctcc cgggtccacc ccggttccg gacgccgtac   2520 cggccgacga tcctgctcgg cgtcgccatc gcgatcctcg ccggcttcac cccgctgaac   2580
gagctcgcgg cgctggtgaa catcggcacc ctgttcgcct tcgtgatcgt cgcgatcagc   2640
gtgatcatcc tccgcaggac ccggcccgac ctgccccgcg ccttccgcac gccctgggtg   2700
cccgtgctgc cgatcgtctc ggtcgccgcg tccctgtggc tgatgctgaa cctgccggcc   2760
gagacctggg tccgcttcgg catctggatg gcggtcggcg tcgtcgtcta cttcctgtac   2820
agccgcaaac acagccgtct ggccgaggag cgcggcgggg aacggacgtc gtcctgaggc   2880
cggcgcctcc cggcgctacc cgtcccgccg cggcgcccag gcgccgcccg cgggccgcac   2940
cgcgcgcggg ccggtgacgt cagcgcccag ggacgtcacc cggcggcgca gctcgcggtc   3000
ggccgtgacc accaggaccg ggcggtcgcc cgcctccgcc accaggtcga ccatgcggtc   3060
gtcgccgctg cccggggccg ggtccacccg gacaccgggg accgactcca ccccgcgggc   3120
cgccccctcg gtcaccagga cgatctccac cgggcccggg tgaccggca cgccctccgc   3180 ggccagccgg tcgcgcagcc gttccgcggc gccccggcgg tcccgccacc atccgtcggg   3240
caccgacccg accacgttgg cggcgtcgac gatcacgagc aggccggtgt catccatggc   3300
gtcagggtcc cacgcggcgc cccggccgtc cgggtcgcgg gggtgcgacc gcgcgcgggg   3360
gaggacgccc gggaacacat gaacgatcga catatgatgt gtcgagtttc agcgttcccg   3420
cgtcggtgac gcggcgggcc gcaggaaggg gcacctggcg atgcggagaa ggtcggcggg   3480
ccccgtgggc gcctccgtca aggacggacg tgccgccggg gagcaccggg aggccgcgtc   3540
cggggccgcc cacggtgact ggctcacccg cggcaaggac ggccggctga cgctgtacgt   3600
ccccaccgac ggcggtctgc tgcgctggac ggagaccgcc gtgggtggcc ccggctggag   3660
```

```
cggtccgcac ttcgtcccgg tggccgggct gacgcacctg gcggtggctc agggagccaa   3720
cggctacgtc cacttcctcg gccgcaggga gcgcgagggc gccgactcca cgccgggcgt   3780
ggacatcgtg cacgcgatcc agtaccagac cggactcgcc ttcagcgact ggcggtccct   3840
cggcaacccg caccgggtcc cggaggagcc cggaccgctc gccgtgccgg tcggggcggt   3900
cgcccgggac ggcaccgtgc acgtgttcgt gcggggcgcg cacggagggc tgatgctgcg   3960
gcgcgaggcc ccgaacggca agtggaaggc gtgggaggac ctgggcggcg gcggcgccgg   4020
cgcccagccc gcggcgctcg cgctcaccga cgggcggatc gaggtctgcg tggccgccga   4080
gacgggcgtg ctggcgtgga gccagtccaa gcccggcggc gacttcaccg gccccggggg   4140
tttctcgctg cgccccgtgc cgggcacggt cgcggccctg gagaccggtc cgggccgggc   4200
cacgttcttc tggacggacg ccgagagcgg cggtgcggcg gcctggcggg cggggcgtg    4260
gcccgtcgcg ctgggcggta ccccggccga gcggccgtgc gcggtgctcc gcacgtcgct   4320
ggacggctac gactgtgtcg tcctcgccta ccgtgaccag gacggcacgg ccgtgctcgg   4380
catgggcggc acgagaaacg aggccgccgg cttctggtgg tacgcgctga ccgagtcctg   4440
ccagggcgct ccgccctggg ccctggacgg gcggggccgc gtggtgatgg cgctgatcgg   4500
cgccgacggc aggcccaggg tcgcccgcca ggaggacggc gacggcctct cgctcacccg   4560
gtgggacgtc ctcgggggct gagcgcgccg tcgccgtgcc ggaggtcagc cgcccgtcgc   4620
gggcgacttc ttcgcggact cggggatctc cgcgtcggag cggatcgcct ccacagctg    4680
gtcggcctgc gggtgcgcgg ccaccacccg gttcgggtcg gtcttgtcgt acgccacggg   4740
gagcatgacg gtctccatgg acgccgggtc gaccccgttc atgctgcgcg cgaagtccgc   4800
caggctggtc agcgaggcca gctcggagtc ggtggtcagg gccgaggtca gggtgtcggc   4860
gatcttgtac gtcttggtgg ggctgccgaa caggtcctgc ttcttcacct cgctcagcag   4920
ggcgatcatg aactgctgct ggaggcctat gcggcccagg tcgctgccgt cgccgacgcc   4980
gtgccgggtc cggacgaacg ccagggagtc ggtgccgtcc agcttgtgcg tcccggcgct   5040
caggtccagg ccgctcgtgc tgtccttgat gggctcgtcg acggtgaccg tgacgccgcc   5100
gatcgcgtcg accagcccct tgaagccggc gaagtcgatc tccatgtagt ggtccatgcg   5160
gacgccggac atcttctcca cggtcttgac cacgcaggcc gggccggccg tcgagtacac   5220
ggagttgaac atgacgcgct cggcctgcgg aagggcggag ccgtccgcct tggtgcactc   5280
cgggcgggtg acgagggtgt cgcgcgggat gctcacggcg acggcctgcc ggcggccctc   5340
cgggatgtgc atgaccagcg cggtgtccga ccgggcgccc gccaccttgc cggtgcccag   5400
gccggcgttg tctccggcac gcgagtccga gccgaggacc agcacgttct gtccggaggt   5460
cggcagcttc tcggggcggt cctcgccgag ggcctcgtcc aggtcgaccc cgtcgatgtt   5520
cccgttcagg tcgctgtaga gccagtagcc ggtgcccccc gcggcgagca cgacggccag   5580
caggacagc aggacgatgc gtcccagcg ccggcgcttc ggccggcggc gtccgccgcc     5640
ggactcgggc tgcgcacgcc gggactccgt ggtggcgctg tgcgtcatgg ttcttgggtt   5700
cctctcctca cgggctccgc gcggcggagt ggggcccggg tggggggaga ccggtccaca   5760
gatgcgttca cgtcagtggg agaactatag gcagcggtcc acggcacatc ctgcacgggt   5820
ggaattagca cggctcagcg atgaatgcca catgaaccga ccttgaccac tcttaaggct   5880
ggaataagat gtgtcgggcc tgtgaccgtc gtggagggg gctttcacga ggtcggaggt    5940
gctggtgggg cggagcggcc ggaagccgcg aagcctcaca taaggggtgg gcgtccggtg   6000
tggacgattt ggtgtcccgg cgggcgaaat gtcttggtag gagtacgagt tggtggttca   6060
```

```
gccgcgtctg agtattgtcg tgcccttcca ggacgtcgag gtgtacctcg ccgagtgtct   6120
ggaatcgatc gcgcggcagt cgttccgcga cttcgaggtc atcctggtcg acgacggctc   6180
caccgacggg tccgtgcgga tcgcggcgga cttctgcgcc gccgaccgcc gtttccggct   6240
ggtccgccag cacgcccacg gaccgggcca cgcgcgcaac accggactgc ggaacacgca   6300
ccccgcggcg gagttcctcg ccttcgtgga cggtgacgac gtcatcccg agtacgccta    6360 cgaactcctg gtgcgcacgc tcgaggagtc cgagtcggac ttcgtctcgg caacgtgca    6420 gatgatgaac tccaccaaga agtggcagtc accgctgcac aagggcccca tgcagaagaa   6480
ccggcgcggg acgcacatca cgaagttcga cgcgctgatc tacgaccgca ccgtctggaa   6540
caaactcttc cggcgctcct tctggaacca gaactccatc aggttccccg aaggcgtgct   6600
gtacgaggac tcgtgggtca acatgtacgc ccacttccgc gccgccaagg tcgacgtcat   6660 cacgacgtc gtctatttct ggcgccgccg ggacggcgga gcggcgccct ccatcaccca    6720
gcgccactcc gaactgtcga acctccggga ccgggtcgcg gccgtgcagt cggtgagccg   6780
cttcctcggc gaccggcgct cgcgtgagta cgcggacagc aagcggaagt acgatctcgc   6840
ctgcctgaag tccgacctcc tgctccatct gaaggtgctc ccggacgcgg acgaggagta   6900
ccagcacgcc ttcatgaagt gggccaacga gttcctcgac gagacggatc tcaccatcat   6960
cgacgagctg cccgcggact cccgcgtcaa gtggctcctg gtgcgcgagg agcggctggc   7020
cgaactgctc gaggtcatcg agttcgagcg ccgcggcggt cccatgcccg tgcagcggcg   7080
tttccggcgc tacctgaact acccgtacct cgggaccgg ggggtgggcc tcgacaagaa    7140
ggcctaccgg ctggacaagg agctctcgct gcacggctcg ctgtccggag cccgctggag   7200
caccggctcc gacctgctca ccctcaccgg aacggcgtac gtccgcttca tcaacgtgca   7260
caagaagcac atgtcggtga aggcgatcgc cctgcggaac aagaagcagg ggcgcatgca   7320
gatcacgacg gcgaagaccg tctacgcgcc gcaggcgacc gaggacagta agcagaatcg   7380
ttactgctat gactgggccg gcttcgaggc gcgcatcgac accacccgcc tcaagcgcaa   7440
gggccagtgg gtcgagggca cctgggacgt ggccgccggt gtcctcagcc ggggactgtt   7500
ccgctaccgg ggcatcgacc ggggcggcgc gggcagcgcc gccaacccgc cctaccgcta   7560
cgtcgacaag aacacccgca tcctcccggt cttcctccag ggcaaactca agctgcgcgt   7620
cgagatcgtg cgctgccgga tcaccaagca ccgtgtcgtc ggcgaccagc tggagctgcg   7680
cggcgtctac ctcggcccca aggtcccgga gtggggcaag ctccgcgtca ccagcatgag   7740
cggcgcggga cgccacgacg cacgcgtcca cttcaccccg ggcggtgagg gctggtgcac   7800
cttctccgcc aagctccccc tgagccgtct ggtgccaag tcccgcgtcc aggcgggaac    7860
cgacgcggac gtcccgcagt cctggggcat gggcagcaac ggctggaaga ccaccttcca   7920
cgtcgagggc cgcaagtcgg ccatctatcc cgtgatggcg gaggagaccc cggacgggca   7980
ctactccatg ccgtcctccc tgcagacccc ggagcgcgac cgggagatcg tcgtgcaccg   8040
caacggctcc ggctatctcg tgctcttcga acgagcgacc ctgcccctgg cgacccggtg   8100
cgactggcag gaggacggct cgctgtggat ccagggccgt tacctggccg cggaccagct   8160
gaccccggag cagtaccgct ccgcccacct cgtggtgcgc tcgcgcgccc acggcgcgga   8220
acgctccgta ccgctcacct gggacgggca cgagttccgc tgcgtcctgg ccccgccgc    8280 gatgcggacc ctggccgggg acatcccgct ggcggccgga cggtgggact tcttcctgcg   8340
ccgccaggac ctgtcggccg tggccgcgca ggaccggctc gaagacctca tggtgaagat   8400
cgagcaggat ctcatcgagg cgttcccgca ggagtacgag agaaacgaac gccgctacga   8460
```

```
gacgcaggcc gaggcctacg accggctgtc gctgctcgtc cactcggcga tgcccgacca   8520
cgcccgcggc ccctaccggc agaagctcct gaggaccaag gcctacccg acgcccggcg    8580 ccggccggtg cgtgacgccg tgctgttcga cgccttcaag ggcacccagt actcggacag   8640 ccccgcgcc ctgcacgagg aactcgtgcg ccgccgcacc ggcctggaac acctctgggt    8700
ggtgcgcgac gaccaggtgc aggtgccgcc cacggcgacg cccgtccgca tgtggtcgcc   8760
ggagtggtac gaggccctcg ccaccagccg ctacgtcgtc gccaacaacc acctcccgga   8820
ctggttcaag aagcgggacg gacaggtcgt cgtgcagacc tggcacggca cgccgctgaa   8880
gaagatcggc cacgacatcg agtccatcca cttcgccgac cagcgctatc tggaacgcgt   8940
cgagaaggag gtgcagaact gggacatgct ggtgtcgccc aacagcttct ccaccccgat   9000
cctcaagcgc gccttcggct tccccggcga gatggtggag agcggctacc gcgcaacga    9060 catcctgcgc cggccggaca ccggggcccg ggagcaggag atccgccgca gcatcgggct   9120
gccggagggc aagcgggtgg tgctgtacgc gccgacctgg cgcgacgacc agttctacgc   9180
gcccggcaag tacaagctgg acttccggat cgacctggcc gccgcgcgtg cgcagctcgg   9240
ccccgaccac gtcctcatgg tgcgccgcca ccccaacgtc gtggaccgg tgccgggcgc    9300 cggcgacgga ttcgtcttcg acgtgtccga ctacccggac atggccgacc tctcgctgat   9360
caccgacgtg atgatcaccg actactcctc cctgatgttc gactacgtga acaccggggcg   9420 gcccatcctg ttcttcacct acgacctgga ccactaccgg acaccctgc gcgggttcta    9480 cttcgacttc gagggcagcg cgccgggccc cctcctctac acgtccgagg aactggtggc   9540
ggcgatccgt gacatcgacg ccatccagga cctctacgcc gagcggtacc gctggttcca   9600
gcgggagttc tgcgacctgg acgacggtta cgccgcggcc cggctcgccg accggatgct   9660
ggtcgcgggc ggcgaccctcg ccccgggca ggcgcacgcg ccggccgtcg gcgcggtcga    9720
cacccggcac accggaaggc cgatgacccc cctccagtgg gggaactcgg agtggttcgc   9780 cggccccgc ccgccggcgg gtctcgtcga cgccgtgccc gcccagcccg ccccggcgta    9840
cgacgccgta ccgcagcacc aggcgggtcc gttcggccat accccgcccg ccggcgaccg   9900
cagctacgaa ggcgtgatcg cgtgacgccg ccgacccgc ccggcgcgag gtcccggcg    9960 tgccgcgcgg tgccggaagg ccccggcccc cgatgaccgc cgtgccgttc gccacgcggg  10020
cgccggccgc cgctgccggt ccgtcgtccg gcggccgccc gggcgcgtcc tcagccggtg  10080
ccggtgtcca cccggatcag cagcgcgcgg tggtcggaga ccccggtgtc gctcacccgg   10140
cacccgagca cgggcagccc ggtgaagagg tagtccagct tgtggtgcga cgtgcgtc    10200 ggccgggccg gccggagggg accggccgtc ccgtcgcact cccggtgcgt gccgtaaggc   10260
tggtcgggcc agacccggga gagcggttg cgctctcccg gcggatccac gttgaggtcg    10320
ccgccgtaga cggtgcgccg ctcgggcacc cgtccacca gggccttcag ctgtccggcg    10380
cggaactcgc ggtccggatg cgccagatcg ccgccgcgcg gggtcagatg cgcggtgcac   10440
accgtgaggt cgtgcgccgc gacgaacgcg cagagtattc cgcgctgcac cccgaccgcg  10500
ggctggggcg cgggcaccgc gcgcacggac gacagcggat acgccgacag cagggcgtag   10560
cccgcggagc cccggccggg cgcccccgca gcgcaccgcgg tgcggcgccc gtcacggccg   10620
cgccaggtgt aggccctgaa ctccgcgtgc cacgacgccc cgagggaggc gcgcaccgcc   10680
tcgacgtccg ccgcgcaggt ctcctgcagg aacagcaccc gggccccgga ttccgcggcg   10740
aggcgttccg tccggccgcg cttggcgtcc tcgccgcccg tgcctcgca gttccattcc    10800 ctgacccgc acatgttcca ggtcgccacg gtcagtgtcc ggtccccggt ggcggagcgg    10860
```

```
tccgctccat tgccgctccg ctcgtgggtc accacggcgg cgagcccgc gagggcggcg   10920 gccgccgtga cggcggcgag caggcgccgt ccgcgcgggc ggggcgaccg ggttcggttc   10980
ctgagcaccc ggccatcatg accgatccgc cgctgaccag ccaaaaccac ccggcgccag   11040
gcgccttccg gcaggtgtcc tcccctgcc cgcgcacccg ccgtcgtcc aagtacctct    11100 gagagtggag tccgtacatg tccaaggcac cctcgaacgg cggcagctg ctcaacggca   11160 tcgaagcctc gggaacgttc ccggtggagt accggttcac ccacgccaag agcggcaacc   11220
ggcacctcgt ggtggtcttc gccaacttct cggcacccga ggactacggc tggtcgaacg   11280
gcgtcttcga caacgtccgt gccaacatcc tgtggatccg tgaccggttc gacgggatga   11340
acgcctacta cctgtgccgg aacatggact tcggtctggc ggactcggtg cagaccctga   11400
tcgcgaacgt caccggggcg ctcgggctga cgccggacca agtcacgctc tggggcggct   11460
ccaagggcgg cagcgccgcg ctgtacttcg gcctgcggta cggctaccgg aacatcgtcg   11520
ccatcgtccc gcagttcctc atcggcgacg ccctggagaa cggcacccg aaggtctccg   11580 cgtacatgct cggcgaaggg gcgcaggcgc acaacgcgcg gatcctggac gcgctcctgc   11640
ccgacctggt gcgcgccaag gccaacccgg gcgccaacat ctacgtgctc tcctccccgc   11700
aggacgagca ttacgccgtg caggtcgagc cgttcctcgg catgttccac ggctacgaga   11760
acttcaattt cctgtacagc gagtcgccga ccatcacggg gcacgccacg cgacccggc    11820 ggaacgtccc ggcgctggtc ggcctgctca acctgctcgc cgacggctac gcccccccgg    11880
tgggcttcac ccgccacgcc gccgaggact tcgaccacga ccggtcggac atcaacgcct   11940
acctcgcctc gacctccaag gtccagggcg ccgacgcgtt cgcgccgccg gtggtgacca   12000
ccccgggctt caacagcgag gtcccgcgca ccggaccgtg gttcaccggg acggcccacg   12060
gagcggtgcg ggtgagcatg tggcgcaacg gcaagttcgt ggcgtcgccc caggtcgcgg   12120
ccgacggcac ctggtcctgg cagccgaccg ggccgtggga ggccgggaag cacatcgtca   12180
agatcttcgc ggtggacccg gcgggcttcc actccgcccg ggtcgagatc cccttcaccg   12240
tggtcgaccg ggatcccgtc cctgcccgc cggtcgtctc cgcaccggtg tccgggcagc    12300
agaccggagc ggcggtcggg ttccacggca gcgcgccggg agcgtcacag gtcggcttcc   12360
gggagaacgg cgtgctcctc ggcgcggtgg ccgtcgcgcc cgacggcacc tggggctggg   12420
accccggccg gccctggccc gagggcagc acctggtcga gatcgtcgcg gtcgacgcgt    12480
acggcatgga gtccgcgccc gccgccgccg gcttcaccgt gctcggccac gcggtgcccg   12540
ccggacactt cacgccgcgg tactgaccga cggcccagga cgacgacaca ccacgagtgg   12600
gaagcagaca tgccgaaaga gcgccgaca acacgcgagc tgatcaccgg gatcgacacc    12660
tccggcgcgt atcccgtcga gtaccggttc acgcacgcca agggggggcaa ccggcacctc   12720 gtcgtcgtgt tcgccaactt cgcggtcaag gacgactacg gctggtccaa cggcgtcctc   12780
aacccggtgc gggccaacat cctgtggatc cgtgaccggt tccgcgacat gaacagctac   12840
tacctgtgcg agggatgga cttctccctg gagcagtccg tgatcgggct catctccaag   12900
gtgatgaacg ccctggaact caccccgag caggtcacga tgtggggcgg ctcgaagggc   12960
ggcagcgccg cgctctactt cggcatgcgc tacggcttcg gcaacatcgt ctccatcgtg   13020
ccgcagttcc tcgtcggcac ctatgtgaag cgggtgcacc ccaaggttgc ccggttcatg   13080
ctgggcgagg cggtgccgga ggagaacgtc cgcgcggtcg acgcgctcat cccggacctg   13140
gcccgttcgg gcgtcgcccg gcactccaac atctatctgc tctcctcgcc gcaggacgag   13200
cagtaccagg agcaggtcga gcctttcctc ggactgttcc aggggtacga caacttcaac   13260
```

```
ttcgtgttca gcgagtcccc ccacatcacc cgtcactcgg acgtcacccg gcgcaacgtc   13320
cccttcctga tgggcctcgt gaacatgctc gccgacggga tgtccccgcg gctgggcctg   13380
gtgcgcaacg ggtacgagga gccggaccgc gacaggtccg ccatcgaggg cttcctggcg   13440
gccacttcgg cggagcggcc cagcgccatc ccgatgcccg tggtgacgca tccgcttccg   13500
cacatggaac tgcccacgga cggcgtgtac ttcacaggga cggcccccgg cgcggtgcgg   13560
gtgagcctgt gggagcacgg caagttcctg ggttcgccgt cggtgcgcc ggacggcacc    13620
tggtcctgga agcgggacaa gccgtggagc aagggcgacc atctggtcaa ggccgtcggc   13680
tgggacgcgg agaagcgccg caccaagggc accgtggtcc cgttcaccac ggtcgccggc   13740
gcgaacgccg ccgcgcccgg ggcaccggcc gccgcgcccc tggcgccggg gcagccgctg   13800
ccggcgccga cggtccacac gccggggggcg tacgagcaga tcaccggcac ggccgtgcgc   13860
ttcagcggct tcgcccccggg cgccgcccag gtgggattca gggcgggggg caccctcctt   13920
ggcacgagcc gggtcgcggc cgacggaacg tgggcctggg actccggctg gccctggcag   13980
gcgggcatgc acaccgtgga ggtgttcgcc gtggacgccg cgggatccga gtcgcccgtg   14040
gcgccggtgc ccttcgacgt catgcacgcc acggcgggcg cctcgccgtt cgcctactga   14100
ccggtcgcca cgcgcggaag ggctcctgga gatcgccggc gatctccagg agcccttccg   14160
cggtctacgg ggactaggcg ggcacgctcg ccgtgcccgg ctccaggaac cgcttcccgt   14220
tcacccgctc ggagacgccc tcgcggtcca ggtacggcgt gatgccgccc aggtggaagg   14280
gccagccggc gccggtgatc aggcacaggt cgatgtcctg ggcctcggcg acgacgccct   14340
cgtcgagcat gagcccgatc tcctgggcca ccgcgtccag gacgcgggcg cggacctgct   14400
cctcggtgag gacggtgtcg ccctgcttca ggagcgcggc gacctccggg tccagctcgg   14460
gcttgccgct gtcgtagagg tagaagccac gcttgccggc ctcgacgacc gccctgaggt   14520
tcggggagac cgtgaagcgc tccgggaacg ccctgttgag ggtctcggac acgtgcagac   14580
cgatcgcggg gccgaccagc tccagcagca ccagcgggga catcggcagg ccgagcggct   14640
cgacggcctt ctccgcgacc tcgaccgggg tgccctcgtc gatgacgttc tggatctcgc   14700
ccatgaagcg ggtcaggatg cggttcacga cgaacgccgg ggcgtccttg accaggaccg   14760
cggtcttctt cagcttcttg gcgacaccga acgccgtggc cagcgccgcg tcgtcggtcc   14820
gctcgccgcg gacgatctcc aggagcggca ggatcgcgac cgggttgaag aagtggaagc   14880
cgacgacccg ctcggggtgc ttcagcttcg acgccatctc ggagacggag agcgaggagg   14940
tgttggtggc gaggatcgcg tgcgccgggg cgaccgcctc gacctccgcg aacacctgct   15000
gcttgacgcc catctcctcg aagacggcct cgatacgaa gtcggcgtcc gcgaagccct    15060
cggccttgtc cagcacaccg gtgaccaggg ccttgaggcg gttggccttg tcctggttga   15120
tccggccctt gccgagcagc ttgtcgatct cggcgtggac gtagcccaca cccttgtcga   15180
tgcgcgcctg gtcgatgtcg gtcagcacga ccggcacctc gaggcggcgc aggaacagca   15240
gcgcgagctg ggaggccatc agaccggcgc cgaccacgcc caccttggtg accgggcggg   15300
ccagcgactt gtccggggcg ccggccggcc gcttgccgcg cttctgcacc aggttgaacg   15360
cgtagatgcc ggagcgcagt tcaccgccca tgatcaggtc ggcgagcgcc tggtcctcgg   15420
cgtcgtagcc ctgctggagg tcgccgttct tggcggcggc gatgatgtcc agggcgcggt   15480
aggcggccgc ggcggcgcgc tgcaccttgg agtcggcgat gaagcggccc ttggcgacgg   15540
cctggtccca ggcctcgccg cggtcgatca ccgggcgctc gatccggatc tcgtccttga   15600
ggacggccgc ggtccagatc agcgactgct ccaggaagtc cgcgccctcg aagatcgcgt   15660
```

```
ccgcgatgcc gagttcgaag acctgcgcgc ccttgagctg cttgttctgg ttgaggctgt   15720
tctcgatgat gaccgagacg gccttctcgg cgccgatcag gttcggcagc agcgtgcagc   15780
cgccccagcc ggggacgaga ccgaggaaga cctcggggag cgagaacgcc gggagggcgg   15840
ccgacaccgt gcggtaggtg cagtgcagac cgacctcgac gccaccgccc atcgccgcgc   15900
cgttgtagta cgcgaaggtc ggcacggcca gcgtcgacag ccgcttgaag acgtcgtggc   15960
cgcccttgcc gatggccagc gcgtcctcgt gccgcttcag cagctcgacg cccttgaggt   16020
cggcgccgac ggcgaagatg aacggcttgc cggtgacgcc gacgccgacg atctcgccgt   16080
ccgcggcctc cttctcgacc cggtcgatcg cggcgtcgat gttcgccagc gactgcgggc   16140
cgagcgtggt cggcttggtg tggtcgtggc cgttgtccag ggtgatgagc gcgaagcgcc   16200
cggcgcccag ggggaggtcg aagtggcgca cgtgcgcgct ggtgacgacc tcgccgggga   16260
acagctcggc cgcacccttc agaagctctg cggtggtgct cacttgtccc cctcgaagtg   16320
cgggttctcc cagatgaccg tcgcgcccat gccgaagccg acgcacatgg tggtgaggcc   16380
gtaacggacc tgcggctgct cctcgaactg gcgggccagc tgcgtcatca gacggacgcc   16440
ggaggaggcc agcgggtggc cgaacgcgat ggcgccgccg tactggttga cgcgcgcgtc   16500
gtcgtcggcg atgccgtagt gctccaggaa ggccagcacc tggacggcga aggcctcgtt   16560
gatctcgaac agaccgatgt cggagatgga cagccccgcc tgggcgaggg ccttctccgt   16620
ggccgggatc gggccgtagc ccatgacctc gggctccacg ccggcgaagg agtaggagac   16680
caggcgcatc ttgaccggga ggccgttctc gcgggcgaag tcctcgctcg cgatgaccga   16740
ggcggtggcg ccgtcgttca gaccggccgc gttgccggcg gtgacccggc cgtggacgcg   16800
gaaggggtc ttcaggccgg ccaggttctc caggtggtg cccgggcgca tcggctcgtc   16860
ggcggtgacc aggccccagc cggtctcacc ggcctcctcg ttggtgcggc gcaccgagac   16920
cgggaccagg tcggcctgga tcttgccgtt ggcgtaggcc ttgcggcct tctcctggga   16980
gcgcacggcg tactcgtcgg cgcgctgctt ggtgatcgag gggtagcggt cgtgcaggtt   17040
ctccgcggtc atgcccatga acagggcgga ctcgtcgacc agcttctcgg agacgaagcg   17100
cgggttgggg tcgacgccct cgcccatcgg gtggcggccc atgtgctcga cgccgcccgc   17160
gatggcgacg tcgtacgcgc cgaaggcgac ggagccggcg accgtggtga cggcggtcag   17220
ggcgccggcg cacatgcggt cgatggagta gcccgggacc gaggtgggca ggcccgcgag   17280
gatgccggcc gtgcggccga tggtcaggcc ctggtcgccg atctgcgtgg tcgcggcgac   17340
ggcgacctcg tcgatcttct tcgggtcgag accggggttg cggcgcagca gctcccggat   17400
cgccttcacg accaggtcgt cggcgcgggt ctcgtggtag atgcccttcg ggcccgcctt   17460
gccgaacggg gtacggacgc cgtcgacgaa gacgacgtcc ctgacggtac gaggcacgat   17520
ggctctcctc ccagggtgcg ggacgctgag cgcttgctta cgccatgcta cttatgagta   17580
acgtgactgc ccagtcccgg cccccgagc ggcgaacatc acacgtacgg cggcgcccgc   17640
caaacgccgg aggggctgga atcagccccc tccggcgttt gaggagcggg aaccctcac    17700
ggtggagccg tggagcctcg cggggtcagg accggggtcg gtaccgggtg cgaccccggc   17760
tgctcctccc cggtgatgac gccgaacagc gtgcgcgcca cctccgcccc gaacccgtgc   17820
acatcgtgac tcatcgcgga cagcgtcgga tgcgtcagcc ggcacagctg cgagtcgtcc   17880
cacgccagca gcgacacgtc gtccggcacc cgcagcccca tctccgccgc caccgacagc   17940
cccgccaccg ccatgatgtc gttgtcgtac acgatcgccg tgggccgttc ccccggcgcg   18000
gccgccagca gcgaacgcgt cgcccgcgcc cccgcgtccc ccgagaagtc cgtggccgtc   18060
```

```
tgccacgccc gcgcgggcgg ctccagcgcc cggaccgcct cgtcgaacgc cgccgtgcgg   18120
atcgaggtgt gcccgagcgc cgccgcgccg cccacccggg cgatccgccg gtgcccgagc   18180
gccgccagat accgcacggc ctccgtcacg gccgtggcgt cgtccgtcca cacggaggtg   18240
agcccgcccg tcagcgccgg gtgcccgacg gccaccgccg gcagcccgag ccgctccgcc   18300
accgccggac gggggtcgcc ggcccggaag tccaccagga tcgagccgcc gatctgccgc   18360
ccgcgccacc acgactccat cagcccgacc tcctcctccg ggctgcgcac cagccgcagc   18420
agcagcgagc aggaccgctc caccaggacg ctctccaccc cggagatgaa ctccatgtag   18480
aacggctcca ggccgagcag ccgggcgggc cggcagaccg cgagacccac cacgtccacc   18540
cgcgacccgg ccagcgtgcg cgcggttcgg ctcggcgccc accccagctc ccgcgccgcc   18600
cggaagatgc ggtcccgggt cgcctccgac agcccgggct tccggttgaa ggcgagggac   18660
acggcgccct tggacacgcc ggcgcgcgcg gcgacgtccc tgatggtgac gcgaggggtc   18720
ggcgttgccg tcatcgagtg ggctccacgc agtacagggc ggaacgggcg gtgtccgggt   18780
ccggagtctt ccaccccgc accccgatgg tcacctgttc cccggggagc agggtcacca   18840
gcccccggtc ggcccgcgcc ccggggtcca gccggtcggc ctggagcagc aggtcccgta   18900
cgagggtgcg ggccgtgacc gtgatcccgt ccggcgcgag ggcgacctcg aactccggcg   18960
gggggtaggg gatctcccgg tccggcgccg ggaagtgcca cgcccgcacc ccgtccgcgt   19020
cggcgaccag gaactccccg gggccgtccg gcagcagttc gaccgggacc tcgaccacgg   19080
ccaccgtccg cccccccggcg tccagcgccg gggccgcctc cgccgatcggg gcgccgtcga   19140 cggacatccg gcgcagccgc agcgttcccc gccagtcctc cgcggactgg ttgaccgccg   19200
ccaccaccag accgtcaccg tccgcgcgca cggtcagcag ccggtccgcg tacagccggc   19260
gcagctcgtg gtagagcggc ttctcccgcc cgtccccgtc gatcgcggcc cacgacgtca   19320
ccggccagca gtcgttgagc tgccagacca ccgtgcccgc gcacaccggc cagtgcgagc   19380
gccagtgctc gacaccggcc gccaccgcac gcgcctggtt gacctgcgtc agatagtgcc   19440
agcggtcgaa gtcgccctcc ggcacggcga agtggcgggc gaggccgcgc tccagcttgc   19500
cgttgccgtc ctccgccttc tggtggtgca gcatgccggg ggagtccggc gcgggtcct   19560 cccccgggcag cgcccgccgc agcgtggcgt gcgcgggagg cgcctgccag ccgaactcgg   19620
ccacgaagcg cgggacgtcg cgccggtagt cggcgtagtc ggcgcggttc cacacctccc   19680
aggagtggtg ggtgccgtgc gccggatcgt tggggtggtg ccgccaggaa ccggaccagg   19740
gactgcccgc cgtgtacggc cgccgtcgggt ccagctccgc gaccaccgcg gcaggacgc   19800 cgaggtagta gccctcgccc caggagtccc cggcgagccc ctgctcccag tcccagtccc   19860
ggaaccccca caggttctcg ttgttgccgt tccacagcac cagggagggg tgcggcatca   19920
gccgtacgac gttctcccgg gcctccgcct ccacctcccc gcgcagcggc tgctcctcgg   19980
ggtaggcggc gcacgcgaac gggaagtcct gccagaccag cagccccaac tcgtcgcagg   20040
cgtcgtagaa gtcctcgtcc tcgtagatcc cgccgcccca gacccggacc aggtccaccc   20100
ccgcgccggc cgcctgctcc agccggtgcc ggtagcgctc ccgggtgatc cggacgggga   20160
acacgtcgtc cggatccag ttgacgcccc gcgcgaacag ccgctcaccg ttgacgacca   20220
gggtgaaccc ggtgccgtgc gcgtcggccg aggtgtccaa ctcaaccgtc cggaacccgg   20280
tcctgcgccg ccaggcgtcc agcgcctcgt caccgtggga caacgtcagc tcgacgtcgt   20340
acagcggctg ttcgccgtat ccgcgcggcc accacaggcg gacgtccggc acccggagcc   20400
gcacggtccc ggccgtccca tcgacccgcg cccggggcgcg cacgcccccg gcgctcgcct   20460
```

```
ccagggtgag cggtgcctcg acccgggagc gctccacgtc gaccgccagc tcgatctgcc    20520
ccaccccgtc ctcgacggtg accagcgggc gcacccgggc gatccgcgcc gtcgaccagc    20580
gctccagccg caccggccgc cagatcccgg ccgtcaccag cgtcggcccc cagtcccagc    20640
cgaacgagca ggccatcttc cgcaggtact ggtacggctc ggcgtacgct ccggggcgct    20700
cgcccagcct gccgcgcacc gcctccgcct cggcgtacgc ggaggcgaac cgcaccgtga    20760
gccggccgct cagtcccgtc acgtcgaagc ggtacgagcg gtgcatgttc cgcgtccggc    20820
ccagtggccg gccgtcgagc aggatctcgg cgacggtgtc gagaccgtcg aagacgaggt    20880
ccgtctgctc gtgcgggccc gtcccggcgg tcagctccgt ctcgtacgtc cactcccgcc    20940
ggcccaccca ggccacctcg gtctcgttgc ggccgaggaa cggatcgggg atcagcccgg    21000
ccgccagcag atcggtgtgc acacacccccg gcaccgaggc ggggagggcg tccccgtgc    21060 cgtccgggtg tcgcaggatc catccctcgg tgagcggtgt gacctgacgc atgcacactc    21120
cctaaaccgg ttgagccttc tctgaagagt ggtctggcat cgttggcgcg attgcgactt    21180
taccggttca gttcagggct gccagagtgc cgaatcagcc atcccactcg tgctcgtccg    21240
tcccgtgaac ggagccgtga tgcatctgaa ccgccgtacg acactcaccg gatcgctcgc    21300
cctgctcgcc ctcctggcct ccgcctgcac gggcacgggg ggttcctcga agggcgcgga    21360
cgccaaggct cccgacgacc cgtcaaaggt caaggggtcc ctcacggtcc tcacccaccg    21420
gaccgatctg gtgcaggacg gacgatgaa gaagtacgcc gccgagttca acgagaccta    21480 tccccggggtg aaggtggagt cgacggcct caccgactac gagggcgagg tcaagatccg    21540
tatgaacacg gagaactacg gcgacgtcct catgatcccg gcggtcgtcg agaagaagga    21600
ctacccgaag ttcttcgcct ccctgggcac caaggccgaa cgcgccgcca gtaccggtt    21660 caccgactac tccaccgtcg acggcaaggt ctacgggcag agcccgtcg gcgtcgtccc    21720 cgggttcatc tacaacaagc gggtgtggag cgaggccggc gtcaccgact ggcccaccac    21780
ccccgccgag ttcctggacg acctgaaggc gatccggtcg aagaccgacg cggtgccgta    21840
ctacaccaac ttcaaggaca tgtggccgct gacccagtgg accaacgtca acggctccgt    21900
cggctgcgac ccgcacgcca ccacgaagct cgccgagggc gacccgtggg ccgaggggc    21960 cgacctgcgc gtgggcgaca ccctgctcca cgacatcgtg cgcggcggac tcgccgagaa    22020
ggacccgacc accaccaact gggagggctc caagcccaag ctggccaagg gcgagatcgc    22080
caccatgtgg ctgggctcct gggccgtcgt gcagatgcgg gacgcggcga agcaggccgg    22140
cgccgacccc gccgacatcg gcttcatgcc cttccccgca cagcgggacg gcacgttctg    22200
cgcggtgacc tccccggact accagcaggc ggtcaacgtc aactccgaca caaggaggc    22260 cgcccgcgcc tggatcgact ggttcaccga caagtccggc tacgccgagg ccaacctcgc    22320
cctatccccc ctgaaggacg ccccgctgcc cgccgtcctc gagccctacg agaaggccgg    22380
cgtgaagctc ctggacctcg aggacagcaa gggcgccgag gtgaagtccc tcgacaaccg    22440
ctccgaggtc ggcatctaca gcccgactta ccgccaggaa tcgtcgacc tcgcccgcgg    22500 cgcccgcaag gcggcctgg acgactacct cggcggcctc ggcgagcgct gggccgaggc    22560
gcgcagcgcg ctgggggcct gatgacggac accacccgca aggcggcgcg gccggttccc    22620
ccggccgcgc ccgccgggcc gggccgcgcg gcgccggccc cgccgcgcac ccggctgtcg    22680
cgccgcctca ccccgtggct gttcctggcc gcaccgctgg ccctgctcct gaccttcacc    22740
tacgcgcccg atcgccaaca tggtcgcgta cagcttcacc gactgggacg gcgtgagccc    22800
ggagctgaac tggacgggca ccgggaacta caccgaactc ctcacccgct ccgagctgtt    22860
```

-continued

```
cgaggtcttc ttcgtcagcg gctactacct cgtcgcctcc gcggtgcaga tcgtgctcgc   22920
cctctacttc gccacggtcc tcagcttcga cgtccgcttc cggaacttct tcaagggcgt   22980
gctgttcttc ccgtacctca tcaacggggt ggccatcggc ttcgtcttcc tctacttctt   23040
ccaggacggc ggcaccctcg actccgtact gggcctgctc ggcgtcgaga ccgaccacgc   23100
ctggctgggc acgccgttct ccgcgaacac ctcgctggcc ggcgtctccg tctggcgcta   23160
cctcggactg aacttcgtcc tcttcctcgg cgcgatccag tccatcccgg gcgagctgta   23220
cgaggcggcc gagatcgacg gcgcgaaccg ctggcagcag ttccggcaca tcatcgcgcc   23280
cggcatcaga cccgtgctga gcctgagcgt gatcctctcg gtctccggct cgctgtcggt   23340
cttcgagatc ccgtacatca tgaccggcgg cgccaccggc acggagacct tcgtgatcca   23400
gaccgtgaag ctggcgttcc agttcaacaa gacgggactc gcctcggccg ccgccgtcgt   23460
cctgctgctg atcgtcctgg cggtcacctg ggtgcagcgg cgcatcgtcc ccgacgagaa   23520
ggtggacctc gtatgacccg ccgtaccgcg gcacgcgccc tggtcctgac gtccctgatc   23580
ctggcgacgc tggtggtgct gctgccgctc gccgtggtct tcctgacctc gctgaagtcc   23640
tccgaggaga tggcgaacgg cagcggaacg ctgacgccgc ccgacgaccc gctgaacttc   23700
ggcaactacg tgacggcgtt ccgggacggc cagatgctgt ccgcgttcgg gaacacggcc   23760
gtcatcctgg tcgtggccgt cggcggaacg atcctgatcg gctcgatgac ggcgtacgcg   23820
atcgaccgct tccggttccg cttcaagaag ctggtcgtgg cgctgttcct gctggccgcg   23880
ctggtccccg gggtgaccac ccaggtggcg accttccaga tcgtcaacag cttcggcatg   23940
ttcgacagcc tgtgggcgcc gatcgccctc tacatgggca cggacatcgt ctcgatctac   24000
gtcttcctgc agttcatccg ctccatcccc gtctccctgg acgaggcggc gcgcctggac   24060
ggcgccaacg cgttcaccgt ctaccgcaag gtgatcttcc cgctgctcaa gccggcgatc   24120
gcgacggtgg tgatcgtaaa ggggatcaac gtctacaacg acttctacat cccccttcctc   24180 tacatgccct ccgaggacct gggggtcatc tcgacgtccc tgttccgctt caagggcccc   24240
ttcggcgcgc actgggagac gatctcggcg ggcgcggtcc tggtcatcct gcccaccttg   24300
atcgtcttcc tgttcctcca gcgcttcatc tacaacgggt tcatgcgggg ggcgacgaag   24360
tagccagcgc ggccaccagc acgggagtga cctggtcgac ctgccacgcg cgtgccccgt   24420
gcgccgtcag cgccgcggcg acggaccgct cgtcgggccc cggcggctcc cagcagaccc   24480
tgcgcaccgt gtccggggtg atcaggttct ccggcggcat gttcagccgc tcggcgagtt   24540
cggcgacccc cgcgcgggcc gccgacagcc gggccgcggc aacggggtcc ttgtccgccc   24600
aggcgcgcgg cggcggaggg ccggtcaccg gctggccggg ctgcggcagc tgggcctcgc   24660
tcagcgcctt cgcgcggtcg acggccgcct gccactgctc cagctggcgc cgccccaccc   24720
gctgcccgaa cccgttgagc gcggccatgg cgtgcaggtt ggcgggcagc gcgagcgcgg   24780
cctccacgat cgccgcgtcg gaaagcacct tgccggggga gacgtcacgg cgccgggcga   24840
tccggtcgcg ggtctcccac agctcccgca ccaccgccat ctggcggcgc cggcgcacct   24900
tgtgcatgcc ggaggtgcgg cgccaggggt ccttgcgggg ctccggcggc ggggccgagg   24960
cgatcgcgtc gaactcctgc cgggcccagt ccagcttgcc ctggcggtcc agctccttct   25020
ccagggcgtc ccgcagatcg accagcagtt cgacgtcgag ggcggcgtac cgcagccagg   25080
gctcgggcag cggacggggtg gaccagtcga cggcggagtg gcccttctcc aggacgaagc   25140
cgagcacgtt ctcgaccatc gcgccagcc cgacgcgggg gaaccggca aggcggccgg   25200 ccagctcggt gtcgaagagg cgggagggca ccatgcctat ctcgcgcaga cagggcaggt   25260
```

```
cctgggtggc ggcgtgcagc acccactcga cgccggacag cgcctcgccg agggcggaca    25320
ggtcggggca ggccacgggg tcgatcagcg cggtacccgc accctcgcgg cgcagctgga    25380
cgaggtaggc gcgctggccg tagcggtacc cggaggcgcg ctcggcgtcc acggcgacgg    25440
gtccgctgcc ggccgcgaag gcggcgaccg cctcggcgag ggcggcctcg tccgctatca    25500
cgggcggaat gccctcgcgg ggttccagca aggggtcgg cgcctccgta acagaagatc     25560
cgccgtcgtc cggaggagcg cctccggtgg tgcgcagtga actgtctgct gcggtgtcgt    25620
gggcgtcggt cacctgtcaa gggtatccgt gccgcgaagg cgcccgtcga cggttgtgct    25680
ccgtgacggg cgccggtggg tcgtattccg gtcagaagag tgaaagaacg tgttcgcttg    25740
gccgtgggcg ggcggatcgg ggacgggcgg atcggggggcg ggacggaagg gtcagtggat    25800
gatgccggtg cgcagggcca cggccaccat gccggcgcgg tcgcccgtgc cgagcttgcg    25860
ggcgatccgg gccaggtggc tcttgacggt cagtgcggac aggcccatcg agacgccgat    25920
cgccttgttc gactggcctt ccgccaccag ccgcagcacc tccacctcgc ggccggacag    25980
ctcgcggtag ccgcccgggt ggctcggggc acccgggggg cggcggtgca ggcgcgcggc    26040
ggcggcgccg atgggagcgg cacccggccg ggtgggagc ccgaggttgg tgcgggtgcc     26100
ggtgacgacg tagcccttga ctccgcccgc gagggcgttg cgcacggcgc cgatgtcgtc    26160
cgccgcggag agggcgaggc cgttgggcca gcccgcggcg cgggtctcgg agaggagggt    26220
gaggccggaa ccatccggca gatggacttc ggcgacgcag atgtcgcggg ggttgccgat    26280
gcggggacga gcctccgcga cggacgaggc ctcgatgacg tcgcgtacgc cgagcgccca    26340
caggtggcgg gtgacggtcg aacggacgcg ggggtcggcc acgaccacca tggcggtcgg    26400
cttgttcggg cggtaggcga ccaggcttgc gggctgctcg aggagaacgg acaccaggcc    26460
tcctggggtg cgggacgggc cggctcgtgg gggtgaaggc gggacgaacc gtgctttcaa    26520
ggtcacagtc gtcttcggca gcaaacctgg tgtcctttaa cgaatgatca cgaagtgatg    26580
agtaacaatc cgggcaattc ggacgcacga tcgatcattc gaagatcgaa cggtttcggt    26640
ctgcgtcgca acgcttccga aagtggccgt atcgacaaag agagatgcag gaggccggtc    26700
gtcgggaccc cgcagcggga ggctcagcgc gactgcggcc ccctccgctg cggcagcgtc    26760 accacgacg cgtcccccgg agcggccggc ggcagcccg cgacctgcgc cagcagatcg      26820
gaccacgcga ccagatgggc ggccgtgtcc ggaacccgc ccagaccctc acgcggcgtc     26880
cacgaggcac ggatctcgat ctgggaggcg gcgggccgcg cggacagccc gccgaagtag    26940
tgcgaactcg cccgcgtcac cgtgccgctc ggctcgccgt acgacaggcc gcgcgccgcc    27000
agcgcgccgg tcagccagga ccagcacacg tccggcagca gcggatccgc cgccatctcc    27060
ggctccagct cggcgcgcac cagcgtcacc agacggaagg tcccccgcca ggcgtcgtgt    27120
ccggccgggt cgcacagcag caccagccgg ccgtcggcca gatcctcctc gccgtcgacg    27180
accgccgcct ccagcgcgtg cgcgtacggg gcgagccgtt tcggcgcggg caccgtctcc    27240
acctcgatct gcggccgcag ccgggcgctc tgcagcgcct cgacagcggc ccggaagggc    27300
ggcggaggcg cacctccgtg cccgggatcc ccccgcccct ccttcggttc gtccattccg    27360
ccagcgccgt ccgacagtcg tccctgagcc gcagccatgc cgggaagatt aagcggaacg    27420
ggcccccggc gcagggaggg acacccgcgc cgcccggcgc tgtccggatc ctgcaccgcg    27480
gccccgcccg ccggacgccc ctggggtccg ggcggcgga cgggtcgtgc gagactggcc     27540
ggtgtgagtg ccaacacgag cccgaagggc cagacgccta ccgcgacccc cgaccccgtc    27600
aagaacgacg ccgtccggga atcagccttc ctcaaggcgt gccggcgcga gccggtgccg    27660
```

```
cacacgccgg tgtggttcat gcggcaggcc gggcgctcac tgccggagta ccgcaaggtg   27720
cgcgagggca tcgggatgct cgactcctgc atgcggcccg agctggtcac cgagatcacc   27780
ctccagccgg tgcgccgcca ccacgtcgac gcggcgatct acttcagcga catcgtcgtc   27840
ccgctcaagg ccatcggcat cgacctcgac atcaagcccg gcatcggccc ggtcgtcgag   27900
cagccggtgc gcacccgcgc cgacctcgcc cggctgcgcg acctgacccc ggaggacgtc   27960
tcctacgtca ccgaggccat cggcatgctg acccgtgagc tcgggtccac cccgctgatc   28020
ggtttcgcgg gcgccccgtt caccctttgcg agttacctcg tcgagggcgg cccgtcccgt   28080
acgtacgaga acgccaaggc gatgatgtac ggcgaccccg agctctgggc cgacctgctc   28140
gaccgcctcg ccgacatcac ggcggccttc ctcgacgtcc agatccgggc cggcgcctcg   28200
gccgtgcagc tcttcgactc ctgggccggc gcgctcgccc cctccgacta ccggcgttcg   28260
gtgctgcccg cctcggcgaa ggtgttccgc gcggtggccg ccacggcgt cccgcgcatc   28320 cacttcggcg tcggcaccgg cgagctgctg ggctcatgg gcgaggccgg cgcggacatc   28380
gtcggcgtcg actggcgcgt cccgatggac gaggccgccc ggcgcgtcgg ccccggcaag   28440
gcgctccagg gcaacctgga cccgaccgtg ctgttcgccg gccgggaggc cgtcgagacg   28500
aaggcgcgcg aggtcctgga caccgccgcg ggcctggagg ccacatctt caacctcggt   28560 cacgagtga tgccctccac cgacccggac gccctcaccc gtctcgtgga gtacgtccac   28620
acgcagacgg cgcgctgacc caccgctcac gcgccggacg cgagtcggaa tccggggcg   28680 gggtactggg cacgggtgcc caccacgttc acccccgggt acgggcaggt ggaggcccca   28740
tgaggctcga gatgttcgac cccgccccga tcggcgtcgt gttcacccag gggccggagc   28800
accggctcgc gtacaccaac gccgtctacc gggagacctt cggcgaccgc ccgctggggc   28860
ggacgatccg cgaggccttc cccgacctcg cgcagtccgg ctacttcgac atcttcgacc   28920
gggtcctcac cacgggcgcg gccgaggtgg tcaccgcgt gccctcgac ctgatctacc   28980 ccggctccac gggcgagggc aggcgctact tcacgttcag catctcccgc gccacgatga   29040
gcgacggccg gccgggagtg ctcggcgtga tcgtggaggt gaccgcgcag gtgaccgccg   29100
cggaacggat ccgtgtgctg gccgaggagc gccgccgcgc gctgcagcgc taccgcagcc   29160
tggtgaacgc cggaacgcag atggtgtggg tggcggacgc caaggcgcgg atcaccgagc   29220
cgagccccgg ctgggaacgc gtgaccgggc agacctggga ggagttccgc ggcgagggct   29280
ggatgaacgc cgtccaccc cgacgaccgcg ccgcctcgt cgaggcgtgg cggcgggcga   29340
cgaccgaaca ggtgccgcgc tggatccaca cctaccggct gcggctggcc gccggcgggt   29400
accggcactt cgtcgtcgac gccgcgcccg tgcgcgacgg gaacacggtg atcgaatggg   29460
tgggcacctg cacggacatc gagcgggaat ggcaggaggg ccgccgtacg gaactgctgg   29520
cgcgggccgc caccgccacg tccggcatcg cgcggctgga cgagatgctc gccgccctgg   29580
ccgatgtgat cgtgcccgac atcgccgaca actgcaccat ccacctcctg ccgcaggccc   29640
tgcaccgtct gccgggcacc ccgctgacca ccgaacgcgt cgccgcggtc acccgcccgg   29700
ggctcccgga cctgccccg caccacgagg agcacctgcg gccggcagc ccgctggccc   29760 gcgccgccga ccgccgcagc ccgctccact tcgtcttccc gccggcgag ccgccggccg   29820 acctcgctcc gctcgacggc gagccctgga tggccgagga cgtcaacagc gtcgtgctgc   29880
tgcccgtcgt cgtcgacggc accaccgccg ccctggtcgc cgtctccacc agcggcgccc   29940
gcccgcccct cggccaggcg gagatcgcc tgctgcagac actcctggaa cgcgcccaca   30000 ccccccctcag caacgccctg gagtaccagc gcacccggca ggtggccctg gccctgcaga   30060
```

```
acagcctgct caccgacccg ccggacgcgc ccggcctgga catcgccgtc cgctaccggc   30120
ccagcaccgc cgccgccgag gtcggcgggg actggtacga cgcgttcgtg ctgcgcgacg   30180
gcgccaccgt cctcaccatc ggcgacgtct ccggccacga cctgccggcc gccgtcacca   30240
tgagccagct gcgcaacatg ctgcgcgggc tcacgctgga ccgccaggaa ccgaccggca   30300
ccatcctgcg ccggctggac atcgccgtgc agaccctcta tacgagtgc accgccacct   30360 gcgtgctggc ccgggtggaa cgcccggact ccggcggcgt ccggctgcac tactccgtcg   30420
ccggtcaccc gccgccgctg ctcgtcgagg cggacggctc cgcgcgcttc ctgaccgggg   30480
cgcggtcccc gatgctcggg ctcgtccccg cgccggagta ctcgagcgcc atggaaccgc   30540
tgccgcccgg ctccaccctg ctgctgtaca ccgacgggct ggtggagcgc cgcgacgagg   30600
atctcaccgt gggcctggag cggctgcggc accacgcctc ggaggcggtc agccgcccgc   30660
tgcaggactt ctgcgacaca ctgctcaccg gccagctcac cgtcgacaac gacgacgacg   30720
tggcgatgct ggtcctgcgc cggtaggagc gtgccgagga cgccactct ggccgatttt   30780 acccttgctt ttccatcggg attcgttctc cggatttccc gatccggcgc cgacggcgag   30840
accgttggga tcaccaatac cccggaattc ccgcctccgc caccgttggg cagcgacgga   30900
tcctgtgata tttcgactac gcgcggtgat gaattggctc ggtgccggtc gcgcccggct   30960
gtagcagttc tggagcgcgt ctggacatcg tcacgagcgc ttgtgattct tggtcctgta   31020
cacgcaagcc ggcgcaacgt ccacgttgcc catcagcggt tatcggcggt ccaccggcgc   31080
gacggtgacc gcgggcgggt actcataggg ggaactgcaa tgaattactc aaaagcagcg   31140
agaggaatgc cgacagccgg acaaggtgcc gttcgggcgg cgcgcgtcgt ccgtgaaagt   31200
ccggcggaat cagaaacggt cacagttcag atagcgtcgt tattaccggg tgagtcgctg   31260
cgctcgaaag ggatcgagca gaaccacgtc gcggcactcg cggaggtaga cgcgccgctt   31320
ccgcccatac tggtggaccg gaagacgatg cgggtcgtcg acgggatgca ccggctcctc   31380
gcggctctgc tcaacggacg gcagacgatc gaggccgaac tgttcgacgg aaccgcggat   31440
gagggattcc tgccgcgccgt ccgggagaac gtggtgcacg gactcccgct gtcgcaggcg   31500
gaccgccggg ccgccgctgc gcgcatcatc gtgtcccacc cgcatctgtc ggacagggcg   31560
atcgcccggg cgtccgggct cggggcgaag accgtgcgcgg ccgtgcggcg cagttcaact   31620
gccgtcgtgc cgcagttgaa cacccgggtg ggccaggacg gcagggtccg gccgctgaac   31680
gggggcgagg ggcggcgcag ggccatggcg gtactggccg aacacccga cgcgtccctg   31740 cgcgaggtcg cccgtctgtc cggggtgtcg cccgcgacgg tcagcgacgt acgccggcgg   31800
ctggccgccg gcgagtcgcc cctgccgtcg agacgggaac cggccgaacc gcggacgggc   31860
gccgactccc accgcaacca gagcttcgtg gatcccgtcc cggtgctgga gaagctgctg   31920
cgcgacccct ctctgcggca caaggagggc ggccgccagc tgctccagct gctccgccag   31980
aacgcggtcg gcgtgcagga cctgatggag ctgtccgacg ccgtgccgtc ccactgcagg   32040
tccctggtga tccatctcgc gcagcagtac cgggacgcct ggcagtcctt cgcggagaag   32100
ctggacgagc ccgcctgcgc ctgtcccggg tgacgaacgg gcggcacgga cccgttcacc   32160
ggacatgacc ggcgccgcgc cgcgttcacg gcgcgccgcc ggcactccca cggcacccgg   32220
accaccgccg cgtatccggc ggacccgggc ccgggcgggc cggattcagc gggcggggc   32280 ccaggtgcca cccgattcca gccacgggga gagctccgcc gccgagtcct tgcgcacgac   32340
cagttcgacg aggccgcggg tctggtcctg accgtgctcg atgcggacgt cctcgatgtt   32400
gacgcccaag tcgccgatcg acgtgaacag ttcggccagg gcgccgggct tgtcggagat   32460
```

```
ggtcaccgag acggtcgcga gctccgtccg gcgcgtaccg ggtttgcgca cgatcctggc   32520
gcaccccgg ttccctccc gcaacagctc ctcgagctcc tcctgcgcgc ggcggcggac    32580
cagcgggtcg gcgtcggaga cggcgcgcag gcgccgacg gcccggccca ggccggcggc   32640
gagggagtcg agaacgtccg ccacggccgt ggcgttggaa cgcaggatgt cccccagag   32700
ccggggcgtca ccggccgcga tccgggtgac gtcggcgacg ccctgccccg ccagccggac  32760
gctgtcctcc gccgcgtgct ccagccgcgc ggcgagcagg gaggagagcc gatgggcgc   32820
gtgcgagacg agggccaccg cgtggtcgtg cacaccggcg tccatgacca ccggcatgcc   32880
gtcgcacaac gacaccatct ccaggcggt gttcagcacg tcctgcccgg tcagctccga   32940
cggggtgagc acccagggc gcccctcgaa gaggtccgcc cggcggcga gcggcccgga    33000
acgctcggtg ccggccagcg gatggcttcc tatgtagctg gccgggtcgg cccgcatcgc   33060
gcgcacgtcg tcgtgcggga ccttcttgac gctggcgaca tcgaggtagg ctcgggccag   33120
cccgctctcc tgtgcgcgcg cgagcacgcg tccgacctgt gccgggggca cggccagcac   33180
cgccaggtcg acctgacggt ccggtctctc cagggatccc gcgcccatcg cctccgccgt   33240
cctggcggcg ttccggtcga cgtcctccag gtgcacgccg accccgcggc gggtcagcgc   33300
gagagcgacg gacgtgccga tggccccggt gccgatgact gtggtggtcc tcaacgcgcg   33360
ccccccaggtg cggtgatccg aaatcggctc ggacaagtgc cgtgcccggc acgggaaaag  33420
ggaattccca tggcgccgtg cgccgccaat ttaacgcttc ggcgcgcatg ttcaactgcg   33480
gcgtcgcagc ggtcgaacac agtagcggta caccggacca ttgaggcatc gtgctcagtt   33540
ggcgacaccg ggtcggataa acgccggaat ccgaggagtt gacgttgcag tcagcgctga   33600
gacacgacga cctgcatccg atagaagaag tggaaataag ttcgctctcc accgacggct   33660
ccccgcggat cgacggggag agtcccgagc acgtggaaat gctggccgcc gccgacaccg   33720
cgcttccacc gatcatggtg caccgccgca ccgggcgggt catcgacggc atgcaccggc   33780
tgcgcgccgc gatgctgacg ggccgtacga cgatcgcggt gaggttcttc gacggcaccg   33840
aggaggacgc cttcgtcctc gccgtgaagt cgaacatcgc gcacggactg ccgctgtccg   33900
ccgccgaccg ccggcgggcc gccgggcgca tcatggccac ccatccccgg tggtcggacc   33960
ggatgatcgc ctcggtggtc ggcacctccg ccaggacggt cgccgagatc cgccgcgacg   34020
ccggcgccgc cggggcgggg gagcccaccc gcatcggccg ggacggcagg gtacggcccg   34080
tcgacgtgag cgaggccgc agactggccc acgacatgat cgtccgcgac ccgggcctgt   34140
cgctgcgcca ggtcgcccgc gccgccggga tctcgccgga gaccgtcagg gacgtcagac   34200
accggatgct ccgcggtgag gaccggtgc ccgcgccgcg gccgcggacc ctggtggagc   34260
gcggcgcgga ccgccgggcg gagccggccg ggaaggccgc cgcgccgtgc gggacggagc   34320
cgccgcccgc cgtcgtgatg aagcggctga gggccgatcc ggcgctgcgt ctcaacgaga   34380
acggacgcga cctgctgcgg cttctggata tccacacggt ccggctggag gactggaacc   34440
gcattatcga aagcgtgccg ccgcaccgtc tggagacggt ggcgcagctg gcacgctcct   34500
gcgccgacaa atggtccgag atcgcgtcac gcatcgaaag caacgcatca catctggccg   34560
ggtgaacgag gaaacacacg aatccttcga ggagccgtcg gagaaagcgg gacggcccgt   34620
cggaacaccc ttgtggaggg gcaatggaga tacggtcgat cgatcacgtc gaattgttcg   34680
tcgaggacgc ccaggacacg gccaggcaggc tgtgcgactc cttcggcttc gtccgcgtgg   34740
gccgcggcgc cgggaccacc ggactgcgcg gctgcgagtc cgtcctgctg cgccagaacg   34800
acatcgccct gctgctgacc acggccaccg acgccgacca ccgtgccgcc gagtacgtga   34860
```

```
agcagcacgg ggacggggtc gcggtgatcg gcatcggggt ggacgacgcg cgcgccgcct   34920
acgccgaggc cgtgcggcgc ggagccgtcc cggtcgccgc gcccgaggag ttcgggcccg   34980
ccggcgcccg tgtcgtcttc gcctcggtgg cgggattcgg cgacgtggag caccgcttcg   35040
tctcccggga ggaccccgga gcgccgttcg cgcccttcat cgaggagacc ggcgcccacg   35100
gctccggggg catgctgaag cgggtcgacc acttcgcggt ctgcgtcccg gccggcgaac   35160
tcgacgggac cgtccgccgc taccaggagg tgttcggcct cagccagacc ttcgaggagc   35220
ggatcgtcgt cggctcgcag gccatggact ccaaggtcgt gcagagcgac cgcggcgcgg   35280
tgacgttcac cgtcatcgag ccggacacca cccgcgcacc cggccagatc gacgcgttcg   35340
tggcctccca cggcggggcc ggtgtgcagc acgtcgcgtt cctcactgag gacatcacca   35400
ccgcggtgcg cacctgcacc gggcgcgggg tccgcttcct caccacgccg ccgagctact   35460
acgagatgct gccggggcgg ctgggcccgg tcggcgtacc cgtggaggag ctcagcgcgc   35520
tcaacatcct ggccgaccgc gacccgtccg ggatcatgct gcagatcttc accgagtcga   35580
cgcacccgag gcggaccctg ttctgggaac tgatcgaccg ccgcggcgcg cagaccttcg   35640
gcagcaacaa catccaggcc ctgtacgagg ccgtggagcg ccagcaggcg gcggaggcgg   35700
ccgaccagga atgaggaagc tccccgcaga cgcgtgtgga cccggaggac acgccctccg   35760
ggtccacacg cgtctgcggg gccagcgtcg gctacgcccc gaggagccgg ccgccgtgca   35820
gcgtctcccc gtacgcgaac acatggccgg ccccaccctc cacgggcgcg agcagtgcca   35880
gatccgtgcc cggacggccg gagagggcga ccggccgggg accgctccag accggtgaga   35940
actcgacgcc gctcacctcc gaggcgacca ggcggggccg tggcggggcg tcggacggca   36000
cccaccgcga aggacgaga ctgtgcgcca gcggacgtc gtgcagcgcg gcggccgct   36060
cggagcggcg ctcgaccgtg accgacgcct cggcggtgag ccggccgtgg acggagagcg   36120
cgccgtcgaa gcgccccccg ggagcgagcc gtgagcccgc ccggccgacg gtcaccggcc   36180
tggtctggtg gatggcgccg aactgcttgg gcatgccctg gacccagccg cgcaccatcg   36240
gcacgggctg gtcgacccag gcgaacgggc agcgcgccat cggccggccc tcgaacgcgc   36300
acccgaggag gatcaggaac tccgagaacc ggcagacggc cgggtcggcc agctccgcgc   36360
cgtcctcgga gcaccactgc caggtggcga acacggcggc cgccgcaccc ggatccgctc   36420
ccgcgtccag gcccggcggc aggaaacgcc gtgcggcgtc ggggtcgaca cggtagtcga   36480
ccatgaggat ctcgcggag aagtgccacg cggaggcgt gagcatcgac gcctgccccg   36540
aaggggacag gggaaggctg tagccgatgg gcccggcggc cccggccgcg tccggatccg   36600
tcggatgtgt gtgcccggtg gtggccgtca tgggttccct ccgatctgcc ggtccggcgg   36660
gccgccggac catgcctggg tcagccgtcg agcggcgcgt tcgagcagcg ggggcggatt   36720
gaagctgtag gccaggcgca cgctcggctc ccgtgtgccg ccgaagcgcg aacccgcggt   36780
gacgcgcaca cccgcccgct ccgcacgggc gagcagttcg tcctcgccga gcccggtgcc   36840
gcaccggagc cagaggaaga acccgcccctc cggacggctg atccgcaccg ggaggtccgc   36900
cgcctcccgc agcgcgtcga ggagggcgtc gcgccgcgcc ctcagacccg cccgcaacat   36960
ttccagatgc cggtcgtagc cgccgtcgga cagcagccct gcgacggcga gcgaggtgat   37020
gtggttgagc gacccgccgc tgcggaacag cccgtgcgac gcgatccgtt cggccagtgc   37080
cggctccgtc accagccagc ccagccggag ccccggcccc agggtcttgg agaagctgcc   37140
cagccgcacc acgcccggt gtccggcgag ggccgccagt ggcggcgggg ccgggggacc   37200
gtccgtcagg cccagttcgc cgtaggcgtc gtcctcgacg accaggacgc cgtgctccgc   37260
```

```
cgccgcctcc agcagccgca gccggcgctc cagcggcatg gtggcgcccg tcggattgtg   37320
gtgggtcggg gtgaggtaca cgaacgcggt gcggccggtg ccgccttcgc cgccccgcgc   37380
ggtcccggcg agggcgcgcc ggagcgcctc cggcaccatg cccgacgcgt cgagggcgac   37440
ccgcctcagg cgcagcgcgc agtccccgag gatgcgctgc ccgaggtcgt agccgaggcc   37500
ctccacgagc accgtgtcgc cgggcctcgc gagggtggtc gccagcaggt ggagcgcctg   37560
ggacgtgccc gccgtgacga ccacgtgctc cggcccgcac ggggaccgcc cccgcacggt   37620
ggcccgggcg gccagctcgg cgcgcagggg cagggcgccc ggatcgtgtc cgtagcccag   37680
tgccgccgct ccgtactcct ccagcgcgcg tgcgtaggcg tcccgcacca gccccaccgg   37740
cagcagcgcc ggttcgaggt agccgggccc caggtcgagg acgcccgcgg gggcgacctc   37800
ctgcaccaca ccgcgacgcc accgccgcgt gtgcgacaac gggcgggccg tgccgtacgg   37860
cagggtcccc tcgccggcag cggtcatcag cggggtgtca gcacatggcg caacgcccgt   37920
acgcactggg ccagcggggc ggacgcccgg gcgagcgcca ggcgcagcgt gcggtcgccg   37980
cgggcggggt cagcccagta gaaggcacgg cagggcaggg cgtacacatg gtgctcgcgc   38040
agcgcctccc agacctcggt cccggtcaga tgcctgatca gcacccgctc cacactgggc   38100
cggctgtccg ggtcgggcac cccggtggtc gacaggtccg ccagcccggc gcgcaccacc   38160
gaccgctggg cggcgatgaa ctcgtgcagc tccgtcagcc cgccggcggc ggcgtcctcg   38220
gagaagcggc ggaccatccc gaggatcagc ggggagacgc ccagcaggat gtcggagtag   38280
atcttctcca ccggcaggcc caggttctcg gagtggacca gcatgccgac cttgaggtcg   38340
agggtcggcc agagcttgcc cgtgtcctcg atgacgaccc agcgcacatc gctggcgtcg   38400
aggatctcgt agtggtcgta ctgggcgcgg gtgtcgaagc cgcggaagga cgtgtcgagg   38460
gcgaggatca cgccgtgccg tgcgcactgc ccggccagcc ggcgcagccg ctccgccgac   38520
acgacccggc ccgtcgggtt gttcggcgtg gtgacgaaga cacagcccac ggactcgagc   38580
agctccgcgg gcaggtcgtc ggcgtgcagc ggatcctcct ccaggggcac cagacccagg   38640
cggttgccgc gcaacaggtc ggcgatgttg tcgaaggtgg ggtggaccag cgccacggag   38700
tccgtgaccg acgccagggc gcgggagagg atctccatgg ccaccgacga ggagtagcag   38760
ctcagcacac ggccgggtgc ggacgggtag cggtgctggc cgagggcctt gaagaaggcc   38820
gcgtgggcct cgcgttcgag ctgctcgacg gggcgcttct cgccgtcctc gaaaagcagc   38880
gggagatcat tgacgatctt gctctggccg ggagtgagcg gctgccgggc atgcccgtcg   38940
gcgatgttga actcgctgtt gagtgcgagg aattccagtt gggtgaggtt ctccgcgcct   39000
gatccggcgt gcgcagcgtg ggccttgctt tgcagtgttc cggacacagg tatgcctctc   39060
tgggatgtga gggtttccag aagcggagcg gacgtaaatg agcggcccac tctacggcct   39120
tcgccctccg gctgaaatgc ctcttctttt cggcaccgtg ttcaactgcg gtggtgcggc   39180
agtcgaacga gccgtctcgc ccgccgtatc ggccggacat cgcgttccga cggtgacgcg   39240
cgtgcggttc ccgtgtccaa ctgacctgag ggcgcagttg gacgggccac ggcacacgg   39300 ccgcccgatc cttgtcggac gggcccgggc acgcgaaagt ggacgtgcgg gatctgtgtt   39360
ccgccgccgg tgtctcttcg taagccgtga agtgggggcct tgatggaatt gtcgctcgat   39420
gaattcgcgt cgctcgcccg ggaacggctg gaccccggccg tctgggatttt catcgaaggc   39480 ggcgccggag aggaacgcac gctccgcgcg aacaccgcgg cattcgaccg cgtcccgctg   39540
cggccgtcgg tgctgcgcgg cgcgggcagc ccgcacaccg gcaccacgat cctcgggcgg   39600
acgtgggacg cgcccctcgc ggtcgccccg gtggcctacc acacgctcgc ggacccggcc   39660
```

```
ggtgaggtcg ccaccgtccg gggaacggcg gccgccgccg gactcccggt cgtcgtcagc   39720
accttcgcgg gccgcacgtt cgaggacatc gccgccgagg ccaccgtccc gctctggctc   39780
caggtgtact gcctgcggga ccgctccctc acccgaggcc tcatcgaacg cgccgagaac   39840
gcgggcttcg aggccctggt cctcacggtc gacgcgccgc acctcggccg ccggctgcgg   39900
gacctgcgca acggcttccg gctgcccgcc ggcacggtcc ccgccaacct cccggtggac   39960
ggattcgcgg accccgcggc gcactcccgc gccgacttcg accccggcct ggactggtcg   40020
gtggtggagt ggctgcgctc ggtctccgaa ctgccgttgc tcgtcaaggg gatcctcacc   40080
ggcgccgacg cggtgcgcgc ggccgaggcc ggggtggacg gcgtcatggt ctccaaccac   40140
gggggccgcc agctcgacgg agtgccggcc accctcgacg tcctgcccga ggtcgccgag   40200
gcggtcggcg gacgcctccc cgtcctcctc gacggcgggg tccgccgggg gcgggacatc   40260
ctggcggcgc tcgcgctcgg cgccgacgcg ccctcgtcg gccgccggt gctgcacggc   40320
ctcgcggccg gcggggccgg cggggtgacc ggcgtcctct ccgtcctcct ggaggagctg   40380
acggacgcga tgtcccttgc gggcctgagg accctcgccg acatcggccc ctcactcgtc   40440
ggcccgggctc ctgaccaccc ccgccgaagc accgtgacg ccgggaaggg cgcggggagc   40500
gaccggcgca ccgccgccgg gggaggggcc gggctgcgcc tcgcggacct gcacccgagt   40560
gtcgccgacc cggtcatgga caccatgaac ttcctcaacg aggtgacact gcgctacccc   40620
gaggcggtgt ccttcgcccc cggacggccc tacgcggagt tcttcgagac cgagcaggtc   40680
ttccgccatc tgcgccgcta cctcgaccac ctggccgagc agggccgttc gcccgcgcag   40740
gtgcgcgacg cgctgttcca gtacggtccg tccgccggtg tgatccgcga gctgatcgcc   40800
cactcgctgc gggtggacga gggcatcgac gtgtcgcccg agtcgatcgt ggtgacggtc   40860
ggctgccagg aggcgatgtt cctgacgctg cgcgcgctca tgtccggccc ggacgacgtg   40920
ctgctcgtct ccagcccctg ctacgtgggg atcaccgggg ccgcccggct gctggacgtc   40980
gcggtgaccg ccgtcgagga gggcgaggac ggcctgtcgt gcgacgccct cgaggccgcc   41040
gtctcggcgg agcgggcgcg cggcaggcgg ccgcggggccg tctacgtggt cccggaccac   41100
tcgaacccgt ccggcgcgac catgccgctc gaggcccgga agtccctcct ggagctggcg   41160
cagcggctcg acgtcctcgt cctggaggac agcccgtacc ggcacgtcag cccgggcacg   41220
caggtggcgt ccctgaaggc cctcgaccgg acacggcgag tgatccacct cggttcctac   41280
gccaagaccg tcttccccgg ggcacgcctc gggttcgcgg tcgccgacca gccggtgctg   41340
gcgccggacg gcggcacgag tctgctggcg gacgaactcg ccaagatcaa gagcatggtc   41400
acggtcaaca cctcgccgct cagccaggcc gcggtggcgg gcgcgctgct ggagtcgggc   41460
ggccgtgtct cggagctcaa cgcccgcaac gccgcccact acggggaggc catgcgcttc   41520
accctgcagt gcctggagcg ggagttcccg gccgcgcggc ggaccccggct cggcgtccgc   41580
tggaacgcgc ccagcggcgg gttcttcctc accctccagg tgccgttccg cgcggacaac   41640
tccgcgctgg cccggtccgc gcaggacttc ggggtcatct ggacgccgat gtcgtacttc   41700
tatccgcagg gcggcggcct gcacaccctc aggctctcca ccagctacct gacccacgcc   41760
gacatcgaga agggcatctc ccggctggcc gggttcatcg agttcgagtg cggggacccg   41820
gtggcctgaa ccgccgcgac gacgaagggc cccggccgcg ccggcgggc ccttcgtcgg   41880
tcgcgacgct caggacggat gcggctcctc ccagaacatg ctgtcggacg aggcgacgag   41940
accgccgtcg aagagcggga cgtcctcgcc ggcgtactct cccagctgcg cccgggtctg   42000
cacctgcgag ccctcctgca tcgcccggct caccgccgac gaccggaaca gcggggccat   42060
```

```
gttctcctcc tgccgcccgg ccatgtcgtc gacggcgtcg gcgaactccg ccgactgctg   42120
cttgagccgc aggacgctcg actcggcgtc ggagaggtcg aagtccgtgc tggacatgcc   42180
cgccaccagc tccacgaacg actccagctc ggcgtggctg ctccgggtga ccttcttcgc   42240
cgtccagaag taggagtcct cgtcgacgtg catgtcgtag aacgaggtca ggaactcgta   42300
gaagacgccg tactcccgcc ggtacccggc ctcgaactcg tcgaaggccc gccgctcgtc   42360
gatccgcccc gccagcacgc tgttgaggga gcgggcggcc agcagcgcgc tgtaggtggc   42420
cagatggacc ccggaggaga agacggggtc gacgaagcac gccgcgtcac cgacgagcac   42480
catccccggc cgccagaagg tcgtgtggtg gtacgagtag tccttgcgca cccgcagctg   42540
cccgtactga ccggtcgtga cccgggtggc gtccgccagg tactccttga tcatcgggca   42600
ttcgtcgatg aggccgcgca gcgcgctctc cgggtcgccc tgcaccttgg ccgcgtcctc   42660
ccggcggacg accgcgccga cgctggtcag cgtggagctg agcgggatgt accagaacca   42720
gccgctgccg aacgccacac agaggatgtt gccggcgtag ggcgccggca tccgcttgcc   42780
gttctcgaag tagccgaaca gcgccaggct cttgaagaag tccgagtacg tgcgcgagcc   42840
gccgacccgc ttgtggatgc ggctggtgtt gcccgaggcg tccaccacgt accgggccga   42900
cacctcgtgc tccgtgccgt ccgggtcggt gtaccgcagc ccgcgggccc gcccgtcggc   42960
gtcgtccacg acatcggtga ccgtgcggtc ctggcggacc acgacaccct tgcgggccgc   43020
gttgtccagc aggatcttgt cgaatttgct ccgctccacc tgataggcga acgaggtcgg   43080
tccggagacc ttggacgaga cggagaagga gaaattccac ggcttgggc tcgcaccccca   43140 ccggaacgtc ccaccgcgct tgtgcggaaa accggcggcg gcgagttcgt cggtgacacc   43200
gagcagatgg cagatgccgt gaatggtcga cggcagaagc gactcgccta tctggtacct   43260
ggggaaggtc tccttttcga gcagcagcac actgtgcccc tgcatggcca ccagggtcga   43320
gagcgtcgac cccgaagggc cgccgcccac gaccacgacg tcgaattcct cgtgctgtcc   43380
tgtactcatt cggcctcccg gcacgcactg atgcggtcat cgcgctggtg actcttttgt   43440
cagggttcca caggactcaa aggggccaaa gggtggacga cattccgtga atggacagcc   43500
gggcccgggc gcgcgcacgc aaaggcgccg ccggggaatt cccggcggcg cccggaccgg   43560
cgtcgggtga gacgggggtc aactcacccg gcgccggatc cgccacaccc gaacaccgt   43620 gaggattccg ctgagtgcca catagatcgc ggtctccagc cactggaacg cccagtagcg   43680
gctgctgggg tggtacagga cgtcgacgtg caggtcgtgt tcggcgaggc acaccgcggt   43740
gtcgccgaac gtgccccccg cgccggtctt gggcgggtcg tcgaggcagc cgttgaactc   43800
gctggaggcg agggtcctgc cgtccgcggt gcgcagcgga ctggtctcgg cgatccacgc   43860
gtccggcgcg tccgggatcc gcaccccgcc gatgacggat ccgccgccga tactgcccag   43920
gttctgcgcc gagttgatcg cctcggccgt catcgccagc gtcgtcctgt ccggcggcat   43980
caggctgggc cgcaccacgt tcgggaagaa gaactggaag gcgatgaaga ccaccagcgt   44040
caccgccatc gcgggcaggg tccgccgcag caggagcccg acgacggtgc cgaacgtgaa   44100
ggccagcgcg gcgtagccga tcggggcgat gttgcgcgca ccgaacacga aggtgtcgaa   44160
ctgctccttg acgacgtcgt cgaagggccg ggccgcccag gtgagcaggg ccgcggccgc   44220
accggtcacg atcaccgagg ccgcgccgat gagcaggatc ttgctgagca gccagcgcgg   44280
ccgggtgacg ctctggttcc acaccagccg atgggtgccg ttctcgagtt ccctggcgat   44340
caggggagcc ccccagaagg tgccgatgag cgcgggatc agggccaggc cggtcgccag   44400
gaacagcagg gtgttctgga aggtgctgcg gaactggctc ctggcctggg cgcagttggc   44460
```

```
cgagttgtcg cagttggcct ggtagacgtc atgggcgtca cggatgtccc cgcccaggta   44520
gagcaggtag acggcgatca cggccagcgc gccggcgccg aacagggcct ggacgcggaa   44580
ctgccgccag ctgagccaca tcatcgggtg gccccccagg ctgcggcctc ggtgcgggcg   44640
gcgggaacgg cggccgcccg ggtcatgtag gcgagcacga gttcctcgag ggtgaccggc   44700
tcggaccggt agggcagtgc ctcggtcgcg gcgccggtgc ggacgaccgc gctgctgtgc   44760
ttgccgctgt gctcgaccga gatcacctcg atcccggcgg gcggctggtc gaactcgccg   44820
cgggccgcga ccagccgggc gtgcccggcc agcagctccc gggtgtcgcc ggcgacctgc   44880
acccgggcgt cgcacagcac gatgagatag tcgcagacct gctccacgtc accgaggagg   44940
tgcgaggaga ggacggcgct ggcgccgagc tccagcacga actccatcag gttctgcagg   45000 aaccccggc gcgccagggg gtccagggcc gccgccggct cgtcgaagat cagcagctcc   45060
ggccgcttgg ccgccgcgat ggtcagcgca agctgcgcgc gctggccacc cgagagctgc   45120
ccggccttct gcccggcgct gagccccacc tggctgatgc gccgctctgc caggaccggg   45180
tcccagcccg ggttcatctt cgcgccgaac ttcaggtgct ccgccacggt gaacgcgccg   45240
tacaccggcg tgttctgcgc gacgaacccc acccgggcca ggtgcgacgc gttggccgcc   45300
ggacgcgagc cgaggacgct cagtgagccg gacgtcggtt cggtcagccc gcaggccagg   45360
tgcaggaggg tcgatttgcc ggccccgttc gggccgacca gtccgatgac acggccggcg   45420
gggacgctga ggtgcacgtc gctcagggcg agcttgccgc ggcggccgta cttcttcgtc   45480
aagccctccg cgtgaagcac gggagggggag tctgcgtgtg gcatgactcc atcctcgaat   45540
tccgccccgt tcacggcatc agtccaaagc acggttcccg ttgccggcgg ccgtactttc   45600
ggccggtcgg ccacggccct gctggtgggc gaactgggtg cggtacagct cggagtagag   45660
accgccgccg gccagcagct ggtcgtgggt gccccgctcc tggatccgcc cgtcgtcgat   45720
gacgaggatc tggtcggcgt cctggatggt ggacagccgg tgcgcgatga cgagcgaggt   45780
gcgcccggtc agggcggtct tgagggcccg ctggatggcc agctcggact cggagtccag   45840
gtgcgccgtc gcctcgtcca ggacgacgat cggaggcgac ttgagcagga gccgggcgat   45900
ggccagccgc tgcttctcac cgccggacag ccggtagccg cggtcgccga cgaccgtgtc   45960
gagaccgtcc gggagctggg agatcgtcgg ccagatccgc gccgcctcgc acgcctggac   46020
gatctcgggc tcggaggcgt ccgggcgggc gtacagcagg ttggcccgga tggtgtcgtg   46080
gaacaggtgc gcgtcctggg tgaccacgcc gaccgtgttc tgcagcgagc cgagggtcag   46140
gtcgcggacg tcgtggccgc cgatccgcac cgttcccgag gtggcgtcgt agagccgtgg   46200
caccaggtgg gtgatcgtgg tcttgcccgc gccggacggg ccgaccagcg ccgtgagccg   46260
gccggccggg gcgtggaagc tcacgtcgtt gaggaccagc gcgccggggc cctgctcgct   46320
cttgcgctgc ggcatcaact ccagtgaggg caggacact tcctcggcgc tggggtagcg   46380
gaaggcgacc tggtcgaact cgacgggggg agcggtgccg tcgccgttcg ccgaggcgcg   46440
ggccggcagg gggcgggcgc cgggacgctc ggtgatcagc ggcttcaggt ccagcacctc   46500
gaagacgcgg tcgaagctga ccagcgcggt catgacgtcg ctctggatgt tcgtcagctg   46560
gttgacgggg ccgtacagca tcagcagcag ggcgaccatg ccaccagcg tgccgatctg   46620 cagcgagccg tcgatgacga accagccgcc gaagccgtac accatcgccg tggtgacggt   46680
ggtgagcagg gtgacgagga tgaacagcag ccgtgcgtgc acgtccatcg agatcgcgat   46740
gtcccggacg aggcccgcct tcttggagaa ctcggcggac tcgtcctccg gacggccgta   46800
gagcttgacg agcatcgcgc cggagatgtt gaaccgctcg gtcatcatcg agcccagctt   46860
```

```
ggcgtcgttc tgcatgccgg cgcgggccag cttctccagc cgctgggcga tgatcttccc   46920
ggggatgaag aacagcggga tcatgatcag cgccgccacg gtgatcggcc acgagaggta   46980
gagcatcgcc gcgagcacca ggaccagcgt cagcagcgtc gacagcgact gcgacagcag   47040
cgaggtgagg gcctgttggg cgcccacgat gtcggtgttg atccggctga ccagcgaccc   47100
ggtctgggtg cgggtgaaga cgccaccgg ctgccgctgg atgtgggaga acaccgcggt    47160
ccgcaggtcg aagatgaggc cctggccgac ccttccggag aaccacgtct gcgtgtagac   47220
cgccacgacg ttcagcaggg ccagtccggc gacgagcccg gcgaggccga acacgacgga   47280
cgtcttcccg gggatgatgc cgtcatcgat gatcattttg agggtcagcg ggatcgacac   47340
cgtgatcagg gagtcgacga tcgtcgccac catgaccatc gccatggccc ggcggtagcg   47400
catggcgtag ggaatgatcc gcttgaacgt gccggacctg accggctgcg ggtccaccag   47460
tccttcgacc cgcagtccga tcgtgccat cgtcgggtcg tgtcccacgg tcacggagac    47520
tctcctcagt gtgtgtcgcg tcgctatgtg tcgcgtcgct gtgtggcgcg tcgctgtgtg   47580
tcgtcggggc gtcgcgtcag tgcttgtcga ggaactcgac gatcgccgcg ttgaccgcgt   47640
cgggccgctc gaagtacccg aggtgcccgc agtccgggat ctccacgaga tcgcagtcgg   47700
gaacggcctc ggcgacctcc acgcccaggt gcggcggggt gatgaggtcg tcggcgaagg   47760
tcacgacgcg acaggggcg gccaccccgg gcagcgccgg gcggcggtcg tccatgatgt    47820
cggcccaggc gtgccggggcc tgcgcctccc cgccccgga cagctcgaag acgtccagcc    47880
aggcggtcac cgcctggtcg tcgttgagcg tcgcgggcga gaacatccgg aacaccgtcg   47940
acgcggcgtc gtacgcggcc ggcagccgca ccccgctctc caccagtgcc gtctccgccc   48000
gcgtctgggc ccgccgcgcg gcgtccgcac gggcccgggt ggcgatgagc accgcgcacc   48060
gcacgagttc gggatgcccg atcgccagct cctgcgcgat catcgccccc agggaggtgc   48120
ccacgatccg gcacggcgcc agatccaggg cctcgatcag gcccttggcg tcggcggtca   48180
tgtccagcag cgagtacctg cccggcggcg cgtcggacgg cgggacaccc cggtggtcga   48240
agacgaccgt ggagtagccc gccgtgtgca gcgccggcgt ctggtgcagg gtccaggcat   48300
ggccggccga gcccgagccc atgatcatga gcaccggttc gccccggccc gcacgctggt   48360
aggcgatgcg gacgccccc acggtgacga agtgcgggc gcgccggccc gcggtgtggt    48420
ccatgccgcc tctccctcct cgtcgtcgcg ggggccgccc ggtggtaccg gccggccccg   48480
ggggcggctc actatcgcac gcggccacgg ggcggggcag tgtgcgcggg gcacgtccat   48540
ggacaccccc cggcccgcgt ccaactgcgg tgatgccctc agttggacac cggccggccg   48600
cgtccaagca ggcccggccg acggttgatc cgctgtgtgg agctgagcca tattgggccg   48660
ccgtgagcca ctgacgccca ccaagtcccc gcgcttcttc cgcaccggcc gctggcgcg    48720 cccgtcgcgc cgagggaggg accaccttgt cagcttccga ccttccagcc acccggctga   48780
cacccgagaa gatccggtcc tggctcgtcg accgggtcgc ctactacgcc aggctgcccg   48840
ccgaggagat cggcgccgac gtcccgctcg cgcactacgg actggactcg gtgtacgcct   48900
tcgccctgtg cggagacatc gaggacggcc tcggcctcgt cgtcgagccc gtcctgctct   48960
gggacgtcga caccatcacc gagctcaccg accatctcgc cgaactgaca gccgactgag   49020
ggccttcgag ggggaggacg atgcgtcgaa aggacctgga gaggctgacg tccggtcagc   49080
tcggcgtctg gtacgcgcag cagctcgaac ccctgagccc cgtgtacaac atcgccgagt   49140
acgtggagat ccgcggcgac gtggacgtcg ggcttctggt gtcggcgctg cggtctgccc   49200
tcgacgaggc ccagacctac cggctccgct tccggcagga ggacgccggc cccggacagt   49260
```

```
acgtcgacga ctcgctggag cttcccgtcc acgtcgccga cctcggctcc gcaggggacc   49320
cgcgcgccgc ggccgtggag tggatgaccg ccgacctgga ccgccccgcg gaccccctca   49380
ccggcccgct ggccgcccac gccgtgttcc ggctgggacc cggccatgtc tctctggtacc  49440 agcgtgccca ccacctcgtc ctcgacggga ccagcctctc cgtgttcgcc gcccgggtgg   49500
cggacctcta cacggcgtcg gcgtcggggc gcccgcccgc cggcggcgca ccggggccgc   49560
tgtccgtact gctggacgcg gaccgctcct acctccggtc cgaggagtac gcacgcgacc   49620
ggcggttctg gcgcgagtac ctggcggacc tgcccggcca gggcgccgca cgcggggacc   49680
gcacccggtc cctgcccggc cggcccctgc tgcacacgca cccgaacgac gcgtccgccg   49740
ccaccgaact gagggaagcg gcacgccggt tgcgcaccag ccccgccgtc ctgtccctga   49800
cggccgccgc cctgtaccgg caccgtacga ccggacacg cgatgtcgtc ctcggcgttc    49860
ccgtcaccgg gcggaccacc ggacgggaac tcggcatccc cggcatgacc tccaacgtgg   49920
tgccgctccg gctctcccte gaccggggcg tcacggtcgc cgaactcctg cggcgcacct   49980
cccgcaccct gcgcgactgc ctgcgccacc agcggtaccc gtacggcgac atcctcgccg   50040
accaggggct cgtcggccgt ggcgcgctgc gcgatctgag cgtcaacctg atgttcctga   50100
accggccgct gcggttcggg gacgccgtcg ccacccgcac cggcctgtcg agcggcccca   50160
tcgacgacgt ggcgatcggc gtgtacgacc gggggggacga cggcttccgg acggtcgtgc   50220
agaccaaccc cggcctgcac gaccccgggg cgggagcgga gatctcccgc gcgttccgca   50280
cggtgctcgg ccgcctggcg gcggcaccgg ccgacgcgtt cgccgaccgg atcgacgccc   50340
tcgacgagga ccagcggcgg cgcgtgctcg tcacctggaa ccgcaccgtg acgagcggcg   50400
tcgcccccag cgtcctgagc cggttcgagg agcacgccgc ccgcacccg gacgcggtcg    50460 ccgtggtctg cggcgcgtcg gagaccacct accgcgagct ggacgagcgg gccgaacggc   50520
tggccggagt actgcgcggg cacggcgtcg gacccgaagc ggtggtcgcg gtgtgcctgc   50580 cgccccggacc cgccctgctg accgcgttcc tggcggcctg gaaggccggc gccgcgtacc   50640
tgccgatgga cccggggcat cccgcggagc gggcccgcct cacccctcgcc gagagccggg   50700 cgaccgcgct gatcgccacc ggcgagccgc tgcgcgacct ggcagggagc ggcatcgccg   50760
ccctcgaccc ggacgacctg ccggtcaccg ccccggcggc cccggcggca ccggcccccgc   50820 tgcccgccca actggcctac ctgatcttca cctcgggctc gacgggcgtc cccaagggag   50880
tcgccgtcac ccacggcgcc ctggccaact acacggtctg ggcggccgag ttcttccgga   50940
tgcgccccgg cgaccactca cccatgcatt cgtcgacggc cttcgacctg gcggtcaccg   51000
gcgtcctggt gccgctggtg tgcggcgagg ccgtggacat cagccccgag ggcggcgcgg   51060
cggggctggc cgcactgacc agggcccgag ccggagaacc gttcggcctg gtcaaggtgg   51120
tgcccggaca tctgccgctg ctcaccgaaa ccctcaccgt cccggaacgg gcctcggcga   51180
cacggcgcct ggtggtgggc ggcgaggcgc tgcccggggc ccatgtacgg gcatggctgc   51240
gcgacgcgcc ggacacggtg gtggtcaacc actacggtcc caccgagacg accgtcggct   51300
gctgcgtgtt cgaggtgccc tccggacgac cggtcggcga ccgggtgccg atcggccgtc   51360
cgatcgccaa cacccgtctc tacgcgctgg acgacgcgct caaccccgta cccgtcggcg   51420
cactggggga gctgtacgtc gcgggcgccg gactggcccg cggctacgcc cggcgcgcgg   51480
gaccgaccgc ggaacggttc gtggcctgcc ccttcgggcc gcccggacag cgcatgtacc   51540
gcaccggcga cctggtgcgc tggaccgccg cggccagct cgagttcgcg ggcccgggccg   51600 acgaccagat caagatcaac ggataccggg tcgagcccgc ggagatcgag gccgtactgt   51660
```

```
cccggcaccc ggcggtcgcc cgtgccgtgg tggtgccccg caccaccgac cgcgacggcc   51720
ccccgcaact ggtcgcctac gtggtgcccg ccggggggaa ggaagccgac acccgggaag   51780
tgcgccgctt cgccgcacac gcgttgcccg cccacatggt ccccgcgacg gtggtggcgc   51840
tcgacaccct gccgctgacg gcgaacggga aggccgaccg gagcgccctg ccggcacccg   51900
accccggcac ctcggaccgc gcgccgcgca gccccggca gacgatcctg tgcgagctgt    51960
tcgccgaggt cctcggcctg ccacgggtgg gcaccgacga cgacttcttc gccctcggcg   52020
gccactccct gcccgccacc cggctcatcg cccgcatccg ggccggcctc ggcgtcgagg   52080
tgccgatgaa ggcactgttc gcggcgccga cggtggcggc ccttgacacc tggcttgacg   52140
acgacggccc gacccggccc cccgtccggc cggcgccgcg ccccgacccc ctcccgctgt   52200
ccccggcaca gcaccgtctg tggttcctgc accgcatgcg gggccagtcg gcgacgtaca   52260
acgtccccct gggactgcgc ctgaccgggc cactggaccg ggaggcgctc caggcggcac   52320
tgtgcgacct ggtggagcgg caccagacac tgcgcaccgt ctacccggac accgacgggg   52380
tgccccgcca gcggatcctc gcccccgagg aggcccgccc ccgtctggag acgtccgagt   52440
gggacggacc cggggggactg gagcgcgccg cgcggtacgc cttcgacctc cgccacgagc   52500 tgccctgcg cgccgaactc ctcacggtgg ggccgcggga gcacgtcctg ctgctgatcg   52560
tccaccacat cgccgccgac gcctggtcga tgtccccgct ggcgcgcgac ctggccaccg   52620
cctacgccgc ccgcagccgg ggcagggcac ccgattggcc gcgactgccg gcgcagtacg   52680
cggactacac cctgtggcag cgccagttgc tcggcgcggc agacgacccg ggcagcctgc   52740
tcggcagcca gatccgctac tggcgcgaac aactcgacgg gcttccggcc cggttggaac   52800
ttccggccga ccgccccgc cccgccgtgg cctcccaccg gggcgccagg ctcccgatcc    52860
ggctggaaca ggacctgcac caggccctga cccgactcgc ccgacagcag ggcgccaccc   52920
ttttcatggt gctgcacgcc gccgtggccg cactgctgac ccggcttggc gccggcaccg   52980
acatcccgct gggcgcgccg atcgcggggc gtaccgacga ggccctcgac gacctcgcgg   53040
gctgcttcgt caacacgctg gtactgcgcg ccgacacctc cggcaatccc gccttcgacg   53100
acctcctcca acaggtccgg aacaccgacc tggccgccta cgagcaccag gacgtcccct   53160
tcgagcacct cgtcgaggtg ctcaaccccg aacggtccca ggcccaccat ccctgttcc    53220 aggtcggact cggcctgcag aacgtctcgc cccccaccct tggactcccc ggcctcgaca   53280
cccgcccgga gccggtcgac accggcaccg cacggttcga cctgatgctc aacctcaccg   53340
acacccacac cgacgacgcg accccggccg gcgtgaccgg aacggtcgag tacgcgaccg   53400
acctcttcga cgccggcacc gtccgcaccc tcgtcgaccg gctcgtacga ctgttggagc   53460
aggtggcgga cgaccccgg cggcgcctgg gcgacctgga cctgctgacc gccgaggagc    53520
ggcgcgggct ggtggccgag accaccgccg ccgaggggtc cgaggcgacg cttcctgagt   53580
tgttcgcggt gcaggcggcg aggacgcctg atgcgacggc ggtgacggcg ggcggggtgg   53640
agttgtcgta cgcggagctg gacgcgcggg cggagggtt ggcgcggggt ctggtggggc    53700
gtggtgtggg tcctgagtcg gtggtggggg tgctgctggg gcggtccgcc gatgtggtgg   53760
tggccgtact ggcggtggcg aaggcgggcg gtgcgtatct gccggtggat ccggactatc   53820
cggcggatcg tgtggcgttc gtgctgtccg acgcgggggc ggagtggggtg gtgacgtcgg   53880 cggagttcgc gccggtcctc cccgctggtg tggcggccgt gacggtcgac ggggccggtt   53940
cggggccggt gttcgactcg gtgccgttgc cgacggtacg cccggaccat ccggcgtatg   54000
tgatctatac gtcggggtcg acggggcggc cgaagggtgt ggtggtgcca caccgcagtg   54060
```

```
tggtggcgct gtttgctgcc acccggggggg tgttcgagtt cggtgctggg gatgtgtgga    54120
gctggttcca ttcgctggcg ttcgatttt cggtgtggga ggtgtggggt gcgctgctgc    54180
atggtgggcg ggttgtggtg gttccgttcg atgtgtcgcg gtcgccgcgt gagttcgtgg    54240
agttgttgga gcgcgagcgt gtgacggttt tgagtcagac gccgtcggcg ttctatcagc    54300
tgatgggtgt gggggggtggg ctgccggctc tgcgcacggt ggtcttcggc ggtgaggcgt    54360
tggagccggg gcggctcgac ggctggtggg agcggttcgg ggaggcgggg ccgcggttgg    54420
tgaacatgta cggatcacg gagacgacgg tgcatgtgac gcaccaggat ctgcgcccgg    54480
acaccgccgc cgacggcagc gtgatcgggc ggggtctgcc ggggttgtcg gtgttcctgc    54540
tggatgagtg gctgcggccg gtgccggtgg gtgcggtggg tgagatgtat gtggccgggg    54600
cgcaggtggc gcgggctat cggggtcgtg ccgggttgac gggtgagcgg ttcgtggcgt    54660
gtccgttcgg tgcggcgggt ggccggatgt atcggacggg tgatcgggcc cggtggtcgc    54720
gggatggccg gctggtgttc gcggggcgtg cggatgagca ggtgaagatc cggggggttcc    54780
ggatcgagcc gggtgaggtc gaggcggtgg tggcgggcca ccgcgacgta gcgcaggtgg    54840
cggtggtggc gcgtgagggc ggtccggggtg ggctgcggct ggtcgcctac atcgttgctg    54900
ccgaaggcac tgacggactc gcggaccggg tgcgcgtgtt tgcgggggag cggttgccgt    54960
cgtacatggt gccgtccgcg ttcgtggttc tgggcggcct gccgttgacg gtcaacggca    55020
aactcgaccg caccgcactg ccggagccca cgtacaccgc cggtggcggc cgtgccgcgg    55080
cgacggccga ggaagaactg ctctgccagg cgttcgccga ggtgctcggc ctgccgaccg    55140
tcggcgtcga cgacgacttc ttcgccctcg gcggccactc cctgctcgcg acccggctca    55200
tcgcccgcgt ccgcgcctcg ctgcgagaag aactgccgat cgaggaactg ttcgcgactc    55260
ctacaccggc cgcgctcgcg gcctggcttg ccgagcacgg cggcgggacg cggagcacca    55320
ggcccgcgct gcgcccgatg cgctgaagga aaggggttcc acatgattcc cgcgtcgttc    55380
gcccagcggc ggctgtggct gcagtggcgg atcgaggggc ccagcgccac gtacaacagc    55440
cccaccatcc tgaggctgac cggacgactg gaccggcagg cactcgcctc cgcgctccgt    55500
gacgtcatca cccggcacga agcgctgcgc accgtcttcc gggaagccga cggcgagccc    55560
caccagcgga tcgtccctct cgcggaactg gactgggcac tgcacgtggt cgaggtgatc    55620
ggcggcgccc acctccgtc gcaccaacgc ctgtacaccc acgaggagtt gcgctgggac    55680
gagccggtcc tggacctgcc gaccgtcgag ccggcgagcg acctgccggc cgaacggatc    55740
gacgcggcgc agctgaccgg cgccgtcgcg cgcgtggccg cccacacctt cgacctctcc    55800
acggaaatcc cgatacgggc atggctgttc gccatggctc ccgacgaaca cgtactggtg    55860
acggtcgtcc accacatcgc caccgacgga tggtcggccg gacccttcac gcgtgacctg    55920
tcgacggcgt acaccgcccg caatcacggc cgggcaccgc agtggtctcc gctgccggtg    55980
cagtacggcg actacaccct gtggcaacga gagctcctcg gcgaccggga cgaccccggc    56040
agcgtcctct cccgccagat cgcctactgg cgggagaacc tggagggagc tcccgaggag    56100
ctgaccctgc cgttcgaccg tcctcgcccc gtggaacctt ccaccgcgg gcacgcggtc    56160
acgatcggac tgcctgccca aaccacgcc gcactggccg cggtggcccg acggcaccgg    56220
gccactctgc ccatgctgtt ccaggccgga ctcgcggtga cgctgtcacg gctcggcgcc    56280
ggccacgaca tccccctcgg gacgccgacc gcgggacgct ccgacgaggc gctcgacgac    56340
ctgatcgggt tcttcgtcaa cacccctggtg atcgggcgg acctggccgg cgacccgacg    56400
ctcgccgagg tgatcgaccg ggtgcgcacc accgccgtac gcgccttcgg ccaccaggac    56460
```

```
gtgccgttcg agcggctcgt cgaggagttc gccccacccc gctccctcgc ccggcacccc    56520
ctgttccagg tcgtcctcgc cccgctcgac gacggtgccc ggctggacat ccccggcctg    56580
cgcggcgagg tgctctccat cggccgctcc accgccaagt tcgacctcga ggcgacgctg    56640
ggcgaggcct tcgacgacga cggcgaggct gccgggatac gcggtgtggt cacgggctcg    56700
gcggacctgt tcgaccagag cacggtcgag cggatcgcgg gctgtctggt acgggtgctc    56760
acggcgttcg ccgccgaccc ggagcagcac gtcggctcgg tcgacatcct gggcgcggac    56820
gaacgctcgc ggctggtgga ggggttcaac gccacggcgg ttcccgtgcg ggacgcctcg    56880
ctgccggaga tgttcgcgcg acagttggcg gcctgcccgg acgcaccggc cgtggtgtgc    56940
ggcgcgaccg agctgtcgta cgccgagctg gacacgcgct cggaccggct ggcacgcgct    57000
ctggtggccg agggagtcgg tcaggagtcg gccgtcgcgg tcctgatgga acgctcgatc    57060
gacctcgtgg tggcgctgct ggcggtggtg aaggccggcg gagccttcgt gccgctggac    57120
acggggtggc ccgaggcgcg caagcgcgcg gtgatcgagg acgcgggcgc ctccgtgatg    57180
gtcgtggacg acaaggcggc cgggcatgag cagttcgggg cctcgttggt tgcggtcggg    57240
tccggggcgg actccgacgt ggtgctgccc gcttcggtgg ctccgggtgc tgcggcgtat    57300
gtgatgtata cgtcgggttc gacggggtg ccgaagggtg tggtggcgac gcaccgggac    57360
gtggtgcggc ttgcgaagga ccggtgctgg ggtgcgcccg cgcgggtgtt gttccatgcc    57420
ccgcatgcgt tcgacgcgtc gtcgtacgag ttgtgggtgc cgttgctgtc gggcggcacg    57480
gtggttgtcg ccccggacga ggcgatggac ggggcggtgt tgcggcgtct ggtttcggac    57540
cacggggtgt cgcatgtgca tgtgaccgca ggcttgttga gggtgctggc ggatcaggac    57600
ccgggctctt tctcgggcgt gcgtgaggtg ctgaccggtg gtgacgtggt cccggccgag    57660
tcggtgcggc gggtgctgga cgccaacccc ggcgtgacgg tgcggcagtt gtacggcccg    57720
accgaggtga ccctgtgcgc gacgcagtac gaggtcgcgg acgccgccga ggtcgacggt    57780
gtgctgccga tcgggcgccc cctcgacaac acgcgcgtct atgtgttgga cggtgcgctg    57840
agcccggtgc cggtcggtgt cgccggtgag ttgtacgtag ccggtgccgg cgtcgcgcgc    57900
ggttacctgg gtcgcccggt gttgacgggt gagcgtttcg tggcctgccc cttcggggcc    57960
accggtgagc ggatgtaccg cacgggcgac ttggtgcgct gggacgccga gggccggctc    58020
gtcttcatgg gccgggccga cgaccaggtg aagatccgcg gtttccgggt ggagccgggc    58080
gaggtcgaga cggtggtggc cgcccatccg gcggtcggcc aggcggccgt cgtcgtacgg    58140
gaggacaccc cgggcgacaa gcggctggtc gcctatctgg tgccggccgg gaccgagacg    58200
tcgctcgccg acgcggtgcg cgcccacacg gccgaacggc tcccggagta cctggtcccc    58260
tcggccttcg tggagctgga gaacctgccg ctgacgccca gcggcaagct cgaccgcaag    58320
gtcctgcccg caccgctgta cgcctccggt gccggccgtg aaccggccac cgtacgcgag    58380
gagttggtgt gccgggcgtt cgccgaggtg ttggggctgg cgtcggtcgg ggtggaggac    58440
gatttcttcg ctctcggggg tcattccctg ttggcggtgt cgttggtgga gtggttgcgt    58500
cggcgtgggg tgtcggtgtc ggtgcgggcg ttgttcgtga cgccgacgcc tgccgcgctg    58560
gcggcggtgg cggggccgga gttggtggag gtgcccccga acctgatccc ggagggcgcg    58620
tcggagctcc gtccggagat gctgccgttg gtggagctgt ccgaggcgga ggtcgcccgg    58680
gtggtggccg cggtgccggg cggcgcggcc aatgtccagg acgtgtatcc gctggcgccg    58740
ctccaggagg gcatcttctt ccaccacttg atggcggagc gggacggtga ggacgtctac    58800
gcgatgccct tcaccctccg gttcgcggag cggtcgggtc tggatgcgtt cctggggggcg    58860
```

```
ttgcagcggg tggtggaccg gcacgacgtg taccgcacgt cgatcgtctg ggaggggctg    58920
cgggagccgg ttcaggtggt gtggcgccgc gccgagctac cggtcaccga ggtggttccg    58980
gacgccagcg gtgagagcga cgcggccggg cgccccgcca cgctgatgac ggctgtgggc    59040
ggccgtatgg agctggaccg cgcccctctg ctgacggtgc acatcgcggc cgaaccggac    59100
ggcgacggat ggcaggccct ggtacggatg caccacctgg tgcaggacca caccgccctg    59160
gaagtggtgc tggacgaggt ccgggcgatt ctggcagggc gggcggacga actgcccgcg    59220
ccggtgccgt tccgggactt cgtcgcgcag gccaggctgg gcgtctccga ggaggcgcac    59280
cgggagtact tcacccggct gctcggcgac gtcaccgaga ccacgccccc ctacgggctg    59340
ctcgacgtgc acggcgacgg caccgggatc gcgcagggcc ggctgaccgt ggagagcggc    59400
ctggccgcac gtgtgcggag ggcggcccag tcgctcgcgg tcagcccctgc gacggtgttc    59460 cacgtcgcat ggggacgtgt gctggcggcg gtgtccgggc gcgacgacgt cgtcttcggc    59520
acggtgctgc tgggccgggc gaccgtcggg gccgaccgtg tgccggggct gttcatgaac    59580
accctccccg tcagggtgag gaccgccggc cggaccgtgc gtgacgcgct ggacgacatg    59640
cgcgagcagc tcgccgagct gcaggtccac gagcacgcgc cgctgacact ggcgcaggag    59700
gccgccgacc tgcccaccgg cagtcccctc ttcacctcga tcttcaacta ccggcacctc    59760
caggccgacg ttccccggtc cggtaccggc atcgaaggcg tcgacgccac tgcgacgagg    59820
gacgccacga actacccct cgacctctcc gtcaaccaga gcggctccgg cttcgaactg    59880
gtcgtggagg cgacggcacc ggtggatccg cggcggtgt gcgggctgct gcacgcctcg    59940
gtggcgaacc tcgtcacggc gctggaggac accccggatc tgatcctcgg ggcgctggac    60000
gtcctcgatg ccgagtacac cgccttgctg cggcaggtca acgacacggc cgcgcccgct    60060
ccggccggcc ttgttccggc gctgttcacc gcgcaggcgg cacggctgcc cgaggcggtg    60120
gcgctggtcg gcgccggcgt cgagctgagc tacggcgagg tcgaggcccg ttcgaaccag    60180
tgggccaggc atctgatcgc cgcgggggtg ggcccggagt cggtggtcgc cctggtgctg    60240
gaacgttcac cggatctgct ggtggcgatt ctcgcggtgc tgaaggccgg tggagcctat    60300
ctgcccatcg atcccgatca gcctgccgaa cgcgtggcgt tcatgatcga ggacgccgca    60360
ccggtgctcg tgctcgacga gtccgccctg caggcggggg ccggcgaccg tgccgactcc    60420
gcggtgtccg acgccgaccg gctcgccccg ctgctgccca ctcacccggc ctacgtgatc    60480
tacacatcgg gctcgacggg gcggcccaag ggcgtcgtcg tcacccacga ggggttcgcc    60540
aatctctcgc tgagccaccg ccggttcgag gtcggaccgg gcagccgggt ggcgcagttc    60600
gcctcggcgg gcttcgacat gttctgcgag gagtggctgc tggcgttgct gtcggggcg    60660 gccctggtga ccgtccccgc cgaccggcgg ctcgcgcgcg acttcgcgga gttcctggcc    60720
gaatctgggg tgacccatgc gacgttgcca cccgccgcgg tggccacgct tccggagggc    60780
gccctcgacg acggcttcgt cctggacgtg ggcgagagg cgctgccggc cgagacggtc    60840
tcccgctggg cggccggccg gaagatgttc aacagctacg ggcccacgga gaccacggtg    60900
aacgccgcca tatggcgctg ccgttcaggt ctggcagccg gggcggaggt gcccatcgga    60960
cgcccgatcg tcaacacccg ggtccatgtg ctcgacgacg cgctgcgcc cgtaccggcg    61020 ggcgtgctgg gcgagttgta cgtgaccggc acggcctgg cacgcggcta cctgggtcgc    61080
gccggcctca ccgccgaacg gttcgtggcc tgcccgttcg agccgggaca gcggatgtac    61140
cgcaccggca ccgggtgaa gtggaacgcc gacggcgacc tggtcttcgc cgggcgtgcg    61200
gacgaccagg tgaagatccg cgggttccgg atcgagccgg gtgaggtcga ggccgtactc    61260
```

```
gcggcccatc cgtgggtgga ccgggccgcg gtcgtcgtgc gcgaggacac ccccggcgac   61320
ccacggctgg tcggctacgt gatccccgcc gaagacatcg atacccatga actgccctcc   61380
ctgctgaccg agttcgcggc gcagcggctg ccggcgcaca tggtgccgtc ggccgtgacg   61440
acgctcgacg cgttcccgct gacaccgaac gccaagctgg accgcaaggc cctgccccgg   61500
ccccggtaca cggctgccgc cggggcgggc cgcgccccgg ccgacgtgcg cgaggagacc   61560
atctgcgccg ccttcgcgga ggtcctcgga ctggaccggg tggggtcga cgacgacttc   61620 ttcgccctcg gcgggcactc gctgctggtc gtctcactcg tggaacggct cgcccggcgc   61680
ggggtgtcgg tctccgtgcg ggccctgttc acgacaccga cgcccgccgg actcgcggcg   61740
gccgcgggcc cggaggcggt cgacgtgccg cccaacctga ttccgcacgc ggcgaacgag   61800 atcaccccg agatgctgcc gctggtcccg ctcaccacgg ccgagatcga acgggtgacg   61860
gccgcggtgc ccggcggcgc gcccaacatc caggacgtgt accccctggc accgctccag   61920
gaaggcatct tcttccacca cctgacgcg gaccgggacg gcacggacgt gtacgtcacg   61980
ccgtcgaccc ttcgcttcga ctcccgcagc cgactcgact ccttcctcgc cgccctccag   62040
aaagtcgtcg accgcaacga cgtgtaccgc acggcgatcc tgtgggaagg gctgcgcgag   62100
ccggtccagg tcgtcgtacg ccacgcggaa ctgccggtca ccgaggagcc ggcggagcgg   62160
ctgctcgcgg ccggcggcgg ctggatggac atcggacggg ctccgctgct cgacgtacgg   62220
acagcggccg aaccggacac cggacggtgg ctggccctcg tacgcgtcca ccacctggtg   62280
caggaccaca cggcatcgga cgtgctcctc gacgaggtgc gcgccttcat ggccgggcag   62340
gccgaccgcc tgcaaccagc cgtgccgttc cgcgagttcg tggcacaggc acggctcggc   62400
atgccgaggg aggagcacga gcggtacttc accgggcttc tcggtgacat caccgaaccc   62460
accgcgccct acggcctcat ggacgtgctc ggagacggcg gcgccgcccg gacgggccga   62520
ctgcccgtcg aacccggcct ggccggcgcg gtacgggagg tggcgcgtgc tcggggcgtc   62580
agcccggcga ccgtgctcca ccttgcctgg gcgcgtgtgc tggcggccgt ggccggccgc   62640
caggatgtcg tcttcggcac ggtgatgttc ggccggatgc actcgggcga gtccgccgac   62700
cgggtcgccg gcctcctcat caacacccctg ccggtacggg tgaacacggc gggagcgggc   62760
gtcggcgagg ccctgaccgg gctgcgtgac caactcgcgg acctcctcgt ccacgagcac   62820
gcctcactgg cactggcgca gtcggcctcc ggcctgcccg gaggcgggcc gctgttcacc   62880
tcgctcttca actaccggca tctccagggc acggacgccg gcgggacgga actgacggc   62940 atcgaggtgc tgtccgtcca cgaccacacc aactatccgc tcaccgtctc ggtggaccag   63000
agcgccaccg gcctggagct ggtggtggag tccgtggcac aggtggacgc gacggaggtg   63060
tgcgggctgc tgcacacctg cctggcgaac ctggtcaccg ctctgaccga ttccccggac   63120
gtccccctcg gcgcgatcga cgtcctcgac gccgcgtacg ccgcccgcct gtgccggagc   63180
gacgaggaca cggcgggacc ggtgccgggg gcgtcggtgc cggagctgtt cgccgcgcgg   63240
gcccggttgt caccggatgc ggtggcgttg gtgggcggcg gtgttcagct gagttacggg   63300
gaggtggagg agcgggcgaa ccgtctggcg cggaagctga tcgcgcgggg tgtaggcccg   63360
gagtcggtgg tggctctggt gctggagcgt tcaccggaag tggtcatcgc cgcgttggcg   63420
gtgctgaagg cgggcggcgc ctacctgccc gtcgatcccg ggcagcccgc cgagcgcatc   63480
cggtccgtga tcgaggacgc cgcccccggtc ctggtgctgg accaccggga cttcctggcg   63540
gagaccgccg actacgacgc ggcaccggtc acggacgccg accgcgtctc cccgctgctt   63600
ccctcccacc ccgcctacgt gatctatacg tcggggtcga ctgggcggcc gaagggtgtg   63660
```

```
gtggtgtcgc accgcagtgt ggtggcgctg ttcgttgccg cgggtggggt gttcgagttc   63720
ggtgccgggg atgtgtggag ctggttccat tcgctggcgt tcgattttc ggtgtgggag    63780 gtgtggggtg cgctgctgca tggtgggcgg gttgtggtgg ttccgttcga tgtgtcgcgg   63840
tcgccgcgtg agttcgtgga gttgttggag cgcgagcgtg tgacggtttt gagtcagacg   63900
ccgtcggcgt tctatcagct gatgggtgtg ggggtgggc tgccggctct gcgcacggtg    63960
gtcttcggcg gtgaggcgtt ggagccgggg cggctcgacg gctggtggga gcggttcggg   64020
gaggcggggc cgcggttggt gaacatgtac gggatcacgg agacgacggt gcatgtgacg   64080
caccaggatc tgcgcccgga caccgccgcc gacggcagcg tgatcgggcg gggtctgccg   64140
gggttgtcgg tgttcctgct ggatgagtgg ctgcggccgg tgccggtggg tgcggtgggt   64200
gagatgtatg tggccggggc acaggtggcg cggggctatc ggggtcgtgc cgggttgacg   64260
ggtgagcggt tcgtggcgtg tccgttcggt gtggccggtg ggcggatgta tcggacgggg   64320
gatcgggccc gctggtcgcg ggagggccgg ctggtgttcg cggggcgtgc ggatgagcag   64380
gtgaagatcc gggggttccg gatcgagccg ggtgaggtcg aggcggtggt ggcgggccac   64440
cccgacgtgg cgcaggtggc ggtggtggcg cgtgaggggcg gtccgggcgg gctgcggctg   64500
gtcgcttaca tcgtgccgga accggccgag caggctgagg gtttctcgga gcgggtgcgg   64560
gtgtatgcgg gggagcggtt gccgtcgtac atggtgccgt ccgcgttcgt ggtcctggac   64620
ggcctgccgt tgacggtcaa cggcaaactc gaccgcaccg cactgcccga accggacaac   64680
gcggtcgtga gcgccggacg cgccccgtgt accgccagg aagagctgct gtgcgccgcg    64740
ttcgccgaag tgctcggctt ggaccaggtc ggcgtcgacg acgacttctt cgccctcggt   64800
ggccactccc tgctggccgt gtcgctggtc gaatggttgc gacagcgcgg cgtctcggtg   64860
tccgtgcggg ccctcttcgc ctccgcgacc ccggcccgcc tggccgaagt ggccgggccc   64920
gaccggatcg aggtgccgcc ccgccgcatc ccgacggtg ccacccggat cacaccggac    64980
atgctccccc tggccgagct gacggaggag gagctggccc gcgtcgaggc ggccgtcccc   65040
ggcggcgcgt ccaacatcca ggacgtgtat ccctggcgc ccctgcagga ggggctcttc    65100
ttccaccatc tgatggccga ccgggacggc acggacgtct acgcgactcc gatggtgctc   65160
acgatcgcga cccgggagag gctcgaggac ttcctcacgg cgctgcggcg gatggtggtc   65220
cgcaacgaca tctaccgcac cgcgatcgtg tgggagggtc tgcgcgaacc ggtgcaggtg   65280
gtcgtgcgtc acgcggagct gccggtggag gagatcgcgc ccgccccgga cggatcggac   65340
gccgtcgacc ggctgctctc gacgggcgag tccgccatgg acctgacgcg ggcgcccctg   65400
ctgcgggtgc gggtgatgga ggccccgac ggtggctgga cggttctcct gcgcatccac    65460
cacctggtcc aggaccacac caccttcgac gtggtgctcg acgaactccg cgcgttcatg   65520
aacgggcggg gcgggacgct gcccgccccg gtgccgttcc gcgagttcgt tgcccgggca   65580
cggttcgggg tgtcgcggga ggagcacgag cggtacttca ccgacctgct gggcgacgtc   65640
accgacacca ccgccccgta cggcctgacg gacgtctacg gtgacggaac ggaggccacg   65700
caggtccggc tcacggtgga cgacaccctg accggccggg tccggagcct ggcgcggtcg   65760
cacggcgtga gccgcgcgac gctgttccac gtgcgtgggg cacgggtgct cggcacactg   65820
tcgggacgcg acgacgtcgt gttcggcacg atcctgttcg gacggatgaa cgcgggcgcc   65880
ggcgccgacc gcgctcccgg cctcttcatc aacaccctcc cggtgcgcat gcgtccggcg   65940
ggaaggagcg tggccgaggc cctcacggac atgcgcggcc agctgcccca gctgatggtc   66000
cacgaacacg cctcgctcac cctggcgcag cgtgccggcg gcgtgccggc gagcagcccg   66060
```

```
ttgttcacct cggtgttcaa ctaccggcac aacctgccga ccgagcggca ccccggtgcc   66120
gacctcgacg gcgtcgacct cctcctgcac cgggactact cgaactaccc gatggtcgtg   66180
tccgtcgacg acgacggcac aggcttcgag gtggagatcg aggccgtcgc cccgtcgat   66240 cccgaggggg cgggcggact gcttctcacc tgcctggagg gcctggcggc cgcgctggaa   66300
gacgcaccgg ccacaccact caccgggatc gacgtactcg gctcgaccga gcgcacacgg   66360
attctgaccg gatggaacga cacgacggca cccgtgtcgg gtgtgtcggt cccccgggcc   66420
ttcgccgcac gcgtggcggc gcatccggac gcggtggccg tggtgagcga cggcgtacgg   66480
ctcacctacc gcgaactgga cctgcgatcc gaccggttgg cgcgggcgct gatcaggtcg   66540
gacgccgggc cggagccggt tttcgccgtg ctgatggagc gctccgccga tctggtggtc   66600
gccctgctcg ccgtgctgaa ggccggcggt gcctttctgc cactggacgc gacatggcca   66660
caggccagga tgcggtcggt catcgaggac gcggccgcgt gcctcgtcgt ggtgagcgag   66720
acgtgggccg gcatgacctc cgggatcacc gaggtcgccg tggacgccgg ctccgacgag   66780
gggcacctcc ccgtcgtacc ggaggcggcg accgcgtacg tgatgtacac atcgggttcg   66840
gcgggcgtgc cgaagggtgt ggtagcggca caccgggatg tggtggcgct cgccggggat   66900
cgttgctggg gtgcgcccgc gcgggtgttg ttccacgcgc cgcacgcctt cgacgcgtcg   66960
tcgtacgagt tgtgggtgcc gctgctgtcc ggcggcacgg tggtggtggc gccggacggg   67020
cgtatggaca ccacggtgtt gcgtcgtctg gttctcgacc acgacgtgtc gcatgtgcat   67080
gtgacggcgg gactgttgcg ggtgctggcg gatcaggacc cgggttgctt cgcgggcgtg   67140
cgtgaggtgc tgacgggcgg ggatgtggtt ccggccgagt cggtgagacg ggtactggac   67200
gccaatcccg atgtcagggt tcggcagttg tacgggccga ccgaggtgac cctgtgcgcg   67260
acgcagtacg aggtcgcgga cgccgccgag gtcgacggtg tgctgccgat cgggcgtccg   67320
ctcgacaaca cgcgtgtgta cgtcctggac ggtgcgctga accccgtacc ggtcggtgtc   67380
gccggtgagc tgtacgtggc cggtgccggt gtcgcgcgag gctatctggg acggccggtg   67440
ctgaccggtg agcgtttcgt ggcgtgcccg ttcgggggtg ccggtgaacg gatgtaccgc   67500
accggtgacc tggtgcgctg ggacgccgag ggccggctgg tgttcgtggg gcgtgcggac   67560
gagcaggtga agatccgcgg gttccgggtc gagcccgccg aagtggaggc ggtcctcggt   67620
gcccatcccg ccgtcgggca ggcggccgtc gtggcgcggg aggacacccc ggggggacaag   67680 cggctgatcg cctacctggt cccgcagaac gagggcgaga ccctcgacgg cccggtccgg   67740
gagtacgcgg ccgagcggct gccggagtac atgctcccgg cggccttcgt ggagctggat   67800
accctgccgc tgacggtcaa cggcaagctc gaccggaagg cgctgccgc accgcggtac   67860 tccccggaca cgggccgggc gcccgcgacc gctcgggaag agctgctgtg tcacctgttc   67920
gccgacaccc tcgggctgcc ccgggtcggc gtggacgacg acttctttct gctcggcggg   67980
cactcactgc tggccatgcg actggtgagc cgggtgcgcg aggtactggg cgtggagatg   68040
ccgctccggg cgctgttcga ggcccgtaca ccggcggggg cggccgcccg gtcggtcagg   68100
gcgacacctg gccggacggc gctgaaggcc ggcgcccggc cggagcggat tccgctgtcg   68160
tacgcccagc gacggctgtg gttcctgggg cagttggagg ggccgagccc ggcttacaac   68220
atcccgctgg ccctgcgcct gacggggacg ctggaccggg acgccttcgc cgccgccctg   68280
cgcgacgtgg tcgagcgcca cgaggtggtg cgcacagtca tccggacggc cgacggagaa   68340
ccgttccagc gggtgctgtc gccggaggag gcggcgttcg agctggagat cgtcgaggtg   68400
gcgaccggcg aactggccgg ccgggtggcg ggggctgccc ggtacgcgtt cgatctcgcc   68460
```

```
gcagaacccc cgctgcgcgc gaccttgttc acggcggcac cggacgagca tgtgctggtc   68520
ctggtgcttc accacatcgc cggcgacgcc tggtcgatgg agccgctggc gcgtgacgtg   68580
tcggcggcgt acacggcgcg gctggcgggc gacgcccgg  tgtgggagcc gctgccggtg   68640
cagtacgccg actacgcgct gtggcaacga gagctgctcg gcgacgaggc ggacccgcgg   68700
agcctgctgt cacgccaggt cgcccactgg cgggagaccc tggccggcat acccgaggaa   68760
ctgaacctgc cgaccaccg  gccccgtccc gcggagatct ccctcctcgg ccgacgcgcc   68820
cgggtcgaga ttcccgccga actgcacggc ggactgctgg aagtggcacg cgcggagggc   68880
gtcaccgtct tcatggccct gcaggccgcg ctggccgtga cgttgtcgcg cctgggagcg   68940
ggcacggaca tcccggtcgg cgtggccgtg gcgggccgta ccgacggggc ggtgaggac   69000 ctggtcgggt tcttcgtgaa caccctcgtc ctgcggacga cctctccgg  cgaccccacc   69060 ctcaccgagg tgctgcggag ggtccgcgag acgtccctga gcgcgttgac gcaccaggac   69120
gtcccgttcg agaaactggt ggaggagctg gccccgccc  gctccctcgc ccgccatccg   69180
ctgttccagg tcatgatgac cctgcagaac accggcaacc ccgccgacgc ggccctgccg   69240
ggcctgacgg cgacccctct ggccacggac ggcacggcgc tcaggttcga cctcgacctg   69300
aatctcggtg aggccttcga cgaggccggc gatcccgcgg gcatcaacgg ctcgctcatc   69360
gcctccgccg acctgttcga ccagagcacc gtggaacggc tgacgagca  actgcttcgc   69420 gtactgcgga cgatgacggc gcaccccgcc accggatcg  ccgacgtcga cgtactcggc   69480
ccgcaggacc gccgacgggt gctgacggag tggaacggca cggcggtggc cgtggcgac   69540 gtgtcggtgc ccgaggcgtt cgcgcgctcc gcggcggccg atcccggagc cctcgccgtt   69600
cagtgtgatg acttccggct gcagtacgac gaggtggacg cgcggtccga tgagcttgct   69660
cgacggctga tggccgcggg agtgcgaccg gagtcggtcg tcgcggtggc catggagcgg   69720
tcggccgacc tggtggtggt cttcctcgcc gtgctgaagg cgggcggcac ctatctgccg   69780
ctggacctcg gctggccgac ggcccggatg cgcgcggtgg ccgaggacgc cgacgcgcgg   69840
tgcatcgtca cccatcaggc caccgccgga cacgagttcg tccgtacgac cgcgctgagc   69900
gaggtacggg tcgacgtcat cgcggggccc gccgccgagg tgacgctgcc cttggtcgat   69960
ccgggtgccg cggcgtatgt gatgtatacg tccgggtcga cgggtgtgcc gaagggtgta   70020
gtggcgacgc accgggacgt ggtgcggctt gcgaaggacc gttgctgggg tgaccccgcg   70080
cgggtgttgt tccacgcgcc gcatgcgttc gacgcgtcga cgtacgagtt gtgggtgccg   70140
ttgctgtccg gcggcacggt ggtggtggcg cccggcgagg cgatcgacgg agcggtgttg   70200
aggcgtctgg tctcggttca cgggttgtcg catgtgcatg tgacggcagg cttgttgagg   70260
gtgctggcgg atcaggatcc cggatgcttt gccggtgtgc gtgaggtgct gaccggtggt   70320
gacgtcgtcg cggccgagtc ggtgcggcgg gtgctggagg ccaaccccgg tgtcggcgta   70380
cggcagttgt acgcccgac  cgaggtgacg ctgtgtgcga cgcagtacga ggtggccgat   70440
gccgccgagg tcgacggtgt gctgccgatc gggcgtccgc tcgacaacac gcgcgtctac   70500
gtgttggacg ggtcgctgag cccggtgccg gtcggtgtgg ccggtgagtt gtacgtcgcc   70560
ggtgccggtg tcgcgcgggg ctatctcggt cgccctgtcc tgaccggtga gcgtttcgtg   70620 gcctgccct  tcgccggtgc cggtgagcgg atgtaccgca ctggcgactt ggtgcgctgg   70680
gacgtcgagg gccggctcgt cttcttgggc cgtgccgacg agcaggtgaa gatccgcggt   70740
ttccgggtcg agccgggcga ggtcgagacg gtggtggccg cccatccggc ggtggcgcag   70800
gcgaccgtac tggtccggga ggacgtcccc ggtgacaagc ggctggtcgc ctacctggtg   70860
```

```
ctcgccgggg cggagacagc ggctgtcgat gcggtccaca cccatgtggc cgagcagttg    70920
ccgtcgtacc tggtcccctc cgcgttcgtg gagctggaga ccctgcccct gacgcccacc    70980
gggaaggtgg accgtgcggc gctccccgcc cctcggtaca ccgcaggcac gggccgggct    71040
cccgccgacg cccgcgagga gttggtgtgc cgggcgttcg ccgaggtgct ggggctggcg    71100
gcggtcgggg tggaggacga tttcttcgct ctcggcggcc actcgctgct ggccgtgtcg    71160
cttgtcgaat ggttacgccg gcgtggggtg tcggtgtcgg tgcgggcgtt gttcgtgacg    71220
ccgacgcctg ccgcgctggc ggcggtggcg gggccggagt tggtggaggt gcccccgaac    71280
ctcatcccgc ccggagcgga cgagatcaca ccggagatgc tgccgctggt cccgctcacc    71340
acggccgaga tcgagcgggt gaccgccgcc gtgcccggcg gcgcgcccaa tatccaggac    71400
gtgtaccccc tggcgccgct ccaggagggc atcttcttcc accacttgat ggcggagcgg    71460
gacggtgagg acgtctacgc gatgcccttc accctccgtt cgccgaccg gtcgggcctg    71520 gatgcgtttc tgggcgcgtt gcagcgggtg gtggaccggc acgacgtgta ccgcacctcg    71580
atcgtgtggg aggaactgcc gcaacccgtc caggtggtgt ggcgcgacgc cgagcttccg    71640
gtcaccgaga tcatcctcga ccccgaaggc ggtgaggacg ccgtccggca gctgctggcg    71700
gcggccggaa gctggatgga ggtccaccgt gcgcctctgc tgacggtgca caccgcggcc    71760
gagccggacg gcgacggatg gctggccctg gtacggatgc accacctggt ccaggaccac    71820
accgcactcg acatcgtcct cgacgagatc aaggcgatcc tcgccggacg ggcggacgag    71880
ctgcccgcgc cggtgccgtt ccgggacttc gtcgcgcagg ccaggctggg cgtctccgag    71940
gaggcgcacc gggagtactt caccaggctg ctcggcgaca tcaccgagac caccgccccc    72000
tacgggctgc tcgacgtccg cggcgacggc acggacctcg cccaggccag cgcagggtg    72060 gacgaagcgc tgacacggcg cgtccaggcc ctcgcccgct ccgggggggt cagccccgcg    72120
acggtcttcc acctggcgtg ggcccggatg ctgtcggcgg tgtcggcccg cgacgacatc    72180
gtcttcggca cggtactgct ggggcgtgcg accgtcggag ccgaccgtgt gccgggactg    72240
ttcatgaaca cccttcccgt cagggtcgat ccggccggac ggacggtcgg acaggcgctg    72300
gccggcctgc gcgaccagct cgccgaactg ctggcgcacg agcacgcgcc gctgaccctc    72360
gctcaggcgg ccgccggcct gccggccggc agccccctct tcaccgcgct gttcaactac    72420
cggcacagca agccgcccgt ccacgagccg gacggcgtac tcgccgacgt cacgactctc    72480
ttcacgcagg aacgcaacaa ctacccgctg gcgcgtctccg tcgacgacga cggccagtcg    72540
ttcggcatca ccgtggacgt cgcgtatccg gtcgacgccg gcaaggtcgc cgcgctgctg    72600
gagacgacac tcgcccacct caccacggcg ctggaggaca ctcccgacct cccgctgctg    72660
tcggtcgacg ttcccggagc cgcgcgcccg gcgaccccg acggaaacag ggccggacgg    72720
cgggccgtgc tcgtacccga ggccggaaac cggacgacgg ggggctccgg acgcgccccc    72780
gccaccgccc aggaggaact gctctgccag gcgttcgccc atgtgctgga cgtgcggcag    72840
gtcggccccg acgacgactt cttcgccctc ggagggaact ccctggtggc gacacgctg    72900 gtcagccggt tgcgtacggt gctcggaagg gaagtgtcca tccgggcgct gttcgaggcg    72960
ctgacgccgg cccgtctcgc cgaacggctg agcccggtcg cccccgaccg ccccgccctc    73020
actccgcgga aacgcccgga gcgggtgccg ctgtccttcg ctcagcgccg gctgtggttc    73080
atcgggcagc tcgagggctc cagcgccagc tacagcaaca ccaccgccct ccggctgcgc    73140
ggcacgctgg accgggaggc gatggacgcc gccctgcggg atgtgatcgg ccgccacgag    73200
gtgctgcgga ccgtgctccc ggccgaggac ggcgagcccc accagcggat cctcgaggtc    73260
```

```
gaggagacgg ccttcgggct gaccgtcgtg gacaccgcgg ccgcggaggt cgccgccacg   73320
atcgaccgcc tggcgggcca cgacttcgac ctcgccacgg agatccccct ccgggcatgg   73380
ctgctggccc tgtcgccgga cgagcacgtc ctcgtactgg cggtgcatca catcgcgacc   73440
gacggctggt cgaccgcggc cctcgcacac gacatgtcca ccgcctacgc ggcgcgcctg   73500
gagggccggg cacccgactg ggcgccgctg ccggtgcagt acgccgacta cgcgctgtgg   73560
cagcacgaac tgctcggcga cgcggacgac ccggacagcg tccgctcccg gcaactggcg   73620
ttctggcggg agacgctcgc gggtgcccca gacgagacgg cgctgccgac cgaccgcccg   73680
cgccccccgg tggcgaccca ccggggagac gagatcgcgg tggaactccc cgcggagctg   73740
caccggcgga tcgcggagct ggcggccacc gaacaggtca ccgtcttcat ggtgctccag   73800
gcgggcctcg cggcgctgct gagcaggctg ggcgcgggca ccgacatccc gatcggcacc   73860
gcactggccg gccgcaccga cgacgcgatg gacgacctga tcggcttctt cgtcaacatg   73920
ctcgtcctgc ggaccgacgt gtcgggcgac ccgacgttcg ccgagctgct gcggcgggtg   73980
cgcgagaccg acctggcggc gtacgcacac caggacctgc ccttcgacca ggtggtggag   74040
gaactcgtcc cggaccgctc cctggcccgg cagccgctct tccaggtggc gctcgacgtg   74100
cagaacgtcc ccgaaggcgc gctgcggctg cccggtctcg acgtggccgg cgagcccttc   74160
gcccacggca cggccaggta cgacctcgcg ctgagcctgt cggaacgcca cgacgaccag   74220
ggcgcaccgg acggcatgta cggcacgctg acgacggcgg ccgacctgtt cgagcgggcg   74280
acggccgaac gcatcgccgg ctacctggtc cgcgtcctca cggcggcggt cgccgagccc   74340
gaagcgccgc tcgccgcact ggagttgctc accggggacg agcaccggcg gatcgtggag   74400
gactggaacg acacgcgggg gccggtgccg gacgggctgg tgccggaact gttcgccgcg   74460
caggcccggt tgtcgccgga cggtggcg ttggcgggcg cgggcgtcga gttgagctat   74520
cgggaggtgg aggagcgggc gaaccgtctg gcgcggaagc tgatcgcgcg ggatgtgggc   74580
ccggagtcgg tggtggctct ggtgctggag cgttcgcccg agttggtcat cgcggtgctg   74640
gcggtgctga aggcgggcgg cgcctacctg cccatcgatc ccgggcagcc cgccgagcgc   74700
atccggtccg tgatcgagga cgccgccccg gtgctggtca tcgacgaccc cgacttcctc   74760
gcggagaccg ccgaccacac cgcggcaccg gtcacggacg ccgaccgcgt ctccccgctg   74820
ctgccctccc accccgccta cgtgatctac acctcggggt ccaccggacg gccgaagggt   74880
gtggtcgtca cccacgaggg gtgcgcgaac ctttcggcga gccacgactg gtacggagtg   74940
gcggccggga gccgggtggc gcagttcgcg tccgtcggct tcgacatgtt ctgtgaggag   75000
tggctgctcg cactgctgcg cggcgcgacg ctggtgaccg tgcccgcgga ccggcggctc   75060
ggaccggacc tcggccactt cctggtggac cagggagtga cccacgcggc actgccgccc   75120
gcggtggcgg cgacgatccc cgacggcctg ctggacccgt cattcgtgct cgacgtcggc   75180
ggcgaggcgt gcccgcccga gctggtcgaa cgctggacgg cggacggccg caccatgttc   75240
aacgcctacg gccccaccga ggcgaccgtg gacgccacgg tgtggcggtg cgcccccggc   75300 ctggacgcg gagcggccgt gccgatcggc agacccgtcc tcaacacccg cgcctatgtg   75360
ctggacgacg cgctgcggcc cgtgccggtg ggcgtcgtgg gcgaactcca cctcgccggc   75420
tcgggcctgg cgcgcggcta cctgggccgg accggactga cggcggaacg cttcgtggcg   75480
tgcccgttcc agccgggccg gcggatgtac cgtacgggcg accgggtcaa gtgggacgcc   75540
gacgggcagt tggtgttcgc gggccggcg gacgaccagg tgaagatccg ggggttccgg   75600
atcgaacccg gcgaggtcga ggccgtactc gcgtcacatc ccgacgtggc ccggggccgcg   75660
```

```
gtgaccgtac gggaggactc acccggcgac ctgcggctcg tggggtacgt ggtccccgcc      75720
gaagacgtcg acgccgggga acttccgcgc acggtgcgcg ggttcgccgg ggagcggctg      75780
ccgtcgtaca tggtgccgtc ggccgtcgtg ccgctgacg  ccctgccgct cacccccaac      75840
ggcaagctgg accgcagggc gctgcccgca cccgactacg gcgcggcagc taccggccgc      75900
gcgcccgcca ccccgcagga agaactggtg tgccgggcct cgccgacat  cctcggcctt      75960 cccgcggtcg gggccgacga ccacttcttc gcgctcggcg ggcactccct gctggccacc      76020
cggttgctca gccgcgtacg gacgcggct  ggcgtcgacg taccgctccg ggtgctcttc      76080
gcgaacccca ccccgccgg  cgtcgccgag tggctgacgg cgcacaccgg cacaccgaag      76140
aagaccaggc cgacgctgcg gccgatgcgt acgcagaaga aggagttctc atgattccgt      76200
tgtcgttcgc gcagcgccgc ctgtggttcc tctggaagct ggaggagcc  gccaccacct      76260 tcaacatccc gctgaccctc cggctgcgcg gcacgctgga ccgggaggcg atggacgccg      76320
cactgcgcga cgtgatcggc cgccacgagg tgctgcgcac cgtcctcccc gccgtcgacg      76380
gggagccgta ccagcggata ctgcccctgc gggagacggg cttcgaactg ggagtcgtcc      76440
aggtgccgcc ggaggacgcc gaggccgcgg tgcggcgcgc gagcacgtac gccttcgacc      76500
tggcggagga gatcccggta cgcgccgacc tgttcgaagt gggtccggac gagcacgtgc      76560
tggccctggt ggtgcaccac atcgccgcg  acggctggtc catcgggccg ctgatgcgcg      76620
atctctccac cgcctacacg gccggctgg  cgggccgcgc gccgcggtgg gagccgctgc      76680
ccgtgcagta cgccgactac gccctgtggc agcgggagct cctcggcacc ggcgacgacc      76740
cggagagcac gctgtcggag caggtggcgt actggcggcg caccctggcc ggcgcaccgg      76800
aggaactgga actgcccacc gaccggccgc gtccggcgca gaccaccccc cgagggcaca      76860
ccgccgaact ggagctcccc gcggacaccc accggcggct gcgggaactg gccggggacc      76920
acggggccag cctgctcatg gtggcgcagt ccgcgttggc ggtactgctg tcccggaccg      76980
gtgcgggcga ggacctcccg atgggcaccc tggtcgcggg acggaacgac gaagggctca      77040
acgacctcgt cggcttcttc gtcaacaacc tggtgatccg tgccgacctg tcgggcgacc      77100
cgaccttcac cgaggtgctc gagcgggtcc gtgaggcatc cctggacgcc tacgaatacc      77160
aggacgtgcc cttcgagaag ctggtcgagg aactgtcacc cacccggtcg ctggcccggc      77220
accccctgtt ccaggtgatg gcggccgtgg agaccgggga cccgatgtcc accggaccgg      77280
gcggtggccc cgccctggaa ctccccgggc tccgcgtcga gatgctctcc gacgaccagc      77340
aggcccgcga cctcgacctc gacctggtgc tgcgcgagac gcacgacggc gacgggcggc      77400
ccgcgggact gcgcggcgcc ctcatcggcg cggccgacct gttcgacgcc ggtacggtcc      77460
agcggatcgc cgacatgctg gcacgcgtcc tcgaacaggt cgccaccact ccgacggccc      77520
acgtccgctc cctggacgta ctcgatccgg aggagcagcg gcggcttctc ggggtgggga      77580
gtggtgcggt ggtggaggtg ccgggggggtt cgctcccgga gttgttcgct gcgcaggctc      77640
ggttgtcgcc ggatgcggtg gcgttggtgg cagcggtgt  cgagttgagt tatcgggagg      77700
ttgacgcgcg ggcgaatcgt ctggcgcgga agttgatcgg gcggggtgtg ggtccggagt      77760
cggtggtggc tctggtgttg gagcgttcgc cggagttggt gatcgctgtg ctggcggtgt      77820
tgaaggcggg cggcgcgtat gtggccgttg acccgggaca acccgccgat cggatccgct      77880
tcgtgatcga ggacgcctca cctgtcttgg tgatcgacga cctgaatttc ctcgccgaga      77940
ccgaggactt cgacgacttt ccggtcacgg atgccgaccg tatctccccc ctcctcccct      78000
cccatccggc gtacgtgatt tacacgtcgg gttcgacggg tcggccgaag ggggtgctga      78060
```

```
tctctcatgc ggcgtgtgtg agttatgtgg cgagtcatgt ccggtatggg gtgagtgaga    78120
gcagtcgggt ggcgcagttc gcgtcggcgg ggttcgacgc gttctgcgag gagtggtggc    78180
tggcgttgct gggggggcggg gcgctggtgg tggtgccgtc ggagcggcgg ctgggtgagg    78240
agctggtgcg gttcctgctg gaggagcgcg tgacgcacgc gacgctgccg ccggcggtgg    78300
cggtgctgat gcgggaggag gcactggccc cggggttcgt gctggatgtg ggggtgagg     78360
tgtgcccgcc ggatctggtg gaccgctggg tggcggccgg ccggacgctg ttcaacagtt    78420
acgggcccag tgaggcgacg gtgaatgtca ccgtctggca ggcagtggac gggagtctgg    78480
gcgccggggt gccgatcggt cgtccggtgg gcaacacgcg gctgtacgtg ctggacgacg    78540
ggttgcgtcc ggtcccggtc ggtgtgctcg gcgagttgta cgtctcgggc gtgcagctgg    78600
ggcggggcta tctcggacgt gcgggcctga ccgcggagcg gttcgtggcc tgtccgtatg    78660
cctccggcga gcggatgtac cgcaccggta accgggtgaa gtggaatgcc gagggcgagt    78720
tggtgttcgc ggggcgtgcg gacgaccagg tgaaggtccg gggtttccgg atcgagccgg    78780
gtgaggtcga gaccgtactc gcggcgcacc ctgccgtcgc ccatgccgcc gtcgtcgtac    78840
gcgaggacac cccgggcgac aagcgcctca ccgcctacgt cgtcccccgt acgccgggaa    78900
cgggcgtcgg tgctgccgcg gtcgcccgtg tggcggagcg ccttccggcg tacatggtgc    78960
cgtcggcggt cgtggagctg gacgcgttgc cgctcaccgc gaacggcaaa ctggaccgcg    79020
aggccctgcc cgtccccgag taccagggcg ccggtggcgg gcgggcgccc gagaacgccc    79080
aggaagagct ggtgtgccag gcgttcgccg aggttttcgg agtggaccgg gccgcggtcg    79140
gggtggagga cgacttcttc gcactcggcg gccactccct gctggccgtg tcgctggtcg    79200
agtggttacg ccggcgcggc gtctcggtgt ccgtgcgggc gctgttcgtg tccgcgaccc    79260
ccgccgcgct ggcggcggcg gccggaccgg aaccggtgac ggtgccgccg aacctgatcc    79320
cggacgcgc gaccgagatc acgccggaca tgctgaccct ggtcgagctc accgaggagg    79380
agatcgcccg ggtggcggcg gcggtgccgg gaggcgccgc caacatcgcg gacatctacc    79440
ccctggcgcc gctccaggag ggtctcctct tccaccacct catgaccgac ggcgacggca    79500
cggacgtcta catcactccc gccgtcgtcg agttcgactc gcgtgaccgc ctcgacgact    79560
tcttcgccgc gctgcgctgg atggtggacc gccacgacat ctaccgcacc gccgtggtct    79620
ccgacgggct gcgggagccg gtgcaggtcg tggtgcggca cgccgaactg accgtcgagg    79680
aaacggttct ggacgccgac gggcggqacc ccgtcgaaca gatgctggcc ctcggcggac    79740
gccgaatgga gctgaaccgg gtaccgctga tgtccgcgca catcgccgcc gacccgggcg    79800
gcgaccggtg gctggccctg ctccgcatcc accacctgct gcaggaccac accacccagg    79860
acgtcctctt cgacgatctg tgggccttcc tggccggccg ggccgacgcg ttgccgccgc    79920
cgctcccgtt ccgcgacttc gtcgcgcagt cgcgcctcgg caccccagg gaggagcacg    79980
agcggtactt cgccgagctg ctcggggacg tcaccgagac caccgcaccg tacggcctga    80040
ccgatgtgca cggtgacggc agcggatcgg aacaggcccg gctccggctc gacgacgccc    80100
tggccgcacg cgtccgccgg gccgcgcgta ccctcggagc cagtcctgcg acctgttcc    80160
acctcgcctg ggcgcgtgtg ctgggcgccc tctccggccg cgacgacgtc gtcttcggca    80220
ccgtgctgtt cggggcggatg aacgccggtg agggcgcgga ccgcgtaccg ggcctgttca    80280
tcaacacccct cccggtgcgc gtgcggctcg accggcagag cgtggcggag gcgctgaccg    80340
gtctccggcg cgacctcgcc gatctgctcg tgcacgaaca cgcgccgctg accctcgccc    80400
aggccgcctg cggactgccc ggcggcagcc cgctgttcac ctccatcctc aactaccggc    80460
```

```
acaacacgaa cgggccgcac gagtcccgcg ccgaactgga cggcatgcag gtgctgtccg   80520
cccgcgacct caccaactac ccgctcgccg tggcggtcga cgcggacacg gccggcttca   80580
cggtcaccgt ggacgcggtg acgcccgccg acccggcacg ggtcggcgcg ctgctgacca   80640
cctgctggag gtccctcacc tccgccatcc aggacgaacc ggccacgccg ctccgtatgg   80700
tggaggtcct ggacggggcc gagctgaccg cgctgctgga cggctggaac gacaccgcgg   80760
tgcccgcgcc ggacgcgtcg ctgcccgagg cgttcgccgc cacggtcgcg gccgccccgg   80820
acgccgtggc gctggtgtgc ggcgacgacc ggatcaccta cgccgaactg gacgcccggg   80880
ccgaccggtt ggcccggacg ctggtcgcgt ccggagtgcg tccggagtcg gccgtcgccg   80940
tggccatgga acgctcggcc gacctcgtcg tggcgctgct ggccgtctcc aaggccggcg   81000
gcgtgttcgt accgctggac gcgggatggc ccgccgcccg gacgcgcgcc gtgatcgagg   81060
acgcggacgc ctgcctggtg ctggtggacg ggacgacggc cgggctggag gccggggtcg   81120
cgctgctgcg ggtcgacgcc acgacggaca ccgtggtgga cctgccgggt ccggtcccgc   81180
ccgacggggc cgcgtacgtg atgtacacct cgggctcgac gggcgtaccg aagggtgtgg   81240
tgaccacaca caaggacctg gtgcgcctgg ccacggaccg gtgctggggg accaccccgc   81300
gggtgctgtt ccacgccccg cacgcgttcg acgcctcctg ctacgagctg tgggtgccgc   81360
tgctgtcggg cggcaccgtg gtgatcgcgc gcgggagcg cgtcgacgcg cgctgatgc   81420 ggcggttgac caccgcgcac cggctgacgc acgtccatgt caccgccgga ctgctgcggg   81480
tgctggccga cgacgacccc ggctgcttcg acggcgtgcg cgaagtgctg acgggcggcg   81540
acgtggtgcc cgccgacgcc gtgcgccgca tcctggacgc caacccgcgg gccgtcgtgc   81600
ggcacatgta cggacccacc gaggtgacgc tgtgcgccac ccagcacgag gtcgccgacg   81660
ccgccgaggt ggacggcgtg ctgccgatcg gccggccgct cgacaacacc cgcgtgtacg   81720
tcctggacga cggtctcaac gtggtgcccg tgggcgtcac cggggaactc tacgtggccg   81780
ggtccggcct cgcccgcggc tacgccaacc gcgccgagtc gacggcggag cggttcgtgg   81840
catgcccgtt cgggccgggc gaacggatgt accgcaccgg tgacctggcc cggtggacac   81900
cggacgggcg gctcgtcttc gcgggccggg cggacgacca ggtgaagatc cgcgggttcc   81960
gggtggagcc gggcgaggtc gaggcggtgc tcgccgcgca cccggccgtg gcgcaggcca   82020
ccgtcgccgt acgcgaggac accccgggg acaaacggct gatcggctac ctggtgccgg   82080
tggaacaggg cagtgcgctc accgccgcgg tacgcgcgta cgcggccgag cgcctccccg   82140
agtacctggt tccggcggcg ttcgtggagc tcgacgcctt cccgctgacg gtcaacggga   82200
aggtggaccg ggcggcgctg cccgcgcccc ggtacctgac gggagccggg cgtctgccgg   82260
ccgacgcccg cgaggaactg ctgtgccagg tgttcgccga ggtcctcggg ctgcccgcgg   82320
tcggtgtgga cgacgacttc ttcacccctcg gcgggcactc cctgctggtg acccgcctgg   82380
tgagccgggt acgcgcgacc ctggacgtgg aactccagat ccgtacggtc ttcgaagcgc   82440
cgacgcccgg ccggctggcc gcccggctga ccgagaccgc cgtacccgga cgcaaggcgc   82500
tggtggcccg gacccggccg cagcggacac ccctgtcctt cgcccagcaa cgcctgtggt   82560
tcctcgcgca gttggagggg ccgagcccga cgtacaacct tccgctggcg ctgcgcctga   82620
ccgggacgct ggaccgggag gcgttcctgg ccgcgctggg cgacacggtc gcacgccacg   82680
aggtgctgcg caccgtgttc gaggtggccg acgacggcac cccttaccag cgggtcctcc   82740
ccgccgacgc gaccgggttc gcgcccgagg tcgtggaggt gccgtccgac gggctcgccg   82800
acgcgctcgc gcgtgcggcg gcgtacgcgt tcgatctggc cgtggagacc ccgctgcgcg   82860
```

```
ccacgctgtt cgcggtggcg ccggacgagc atgtgctggt cctggtggtc caccacatcg   82920
ccggtgacgc ctggtcgatg gagccgctgg cgcgcgacgt gtcgacggcg tacgcggccc   82980
ggctcgtcgg ggacgcccca cgctgggagc cgctgccggt gcagtacgcc gactacaccc   83040
tgtggcaacg ggaactgctc ggcgacgagg acgacccgga cagcctgctc tcacggcagg   83100
tgagccactg gcgggacgcc ctctcgggag cgcccgagga actggacctg ccggccgacc   83160
ggccgcgacc cgccgagttc tcccaccgcg gccgcaccgc cgggctcgag ttccccgccg   83220
agctgcatcg acgactgcgg gaggtggcac gcgccgaggg cgtgacggtc ttcatggtgc   83280
tccaggccgc gctggcggtg acgctgtcac ggctcggcgg cggcaccgac atccccatcg   83340
gcacggccgt cgccggccgt accgaccagg cactggacga actggccggc ttcttcgtca   83400
acaccctggt cctgcgcacc gacctctccg ggaacccgac gttcgccgag acgctccacc   83460
gggtgcgcga cgacctcctg acggccctgg cccaccagga cgtgccgttc gagcgactgg   83520
tggaggaact ggccccggtc aggtcactga ccaggcaccc gctgttccag gtcatgctga   83580
ccttgcagaa caccgcgcgg gccggcggcg gagcgtccgc cgcgctgccg ggcctggaga   83640
cggccgtgct gccgacgggg gcgacggccg ccaagttcga cctcgacctg gccctcgccg   83700
agaccttcga cccggagggc gcccccaccg ggatgcacgg cacgctcgtc gccgccgccg   83760
atctgttcga ccaggaaacg gccgaccggc tcgtcgcctg cttcactcgg gcgctcgaag   83820
cactgaccca ccgcacggac ctgcggcttg gcgaggtcga cctgctggac gaggcggagc   83880
tgtccaccct cgtcgaggac tggaacggcc cggcgctccc gacgtccgag gcgacgcttc   83940
ctgaactgtt cgcggtgcag gcggcgagga cgccggacgc gacggcggtg acggcgggcg   84000
gggtcgagtt gtcgtacgcg gagctggacg cacgcgccga ccggttggcg cgtggtctgg   84060
tggggcgcgg tgtgggccct gagtcggtgg tgggggtgct gctggggcgg tccgccgatg   84120
tggtggtggc ggtgctggcg gtggcgaagg cgggggggtgc gtatcttccc gtggacccgg   84180
actatccggc ggatcgtgtg gcgttcgtgc tgtccgacgc gggggccgag tgggtggtga   84240
cgtcggcgga gttcgcgccg gtcctccccg ctggtgtggc ggccgtgccg gtcgacgggg   84300
ccggttcggg gccggtattc gactcggtgc cgttgccgac ggtacgcccg gaccaccccg   84360
cctacgtgat ctacacctcc gggtcgacgg gacggccgaa gggtgtggtg gtgccacacc   84420
gcagcgtggt ggcgctgttc gccgccgccc gggagatgtt cgccttcgga gcagacgacg   84480
tgtggagcgg cttccactcg ttcgcgttcg acgtctccgt atgggagatg tggggtgcgc   84540
tgctgcacgg cggacgcctg gtggtggtgc cgttcgacgt ctcgcggtcg ccgcgcgagt   84600
tcgtggaact gctggaacgc gagcgtgtga ccgtcctgag ccagacgccg tcggcgttct   84660
accagctgat gggcgcgggg ggcgcgctgc ccgacctgca caccgtggtc ttcgccggtg   84720
aggcactgga gccggcgcgg ctcgacggct ggtgggagcg gcacggcggg accgggccgc   84780
ggctggtcaa catgtacggg atcacggaga cgacggtgca cgtcacgcac cacgacctcc   84840
gcccggacac cgccgcggac ggcagcgtga tcgggcgggg tctgcccgga ctgtcggtgt   84900
tcctgctgga cgagtggctg cggccccgtcc cggtgggcgt gacgggtgag ttgtatgtgg   84960
ccggcgcgca ggccgcgcgc ggctatctgg ggcgtgccgg gctcaccggc gaacggttcg   85020
tcgcctgccc gttcggtgag gccgggggcc ggatgtaccg gtcgggtgac cgggcccgct   85080
ggtcgcgcga cggacggctg gtgttgcgcg ggcgtgcgga cgaacaggtg aagatccgcg   85140
ggttccggat cgagccgggt gaggtcgagg cggtgctggc gggccacccc gacgtggcac   85200
aggccgcggt cctcgtgggc gacgacaccc tcggcggcag gcggctgatc ggctatgtga   85260
```

```
cccccggtgg gaccaccgag gacgccgacg gcctggcgga tgcggtgcgc gtgtacgcgg      85320
gggagcggct gccgtcgtac atggtgccgt ccgcgttcgt ggtcctggac ggcctgccgt      85380
tgacggtcaa cggcaaactc gaccgcaggg cgctgccggc cccgcccac accgccggtg       85440 gcgggcgggc cgcggcgacg gtggaggagg aactgctctg ccaggggttc gccgaggtgc      85500
tgggcctgcc ggccgtcggc gtcgacgacg acttcttcgc cctcggcggc cactccctgc     85560
tcgccgtgtc gctcgtggaa tggctgcggc agcgcggggt gtccgtctcg gtgcgcgccc     85620
tgttcgtgac gccgacccc  gcggggctgg ccgccgtcgc ggccgcgccg gcggtggtgg     85680
tgccgccgcc cggcatgatt cccgagggcg ccacggagat caccccggag atgctgcccc     85740
tggtcgacct gaccgaggac gagatcgccc gggtgacgga gacggtgccg ggcggcgcgg    85800
ccaacgtcca ggacgtctac ccgctcgccc cgctccagga agggatcttc ttccaccacc    85860
tggtggccga ccgggacggc acggacgtct atgtgacccc gaccgtgctc gacttcgaca    85920
cccgggagag gctcgacgac ttcctcgcgg ggctccagtg ggtgatggac cggcacgaca    85980
tctaccgcac cgcgatcgtg tgggaaggac tgcgcgagcc ggtgcaggtc gtgtggcgcc    86040
gcgccgggct gccggtccag gagagggagc tcgaccggc  cggtccggag gcggtcgagc     86100
agctgcgcac ggcggccggc ggccggatcg aactggacgg cgcgcccctg ctgcgggtgg    86160
acgtcgccgc cgcccccgaa ggcggctggc tgatgctgct gcgcatccac cacctggtcc    86220
aggaccacac ctccgtggag gtgttgctcg acgatctgcg ggcgttcctg gacggcgacg    86280
ccgaccggct gcccgcgccg gtgccgttcc gcgacttcgt cgcccaggca cggctcggga    86340
cgcccaggga ggagcacgag cggtacttcg ccgagctcct cggcgacgtc acggaaccca    86400
ccgcgcccta cggtctgacg gacgtgcgcg gcgacgcga  ggggtcccgg cacgcccggc     86460
tgcgggtcga cgacgccctg acggggcgga tgcgggaggt ggcgcggtcg ctcggggtga    86520
gcccggcgtc cctgttccat ctggcgtggg cgcgcgtcct cggcgcggtg tcgggccgcg    86580
acgacgtggt gttcggcacg ctgctcttcg gacgcatgaa cgcgggcgcg ggcgccgacc    86640
gtgcccgggg cctcttcctc aacacccgc  cggtgcgcgt gcgcatggcc gggaagagtg     86700
tgaccgaggc cctgaccgaa ctgcgccacc agctcgccga cctcatggtc cacgagcacg    86760
cgccgctgac gctggcccag tccgccaccg gactgaccgg tggcggcccg ctgttcaccg    86820
cgctcttcaa ctaccggcac aaccgggagg cacccgagcc cggtgagggc atcgagggcg    86880
tccggaccgt ctacacccgg gagcacacca actacccgct gcacgtggcc gtcgacaacg    86940
acggatcgag cttcgacatc accgtcaacg cggtggcgcc cgccgacccc gacgaggtct    87000
gcgcgctcct gcacaccggc ctcgccaacc tggtcaccgc ccttgcggaa gcccccggga    87060
ccccgctggc gggactcggc gtgctggacg agcgcacccg cacccggatg cggaccgagt    87120
ggaacgacac agccgtcgac gtgccggacg tgaccgttcc ggcggcgttc tccgcgcagg    87180
cggcacgcgt accgcaggcc accgcgctgg tctgcgggga cgtggagatc ggctacgccg    87240
agctggacgc ccgcgcggac cggctggcgc gggtcctcgt cgaggcgggt gtggcggcgg    87300
agtcgaccgt cgcggtggtg atggaacgat cggtcgacct ggtggtgacc ctgctggccg    87360
tgctcaaggc cggcgccgtg tacgtgccgc tggacgcggg ctggccggtg gccaggatgc    87420
ggacggtggt ggaggactcc ggcgcccggt gggtggtggt gcatgagccg acgtccggcc    87480
acgagttcct gcgcggcctc ggcattccga cactctcggc cgacacggac gccgacgcgg    87540
aggagtgcgt tcttccccag aggtggtccc cgcgccaggc ggcgtacgtg atgtacacat    87600
cgggctcgac gggcgtgccg aagggtgtgg tggcgacaca tggggacgtg gtgcgcctgg    87660
```

```
ccacggaccg gtgctgggga gccaccccgc gggtgctgtt ccacgccccg cacgcgttcg    87720
acgcctcgac gtacgagctg tgggccccgc tgctgtccgg cggcacggtc gtcatcgccc    87780
cgaacgagcg ggtggacccg gtggtgctgc ggcgcctggt caccggccac gggctgaccc    87840
atgtgcacgc caccgcaggg ttgttgaggg tgctggccga tcaggacccg ggctgcttca    87900
ccggagtacg ggaagtgctg accggtggtg acgtggtccc ggccgagtcg gtacggcgcg    87960
tcctggacgc caacccggt gtggtcgtac ggcagttgta cggccccact gaggtgaccc    88020
tgtgcgcgac acagtacgag gtcgcagacg ccgccgaggt cgacggcgta ctgccgatcg    88080 gacgcccct cgacaacacg cgcgtctacg tcctggacgg ggctctgaac ccggtgcccg    88140
tcggtgtcgc cggtgagctg tacgtagccg gtgccggcgt cgcgcgaggc tatctcggcc    88200
gccccgtcct gacgggcgag cgtttcgtgg cctgcccgtt cgagacctcc ggggaacgga    88260
ggtaccgcac cggcgacttg gtgcgctggg acaccgaggg ccggctcgtc ttcttgggcc    88320
gtgccgacga gcaggtgaag atccgcggtt tccgggtcga gccgggcgag gtcgagaccg    88380
tggtgacggc ccaccccgcg gtggcgcagg cgaccgtact ggtccgggag gacgtccccg    88440
gtgacaagcg gctggtcgcc tacctggtgc ccgccgaccc gggggccgcc gtgggcctca    88500
ccgtccgggc gtacgccgcc gaacggctgc ccgagtacat gctgccctcg gccatggtgg    88560
aactggacgc cctgccccctg accccaacg gaaaggtgga ccgggccgcc ctgcccgccc    88620 ccgactacg ggccggcgcc ggacgagtgc ccgccgacgc ccgtgaggaa ctgctctgcc    88680
aggcgttcgc cgccgtgctc ggactgccgg cgttcggcgt ggacgacgac ttcttcgcca    88740
agggcgggca ctccctgctg gccaccgtcc tggtcggccg gatccgcgcc acgttccacg    88800
tggagatgac gatcgtcgcg ctgttcgacg ccccccacccc ggcgagtctc gcgcgctggc    88860
tcgtccaggc ccggcccggc cggatcgaac tggccgcgcg ggaacggccg gagcgggtgc    88920
cgctctcctt cgcgcaacgc cgtctgtggt tcctgggaca actggagggc cccggcgcca    88980
cgtacaacat cccgctgctg acgcggatca ccggaccgct ggaccggacc gcggtggacg    89040 ccgcctgcg cgacgtcctc gaccgccacg aggtgctgcg cacggtctac gcggtgcacg    89100
gcggcgaacc ccaccagcgg agccgccccg tcgacacctc cggcttcgca ctgcccgtcg    89160
tcgacgtggc ccccggcggc ctgaccgatg cgctggaacg ggccgcgggg cacgagttcg    89220
acctctccac ggacatcccc gtgcgggcct ggctgttcgc cacggccccc gaggagcacg    89280
tactggcgct ggtggtccac cacatcgccg cggacgcctg gtcgatggcg cccctcaccc    89340
gcgacttcgc ggcggcctac gccgcgcgcc gcgcgggcga ggaaccggac tggacgccac    89400 tgccccgtgca gtacgccgac tacgcgctct ggcagcgaga cttgctcggc gacgagggcg    89460
acccggacag cctgatctcc cagcaggtcg cctactggcg ggacaccctg gacggcgcac    89520
cggaggaact cgcgcctgccg gccgaccggc cgcgccccgc gacggtgtcc taccgcggcc    89580
acctggcccc cgtcgagatc cccgccgacg tgcacggacg cctgcagcag gtggcgcgcg    89640
agcacggagt gaccctgttc atgacggtgc agaccgcgct ggcggtgacg ctctcacggc    89700
tgggcgccga caccgacatc cccatcggca ccacggtcgc cgggcgcacc gaccaggcgc    89760
tcgacgacct gatcggcttc ttcgtcaaca ccctcgtcct ccgcacccgc ctgggcggcg    89820
accccacggt caccgacgtc ctgcgccggg tgcgggagac ctcgctcgcg gccttcaccc    89880
accaggacgt gccgttcgag aaactcgtgg aggaactcgc cccgagccgc tcgctggccc    89940
ggcaccccct gttccaggtc atgctcaccc tgcagaacgc cggacgccc ggcggaggcc    90000 cgtccgcggt gctcccgggc ctgcggaccg agtcgctgcc caccgacgac gtggcggcca    90060
```

```
agttcgacct ggacatcacc atgggcgaga ccttcgacgc cgtgggcgcc ccggcgggca   90120
tccagggcat gctggtcgcc gccgccgacc tgttcgaccc ggcgacggcc gaacggatcg   90180
ccgactccct ggtccggtg ctgaagctga tcgccgagga caccggcacc cgcctgagcg    90240
ccgtggacct gctcgacgcc ggcgagcggc gacgggtcgt cgaggagtgg aacgacaccg   90300
acgccccgcc accgccctg tccgtccccg ccgcgttcga ggcgcaggcg gcgctgaccc    90360
ccgacgccgt cgccgtactg ggcggcgaca cccggctgac ctacgccgag ctgaacgcgc   90420
gggccaaccg gctggcccgg ctgctcgtcc ggcacggcgt cggaccggag tcgtccgtcg   90480
ccgtgtgcct gcggcgctcg gccgaactgc ccgtggccct gctggcggtg ctcaaggccg   90540
gcggcgcgta cctgcccgtc gaccccggcc atccggccga gcgcgtcgga cacgtcctcg   90600
acgacgcccg cccgccctg ctgctcaccg accgggcaac cgcggccgac ctgccgggac    90660
cggaacacct cgtcgtggac gacccccgta cggcggcgga actccaggcg ctggacaccc   90720
acgacctgac cgctcgggag cgcctcggcg cgctcctgcc cggcacccc gcctacgtga    90780
tccacacctc ggggtccacc ggtcggccca aggggtggt cgtcccgcac ggcgccatgg    90840
cgaacttcgt cgcggcgatg cgggagcgct tcccgatgag ctccgccgac cgtctgctgg   90900
ccgtgaccac cgtgtccttc gacatccatg tcctggagct ctatgtgccg ctgctcgccg   90960
gcgccggggt cgtggtcgcc gaggacgcgg acgtgcggga cccggccgcg gtggccgcgc   91020
tgatcgaacg gttcggcgtg accgtgatgc aggcgacccc ggcactgtgg caggcactgc   91080
tcaccgagca cgccgggtcc gcgagcgggc tgcgcctgct cgtgggcggc gaggcactgc   91140
ccgccgccct ggccgcccgt atggcggccg tcggggacac tgtcaccaac ctgtacggcc   91200
cgaccgaggt gacggtctgg gcgaccgcgg ccggcctgac cgcggacgac ccggactccc   91260
gggtgccgat cggccggccg ctgcccaaca cccgggcgta cgtcctcgac gacgcgctgc   91320
gtccggtgcc gccgggctcc ccgggcgagc tgtacctcgc cggagtccag ctggcacgcg   91380
ggtacctggg gcgtccggcg ctgtcggcgg aacggttcac ggcctgcccg ttcgcctccg   91440
gcgagcggat gtaccgcacc ggtgacctgg tccggtggcg cacggacggc gcactggaat   91500
tcctggagcg cgcggacgac caggtcaaga tccgcgggtt ccgcatcgag ctcggtgagg   91560
tcgaggccgt actcggcgcc cacccggcgg tccaacgggc cgcggcagcg gtgcgggagg   91620
acacgccggg cgaccggcgg ctcgtcggct acgcggtggc ggacaccccg gacccgcggg   91680
ccctggccga agcggtacgg gcccacgccg ccgaacggct gccctcctac atggtgccct   91740
cggcggtcgt ggtgctggac gcgctgccgc tgaccgcgaa cggcaaactc gaccgcaagg   91800
cactgcccgc acccgacttc gaggcggccg ccggctcggg ccgggcaccg gcgggcccgc   91860
gcgaagaact gctgtgcgcg gccttcgagc gggtgctggg cctcgaacgc gtcggcgtgg   91920
acgacgactt cttcgccctg gcggccact cgctgctggc ggtctccctc gtcgagcacc    91980
tgcgcgagcg cggggtgtcg gtgtcggtgc gggcgctgtt ccagagcgcc accccgccg    92040
gactggcggc cgcttccgga gcggcggacc aggtgaccgt ccgccgaac ctcatcccgc    92100
ccggcgcgac cgtgatcaca ccggacatgc tcacctggc cgacctcacc gaggcggaga   92160
tcgcccgggt cgtcgacacg gtgcccggcg gcgcggccaa catcgcggac gtgtacccgc   92220
tggccccgct ccaggaaggc atgttcttcc accacttgat ggccggcggc gacgacggcg   92280
acgtctacgt gctgccgacc gtgctggggt tcgactcgcg ggaccgcctc gacgccttcc   92340
tctcggcgct gcagcaggtc gtcgaccggc acgacaccta ccggaccgcg ttcgtgtggg   92400
aaggactgcg cgagccggtg caggtcgtgt ggcgaaacgc cgcactgccc gtcgacgagg   92460
```

```
tcgtcctcga caccgcggag gacccggccg gacaactgct gagcggagcg ggagcctggc   92520
ggacactgaa ccgggcaccc ctgatgcgcg tccggatcgc cgccgaaccg ggcaccggcc   92580
gatgggtggc actgctgctc atccaccacc tggtacagga ccacaccgcc ctggacgtgc   92640
tcctccacga ggtgagcgcg ttcctttccg gcgacgccgc cgacctgccg gaacccgtgc   92700
cgttccgcgg gtacgtggcg caggcgcggc tgggcacggc gcgcgaggag cacgaggcct   92760
acttctccgg cctgctcggc gacgtgaccg aacccaccgc cccctacgga ctcctggacg   92820
tgcacggtga cggcggcccg gagacacgcg cccagcactg ggtcgacgat gcactggccg   92880
cacgggtgcg cgggctggcc cggtcgaagg gggtcagcgc ggccaccgtc ttccacctgg   92940
cgtgggccag ggtgctcggc gcgctggccg gccgcgacga cgtggtgttc ggcacgatcg   93000
tcttcggccg gatgaactcg ggcacgggat ccgccagggt gccgggcctg ttcatgaaca   93060
ccctgccggt acgcgtccgc ctcggcgccg gcgccgccga cgccgcgctc acggacatgc   93120
gggaccagct cgccgagctg atggcgcacg agcacgcacc gctcacgctg gctcagtcgg   93180
tcagcggcgt gcagggcggc accccgctgt tcacctcgct cttcaactac cgcttcaccg   93240
cggctccgga caccgaaccc gccgccgggg aggcaggccc cctggacggc atcggtctgc   93300
tggcgtaccg ggaacagagc gagtacccgc tgaccatgtc cgtggacgac gccggggagc   93360
ggttcctgct gaccgccgac gcccacgccc ggccgacccc gaccaggcc tgccgactgc   93420 tccacacctg cctggagagc ctggtcacca ctctcgaggg cgctccgcac acggggctcg   93480
ccgcggtgga cgtactcgac ccggatgagc accggcggct tctcggggtg gggagtggtg   93540
cggtggtgga ggtgccgggg gtgtcgttcc cggagctgtt cgccgcgcag gctcggttgt   93600
cgccggatgc ggtggcgttg gtgggcagcg gtgtcgagtt gagttatgcg gaggtcgagg   93660
cccgggcgaa tcgcctggcg cggaagttga tcgggctggg tgtgggtccg gagtcggtgg   93720
tggctctggt gctggagcgt tcgccggaac tggtcattgc tgtgctggcg gtgttgaagg   93780
cgggcggcgc gtatgtggcc gttgatccgg ggcagcccgc cgatcggatc cgtttcgtgg   93840
tcgaggacgc ctcaccggtg ttggtgatcg acgacgtgga cttcctgacg gagaccgccg   93900
atttcgacgc ggctccggtg tcggacgccg acaggctgtc cccgcttctg ccgtcccatc   93960
cggcgtacgt gatctatacg tcggggtcga cgggtcggcc gaaggggggtg ctgatctctc   94020 atgcggcgtg tgtgagttat gtggcgagtc atgtccggta tggggtgggt gagggcagtc   94080
gggtggcgca gttcgcgtcg gcggggttcg acgcgttctg tgaggagtgg tggctggcgt   94140
tgctcggggg tggggcgctg gtggtggtgc cgtcggagcg gcggctgggt gaggagctgg   94200
tgcggttcct gctggaggag cgcgtgacgc acgcgacgct gccgccggcg gtggcggtgc   94260
tgatgcggga ggaggcactg gccccggggt tcgtgctgga tgtgggggt gaggtgtgcc   94320 cgccggatct ggtggaccgc tgggtggcgg gtggccggac gctgttcaac agttatgggc   94380
ccagtgaggc gacggtgaat gtcaccgtct ggcaggcagt ggacgggagt gtgggcgccg   94440
gggtgccgat cgggcgtccg gtggggaaca cgcgggtgtt cgtgctggac gacgggttgc   94500
gtccggtccc ggtcggtgtg ctgggcgagt tgtacgtctc gggcgtgcag ctgggcgggg   94560
gctatctcgg gcgtccggc ctgaccgcg agcggttcgt ggcatgtccc ttcgacccgg   94620
ggcagcggat gtaccgcacc ggtgaccggg tgaagtggag cgccgacggt gagttggtgt   94680
tgcggggtcg tgcggacgac caggtgaaga tccggggttt ccggatcgag ccgggtgagg   94740
tcgagaccgt actcgcggcg caccccgccg tcgcccatgc ggccgtggtc gtacgcgagg   94800 acaccccccgg cgacaagcgc ctcaccgcct acgtcgtccc cgcgcacgac acggacttcg   94860
```

```
ccgacgtgcc cgagacgctg cgtgcgtacg ccgccgagca gttgcccgcg tacatgctgc   94920
cctcggcgat cgtggagctg gacgtcctcc cgctcaccac caacggcaaa ctggaccgca   94980
aggcgctccc cgcccccgag tacgcggccg gcgcgggcag ggctgccgcc gacgcccgcg   95040
aggaactgct gtgcggggcc ttcgcccagg tgctgggcct cgaacgcgtc ggcgtggacg   95100
acgacttctt cgcactcggc ggccactccc tcctcgccac ccggctggtg agccgggtgc   95160
gcgccgtgct ggacgtggag ctgccgatcc gggcgctgtt cgagacgccc accccggcgg   95220
ccctggcccg cggactcgct cacgccgcgc cgggacgtgc ggcgctggag ccgcgggagc   95280
ggccggcgcg ggcgccgttg tccttcgcgc agcggcggtt gtggttcctc ggccggctgg   95340
acgggccgaa cgccacctac aacatccccc tcgccctgcg gctcaccggg gagctcgacc   95400
gggaggcgct ggccggcgcg ttccgggacg tgatggagcg gcacgaggtg ctgcggacgg   95460
tgttcgccac ggccgacggt gagccgtacc agcaggtgct gccggtcgac gcggccgggt   95520
tcgcactgcg ggtcgccgac gtcgacgtgg acggactcga cggggcggtg acggaggcgg   95580
ccggccacgc gttcgacctc tccgccgaaa tcccctccg agcctggctg ttcgcgaccg   95640
cgcccgagga gcacgtgctc ctcatggtgg tccatcacat cgccggagac gcctggtcca   95700
tggagccgct ggcccgtgac atggccgccg cctacgcggc ccgccgtgag ggccgtgagc   95760
cgggctgggc gccgctgccg gtccagtacg tcgactacgc cctctggcag cgtgacgtgc   95820
tggaccacga gggcgactcc ggcagtgtgc tgtcccgcca ggtggcgtac tggcgggacg   95880
ccctcgccgg ggcgcccgag gaactggagc tgcccgcgga ccggccgcgg ccgccgagg   95940 tgtccacccg cggacaccag gccccgtgc tggtgcccgc cgaggtccac gaacggctgc   96000
tggaggtggc gcggggagag ggcgtgaccg tcttcatggt gctccaggcc gcgttcgcga   96060
cactgttgca ccgcctcggt gcgggcgacg acgtccccgt cggcgcgtcc gtcgcgggcc   96120
ggacggacga gggcctcaac gacctggtcg gcttcttcgt caacacgctc gtgatccgca   96180
ccgacctgtc cggagacccg accttccgcg aactgctcgg ccgggtccgg gcggtgagcc   96240
tgtcggcgta cgagaaccag gacgtgccgt tcgagcggct ggtggaggag ctcgcaccgg   96300
ccaggtcact ggcccggcac cccctgttcc aggtcatgct cacactgcag aacacgggcg   96360
gaccgggcgg tggtccccgcc gtggacctgc cgggtctgcg gaccgactcg ctgtccgccg   96420
gaagcgtggc ggccaagttc gacctggacc tgtccgtcgg cgagacgctc gacgccaccg   96480
gtgctccggc gggcatcgag ggcgtgctcg tcgccgccgc cgacctgttc gacccggcga   96540
ccgtcgagcg catcgcgggc cgcctggtac ggctcctgga actggtcgcc ggggacaccg   96600 acatgccccct gagcgcggtg gacgtcctcg acgcggacga acggcgccag gtcgtcgagg   96660
agtggaacgg caccgacgcc cccctgcccg cccggtccgt ctccgacatg ttccgggcgc   96720
aggcggccgt gacgcccgac gcggtggccg tgctgtgcgg cgacgaccgg ctgacctacg   96780
ccgagctgga cgcgcgggtg aacaggctgg cccggctgct gatacggcgc ggtgtcggcc   96840
cggaggcccg ggtggcggtc tgcatggaac gctcggccga cctgctcgtg gcgctgctcg   96900
cggtgctgag gaccggagcc gcctatctgc cggtcgaccc gggccacccg gccgaacgcg   96960
tcgccttcat gctcgacgag gcccggcccg cgctgctcct caccggtcgc ggtaccgccg   97020
tcgaggcgtt cgggccggaa cgcgtcgtcg tggacgaccc ccgtaccgtc gccgaactcg   97080
cggatctgga cgcgcgcgcc gtcaccgacg cggaacgcgt caccccgccc ctcccggacc   97140
acccggccta cgtgatctac acatcgggct ccacggggcg gcccaaggga gtggtcgtca   97200
cgcacggcgc catggcgaac ctcgtcgcca cgatgggccg gcggttcccg atggacaccg   97260
```

```
aggaccgcct gctggccgtg acgacggtga ccttcgacat ccacgtcttc gagctgtacg    97320
ttccgctgct cgcgggcgcc gccgtcgtga tcgccgtgga cggggacgtg cgggacccgg    97380
cggccgtcgc cggactcgtc gaacggttcg gggcgagcct gatgcagggc accccggccc    97440
tctggcacgg gctgctgacc gcacacgccg aggcggcacg gggactgcgg ctgctcgtcg    97500
cgggcgaggc gctgtccggc tccctggccg cccgcatggc ggccgtcggg agcacggtga    97560
ccaacctgta cggcccgacc gaggcgaccg tctacgcgac cgccgccggc gtggaggcgg    97620
ggacgacggt tcccaggtg ccgatcggac gccccatcga caacacgcgt gcctatgtgc    97680
tcgacggacg gctccagccg gtgccccggg gtgtctccgg agagctgtac ctggccgggg    97740
cgcagctcgc ccgcggatac ctggaacggc ccgggctgtc cgcggagcgc ttcgtggcct    97800
gccccttcgg ggcggcgggc gaacggatgt accgcaccgg tgacgtggtg cgccggcgga    97860
ccgacgggca gctggagttc cggggccggg cggacgacca ggtgaagatc cggggattcc    97920
ggatcgagcc gggcgaggtg gaggccgtac tcggcgccca cccggcggtc ggccgggccg    97980
ccgcggtggt gcgcgaggac gtaccgggcg acaagcggct cgtcgcctac gtcgtggccg    98040 ccggcccga cgacgcggc cccgacgacg gcggccccga cgacggcggc ctcgccgccg    98100
tggcgcacga ccacgcggcc gagcacctgc cgtcgtacat ggtgccctcg gcggtggtgg    98160
tcgtggacgc gctgccgctg acctcgaccg ggaaactcga ccgcagggcg ctgccggccc    98220
cggcgtacac cgccggtggc gggcgcgccg cggcgacggt ggaggaggaa ctgctctgcc    98280
aggggttcgc cgaggtgctg ggcctgccgg ccgtcggcgt cgacgacgac ttcttcgccc    98340
tcggcggcca ctccctgctc gccgtctccc tggtggagtg gctgcggcag cgcggactcc    98400
cggtgtcggt ccgcgcgctg ttcacgacgc ccaccccggc cggactggcg gcggccgcgg    98460
gaccggagac ggtggtggtg ccgccgaacc tgatccccga cgacgccacg gagatcaccc    98520
cggagatact gaccctggtc gacctgaccg aggacgagat cgcccgggtg acggagacgg    98580
tgccgggcgg cgcggccaac atccaggacg tctacccgct ggccccgctc caggaaggca    98640
tcctcttcca ccacctgatg ctcgaccggg acgccacgga cgtgtacgtg acacccacgg    98700
tgatcgggtt cgactcacgg cggcgcctgg acggcttcct ggaagcgatg cggtgggtgc    98760
tggagcggca cgacgtgtac cgcacggcgt tcgtctccga cgggctcccg gaacccgtcc    98820
aggtggtgct ccgccacgcc gggctgccgg tcgaggaggt ggtgctggac cccgcgggcc    98880
cggacgccga acagcagctg gcggccgccg tgcgcggcag gctggacctg caccgggcgc    98940
cgctgatcac gacgcacgtc gccgccgacc cgcggaccgg cggccggtgg ctgtgcctgc    99000
tccgcgtcca ccacctgctc caggaccaca cgggcctcca gatcatgctc gacgagctgc    99060
gggcacacct ggcgggacgg acggagcacc tgccggagcc gctgccgttc cgcgacttcg    99120
tggcgcaggc acggctcggg gtgcccaggg agcagcaccg gcgccacttc accggcctgc    99180
tcggcgacgt caccgagccg accgcgccgt acgggctggt cgaggtgcac ggcgacggca    99240
cggcggtggc acaggcaagg ctccgggtcg acggcgaact gaccgtccgg ctcaagggg    99300 tcgcgcggtc gctgggggtg agcccggcga cgctcttcca cctggcgtgg gcgcgtgtgc    99360
tcggggccgt gtcggccgc gacgacgtgg tgttcggcac catcgtcttc ggccggatga    99420
actccggggc cggcgccgac cgcgtacccg gactgttcat caacacccctg cccgtgcggg    99480 tgcggctggc cggcgcctcc gtcggggagg cgctgaccgg gctgcggcac cagctcgccg    99540
acctgatggt ccacgagcac gcgccctgg ccctcgccca ggcggccagc ggcatgcccg    99600
gcggcccgct gttcacctcc ctcttcaact accggcacaa ccaggacgtg ccccaggaga    99660
```

```
ccgccgggc  gatggacggc  atggggctgc  tgtccgaccg  ggacatcacc  gactacccgc    99720
tcgccgtggc  tatcgacgtc  ggcggggag   gcttcaccat  cgccgtggac  gcggtggccc    99780
ccgccgaccc  cgaccaggtc  tgcacgctgc  tgcgcacctg  cctggacaac  ctggtcacgg    99840
ccctcgagga  ggcccccgac  acgccgctgc  ggagcctgga  cgtactgggc  ggcgccgaac    99900
tctccgagct  ggtcgaggga  cacaacgcca  cctcggtcgc  gagagcggac  gtctcggtgc    99960
cggaggcgtt  cgcgcggcgg  acggcggccg  atcgggacgc  cgtggcgctg  gtctcggact   100020
ccggcgaagt  gacgtacggc  gaactggacg  cacgtgccga  tgagttggcg  cgggcgctgg   100080
tcgcctcggg  cgtgggccg   gagtcggtgg  tcgccgtgct  gatggaacgc  tcggccgatc   100140
tggtggtggc  gttgctggcg  gtgttgaagg  ccggcggcgc  gtatctgccg  ctggacgtga   100200
ggtggccggt  ggcacggatg  cgcgcggtga  tcgaggacgc  cggggccacg  tcggtcgtcg   100260
tgcacgacgc  gacggccgga  cacgacctcg  gccgtaccac  cggtctcgac  gtgatcccgg   100320
tcgccgccgg  ggcggactcc  gccgtggtgc  tgcccgccgc  tgtggctccg  ggtgctgcgg   100380
cctacgtgat  gtacacgtcc  gggtcgacgg  gggtgccgaa  gggtgtggtg  gcgacgcacc   100440
gggacgtggt  ggcgctcgcc  ggggaccggt  gctgggagc   caccccgcgg  gtgctgttcc   100500
acgccccgca  cgcgttcgac  gcctcgacgt  acgagctgtg  ggtgccgttg  ctgtcgggcg   100560
gcacggtggt  cctcgccccc  gacgaggcgg  tggacggatc  ggtgctgcgg  acgctggtca   100620
ccggccacga  cctgtcccat  gtgcatgtga  cggcaggctt  gttgagggtg  ctggccgatc   100680
aggaccgggc  tgcttcacc   ggcgtgcgtg  aggtgctgac  cggtggtgac  gtggtcccgg   100740
ccgagtcggt  acggcgcgtc  ttggacgcca  accccggcgt  tgtcgtacgg  cagttgtacg   100800
gccccaccga  ggtgacgctg  tgcgcgacgc  agtacgaggt  cgccgatgcc  gccgaggtcg   100860
atagcgtgct  gccgatcgga  cgcccctcg   acaacacccg  cgtctacgtc  ctggacgggt   100920
cgctgaaccc  ggtgccggtc  ggtgtcgccg  gtgagttgta  cgtagccggt  gccggtgtcg   100980
cgcggggcta  tctcggtcgc  cccgtcctga  ccagtgagcg  tttcgtggcc  tgcccgttcg   101040
gggtcaccgg  tgaacggatg  taccgcaccg  gcgacttggt  gcgctgggac  gccgagggcc   101100
ggctcgtctt  catgggccgg  gccgacgacc  aggtcaagat  ccgcggtttc  cgggtcgagc   101160
cgggcgaggt  cgagacggtg  gtggccgccc  atccggcggt  cggccaggcg  gccgtcgtcg   101220
tacgggagga  caccccgggc  gacaagcggc  tggtcgccta  tctggtgccg  gccgggaccg   101280
agacgtcgtt  cgccgacgcg  gtgcgcgccc  acacggccga  ccggctcccg  gagtacctgg   101340 tccctcggc   cttcgtggaa  ctggagaacc  tgccgctgac  ggtcaacggc  aaactcgacc   101400
gcgaggcact  gcccgctccc  ggcttcccgc  acggggccgg  ggacacggtg  gcccacgggc   101460
cggtggcggc  gctcgaacag  gccatgtgcg  aggcgttcgc  cgaggtgctg  ggcctgccgt   101520
ccgtcggcgt  cgacgacgac  ttcttcgccc  tcggcggaca  ctcgctgctg  gcggtcagac   101580
tggtgcaccg  ccttcgggac  cggggcgtca  ccacatccgt  ccgggacctg  atggccgccc   101640
ccaccgtcac  cgccctgcgc  ggcacgctgg  gcctgtcgtc  agtgcgggac  tcgctcggcg   101700
tgctgctgac  gatccgcggc  gacggcggcc  ggccgcccct  gttctgcgtc  cacccggcag   101760
gcggactcag  ctggtgctac  acgccgttcg  cccagcacgc  gccggacgac  cagcccgtct   101820
acgggctgca  ggcccgcgga  gtcgacgcg   gcgcccgtt   cgccggcagc  ctggcggaga   101880
tggccgccga  ctacatcgag  cagctgcgcc  aggtgcagcc  ggccggcccc  taccacctcg   101940
tcggatactc  cttcggcgcg  gccccggccc  acgagatcgc  cgtccagctg  cgcgaacagg   102000
gcgaggaggt  ggccgcctg   gtcatcatgg  actcgttccc  gctcgaccgg  gagatcgcgg   102060
```

```
ccaccggcgc cgaggacggc gcggccccg  gcgggacct  gtcgtgggag ggcgcgatcc 102120
gggcggagtt cggtcatctg ctcggcgggt tcaccgacga ggagatcgcc gtcgtcgcgc 102180
ggaccttcga gaacaacacc cggatcaggg cggcgcacac caccggccgg ttcgacggcg 102240
acgcgctgat cctcacctcg gcggacagca cgacggagga cgggccgctc accgcgaaat 102300
gggcgcccca cgtcttgggc gagctgaccg aggtgtccat cccgtgcgga cacgtggaca 102360
tggtccgccc cgacatgatg ggcctggcgt ggcaggccat ctcggcctgg ctgaagtccc 102420
cgttgaccag aggaacggag agaacagaca tgcgacggac gtctctgctg tgcgtccccct 102480 tcgcgggcgc cggggcctcg ttcttccacc cgtgggcggc gctgacggac gggaacccgc 102540
ggatcgtggc cctccagctg ccgggccggg agtggcggct ctccgaggag ccgtaccggg 102600
acgtggcgcg ggccgcggcc gaactgcttc ccgtggtgac cgaggagatc ggcccggacg 102660
accgggtcgt gatcttcggg cacagcctcg gcgcggtgct cgcctacgaa ctcgcgcacc 102720
tgctggtcga ccgcaccggg gtcgacgtgg cccggctctt cgcgagcggc tcaccgggcc 102780
cctggacccg gcggacccgc cgggccaccg gcctgcccga cgaggagttc ctgctgcgcg 102840
tcaaggagtt cgccggctac gaccacgagg cactgtccca tccggacatg cgcgagctga 102900
tcctgccgac cctgcgggcg gacgtcgaga tgcacgagaa ctacgtcccc gccggcgacc 102960
ggccgctccc ggtccccgtc accgcggtgc gcggcacccg cgacgacctg gtcacggccg 103020
agcagaccgg cgaatgggcc agggcgacca cgccgggtt  cacccgggcc gaggtggagg 103080
gcggacacat gtacatcgcc gaggacccg  gcagcctgct gcgtctcgtc gacgacgcgc 103140
tcgcccggta ggagccgcca tgcagctcgc cggcaagacc gcgatcgtca ccggggccgc 103200
acgcgggctg gggcgcgcct gcgcggtcgc cttcgcccgt gagggcgccg acctcgtcct 103260
cctcgacctc tgcgcggacc tgcccggcgt tccgtacccg ctcggcggcc ccggccagct 103320
cgcccacacc gccgacctgt gccgcggca  cggcgcggcc gtcctcgtcc ggcaggccga 103380
cgtacgggac ctcggcgcgc tgcggcacgc cgtggacgac gcccacggcc ggttcggacg 103440
catcgacgtg ctgctcaaca acgcccggat cgccgcgccc tccggcaaac ccgtcgacga 103500
gatcgacgag gacgagtggc agctgatgat cgacgtggac ctgtccggcg cgtggcgcgc 103560
gacgaaggcg gtcggcaaga tcatgaccgc ccagcgggcc ggcagcatca tcaacgtcgc 103620
ctccaccgcc gggcaggtcg gataccgcaa cttcgcgggc tacgtggcgg ccaaacacgg 103680
tgtcatcggg ctcaccaggg ccacggcgct cgacttcgcg ccgatgaggg tccgcgccaa 103740
cgccctgtgc ccgggctcgg tccgggacga ccctgccgtc gagggccgga tgctctccga 103800
gatcgccagg tccctccagg tgccggtcgc cgaacacgag gaggccttcg tccagtcgca 103860
gcccatgaac gccctgatcg agcccgatga cgtcgcctcg gccgccgtct ggctcgcctc 103920
cgacggatcc cggcaggtca cggggtcggt catcaccgtc gacggcgggt tcaccactcg 103980
ctgaaccaca gggagaggga cgtggtcact gtccagtcag ccgaggacgc ccggcactgc 104040
cacgcgctgc gcgtccgcct cggggcctcc gaccgcgtgg acgcgccctg ggtggaacgg 104100
gtgcccttcg cgagcgacga gccgggcgcc gcacggcacc cgcgccgcga actgcccgg  104160 ccggtcgacg cgggccgcgg atcgcgcgcc gtgctgctcg tctacaccga cggccgggcc 104220
gacctggtcg tcgtcgccca ccggtccgcg tacgccagc  gggcgctgcg ccgcctggcc 104280
gccgcgctgc tcgaccccgc gcggccgcgc ccggcccgcg gacagggcgc cgtgccgagc 104340 ggctccggc  acacgcccga ctgggggctg gcggccccg  cacaggggga cgcgcgggac 104400
ggccaccggg tcgcgctgcc cgagggcacg tcccgtgaac ccgagggctg gctcgccgcg 104460
```

```
ctcgcccagg tgctctcccg gtacgagccg gagcgcacgc cggaggccac ggccctggac 104520
gccggggacc gggccgcgtc cccgccggcc acgccggtga gcgccgggct ggtcttcgac 104580 ctcggggcg aaggcgagta cgtgccctgc ctggcgcccg tcttcccgct cacggtcacc 104640
gtcggcgagg acggtctccg ctgcgaccac cggctcggcg acgtcagcac gccgatcgcc 104700
gaacagttcg tgcgccacct cgtcgaggcc caccgccgcc tcaccggccc gcccggcatc 104760
ctcgacccgg cggagcacga acggatcctc cggctggggc gggcggcaca gccgctgaag 104820
agcacaccgc gccggatacc ggacgtgttc gccgagcggg ccgcgaacg ccccgacgcg 104880 ctggccctcg tggacgggga ccgcacggtg acctaccgcc ggctcgacga gtggtccgac 104940
cggctcgcgc acggcctgcg cgccgccgga gcgggcgacg gcaccctggt cggtgtctgc 105000
ctggagcgct cggcgcaact cgtcgcgtc ctgctcgccg tcctcaaggc cggggcggtc 105060
tacgtgccgc tggaccccggc ctacccggcg gaccggctcg cgtacacggt ggaggactcc 105120
ggcacggacg tcgtggtcac cgagtcggcc gggttccccg gctccccggg cgtccggtg 105180 ctcaccccg cccaggtgct ggagtcgggc ggcgccgcgc cggacggtcc ccccgcgacc 105240
ggcgcaggcc cgcaggaggc cgcgtacgtg atctacacgt cgggctccac cggaaggccc 105300
aagggggtgc tggtcccgca cgcccacgtc gtcgccctga tggacgccac ccgcgacgac 105360
ttcacgctcg gcgccgccga cgtgtggacg ttcttccact ccgtcgcgtt cgacttctcg 105420
gtctgggaga tctggggctg cctgctgacc ggcggccggc tcgtcgtcgt cccgtactgg 105480
gtgtcgcggt cgcccgagca gttccacggc ctcgtcgccg ccgggggggt caccgtgctc 105540
agccagacgc cgtccgcctt cacccagttc gcggccgccg accgcgacac ggcggagccg 105600
ctcgcggtgc ggctggtggt cttcggcggt gagccgctgg acaccccggag cctgctgccc 105660 tggctggacc ggcaccccgg ggaccgctgc cggctggtca acatgtacgg gatcaccgag 105720
accaccgtga acgtcaccgc ggagaccgtc acccggcggc tcgccctggc cggatcccgg 105780
tccgtgggcc gggcgctccc cggctggcgg gtgtacgtcc tggacgcgcg ggggcggctc 105840
gcgccacccg gagtggcggg ggagatccac gtcggcggcg ccggagtggc gctcggctat 105900
ctgcgccgcc ccgacctcac acgggagcgg ttccgccccg atccgttcgg cggcgggcgg 105960
atgtaccgga ccggcgaccg gggccggctg cgccgacg cgcccctgga gcacctggga 106020
cgcctcgaca accaggtcaa gctgcgcggg ttccgcatcg agctggacga gatccgcacg 106080
gtgctggccg aatgccccgg cgtgaccgcc gccgccgtga cgttccgtca gaccgacccg 106140
ggggacgcgg cgaccggccg gctcgacgcg tacgtggtcc tctccgaggg ctccacggcg 106200
gacgtgaggg agcgggccgc gcgcgtcctg cccgcccaca tgctgccctc caccctgacg 106260
gcgctgcccg cgctgccggt gacggcgaac gggaagaccg acctggccgc cctgccggaa 106320
ccggccgtgg ccgcgtccgg cggggagcg gtccccgcgg gcggcgagga cggtctgtcc 106380
ggcgagttgc tgagcgtgtg gcggcagctg ttcggcttca ccgtgggcct gtccgacagc 106440
ttctgggaac tgggcgggaa ctcgctgctc gccgtgcgga tggcgtcgct gatgcggaa 106500 cggggcctgc cgtcactgca cccgcgcctg ctctacctca acccgacggt gcggcaactc 106560
gcggtcgcgc tcaagggata gccgctcgcg cgccggcgcg gcccgctact cggaggtgct 106620
ctcgacgacg cggttctccc aggcccagac ggcgatctcg gtccggttgc gcaccccgag 106680
cttggtctgg atccccgaca gatggctctt gaccgtgctg agcgagatga acagctcggc 106740
ggcgatctcc tggttggtgc ggccgcgcgc gatggcccgc acgacctcca gcgcgcgccc 106800
ggacagctcc gacgaccgcg cggcacccc gcggggcatc gcctgcgact cgttgaggtg 106860
```

```
tttgagcagg cgcagcgtga ccgacggcga gaccagcgcc tcgccgttgt aggcggcgcg    106920
gaccgcctcg atgagcaggg cgggccccgc gtccttgagg acgaacccgg ccgccccgcc    106980
ccgcagtgcc ccgtacacgt attcgtcgag gtcgaaggtg gtgaccacga tcacccgcat    107040
cgggtcggcc gccttcgggc cggccagcgc gcgggtgacc tcgatgccgt cgagcttggg    107100
catccggatg tccaccaggc acacgtcggg acggagcctt cgggccatcg cgatcgcctc    107160
ggcgccgtcc tcggcctccc cgacgacggt gatgtcccgg ctggtcctcc aggatgagcc    107220
gcagggcccg cggcggatca tcgcctggtc gtcggcgagc aggaccttga tcgtcatccg    107280
ggctccctgg tgggtacggg cagggtcgcc cgcacggacc agccggcgcc gggccggggg    107340
ccggcgtgca gtgagccgcc gagcgtttcg acgcgttcgc gcatgccgac caaaccgtac    107400
cctccacgat ggtgcgaccg ggcggagttc ggcggggcgt cgtcgcggac ctcgaccgtg    107460
acggcgtcgg cgtcgcggcc gacggtgacg tcgatggagt gcgcgtgccg cgcgtgccgc    107520
aggacgttcg tcagcgactc ctggacgatg cggtacacgg tgctggtcac ctcgggcggc    107580
cagcgcgtgt cgtcgtcggg cacgctcagg cgcaccttcg gaccctgccg gctgaagcgc    107640
tcgaccaggg cgcccagtcc ctccggcccg ggcgaggcgg gtgccgcgtc gtccgtgtcg    107700
cgcagcagcc cgacgacccg cgcatcgcg gccatggcct cgaaccccgc ggtctcgatc    107760
tcggtcagcg agtccgacac gtcctccggg ttccggcgcg ccaccacctg ggcggcctgt    107820
gcctggatca gcatccccgt gatgtggtgg gccacgatgt cgtgcagttc ccgggcgagt    107880
tcgagccgtt cggtccggcg gacctgctgg gcggtggcct tcgcgtgctc gtcgagccgg    107940
cgcagcgaca gccccactcc cacggcggcc agccaggcca ccgcggcgat ggccggaacg    108000
gccgtcaccg gccgggtggc gaactgggcg gcgaccagca ggagtcccgc gccccgcgatg    108060 gtccccgccc gcaccggggg cagtgcccgg accgcggacc cgatgagcac cgccaggccc    108120
agcgccgtgg aggggccgag tcccgcgggc agccgggtgc cggcagcag cggcacgagc    108180 accgacagcg cggccacgac gagacccacg accgaggtcc aggtccgctc gcggtggcgc    108240
agcagcgcca gcccgcacac caccacggag gcggcggcgc ccggcaccca ggacgccgct    108300
ccccaggtct gcgcgagggc gacggcctgc acggcgatcg cggtgaggaa ggcgacggcg    108360
agcccgacgt tggagaagac gctcacccat cgcttcggaa tcgccacgtc gatcaggcta    108420
ccgaaccccc gcccgcggtc cgcgccgtcc ggcggggccg cgggcggggc gcccggcggt    108480
tcggaggtac cggtcgcgga ccgggcggtg ctcatggtgt cgaggtctcc ggtcatgcta    108540
ggagtgcggc gggtgggccc aggattcctg cggttcccgg ggagtggcca gcgcgcgccg    108600
gtcgaggagc cgcagcaccg gccccaggac gagggccgcg gtcatcgcga gcgtggccgc    108660
gctcgccacg ccgctcagcc cctccagcca gaaggccacg gtcaccgcga caccgcccac    108720
cgcgatcgcg gcggcccccgc ccgcgggcag cgtccggatc gccgagccga cgagcaccga    108780
cagcgcgagc gccgtggccg gcgcgggctc ctgcggcagg tcgtccccgg cgatccggga    108840
cacggtgacg gcgccggccg tgaggaccag ccccgcgacc gccgtcagcg ccttgaaccg    108900
cgcacggaac agcgccacgg cgctcacgac gacggagacg gcggtgccga acagccacgc    108960
ggtcccgccc cagctggtca tgaacatgaa cgccgtgaag acgatcccca gggcagcac    109020 gacgccagc ccgacgtcga acatccttcc aggtggcctc gtgggcccct ccgctgtatt    109080
catgctcctc aggctaggaa gccggggcgt ccggcgtacc ggccgaaagt acggaacagt    109140
gtggacggag ccgtgctttg gccggttcc ggcggcggtc cgctcagccg ggcacgtgcc    109200
gcgcggacag gtccaggaga cgcccgtcgt gacagcgcgc gaccgcgaga ccgaacagct    109260
```

```
cccgctccac gtccttgcgt tcggccgcgg tgagcaccgg cgggccgccc agccgtccgg   109320
tcagccggtc cagggcgccc agcagcgccg cgtcggggta acggccggcg caccgccgcc   109380
acaccgccag caccgaggcg gcggcgagga ccaccgtgta gcggtcggcg agcgcgaacg   109440
ccgccggcgg ggcgtcgatc gtgatgtcac cggggccgag cgccgcgcac ccgtcccgca   109500
gcgtccgcag ctcgtcccgg agccgggcgg cgaaccggcg gaccgggtcg cggtcgtccg   109560
ccggcacgcc gtccgccagt tcggtgagcg cgccgactac gccgtcgtgg cggggcatgc   109620
cggtgctcag ccggtccggg gcgagcgcgg gcagctcacc gcccgggtcg aacagcgagg   109680
ccggggcgga cggatcggcc agccaggacc tgcgggccag ccggggcagc tgcggaagca   109740
gtgtcaccag ggcggcggtg agcgacacat gggcgaaggt cgcgggggcg acttccccgg   109800
ccagcttctg gaacgtcgcg tacgggcccc gccgcagata ggaccgtgag ccgagcaccg   109860
cccgcaggtc ctcaaacgcg tcgagcagca tccgcgcggt caggtacttc gccgcggggg   109920
cgtagaccgc catcgcctcc ggccgcaggt gcagcgcccg gaggaccacc gcggagaacg   109980
cgtccatggc cagcagatcg gcgtaggagc gggcgatcac cgcgcgcacg tacggcaggt   110040
cggcgaccgt accgccgtag aggcggcgct cgagggagca gcgcatggcg aggcgcagcg   110100
cggtctccag cggtccgacg agcaccgcgg ggcccaccga gcgggtgatc tggtacgagc   110160
gcagcgccac ctcgatcccc tggcccgggg agccgatcag cgccgtcggcg gggacggggc   110220 agtcggcgaa ctccacgccg ccgagctcga tgccgcgcat cccggagctg tggaagcgcg   110280
gcaggtcccg gaccgccgcg gcgggcaggt cgtcccgggt gaggaggaac tggctgtggc   110340
cgcggctgcc cgcgcccgtg ccggtccgtg cgaacagcac catggcctgc gcgcggcgca   110400
cgttcgtcac gatctccttg cggccggtca gccgccagcc ggcgccgtcc ggccgggcgg   110460
cgcactcggc gtgcgcgaag tcgttgccgt gcgccagctc gtggaacgcg cggcgaccc    110520 ggccgttcgc caggagcagg tccgccaccc ggcgccgctg ctcctcgtcg ccggtggtcc   110580
agacgttgac ggaggcgatg agcgagctga agccgtagcc gagaccgagg cacggatccc   110640
gccgccacac cgtccgcagc acctcggcga gccggtcggc gcgctccaga cggccgccgt   110700
ggaccaccgg gacgaactcg gcgttcaggc ggtactcgtc cagcacccgc tcgccctcgg   110760
cgggcatctc ctgtctctcg tcggcggcca gcaccgccgc gtgacccacc gggttgcggt   110820
cgtcccaggg gtcgccgagc aggacgtcca gctccgcggc gcccatcagc ggccgtcctg   110880
ggagccggtc agcggcgcac cgaacgggggt caccgggggcc ccgtcccgcg ccgcccgcg    110940 cacgtgctcc gccagcagtc cgtcgagccc gtcgtccccc ggggccgccg acggcgcgg    111000 tgtccgcagc gtcgtcgcga gcctggcccg cagggcgcgc agcgccgccc tcgcccacag   111060
tccgtcctcc cacaacggct ctcctcgacg gctgtgccgt ccggccgacc aggtgtgcag   111120
gcacgccgcg gccgcgtagc agagttcgta cgcggcggcc gtctcgtagg cggacatcgg   111180
agggtgcgcg gccggggcga ccgccgccat ccgcgcgtgg acctctccgg cggccgcggc   111240
gaccgcgacg gcgtgcgcca cgagcccctc cggggccgct tccccggcga gtgcccggga   111300
caaagcgggg agggactgca ccaccgaaca gccccgccgg acagcagcg tgagtgcccc    111360 gcggtccagc ggcccggcgg gctcgcccac cgccgccgcc ccggccagcc ccttctcgtc   111420
gaccgtgccc gccggtact cccgcaccag ccgcgggaac tgctggacga gcgccgcgcg    111480
gttcaccggg gtgctgccgt cgaacaccga cacgatctgg tggtcgcgcc agatcttctg   111540
gaacgcgccg tgcgcgtaca ccccggtgag gaaggaccgc gcgccgagca gttcggcgag   111600
ttcggcgatc accgcgtcgg tcagtgccgg tgcgacggac ttgaccaccg cggacaccac   111660
```

```
gctcatctcg ccggtgaggg tgtggatcgc gcggctgccg accagcgccg ccgactcggc   111720
ggcggccgtc agcgccgcgc accggccgag gatcgcccgg ggatgggcgc ggtcgaggag   111780
cggacgccgc tggatgatcc gttcggcggc gaacgcggcg gtgatccgca gcgcgtgctc   111840
gcccgccccc agcgacaggg cggcgcacat ggtccgggtg agctgcagcg cgcgcagcac   111900
cgtctcggct ccgccgccct cacggccgaa cagcgcgccg ggagccggca ccgcccctc    111960 gaacgcgatg ccggagatgt cgatgccgcg gatcccatgg gtgggttcct tgggcagcac   112020
atgccaggag ccggggcga gcgcggactt gtccaccagg aagagactct gcccccgccc    112080
ggatccggcg gctccggtgc gggccaggac ggtcagcaga cgggcccggg tggcgttgtt   112140
gacgggccac ttgacgccgt caaggcggcg gccgccgtcc tggcggtcg cggtcagctc    112200 cccgttgagc aggtcggcgc cgtggtccgg ttcggacagc gcccaggcga ccggttcgcc   112260
cgccaggacc gcgtccgccg tggcggtggc ctgcgcggcg tcgcctgcgc accagaccga   112320
cgcggcgccg aggtaggtct tgccgtgcgc gacggcggcg ctcaggtcac ggcgggccac   112380
cgtgcgccac agccgcagca gcacctcgtg gtcggcgccg gcgccgcccc actcggccgg   112440
aacgtagtac gcgggcagcc cgaacgcgtc gagccgcgcg acgagcgtgg cggggaactc   112500
ctcggcggcg tcctccccgg cgacgcggcg ggcgacatcg ccccccgccc cgtccggtcc   112560
ggcgtccgtc aggaacgcgt cgagcgcggc ctcccgcccg gcgcccgtgc cggtgtgcac   112620
cggcgccctc accgcggccc cgccgccggt gcgcgcagcg cgggctccag ctcggcgtgc   112680
agcacggtca tgtcgcccgc gaggaaccgt tcccgcatgg cggtgcgccg gatcttcccg   112740
ctggtggtgc ggcgtacggt gccgcgccgc accagcacga cgttgcgcag ggggagaccg   112800
aacgaagcgg ttgagcctgc gggtgaccgc ggtgacgacc tccggcagct cggtcctcgg   112860
ggtccggggg tgcacctcgt gcacgagcac cacacgctcg tccggcgagc cgaccccgaa   112920
cgcggccccg agctggccgc ccagtgcctg gtgcgcggca cgcgcctcgt gctccacgtc   112980
ctgcgggaag atgttccggc cgtgcacgat cagcagttcc ttgaggcggc ccgtgacgaa   113040
cagttcgccg tcgacgagcg cgcccaggtc cccggtgcgc agccagcccg gtccctcggc   113100
ggagtccgcg aggcgggcgt cgaagacctc cgcgctcagc tccggtctgc cccagtagcc   113160
ccggccgatg ctctccccgc gcagccagat ctcgccgatc ctgccctcgg gcagcggcac   113220
ccgctcccgc gggtcgacga tccgcaggtc gaacgcgtgc ggccggccca gacccatcac   113280
cggcctgccc gccccctcgg ccaccggccg cagctccggc cgctcgccgg actccagccg   113340
cagcgggtcc accgtgagca cggtgggact ggtctcctcg gggacgcagg tcacgtacgc   113400
cgtggactcg gcgaggccgt agccgctgga gtggacgtgg gaacgcagcc cgaggtcgcg   113460
gaaccgttcc atgaaggccc gcacggtcgg cgcgtggatc ggctcggccc cgttgccgag   113520
gtagcgcagg gcggacaggt ccagtccccg cgtcatctcg tcggtgatga cgcgggtgca   113580
gagttcgtac gcgaagttgg gggcgacggt gtaggtgatc cggaaccggt ccagcatgcg   113640
gaaccactcg gccggccgcc ggatgaactg gccggcgtc atcagcgtga ggtgcgcgcc   113700
gcacagcagc gccgcggtga gctgggtgaa caggcccatg tcgtggtgca gcggcagcca   113760
gctgccgaac cggtcctccg ggacgaggcc cacataggtg cagaccgccg agacgttcgc   113820
caggaccgcc ccgtgcgtga ggatcacacc ttcggcgacc cggtggaccg gagctgtact   113880
gcaggaccgc gtccgtgccg cggcgacgtc ccggccgtcc gcccctcc caggcgcgga    113940 ccgcccgccc accgggagca cggcctcgac ggcgagcccc tccgggccgt ggcccctcag   114000
gtgctcggcg acctcggcgc gggctgcgtc ggtggtgagg accaggccgg gcgagcagtc   114060
```

```
ggccgcgatc gccgcgatcc gttcaccggc gctcgccgac ccgcccggca tcggtgaggg   114120
cacggcgaca agaccggcgg tcagacaggc cagatagacc tccgcgaact cgatgcccgt   114180
cggcagggcg acgagcaccc tttccccggg ggccagccgc cgggccagct cccgcgcgcg   114240 caccccgggac cggcgggcca gctccccgta ggtgacgctc tcggggtccg ccccggtgga   114300
gccgtgccag agggtcagtg cggtccgccc gggatgagcg tccgcccgcg cggcgaaggc   114360
cgcgcccaga ctcggatatc cgctgaggtc gacggtcatg gcgtcagcgc tggttttcca   114420
tcgcctcgat gaggctcttc ggccgcatgt ccgtccagtt cttctcgatg tagtcgaggc   114480
agtcctggcg gccggcctct ccgaacacgg acgtccatcc gtccgaacc ttggcgaaga    114540 cgggccagag ggaatgctgg ccctcgtcgt tgaccaggac gagatagctg gcgtcgggat   114600
cctcgaaggg gttcggcacg gcgttgccct ctctcggtga aggaagggg tgcgcggacg    114660 acttgaccgc gttcactat gcccgcgccg ctcgctgacc atcaacggcg gcgaacaccc    114720
cggcgtccaa ccgctcccgt ggcatcactt ggacgaaccc gccccggcac cgcgccgtcc    114780
cggcgccctc accagtccgg ccgggcgcgc ctgccgaaca ggattccgcg cggctccggc   114840 ggcggggag tgcccggggc gcagcgggcc aggcgatcag catgcccgc cacgaagccg     114900 aacacgtgcg cccaggtacg ccaccgtccc ggcgtcggtg acgccctgcc cggacgagta   114960
caccgcctgc agcacgaacc acatgcccag cacgatccac gcgggcagcc gcagcggcag   115020
gaagatcagg aacggcacca gcacccagac ccgcgccctc ggatacagca ccagataggc   115080
gcccagcacc ccggcgaccg ccccggaggc gccgatcagg ggctcgcccg agccggcgtt   115140
cagcacggcg aagccgtacg cggcggcgta accgcagacc aggtagaaga gcaggaagcg   115200
gacgtgcccc atgcggtccg cgacgttgtt gccgaagatc cacaggaaga gcatgttgcc   115260
gagcaggtgc agccagccgc cgtgcaggaa catcgccgtc aggacgctca gctcgggga    115320 cttctcgtag cccggccggt ccaccacgca ccccgggccc tgcgggccca ccccggtggc   115380
gccggtgggc accaggttcg gcatccggtg gtggatcagc tcctgcggga ccacggcgta   115440
gcggtccagg aacgcctgca gatggcacag gtcggccaga ctgctcccgc cggtcagtga   115500
gccgatcacg ccggggtga aggccaggaa gacgacgaag ttggcggcga ggagcgcgta    115560
cgtcacccag ggggtgcgcc gcgtgggggtt cacgtcatgg acgggcatga ccacgtccca   115620
ctagtgcccg gacggccggc ggtgaatccg cggcggcgct gaacaccgcc gtacggacgc   115680
gcgtatgact cggcaaccgc ccggggcgcg gggaaaggcg ccgcggggtc cgacgtgagg   115740
aacaggcgat gaacgaccga gtgccccccg cgatgcacgc gctgcccgac ggcgaggccg   115800
agctcacgct cgtggtgcgc ctcccctggg aggacgtcgc ccggctcggc caggaggcgg   115860
ggcggctcgc ctcccagatg cggcggccgg tgacgctgga ggaggcggtg agccatcggc   115920
tgcggtccgc gcggagcgcg gcgcacgcca agccggcggt gcccgcgccc gcgtcggcgc   115980
cggatgccgg caccccgggt                                              116000
```

<210> SEQ ID NO 50
<211> LENGTH: 35
<212> TYPE: DNA
<213> ORGANISM: Artificial sequence
<220> FEATURE:
<223> OTHER INFORMATION: Synthetic oligonucleotide primer.
<220> FEATURE:
<221> NAME/KEY: misc_feature
<222> LOCATION: (9)..(9)
<223> OTHER INFORMATION: n is c or g
<220> FEATURE:
<221> NAME/KEY: misc_feature

```
<222> LOCATION: (12)..(12)
<223> OTHER INFORMATION: n is c or g
<220> FEATURE:
<221> NAME/KEY: misc_feature
<222> LOCATION: (18)..(18)
<223> OTHER INFORMATION: n is c or g
<220> FEATURE:
<221> NAME/KEY: misc_feature
<222> LOCATION: (21)..(21)
<223> OTHER INFORMATION: n is c or g
<220> FEATURE:
<221> NAME/KEY: misc_feature
<222> LOCATION: (30)..(30)
<223> OTHER INFORMATION: n is c or g

<400> SEQUENCE: 50
atctacacnt cnggcacnac nggcaagccn aaggg                                35

<210> SEQ ID NO 51
<211> LENGTH: 26
<212> TYPE: DNA
<213> ORGANISM: Artificial sequence
<220> FEATURE:
<223> OTHER INFORMATION: Synthetic oligonucleotide primer.
<220> FEATURE:
<221> NAME/KEY: misc_feature
<222> LOCATION: (2)..(2)
<223> OTHER INFORMATION: n is a or t
<220> FEATURE:
<221> NAME/KEY: misc_feature
<222> LOCATION: (2)..(3)
<223> OTHER INFORMATION: n is inosine
<220> FEATURE:
<221> NAME/KEY: misc_feature
<222> LOCATION: (7)..(7)
<223> OTHER INFORMATION: n is g or t
      220>
<221> NAME/KEY: misc_feature
<222> LOCATION: (8)..(8)
<223> OTHER INFORMATION: n is g or c
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is g or c
<220> FEATURE:
<221> NAME/KEY: misc_feature
<222> LOCATION: (15)..(15)
<223> OTHER INFORMATION: n is c or c
<220> FEATURE:
<221> NAME/KEY: misc_feature
<222> LOCATION: (16)..(17)
<223> OTHER INFORMATION: n is g or c
<220> FEATURE:
<221> NAME/KEY: misc_feature
<222> LOCATION: (18)..(18)
<223> OTHER INFORMATION: n is g or c
<220> FEATURE:
<221> NAME/KEY: misc_feature
<222> LOCATION: (19)..(19)
<223> OTHER INFORMATION: n is inosine
<220> FEATURE:
<221> NAME/KEY: misc_feature
<222> LOCATION: (20)..(20)
<223> OTHER INFORMATION: n is a or c

<400> SEQUENCE: 51
anngagnnnc cnccnnnnnn gaagaa                                          26

<210> SEQ ID NO 52
<211> LENGTH: 24
<212> TYPE: DNA
```

<213> ORGANISM: Artificial sequence
<220> FEATURE:
<223> OTHER INFORMATION: Synthetic oligonucleotide primer.
<220> FEATURE:
<221> NAME/KEY: misc_feature
<222> LOCATION: (3)..(3)
<223> OTHER INFORMATION: n is c or g
<220> FEATURE:
<221> NAME/KEY: misc_feature
<222> LOCATION: (9)..(9)
<223> OTHER INFORMATION: n is c or g
<220> FEATURE:
<221> NAME/KEY: misc_feature
<222> LOCATION: (12)..(12)
<223> OTHER INFORMATION: n is c or g
<220> FEATURE:
<221> NAME/KEY: misc_feature
<222> LOCATION: (18)..(18)
<223> OTHER INFORMATION: n is c, g, or t
<220> FEATURE:
<221> NAME/KEY: misc_feature
<222> LOCATION: (21)..(21)
<223> OTHER INFORMATION: n is c or g
<220> FEATURE:
<221> NAME/KEY: misc_feature
<222> LOCATION: (24)..(24)
<223> OTHER INFORMATION: n is c or g

<400> SEQUENCE: 52
ggnaccggnc tnatcggnac ntcn					24

<210> SEQ ID NO 53
<211> LENGTH: 30
<212> TYPE: DNA
<213> ORGANISM: Artificial sequence
<220> FEATURE:
<223> OTHER INFORMATION: Synthetic oligonucleotide primer.
<220> FEATURE:
<221> NAME/KEY: misc_feature
<222> LOCATION: (4)..(4)
<223> OTHER INFORMATION: n is c or g
<220> FEATURE:
<221> NAME/KEY: misc_feature
<222> LOCATION: (13)..(13)
<223> OTHER INFORMATION: n is c or g
<220> FEATURE:
<221> NAME/KEY: misc_feature
<222> LOCATION: (19)..(19)
<223> OTHER INFORMATION: n is c or g
<220> FEATURE:
<221> NAME/KEY: misc_feature
<222> LOCATION: (22)..(22)
<223> OTHER INFORMATION: n is c or g

<400> SEQUENCE: 53
gtgngagacg agngccacng cncggtcgtg					30

<210> SEQ ID NO 54
<211> LENGTH: 27
<212> TYPE: DNA
<213> ORGANISM: Artificial sequence
<220> FEATURE:
<223> OTHER INFORMATION: Synthetic oligonucleotide primer.

<400> SEQUENCE: 54
cacggatcca agcttggttc atgtgca					27

<210> SEQ ID NO 55
<211> LENGTH: 25
<212> TYPE: DNA
<213> ORGANISM: Artificial sequence
<220> FEATURE:
<223> OTHER INFORMATION: Synthetic oligonucleotide primer.

```
<400> SEQUENCE: 55
atcggatcca agcttcacgt gttgc                                          25

<210> SEQ ID NO 56
<211> LENGTH: 32
<212> TYPE: DNA
<213> ORGANISM: Artificial sequence
<220> FEATURE:
<223> OTHER INFORMATION: Synthetic oligonucleotide primer.

<400> SEQUENCE: 56
tctacgtcct ggacagatct ctgaacccgg tg                                  32

<210> SEQ ID NO 57
<211> LENGTH: 32
<212> TYPE: DNA
<213> ORGANISM: Artificial sequence
<220> FEATURE:
<223> OTHER INFORMATION: Synthetic oligonucleotide primer.

<400> SEQUENCE: 57
caccgggttc agagatctgt ccaggacgta ga                                  32

<210> SEQ ID NO 58
<211> LENGTH: 34
<212> TYPE: DNA
<213> ORGANISM: Artificial sequence
<220> FEATURE:
<223> OTHER INFORMATION: Synthetic oligonucleotide primer.

<400> SEQUENCE: 58
tcaaccccgt acccgtcaga tctctggggg agct                                34

<210> SEQ ID NO 59
<211> LENGTH: 34
<212> TYPE: DNA
<213> ORGANISM: Artificial sequence
<220> FEATURE:
<223> OTHER INFORMATION: Synthetic oligonucleotide primer.

<400> SEQUENCE: 59
agctccccca gagatctgac gggtacgggg ttga                                34

<210> SEQ ID NO 60
<211> LENGTH: 25
<212> TYPE: DNA
<213> ORGANISM: Artificial sequence
<220> FEATURE:
<223> OTHER INFORMATION: Synthetic oligonucleotide primer.

<400> SEQUENCE: 60
gtcaagcttg aggaactcgt gctcg                                          25

<210> SEQ ID NO 61
<211> LENGTH: 23
<212> TYPE: DNA
<213> ORGANISM: Artificial sequence
<220> FEATURE:
<223> OTHER INFORMATION: Synthetic oligonucleotide primer.

<400> SEQUENCE: 61
ctgagatcta ctcattcggc ctc                                            23

<210> SEQ ID NO 62
<211> LENGTH: 26
<212> TYPE: DNA
```

```
<213> ORGANISM: Artificial sequence
<220> FEATURE:
<223> OTHER INFORMATION: Synthetic oligonucleotide primer.

<400> SEQUENCE: 62
gcgagatctg gagagtacgc cggcga                                          26

<210> SEQ ID NO 63
<211> LENGTH: 23
<212> TYPE: DNA
<213> ORGANISM: Artificial sequence
<220> FEATURE:
<223> OTHER INFORMATION: Synthetic oligonucleotide primer.

<400> SEQUENCE: 63
ctgacggacg cgaattccct tgc                                             23

<210> SEQ ID NO 64
<211> LENGTH: 8
<212> TYPE: PRT
<213> ORGANISM: Streptomyces fungicidicus
<220> FEATURE:
<221> NAME/KEY: misc_feature
<222> LOCATION: (2)..(4)
<223> OTHER INFORMATION: Xaa can be Leucine or Phenylanine
<220> FEATURE:
<221> NAME/KEY: misc_feature
<222> LOCATION: (7)..(7)
<223> OTHER INFORMATION: Xaa can be Threonine or Tryptophan

<400> SEQUENCE: 64

Asp Xaa Xaa Xaa Val Gly Xaa Val
1               5

<210> SEQ ID NO 65
<211> LENGTH: 8
<212> TYPE: PRT
<213> ORGANISM: Streptomyces fungicidicus

<400> SEQUENCE: 65

Asp Leu Thr Lys Val Gly His Val
1               5

<210> SEQ ID NO 66
<211> LENGTH: 8
<212> TYPE: PRT
<213> ORGANISM: Streptomyces fungicidicus

<400> SEQUENCE: 66

Asp Phe Trp Ser Val Gly Met Val
1               5

<210> SEQ ID NO 67
<211> LENGTH: 8
<212> TYPE: PRT
<213> ORGANISM: Streptomyces fungicidicus

<400> SEQUENCE: 67

Asp Ala Tyr His Leu Gly Leu Leu
1               5

<210> SEQ ID NO 68
<211> LENGTH: 8
<212> TYPE: PRT
<213> ORGANISM: Streptomyces fungicidicus

<400> SEQUENCE: 68
```

```
Asp Met Glu Thr Asp Gly Ser Val
1               5

<210> SEQ ID NO 69
<211> LENGTH: 8
<212> TYPE: PRT
<213> ORGANISM: Streptomyces fungicidicus

<400> SEQUENCE: 69

Asp Phe Trp Ser Val Gly Met Val
1               5

<210> SEQ ID NO 70
<211> LENGTH: 8
<212> TYPE: PRT
<213> ORGANISM: Streptomyces fungicidicus

<400> SEQUENCE: 70

Asp Ala Tyr His Leu Gly Leu Leu
1               5

<210> SEQ ID NO 71
<211> LENGTH: 8
<212> TYPE: PRT
<213> ORGANISM: Streptomyces fungicidicus

<400> SEQUENCE: 71

Asp Ala Tyr His Leu Gly Leu Leu
1               5

<210> SEQ ID NO 72
<211> LENGTH: 8
<212> TYPE: PRT
<213> ORGANISM: Streptomyces fungicidicus

<400> SEQUENCE: 72

Asp Met Glu Ala Asp Gly Ala Val
1               5

<210> SEQ ID NO 73
<211> LENGTH: 8
<212> TYPE: PRT
<213> ORGANISM: Streptomyces fungicidicus

<400> SEQUENCE: 73

Asp Ala Glu Thr Asp Gly Ser Val
1               5

<210> SEQ ID NO 74
<211> LENGTH: 8
<212> TYPE: PRT
<213> ORGANISM: Streptomyces fungicidicus

<400> SEQUENCE: 74

Asp Ala Tyr His Leu Gly Met Leu
1               5

<210> SEQ ID NO 75
<211> LENGTH: 8
<212> TYPE: PRT
<213> ORGANISM: Streptomyces fungicidicus

<400> SEQUENCE: 75

Asp Val Trp Ser Val Ala Met Val
1               5
```

<210> SEQ ID NO 76
<211> LENGTH: 8
<212> TYPE: PRT
<213> ORGANISM: Streptomyces fungicidicus

<400> SEQUENCE: 76

Asp Ala Tyr His Leu Gly Leu Leu
1               5

<210> SEQ ID NO 77
<211> LENGTH: 8
<212> TYPE: PRT
<213> ORGANISM: Streptomyces fungicidicus

<400> SEQUENCE: 77

Asp Ile Leu Gln Leu Gly Leu Val
1               5

<210> SEQ ID NO 78
<211> LENGTH: 8
<212> TYPE: PRT
<213> ORGANISM: Streptomyces fungicidicus

<400> SEQUENCE: 78

Asp Ala Glu Thr Asp Gly Ser Val
1               5

<210> SEQ ID NO 79
<211> LENGTH: 8
<212> TYPE: PRT
<213> ORGANISM: Streptomyces fungicidicus

<400> SEQUENCE: 79

Asp Ile Phe Gln Leu Ala Leu Val
1               5

<210> SEQ ID NO 80
<211> LENGTH: 8
<212> TYPE: PRT
<213> ORGANISM: Streptomyces fungicidicus

<400> SEQUENCE: 80

Asp Ala Tyr His Leu Gly Leu Leu
1               5

<210> SEQ ID NO 81
<211> LENGTH: 8
<212> TYPE: PRT
<213> ORGANISM: Streptomyces fungicidicus

<400> SEQUENCE: 81

Asp Phe Trp Ser Val Gly Met Val
1               5

<210> SEQ ID NO 82
<211> LENGTH: 16
<212> TYPE: PRT
<213> ORGANISM: Streptomyces fungicidicus
<220> FEATURE:
<221> NAME/KEY: misc_feature
<222> LOCATION: (13)..(13)
<223> OTHER INFORMATION: Xaa can be Phenylananine or Leucine

<400> SEQUENCE: 82

Asp Asp Asp Phe Phe Ala Leu Gly Gly His Ser Leu Xaa Ala Thr Arg
1               5                   10                  15

```
<210> SEQ ID NO 83
<211> LENGTH: 16
<212> TYPE: PRT
<213> ORGANISM: Streptomyces fungicidicus

<400> SEQUENCE: 83

Asp Asp Asp Phe Phe Ala Leu Gly Gly His Ser Leu Pro Ala Thr Arg
1               5                   10                  15

<210> SEQ ID NO 84
<211> LENGTH: 16
<212> TYPE: PRT
<213> ORGANISM: Streptomyces fungicidicus

<400> SEQUENCE: 84

Asp Asp Asp Phe Phe Ala Leu Gly Gly His Ser Leu Leu Ala Thr Arg
1               5                   10                  15

<210> SEQ ID NO 85
<211> LENGTH: 16
<212> TYPE: PRT
<213> ORGANISM: Streptomyces fungicidicus
<220> FEATURE:
<221> NAME/KEY: misc_feature
<222> LOCATION: (1)..(1)
<223> OTHER INFORMATION: Xaa can be Aspartic acid or Glutamic acid
<220> FEATURE:
<221> NAME/KEY: misc_feature
<222> LOCATION: (3)..(3)
<223> OTHER INFORMATION: Xaa can be Aspartic acid or Histadine
<220> FEATURE:
<221> NAME/KEY: misc_feature
<222> LOCATION: (10)..(10)
<223> OTHER INFORMATION: Xaa can be Asparagine acid or Histadine
<220> FEATURE:
<221> NAME/KEY: misc_feature
<222> LOCATION: (13)..(13)
<223> OTHER INFORMATION: Xaa can be Leucine or Valine
<220> FEATURE:
<221> NAME/KEY: misc_feature
<222> LOCATION: (14)..(14)
<223> OTHER INFORMATION: Xaa can be Alanine or Valine
<220> FEATURE:
<221> NAME/KEY: misc_feature
<222> LOCATION: (15)..(15)
<223> OTHER INFORMATION: Xaa can be  Valine, Methionine or Threonine
<220> FEATURE:
<221> NAME/KEY: misc_feature
<222> LOCATION: (16)..(16)
<223> OTHER INFORMATION: Xaa can be Serine or Arginine

<400> SEQUENCE: 85

Xaa Asp Xaa Phe Phe Ala Leu Gly Gly Xaa Ser Leu Xaa Xaa Xaa Xaa
1               5                   10                  15

<210> SEQ ID NO 86
<211> LENGTH: 16
<212> TYPE: PRT
<213> ORGANISM: Streptomyces fungicidicus

<400> SEQUENCE: 86

Glu Asp Asp Phe Phe Ala Leu Gly Gly His Ser Leu Leu Ala Val Ser
1               5                   10                  15

<210> SEQ ID NO 87
<211> LENGTH: 16
<212> TYPE: PRT
<213> ORGANISM: Streptomyces fungicidicus

<400> SEQUENCE: 87
```

```
Asp Asp Asp Phe Phe Ala Leu Gly Gly His Ser Leu Leu Val Val Ser
1               5                   10                  15

<210> SEQ ID NO 88
<211> LENGTH: 16
<212> TYPE: PRT
<213> ORGANISM: Streptomyces fungicidicus

<400> SEQUENCE: 88

Asp Asp Asp Phe Phe Ala Leu Gly Gly His Ser Leu Leu Ala Val Ser
1               5                   10                  15

<210> SEQ ID NO 89
<211> LENGTH: 16
<212> TYPE: PRT
<213> ORGANISM: Streptomyces fungicidicus

<400> SEQUENCE: 89

Asp Asp Asp Phe Phe Leu Leu Gly Gly His Ser Leu Leu Ala Met Arg
1               5                   10                  15

<210> SEQ ID NO 90
<211> LENGTH: 16
<212> TYPE: PRT
<213> ORGANISM: Streptomyces fungicidicus

<400> SEQUENCE: 90

Glu Asp Asp Phe Phe Ala Leu Gly Gly His Ser Leu Leu Ala Val Ser
1               5                   10                  15

<210> SEQ ID NO 91
<211> LENGTH: 16
<212> TYPE: PRT
<213> ORGANISM: Streptomyces fungicidicus

<400> SEQUENCE: 91

Asp Asp Asp Phe Phe Ala Leu Gly Gly Asn Ser Leu Val Ala Thr Arg
1               5                   10                  15

<210> SEQ ID NO 92
<211> LENGTH: 16
<212> TYPE: PRT
<213> ORGANISM: Streptomyces fungicidicus

<400> SEQUENCE: 92

Asp Asp His Phe Phe Ala Leu Gly Gly His Ser Leu Leu Ala Thr Arg
1               5                   10                  15

<210> SEQ ID NO 93
<211> LENGTH: 16
<212> TYPE: PRT
<213> ORGANISM: Streptomyces fungicidicus
<220> FEATURE:
<221> NAME/KEY: misc_feature
<222> LOCATION: (1)..(1)
<223> OTHER INFORMATION: Xaa can be Aspartic acid or Glutamic acid
<220> FEATURE:
<221> NAME/KEY: misc_feature
<222> LOCATION: (6)..(6)
<223> OTHER INFORMATION: Xaa can be Alanine or Threonine
<220> FEATURE:
<221> NAME/KEY: misc_feature
<222> LOCATION: (7)..(7)
<223> OTHER INFORMATION: Xaa can be Leucine or Lysine
<220> FEATURE:
<221> NAME/KEY: misc_feature
<222> LOCATION: (14)..(14)
<223> OTHER INFORMATION: Xaa can be Alanine or Valine
```

```
<220> FEATURE:
<221> NAME/KEY: misc_feature
<222> LOCATION: (15)..(15)
<223> OTHER INFORMATION: Xaa can be Valine or Threonine
<220> FEATURE:
<221> NAME/KEY: misc_feature
<222> LOCATION: (16)..(16)
<223> OTHER INFORMATION: Xaa can be Serine, Arginine or Valine

<400> SEQUENCE: 93

Xaa Asp Asp Phe Phe Xaa Xaa Gly Gly His Ser Leu Leu Xaa Xaa Xaa
1               5                   10                  15

<210> SEQ ID NO 94
<211> LENGTH: 16
<212> TYPE: PRT
<213> ORGANISM: Streptomyces fungicidicus

<400> SEQUENCE: 94

Glu Asp Asp Phe Phe Ala Leu Gly Gly His Ser Leu Leu Ala Val Ser
1               5                   10                  15

<210> SEQ ID NO 95
<211> LENGTH: 16
<212> TYPE: PRT
<213> ORGANISM: Streptomyces fungicidicus

<400> SEQUENCE: 95

Asp Asp Asp Phe Phe Thr Leu Gly Gly His Ser Leu Leu Val Thr Arg
1               5                   10                  15

<210> SEQ ID NO 96
<211> LENGTH: 16
<212> TYPE: PRT
<213> ORGANISM: Streptomyces fungicidicus

<400> SEQUENCE: 96

Asp Asp Asp Phe Phe Ala Leu Gly Gly His Ser Leu Leu Ala Val Ser
1               5                   10                  15

<210> SEQ ID NO 97
<211> LENGTH: 16
<212> TYPE: PRT
<213> ORGANISM: Streptomyces fungicidicus

<400> SEQUENCE: 97

Asp Asp Asp Phe Phe Ala Lys Gly Gly His Ser Leu Leu Ala Thr Val
1               5                   10                  15

<210> SEQ ID NO 98
<211> LENGTH: 16
<212> TYPE: PRT
<213> ORGANISM: Streptomyces fungicidicus

<400> SEQUENCE: 98

Asp Asp Asp Phe Phe Ala Leu Gly Gly His Ser Leu Leu Ala Val Ser
1               5                   10                  15

<210> SEQ ID NO 99
<211> LENGTH: 16
<212> TYPE: PRT
<213> ORGANISM: Streptomyces fungicidicus

<400> SEQUENCE: 99

Asp Asp Asp Phe Phe Ala Leu Gly Gly His Ser Leu Leu Ala Thr Arg
1               5                   10                  15
```

```
<210> SEQ ID NO 100
<211> LENGTH: 16
<212> TYPE: PRT
<213> ORGANISM: Streptomyces fungicidicus

<400> SEQUENCE: 100

Asp Asp Asp Phe Phe Ala Leu Gly Gly His Ser Leu Leu Ala Val Ser
1               5                   10                  15

<210> SEQ ID NO 101
<211> LENGTH: 16
<212> TYPE: PRT
<213> ORGANISM: Streptomyces fungicidicus

<400> SEQUENCE: 101

Asp Asp Asp Phe Phe Ala Leu Gly Gly His Ser Leu Leu Ala Val Arg
1               5                   10                  15

<210> SEQ ID NO 102
<211> LENGTH: 16
<212> TYPE: PRT
<213> ORGANISM: Streptomyces fungicidicus

<400> SEQUENCE: 102

Ser Asp Ser Phe Trp Glu Leu Gly Gly Asn Ser Leu Leu Ala Val Arg
1               5                   10                  15

<210> SEQ ID NO 103
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 103
aaggagaaga gccttcagaa ggaa                                          24
```

ENDURACIDIN BIOSYNTHETIC GENE CLUSTER FROM *STREPTOMYCES FUNGICIDICUS*

CROSS REFERENCE TO RELATED APPLICATIONS

This is the U.S. National Stage of International Application No. PCT/US2007/08126, filed Oct. 1, 2007, which was published in English under PCT Article 21(2), which in turn claims the benefit of the earlier filing date of U.S. Provisional Application No. 60/827,666, filed on Sep. 29, 2006, and U.S. Provisional Application No. 60/959,461, filed on Jul. 13, 2007, which are all incorporated herein by reference.

STATEMENT OF GOVERNMENT SUPPORT

This invention was made with government support under grant number GM069320 from the National Institutes of Health. The United States Government has certain rights in the invention.

FIELD

This disclosure relates to antibiotic biosynthesis, in particular, to an enduracidin gene cluster, methods of its use, the proteins encoded thereby, enduracidin analogs, and methods of their production.

BACKGROUND

The global emergence of multidrug-resistant bacterial infections has resulted in enormous healthcare costs and has become a major threat to public health. In the U.S. alone, the total cost linked to antibiotic-resistant infections has been estimated at $5 billion annually (Zinner, *Expert Rev. Anti. Infect. Ther.* 3: 907-913, 2005). Since its launch in 1958, vancomycin was the drug of last resort for treating Gram-positive pathogens such as methicillin-resistant *Staphylococcus aureus* (MRSA) (Barrett, *J. Curr. Opin. Invest. Drugs* 6: 781-790, 2005). However, vancomycin-resistant *S. aureus* strains emerged and over 28% of enterococci responsible for intensive care unit infections in the U.S. are now vancomycin resistant (Tenover & McDonald *Curr. Opin. Infect. Dis.* 18: 300-305, 2005). In addition, resistance to the newest antibiotics to treat these infections, linezolid and daptomycin, has already been described (Mangili et al. *Clin. Infect. Dis.* 40: 1058-1060, 2005; Meka et al. *J. Infect. Dis.* 190: 311-317, 2004; and Tsiodras et al. *Lancet* 358: 207-208, 2001). To stay ahead of the development of antibacterial drug resistances, there is a pressing necessity to identify new antibiotics, especially those with novel mechanisms of action, and methods of producing such antibiotics.

SUMMARY

This disclosure describes the molecular cloning of the enduracidin biosynthetic gene cluster from *Streptomyces fungicidicus*, and the characterization of the individual genes in the gene cluster and the proteins encoded thereby. An enduracidin gene cluster included within a 116 kilobase genetic locus (nucleotide residues 31147-114619 of SEQ ID NO: 49) is disclosed and includes 25 open reading frames (ORFs) referred to as ORF 22 to 46 respectively (SEQ ID NOs: 22-46, respectively). An additional twenty-three ORFs were identified that flank the 5' (ORFs 1-21) and 3' (ORF 47-48) end of the enduracidin gene cluster, respectively. ORFs 36, 37, 38 and 40 are four genes (endA, endB, endC, and endD) which encode two-, seven-, eight- and one-module NRPSs, respectively (EndA, SEQ ID NO: 36; EndB, SEQ ID NO: 37; EndC, SEQ ID NO: 38; and EndD, SEQ ID NO: 40, respectively). Collectively, these four peptide synthetases (EndA, EndB, EndC, and EndD) function to assemble the 17-residue enduracidin peptide backbone.

In addition, this disclosure describes enduracidin analogs and their manufacture. In one embodiment, the analogs are produced by mutant *Streptomyces* organisms. For example, tetrahydroenduracidin A, tetrahydroenduracidin B, deschloroenduracidin A and deschloroenduracidin B are disclosed. Also discussed herein are methods for producing such analogs.

The foregoing and other features and advantages of the disclosure will become more apparent from the following detailed description, which proceeds with reference to the accompanying figures.

BRIEF DESCRIPTION OF THE DRAWINGS

FIG. 2C i includes Enduracidin A and B standards; FIG. 2C ii, methanolic extract of wild-type mycelia; FIG. 2C iii, co-injection of wild-type extract and standards; and FIG. 2C iv and v, methanolic extract of *S. fungicidicus* disruptant strains SfPS18D17 and SfPS18D29.

FIG. 8 is a schematic illustrating the organization of the transposon cassette used to achieve random mutagenesis in the enduracidin gene cluster, including the nucleic acid sequence for a sequencing primer binding site (SEQ ID NO: 103).

FIGS. 9A-9C illustrate restriction fragment analyses. FIG. 9A depicts preliminary screening to choose single Tn5AT insertion mutants from the pXYF24D series, lanes 1, 25 and 26 are molecular weight markers, line 2 is control fosmid pXYF24. FIG. 9B depicts confirmation screening for the pXYF305D and pXYF607D series, lanes 1 and 10 are molecular weight markers, lanes 2 and 11 are control fosmids pXYF305 and pXYF607, lanes 3 through 9 are pXYF305D series, lanes 12 through 21 are pXYF607D series. FIG. 9C depicts a plasmid pXYHaloD series.

FIG. 13A is an HPLC analysis comparing wild type S. fungicidicus extract (upper trace) with the extract from mutant Sf305D6 in which orf45 is disrupted (lower trace), the arrow on the left on the top trace points to the enduracidin A peak and the arrow on the right on the top trace points to enduracidin B; the arrow on the left on the bottom trace points to tetrahydroenduracidin A and the arrow on the right on the bottom trace points to tetrahydroenduracidin B. FIG. 13B is a MALDI-TOF mass spectrum of the peak corresponding to tetrahydroenduracidin A, the arrow shows the $[M+H]^+$ peak. FIG. 13C is a MALDI-TOF mass spectrum of the peak corresponding to tetrahydroenduracidin B; the arrow shows the $[M+H]^+$ peak.

FIG. 14A is a HPLC analysis of extract from mutant Sforf30infd3 in which orf30 had undergone in-frame deletion; the arrow on the left points to deschloroenduracidin A and the arrow on the right points to deschloroenduracidin B. FIG. 14B is an ESI mass spectrum of the peak corresponding to deschlorohydroenduracidin A, the horizontal arrow shows the $[M+3H]^{3+}$ peak, the vertical arrow shows the $[M+2H]^{2+}$ peak (also in inset). FIG. 14C is an ESI mass spectrum of the peak corresponding to deschloroenduracidin B; the horizontal arrow shows the $[M+3H]^{3+}$ peak, the vertical arrow shows the $[M+2H]^{2+}$ peak (also in inset).

SEQUENCE LISTING

Figure 1:
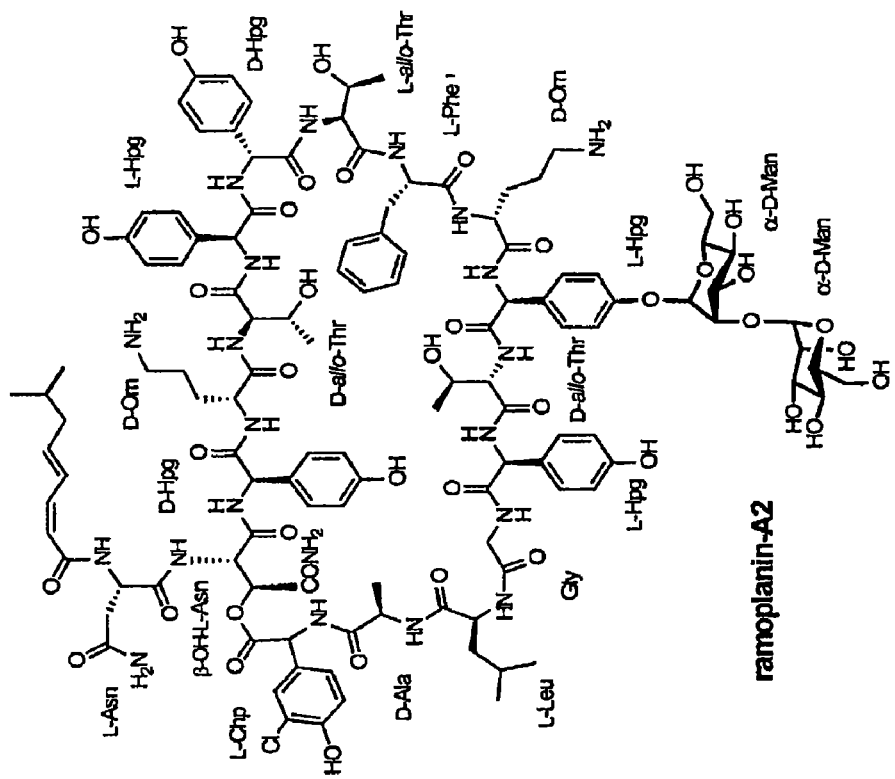
FIG. 1 shows the chemical structures of enduracidin A and ramoplanin A1.
Figure 1:
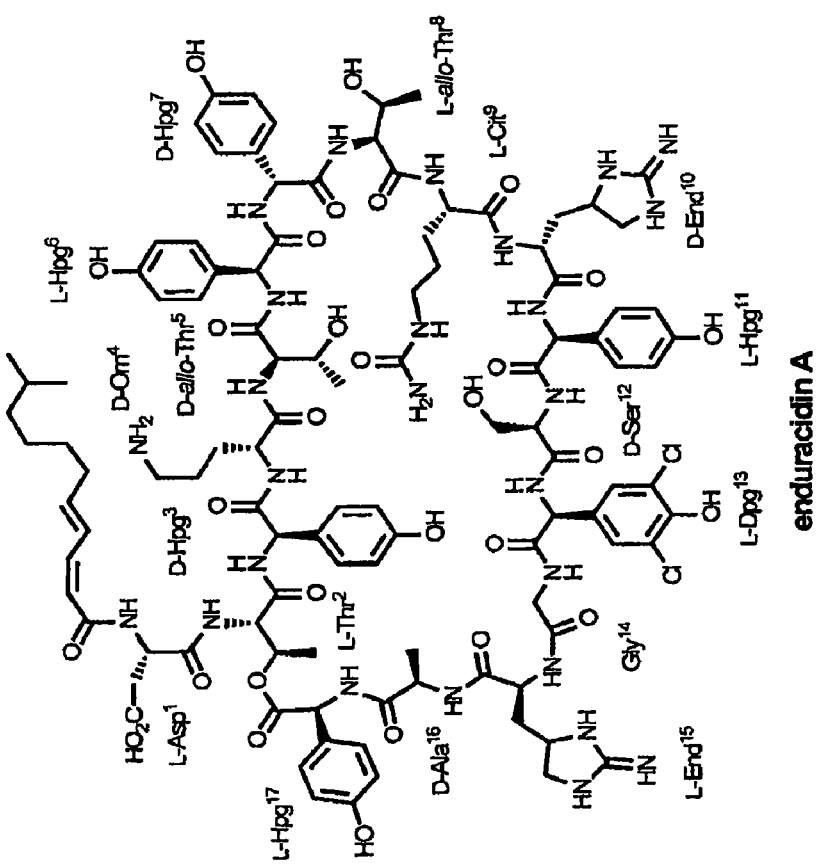

The nucleic and amino acid sequences listed in the accompanying sequence listing are shown using standard letter abbreviations for nucleotide bases, and three letter code for amino acids, as defined in 37 C.F.R. 1.822. Only one strand of the nucleic acid sequence is shown, but the complementary strand is understood as included by any reference to the displayed strand. In the accompanying sequence listing:

SEQ ID NO: 1 is the amino acid sequence encoded by ORF1, corresponding to nucleotides 1 to 1230 of SEQ ID NO: 49.

SEQ ID NO: 2 is the amino acid sequence encoded by ORF2, corresponding to nucleotides 1381 to 2877 of SEQ ID NO: 49.

SEQ ID NO: 3 is the amino acid sequence encoded by ORF3, corresponding to the reverse complement of nucleotides 2896 to 3297 of SEQ ID NO: 49.

SEQ ID NO: 4 is the amino acid sequence encoded by ORF4, corresponding to nucleotides 3461 to 4582 of SEQ ID NO: 49.

SEQ ID NO: 5 is the amino acid sequence encoded by ORF5, corresponding to the reverse complement of nucleotides 4606 to 5688 of SEQ ID NO: 49.

SEQ ID NO: 6 is the amino acid sequence encoded by ORF6, corresponding to nucleotides 6053 to 9925 of SEQ ID NO: 49.

SEQ ID NO: 7 is the amino acid sequence encoded by ORF7, corresponding to the reverse complement of nucleotides 10071 to 10988 of SEQ ID NO: 49.

SEQ ID NO: 8 is the amino acid sequence encoded by ORF8, corresponding to the reverse complement of nucleotides 11118 to 12566 of SEQ ID NO: 49.

SEQ ID NO: 9 is the amino acid sequence encoded by ORF9, corresponding to nucleotides 12610 to 14100 of SEQ ID NO: 49.

SEQ ID NO: 10 is the amino acid sequence encoded by ORF10, corresponding to the reverse complement of nucleotides 14174 to 16303 of SEQ ID NO: 49.

SEQ ID NO: 11 is the amino acid sequence encoded by ORF11, corresponding to nucleotides 16300 to 17517 of SEQ ID NO: 49.

SEQ ID NO: 12 is the amino acid sequence encoded by ORF12, corresponding to nucleotides 17697 to 18734 of SEQ ID NO: 49.

SEQ ID NO: 13 is the amino acid sequence encoded by ORF13, corresponding to the reverse complement of nucleotides 18731 to 21112 of SEQ ID NO: 49.

SEQ ID NO: 14 is the amino acid sequence encoded by ORF14, corresponding to nucleotides 21260 to 22582 of SEQ ID NO: 49.

SEQ ID NO: 15 is the amino acid sequence encoded by ORF15, corresponding to nucleotides 22760 to 23536 of SEQ ID NO: 49.

SEQ ID NO: 16 is the amino acid sequence encoded by ORF16, corresponding to nucleotides 23533 to 24363 of SEQ ID NO: 49.

SEQ ID NO: 17 is the amino acid sequence encoded by ORF17, corresponding to the reverse complement of nucleotides 24341 to 25633 of SEQ ID NO: 49.

SEQ ID NO: 18 is the amino acid sequence encoded by ORF18, corresponding to the reverse complement of nucleotides 25792 to 26454 of SEQ ID NO: 49.

SEQ ID NO: 19 is the amino acid sequence encoded by ORF19, corresponding to the reverse complement of nucleotides 26724 to 27398 of SEQ ID NO: 49.

SEQ ID NO: 20 is the amino acid sequence encoded by ORF20, corresponding to nucleotides 27544 to 28638 of SEQ ID NO: 49.

SEQ ID NO: 21 is the amino acid sequence encoded by ORF21, corresponding to nucleotides 28753 to 30746 of SEQ ID NO: 49.

SEQ ID NO: 22 is the amino acid sequence encoded by ORF22, corresponding to nucleotides 31147 to 32133 of SEQ ID NO: 49.

SEQ ID NO: 23 is the amino acid sequence encoded by ORF23, corresponding to the reverse complement of nucleotides 32266 to 33354 of SEQ ID NO: 49.

SEQ ID NO: 24 is the amino acid sequence encoded by ORF24, corresponding to nucleotides 33630 to 34565 of SEQ ID NO: 49.

SEQ ID NO: 25 is the amino acid sequence encoded by ORF25, corresponding to nucleotides 34644 to 35714 of SEQ ID NO: 49.

SEQ ID NO: 26 is the amino acid sequence encoded by ORF26, corresponding to the reverse complement of nucleotides 35792 to 36631 of SEQ ID NO: 49.

SEQ ID NO: 27 is the amino acid sequence encoded by ORF27, corresponding to the reverse complement of nucleotides 36628 to 37887 of SEQ ID NO: 49.

SEQ ID NO: 28 is the amino acid sequence encoded by ORF28, corresponding to the reverse complement of nucleotides 37887 to 38768 of SEQ ID NO: 49.

SEQ ID NO: 29 is the amino acid sequence encoded by ORF29, corresponding to nucleotides 39403 to 41829 of SEQ ID NO: 49.

SEQ ID NO: 30 is the amino acid sequence encoded by ORF30, corresponding to the reverse complement of nucleotides 41890 to 43404 of SEQ ID NO: 49.

SEQ ID NO: 31 is the amino acid sequence encoded by ORF31, corresponding to the reverse complement of nucleotides 43 to 27398 of SEQ ID NO: 49.

SEQ ID NO: 32 is the amino acid sequence encoded by ORF32, corresponding to the reverse complement of nucleotides 44601 to 45524 of SEQ ID NO: 49.

SEQ ID NO: 33 is the amino acid sequence encoded by ORF33, corresponding to the reverse complement of nucleotides 45559 to 47514 of SEQ ID NO: 49.

SEQ ID NO: 34 is the amino acid sequence encoded by ORF34, corresponding to the reverse complement of nucleotides 47597 to 48424 of SEQ ID NO: 49.

SEQ ID NO: 35 is the amino acid sequence encoded by ORF35, corresponding to nucleotides 48747 to 49019 of SEQ ID NO: 49.

SEQ ID NO: 36 is the amino acid sequence encoded by ORF36, corresponding to nucleotides 49041 to 55346 of SEQ ID NO: 49.

SEQ ID NO: 37 is the amino acid sequence encoded by ORF37, corresponding to nucleotides 55363 to 76194 of SEQ ID NO: 49.

SEQ ID NO: 38 is the amino acid sequence encoded by ORF38, corresponding to nucleotides 76191 to 103151 of SEQ ID NO: 49.

SEQ ID NO: 39 is the amino acid sequence encoded by ORF39, corresponding to nucleotides 103160 to 103984 of SEQ ID NO: 49.

SEQ ID NO: 40 is the amino acid sequence encoded by ORF40, corresponding to nucleotides 104002 to 106581 of SEQ ID NO: 49.

SEQ ID NO: 41 is the amino acid sequence encoded by ORF41, corresponding to the reverse complement of nucleotides 106606 to 107277 of SEQ ID NO: 49.

SEQ ID NO: 42 is the amino acid sequence encoded by ORF42, corresponding to the reverse complement of nucleotides 107274 to 108386 of SEQ ID NO: 49.

SEQ ID NO: 43 is the amino acid sequence encoded by ORF43, corresponding to the reverse complement of nucleotides 108538 to 109083 of SEQ ID NO: 49.

SEQ ID NO: 44 is the amino acid sequence encoded by ORF44, corresponding to the reverse complement of nucleotides 109184 to 111058 of SEQ ID NO: 49.

SEQ ID NO: 45 is the amino acid sequence encoded by ORF45, corresponding to the reverse complement of nucleotides 110866 to 114399 of SEQ ID NO: 49.

SEQ ID NO: 46 is the amino acid sequence encoded by ORF46, corresponding to the reverse complement of nucleotides 114404 to 114619 of SEQ ID NO: 49.

SEQ ID NO: 47 is the amino acid sequence encoded by ORF47, corresponding to the reverse complement of nucleotides 114877 to 115614 of SEQ ID NO: 49.

SEQ ID NO: 48 is the amino acid sequence encoded by ORF48, corresponding to the reverse complement of nucleotides 115590 to 114619 of SEQ ID NO: 49.

SEQ ID NO: 49 is the nucleic acid sequence of a 116 kb genetic locus including an enduracidin gene cluster.

SEQ ID NOs: 50 and 51 degenerate oligonucleotide primers used to amplify internal fragments of NRPS genes corresponding to the region between conserved A3 and T.

SEQ ID NOs: 52 and 53 degenerate oligonucleotide primers used to generate a prephenate dehydrogenase gene fragment.

SEQ ID NOs: 54 and 55 oligonucleotide primers used to introduce BamHI/HindIII restriction sites into a plasmid.

SEQ ID NOs: 56, 57, 58 and 59 oligonucleotide primers used to introduce BglII sites into a plasmid.

SEQ ID NOs: 60 and 61 oligonucleotide primers used to generate orf30Δ1.

SEQ ID NOs: 62 and 63 oligonucleotide primers used to generate orf30Δ2.

SEQ ID NO: 64 degenerate amino acid sequence for an NRPS adenylation domain in an EndA module of an enduracidin gene cluster.

SEQ ID NO: 65 amino acid sequence for an NRPS adenylation domain in an EndA-module 1 in an enduracidin gene cluster.

SEQ ID NO: 66 amino acid sequence for an NRPS adenylation domain in an EndA-module 2 in an enduracidin gene cluster.

SEQ ID NO: 67 amino acid sequence for an NRPS adenylation domain in an EndB-module 1 in an enduracidin gene cluster.

SEQ ID NO: 68 amino acid sequence for an NRPS adenylation domain in an EndB-module 2 in an enduracidin gene cluster.

SEQ ID NO: 69 amino acid sequence for an NRPS adenylation domain in an EndB-module 3 in an enduracidin gene cluster.

SEQ ID NO: 70 amino acid sequence for an NRPS adenylation domain in an EndB-module 4 in an enduracidin gene cluster.

SEQ ID NO: 71 amino acid sequence for an NRPS adenylation domain in an EndB-module 5 in an enduracidin gene cluster.

SEQ ID NO: 72 amino acid sequence for an NRPS adenylation domain in an EndB-module 7 in an enduracidin gene cluster.

SEQ ID NO: 73 amino acid sequence for an NRPS adenylation domain in an EndC-module 1 in an enduracidin gene cluster.

SEQ ID NO: 74 amino acid sequence for an NRPS adenylation domain in an EndC-module 2 in an enduracidin gene cluster.

SEQ ID NO: 75 amino acid sequence for an NRPS adenylation domain in an EndC-module 3 in an enduracidin gene cluster.

SEQ ID NO: 76 amino acid sequence for an NRPS adenylation domain in an EndC-module 4 in an enduracidin gene cluster.

SEQ ID NO: 77 amino acid sequence for an NRPS adenylation domain in an EndC-module 5 in an enduracidin gene cluster.

SEQ ID NO: 78 amino acid sequence for an NRPS adenylation domain in an EndC-module 6 in an enduracidin gene cluster.

SEQ ID NO: 79 amino acid sequence for an NRPS adenylation domain in an EndC-module 7 in an enduracidin gene cluster.

SEQ ID NO: 80 amino acid sequence for an NRPS adenylation domain in an EndC-module 8 in an enduracidin gene cluster.

SEQ ID NO: 81 amino acid sequence for an NRPS adenylation domain in an EndD module of an enduracidin gene cluster.

SEQ ID NO: 82 degenerate amino acid sequence for a peptidyl carrier domain in an EndA module of an enduracidin gene cluster.

SEQ ID NO: 83 amino acid sequence for a peptidyl carrier domain in an EndA-module 1 in an enduracidin gene cluster.

SEQ ID NO: 84 amino acid sequence for a peptidyl carrier domain in an EndA-module 2 in an enduracidin gene cluster.

SEQ ID NO: 85 degenerate amino acid sequence for a peptidyl carrier domain in an EndB module of an enduracidin gene cluster.

SEQ ID NO: 86 amino acid sequence for a peptidyl carrier domain in an EndB-module 1 in an enduracidin gene cluster.

SEQ ID NO: 87 amino acid sequence for a peptidyl carrier domain in an EndB-module 2 in an enduracidin gene cluster.

SEQ ID NO: 88 amino acid sequence for a peptidyl carrier domain in an EndB-module 3 in an enduracidin gene cluster.

SEQ ID NO: 89 amino acid sequence for a peptidyl carrier domain in an EndB-module 4 in an enduracidin gene cluster.

SEQ ID NO: 90 amino acid sequence for a peptidyl carrier domain in an EndB-module 5 in an enduracidin gene cluster.

SEQ ID NO: 91 amino acid sequence for a peptidyl carrier domain in an EndB-module 6 in an enduracidin gene cluster.

SEQ ID NO: 92 amino acid sequence for a peptidyl carrier domain in an EndB-module 7 in an enduracidin gene cluster.

SEQ ID NO: 93 degenerate amino acid sequence for a peptidyl carrier domain in an EndC module of an enduracidin gene cluster.

SEQ ID NO: 94 amino acid sequence for a peptidyl carrier domain in an EndC-module 1 in an enduracidin gene cluster.

SEQ ID NO: 95 amino acid sequence for a peptidyl carrier domain in an EndC-module 2 in an enduracidin gene cluster.

SEQ ID NO: 96 amino acid sequence for a peptidyl carrier domain in an EndC-module 3 in an enduracidin gene cluster.

SEQ ID NO: 97 amino acid sequence for a peptidyl carrier domain in an EndC-module 4 in an enduracidin gene cluster.

SEQ ID NO: 98 amino acid sequence for a peptidyl carrier domain in an EndC-module 5 in an enduracidin gene cluster.

SEQ ID NO: 99 amino acid sequence for a peptidyl carrier domain in an EndC-module 6 in an enduracidin gene cluster.

SEQ ID NO: 100 amino acid sequence for a peptidyl carrier domain in an EndC-module 7 in an enduracidin gene cluster.

SEQ ID NO: 101 amino acid sequence for a peptidyl carrier domain in an EndC-module 8 in an enduracidin gene cluster.

SEQ ID NO: 102 amino acid sequence for a peptidyl carrier domain in an EndD module of an enduracidin gene cluster.

SEQ ID NO: 103 is the nucleic acid sequence of a sequencing primer binding site primer.

DETAILED DESCRIPTION

I. Introduction

Enduracidin is a 17 amino acid lipodepsipeptide produced by the soil bacterium *Streptomyces fungicidicus* ATCC 21013 (FIG. 1). The peptide is isolated from the fermentation broth and mycelia (e.g., the cultured bacteria) as a mixture of enduracidins A and B, which differ in the length of the attached lipid chain (Hori et al. *Chem. Pharm. Bull.* 21: 1175-1183, 1973; Iwasaki et al. *Pro. Natl Acad. Sci. U.S.A.* 101: 14925-14930, 1973). A relative of enduracidin, ramoplanin (FIG. 1), is currently in Phase III clinical trials for the oral treatment of intestinal vancomycin-resistant *Enterococcus faecium* (VRE) and in phase II trials for nasal methicillin-resistant *S. aureus* (MRSA) (Fang et al. *Mol. BioSyst.* 96-76, 2006; Walker et al. *Chem. Rev.* 105: 449-476, 2005).

At present, there is no known form of developed or acquired resistance to ramoplanin or enduracidin. Enduracidin is active towards a wide variety of Gram-positive bacteria, including VRE and MRSA (Goto et al. *J. Antibiot.* 21: 119-125, 1968; Kawakami et al. *J. Antibiot.* 24: 583-586, 1971; Komatsuzawa et al. *J. Antimicrob. Chemother.* 33: 1155-1163, 1994; Peromet et al. *Chemother.* 19: 53-61, 1973; Tsuchiya et al. *J. Antibiot.* 21: 147-153, 1968; and Yourassowsky & Monsieur *Chemother.* 5: 1278-1281, 1972). These peptides disrupt bacterial cell wall biosynthesis but have a mechanism of action that is distinct from the β-lactams and vancomycin. Enduracidin and ramoplanin block the elongation step of peptidoglycan biosynthesis by binding to the transglycosylase substrate Lipid II (Cudic et al. *Proc. Natl. Acad. Sci. U.S.A.* 99: 7384-7389, 2002; and Fang et al. *Mol. BioSyst.* 69-76, 2006). This substrate-binding mechanism is analogous to the vancomycin mode of action but these different peptide antibiotics recognize distinct regions of Lipid II. The promising activity and unique mode of action of enduracidin, coupled with novel structural features and intriguing questions in the biosynthesis, make this peptide an attractive target for further antibiotic development studies.

This disclosure describes the molecular cloning of the enduracidin biosynthetic gene cluster from *S. fungicidicus* ATCC 21013, the characterization of the individual genes in the gene cluster, the proteins encoded thereby, and modification of the gene cluster to produce enduracidin analogs. The chromosome of the native enduracidin producer, *Streptomyces fungicidicus*, or suitable surrogate bacterial host cells harboring the enduracidin gene cluster, can be modified through deletion, replacement or disruption of segments of the host chromosome to result in biosynthetic precursors to, or novel analogs of, the enduracidin antibiotics. Alternatively, specific genes in the end cluster can be deleted or disrupted to alter the processing or synthesis of certain precursor compounds such that alternative species are utilized leading to the biosynthesis of novel enduracidins. Additionally, specific genes in the end cluster can be deleted or disrupted to create a deficiency in precursor compounds that results in the elimination or reduction of enduracidin biosynthesis. The genetic lesion can be complemented by the expression of similar genes from other antibiotic producing organisms, or by the exogenous addition of the missing compound, or an analog thereof, to restore antibiotic formation or generate novel enduracidins.

The enduracidin gene cluster was isolated using a strategy based on its predicted nonribosomal peptide synthetase (NRPS) assembly. The enduracidin biosynthetic gene cluster is 84 kb embedded in a 116 kb contiguous segment of the *S. fungicidicus* ATCC 21013 chromosome, and includes twenty-five open reading frames (ORF). Targeted disruption of NRPS genes (SEQ ID NOs: 36, 37, 38 or 40) in the cluster abolished enduracidin production and confirmed function. The cluster includes four genes, endA-D, encoding two, seven, eight and one-module NRPSs, respectively, and includes unique modules for the incorporation of citrulline and enduracididine. The NRPS organization generally follows the colinearity principle, and starts with a condensation domain (C domain) similar to those found in other lipopeptide systems for the coupling of an acyl group to the starting amino acid. The sixth module of EndB, corresponding to Thr[8], is missing an adenylation domain (A domain) as compared to other NRPS and this module is suggested to be loaded in trans by the single module protein EndD. One of the most striking features of the NRPS organization is the lack of epimerization domains (E domains) in light of the fact that the product has seven D amino acid residues. Sequence analysis reveals C domains following modules corresponding to D amino acids belong to a unique subset of C domains able to catalyze both epimerization and condensation reactions. Other genes directing lipid modification and activation, and formation of the nonproteinogenic amino acids 4-hydroxyphenylglycine and enduracididine are readily identified, as are genes likely involved in regulation of antibiotic biosynthesis and export.

To produce a library of *S. fungicidicus* mutants, an in vitro transposon-based method was devised to randomly insert a selectable marker and oriT element in the fosmid inserts carrying segments of a biosynthetic gene cluster and adjacent regions. This technique can produce millions of random disruption constructs for a given fosmid or plasmid template in a single transposase catalyzed reaction in vitro. This library of mutagenized fosmids was screened by restriction analysis, in conjunction with DNA sequencing using a primer corresponding to a site in the inserted cassette, to find specific disrupted genes. This collection of mutagenized fosmids was then introduced to the parent wild-type *Streptomyces* sp., or other suitable host cells carrying the biosynthetic gene cluster, to create a cluster-wide disruption library. Advantageous mutations were identified leading to organisms that biosynthesize different enduracidin analogs. Exemplary enduracidin analogs that may be synthesized by this method include, without limitation, tetrahydrorenduracidin A, tetrahydroenduracidin B, deschloroenduracidin A, and deschloroenduracidin B.

II. Abbreviations and Terms a. Abbreviations
Am: apramycin
CFU colony forming units
Cit: L-citrulline
Dpg: 3,5-dichloro-L-4-hydroxyphenylglycine
End: D- and L-enduracididine
Hpg: D- and L-4-hydroxyphenylglycine
MRSA: methicillin-resistant *Staphylococcus aureus*
NRPS: non-ribosomal peptide synthetase
ORF: open reading frame
Orn: D-ornithine
PCP: peptidyl carrier protein
PDH: prephenate dehydrogenase
SNP: single nucleotide polymorphism
VRE: vancomycin-resistant Enterococci b. Terms Unless otherwise noted, technical terms are used according to conventional usage. Definitions of common terms in molecular biology may be found in Benjamin Lewin *Genes V* published by Oxford University Press, 1994 (ISBN 0-19-854287-9); Kendrew et al. (eds.) *The Encyclopedia of Molecular Biology*, published by Blackwell Science Ltd., 1994 (ISBN 0-632-02182-9); and Robert A. Meyers (ed.) *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Allelic variant: An alternate form of a polypeptide that is characterized as having a substitution, deletion, or addition of one or more amino acids. In one example, the variant does not alter the biological function of the polypeptide.

Amplification: When used in reference to nucleic acids, techniques that increase the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744, 311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, and/or a change in ionization. Structural analogs are often found using quantitative structure activity relationships (QSAR), with techniques such as those disclosed in Remington (*The Science and Practice of Pharmacology*, 19th Edition (1995), chapter 28). When the changes to the original compound are substantial, or many incremental changes are combined, the compound is no longer an analog. For example, ramoplanin is not considered herein to be an analog of enduracidin: ramoplanin does not have either enduracididine amino acid, includes different amino acids, and though it has a lipid side chain, the chain length is substantially shorter. Analogs of enduracidin may be prepared by addition or deletion of functional groups on the amino acids that constitute the lipodepsipeptides, by substitution of one amino acid for another (excepting the enduracididine amino acids) or a combination of functional group modification and amino acid substitution. Exemplary enduracidin analogs include tetrahydrorenduracidin A, tetrahydroenduracidin B, deschloroenduracidin A, and deschloroenduracidin B.

A derivative is a biologically active molecule derived from the base structure. A mimetic is a molecule that mimics the activity of another molecule by mimicking the structure of such a molecule, such as a biologically active molecule. Thus, the term "mimetic" indicates a definite structure related to activity.

Antibiotic: A substance, for example enduracidin, penicillin or streptomycin, often produced by or derived from certain fungi, bacteria, and other organisms, that can destroy or inhibit the growth of other microorganisms.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T). Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits transcription of the target mRNA.

Binding or stable binding: A molecule, such as an oligonucleotide or protein, binds or stably binds to a target molecule, such as a target nucleic acid or protein, if binding is detectable. In one example, an oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one of ordinary skill in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and the target disassociate from each other, or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

The binding between a protein and its target protein, such as an antibody for an antigen is frequently characterized by determining the binding affinity. In one embodiment, affinity is calculated by a modification of the Scatchard method described by Frankel et al., *Mol. Immunol*, 16:101-106, 1979. In another embodiment, binding affinity is measured by a specific binding agent receptor dissociation rate. In yet another embodiment, a high binding affinity is measured by a competition radioimmunoassay. In several examples, a high binding affinity is at least about 1×10-8 M. In other embodiments, a high binding affinity is at least about 1.5×10-8, at least about 2.0×10-8, at least about 2.5×10-8, at least about 3.0×10-8, at least about 3.5×10-8, at least about 4.0×10-8, at least about 4.5×10-8, or at least about 5.0×10-8 M.

Biological function: The function(s) of a polypeptide in the cells in which it naturally occurs. A polypeptide can have more than one biological function.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Conservative substitution: Amino acid substitutions that do not substantially alter the activity (specificity or binding affinity) of the molecule. Typically conservative amino acid substitutions involve substitutions of one amino acid for another amino acid with similar chemical properties (e.g., charge or hydrophobicity). The following table shows exemplar conservative amino acid substitutions:

| Original Residue | Conservative Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

DNA (deoxyribonucleic acid): A long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Domain: A portion of a molecule such as proteins or nucleic acids that is structurally and/or functionally distinct from another portion of the molecule.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Enduracidin: Enduracidins A and B are 17 amino acid lipodepsipeptides discovered in the late 1960s from fermentations of the soil bacterium *Streptomyces fungicidicus*

B-5477 (ATCC 21013). The A and B peptides are homologs that differ by one carbon in the length of the attached lipid chain. Structurally, the enduracidins are distinguished by $C_{12}$ or $C_{13}$ 2Z,4E branched fatty acid moiety and the presence of numerous nonproteinogenic amino acid residues such as enduracididine (End), 4-hydroxyphenylglycine (Hpg), 3,5-dichloro-4-hydroxyphenylglycine (Dpg), citrulline (Cit) and ornithine (Orn). Seven of the 17 amino acids have the D configuration and six of the residues are Hpg or the chlorinated analog Dpg. Analogs of enduracidin may be prepared by addition or deletion of functional groups on the amino acids that constitute the lipodepsipeptides, by substitution of one amino acid for another (excepting the enduracididine amino acids) or a combination of functional group modification and amino acid substitution. Exemplary enduracidin analogs include tetrahydrorenduracidin A, tetrahydroenduracidin B, deschloroenduracidin A, and deschloroenduracidin B.

Enduracidin (for simplicity, the peptides A and B will be referred to singularly) exhibits potent in vitro and in vivo antibacterial activity against a wide spectrum of primarily Gram-positive organisms, including MRSA. Minimal inhibitory concentrations (MICs) are as low as 0.05 μg/mL and the effect is bactericidal. A study with 100 strains of S. aureus collected from various pathological products, and including 40% MRSA, found MICs ranging from 0.09 to 0.56 μg/mL with no strain able to survive exposure to 1 μg/mL. For comparison, typical MICs for vancomycin toward sensitive strains of S. aureus range from 0.5 to 2 μg/mL. Enduracidin has been shown to be effective in humans for treating urinary tract and skin infections caused by MRSA, but not chronic bone infections. No toxicity or side effects were reported.

Functional fragments and variants of a polypeptide: Included are those fragments and variants that maintain one or more functions of the parent polypeptide. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential function(s) of a protein. See Stryer Biochemistry 3rd Ed., (c) 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. J. Immunol. 159(5): 2502-12, 1997). Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by those well skilled in the art. A variety of methods for labeling polypeptides, and labels useful for such purposes, are well known in the art, and include radioactive isotopes such as $^{32}P$, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, 200, or even more amino acid residues.

Gene Cluster: A set of genetic elements grouped together on the chromosome, the protein products of which have a related function, such as forming a natural product biosynthetic pathway. For example, the enduracidin biosynthetic pathway from Streptomyces fungicidicus can be formed by the gene cluster including SEQ ID NOs: 22 to 46.

Halogenases and halogenase activity: A class of halogenating enzymes responsible for chlorination of amino acid side chains, such as aryl side chains of amino acids for the biosynthesis of nonribosomal peptides. An exemplary isolated protein with halogenase activity (the ability to chlorinate amino acid side chains) is an amino acid sequence at least 80% identical in amino acid sequence to SEQ ID NO: 30.

Heterologous: As it relates to nucleic acid sequences such as coding sequences and control sequences, "heterologous" denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different than the native gene). Similarly, a host cell transformed with a construct which is not normally present in the host cell would be considered heterologous for purposes of this disclosure.

Homologous amino acid sequence: Any polypeptide which is encoded, in whole or in part, by a nucleic acid sequence that hybridizes to any portion of the coding region nucleic acid sequences. A homologous amino acid sequence is one that differs from an amino acid sequence shown in the sequence listing by one or more conservative amino acid substitutions. Such a sequence also encompasses allelic variants (defined above) as well as sequences containing deletions or insertions which retain the functional characteristics of the polypeptide. Preferably, such a sequence is at least 75%, more preferably 80%, more preferably 85%, more preferably 90%, more preferably 95%, and most preferably 98% identical to any one of the amino acid sequences.

Homologous amino acid sequences include sequences that are identical or substantially identical to the amino acid sequences of the sequence listing. By "amino acid sequence substantially identical" it is meant a sequence that is at least 90%, preferably 95%, more preferably 97%, and most preferably 99% identical to an amino acid sequence of reference and that preferably differs from the sequence of reference by a majority of conservative amino acid substitutions. Consistent with this aspect of the invention, polypeptides having a sequence homologous to any one of the amino acid sequences of the sequence listing include naturally-occurring allelic variants, as well as mutants or any other non-naturally occurring variants that retain the inherent characteristics of any polypeptide of the sequence listing. Homology can be measured using sequence analysis software such as Sequence Analysis Software Package of the Genetics Computer Group, University of Wisconsin Biotechnology Center, 1710 University Avenue, Madison, Wis. 53705. Amino acid sequences can be aligned to maximize identity. Gaps can also be artificially introduced into the sequence to attain optimal alignment. Once the optimal alignment has been set up, the degree of homology is established by recording all of the positions in which the amino acids of both sequences are identical, relative to the total number of positions. Homologous polynucleotide sequences are defined in a similar way. Preferably, a homologous sequence is one that is at least 45%, 50%, 60%, 70%, 75%, 80%, 85%, 86%, 87%, 88%, 89%, 90%, 91%, 92%, 93%, 94%, 95%, 96%, 97%, 98%, 99% or identical to any one of the coding sequences.

Hybridization: Oligonucleotides and other nucleic acids hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between two distinct nucleic acid sequences or two distinct regions of the same nucleic acid sequence.

Specifically hybridizable and specifically complementary are terms that indicate a sufficient degree of complementarity such that stable and specific binding occurs between a first nucleic acid (such as, an oligonucleotide) and a DNA or RNA target. The first nucleic acid (such as, an oligonucleotide) need not be 100% complementary to its target sequence to be specifically hybridizable. A first nucleic acid (such as, an oligonucleotide) is specifically hybridizable when there is a sufficient degree of complementarity to avoid non-specific binding of the first nucleic acid (such as, an oligonucleotide) to non-target sequences under conditions where specific binding is desired. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though wash times also influence stringency. Calculations regarding hybridization conditions required for attaining particular degrees of stringency are discussed by Sambrook et al. (ed.) *Molecular Cloning: A Laboratory Manual,* 2nd ed., vol. 1-3, Cold Spring Harbor Laboratory Press, Cold Spring Harbor, N.Y., 1989, chapters 9 and 11.

The following are exemplary sets of hybridization conditions and are not meant to be limiting.

| Very High Stringency (detects sequences that share 90% sequence identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |
| High Stringency (detects sequences that share 80% sequence identity or greater) | |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |
| Low Stringency (detects sequences that share greater than 50% sequence identity) | |
| Hybridization: | 6x SSC at RT to 55° C. for 16-20 hours |
| Wash at least twice: | 2x-3x SSC at RT to 55° C. for 20-30 minutes each |

Isolated: An isolated biological component (such as a nucleic acid molecule or protein) is one that has been substantially separated or purified away from other biological components in the cell of the organism in which the component naturally occurs, such as other chromosomal and extrachromosomal DNA and RNA, proteins and organelles. With respect to nucleic acids and/or polypeptides, the term can refer to nucleic acids or polypeptides that are no longer flanked by the sequences typically flanking them in nature. Nucleic acids and proteins that have been isolated include nucleic acids and proteins purified by standard purification methods. The term also embraces nucleic acids and proteins prepared by recombinant expression in a host cell as well as chemically synthesized nucleic acids.

Nonribosomal peptide (NRP): A class of secondary metabolites, usually produced by microorganisms, such as bacteria and fungi. Unlike polypeptides synthesized on the ribosome, these peptides are synthesized by nonribosomal peptide synthetases (NRPS) from amino acids.

Nonribosomal peptide backbone assembly: The second step in nonribosomal peptide biosynthesis, which includes amide bond formation (condensation) of the peptide sequence.

Nonribosomal peptide synthetase (NRPS): A large multifunctional protein that synthesizes polypeptides by a nonribosomal mechanism, often known as thiotemplate synthesis (Kleinkauf and von Doehren *Ann. Rev. Microbiol.* 41: 259-289, 1987). Such nonribosomal polypeptides can have a linear, cyclic, or branched cyclic structure and often contain amino acids not present in proteins or amino acids modified through methylation or epimerization. In particular examples, NRPS produce dipeptides. Example NRPSs are SEQ ID NOs: 36, 37, 38 and 40.

NRPSs are typically organized into modules. A "module" is a set of distinctive domains that encode all the enzyme activities necessary for one cycle of peptide chain elongation and associated modifications. The number and order of modules and the type of domains within a module on each NRPS protein determine the structural variations of the resulting peptide products by dictating the number, order, choice of the amino acid to be incorporated, and the modifications associated with a particular cycle of elongation. The modular architecture of NRPS (Cane et al. *Science* 282: 63-68, 1998, Stachelhaus et al. *Science* 269: 69-72, 1995; Stachelhaus et al. *Mol. Gen. Genet.* 257: 308-318, 1998; and Belshaw et al. *Science* 284:486-489, 1999) has been successfully used in combinatorial biosynthesis of diverse natural product analogs. In some examples, a NRPS includes one or modifying domains, including, for example, domains able to catalyse epimerization and/or condensation reactions.

Nonribosomal peptide tailoring: The third step in nonribosomal peptide biosynthesis. There are numerous novel precursor amino acids found in nonribosomal peptides and many of these building blocks are formed or modified while attached to PCP domains of specialized proteins or the NRPS. This post-synthetic modification can occur after amide bond formation of the peptide backbone. Exemplary modifications include α-carbon epimerization, N-methylation, heterocyclization of Cys or Ser/Thr residues to thiazolines and oxazolines, and side chain halogenation or hydroxylation. Other modifications such as oxidation, alkylation, acylation and glycosylation can occur after release of the nascent peptide from the NRPS complex and are often necessary for full biological activity.

Nonribosomal precursor amino acid biosynthesis: The first step in nonribosomal peptide biosynthesis. Nonribosomal peptides often possess amino acids not found in peptides and proteins that are assembled on ribosomes. These nonproteinogenic amino acids contribute to the diversity of these peptides and often have roles in their biological activity. Biosynthesis of these amino acids can occur via protein-bound intermediates or as free, soluble species.

Nucleic Acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Nucleotide: This term includes, but is not limited to, a monomer that includes a base linked to a sugar, such as a pyrimidine, purine or synthetic analogs thereof, or a base linked to an amino acid, as in a peptide nucleic acid. A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15, or 20 bases.

Open reading frame (ORF): A series of nucleotide triplets (codons) coding for amino acids without any internal termination codons. These sequences are usually translatable into a peptide. For example, ORF, open reading frame, and enduracidin ORF refer to an open reading frame in the enduracidin biosynthetic gene cluster as isolated from *Streptomyces fungicidicus*. The term also embraces the same ORFs as present in other enduracidin-synthesizing organisms. The term encompasses allelic variants and single nucleotide polymorphisms (SNPs). In certain instances the term enduracidin ORF is used synonymously with the polypeptide encoded by the enduracidin ORF and may include conservative substitutions in that polypeptide. The particular usage will be clear from context.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ortholog: Two nucleic acid or amino acid sequences are orthologs of each other if they share a common ancestral sequence and diverged when a species carrying that ancestral sequence split into two species. Orthologous sequences are also homologous sequences.

Peptide condensation reaction: Refers to the formation of an amide bond between a polypeptide, peptide or amino acid and an amino acid, such as occurs during the formation of polypeptides catalyzed by nonribosomal peptide synthetase (NRPS). A protein that carious out NRPS has this activity, such as proteins with sequence similarity to SEQ ID NO: 36, SEQ ID NO: 37, SEQ ID NO: 38 or SEQ ID NO: 40.

Polypeptide: A polymer in which the monomers are amino acid residues which are joined together through amide bonds. When the amino acids are alpha-amino acids, either the L-optical isomer or the D-optical isomer can be used, the L-isomers being preferred in some instances. The term polypeptide or protein as used herein encompasses any amino acid sequence and includes modified sequences such as glycoproteins. The term polypeptide is specifically intended to cover naturally occurring proteins (whether produced by ribosomal or nonribosomal mechanisms), as well as those that are recombinantly or synthetically produced.

The term polypeptide fragment refers to a portion of a polypeptide that exhibits at least one useful epitope. The phrase functional fragment of a polypeptide refers to all fragments of a polypeptide that retain an activity (such as a biological activity), or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell.

The term substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Probes and primers: Nucleic acid probes and primers can be readily prepared based on the nucleic acid molecules provided in this disclosure. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides, 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (*In Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 17, 20, 23, 25, 30, 35, 40, 45, 50 or more consecutive nucleotides of desired nucleotide sequence.

Protein: A biological molecule expressed by a gene and comprised of amino acids.

Purified: The term purified does not require absolute purity; rather, it is intended as a relative term. Thus, for example, a purified protein preparation is one in which the protein referred to is more pure than the protein in its natural environment within a cell.

Ramoplanin: A peptide related to enduracidin that has been structurally characterized; it was characterized in 1984 from an *Actinoplanes* sp. Ramoplanin includes 17 amino acids, including seven in the D configuration at the same positions as in enduracidin (See FIG. 1). The greatest differences in the peptides are the shorter $C_8$ unsaturated lipid tail, an $\alpha$-1,2-dimannosyl moiety appended to $Hpg^{11}$, and substitution of D-Orn and L-Leu for the D- and L-enduracididine residues at positions 10 and 15, respectively.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. "Recombinant" also is used to describe nucleic acid molecules that have been artificially manipulated, but contain the same control sequences and coding regions that are found in the organism from which the gene was isolated.

Regulating antibiotic production: To cause an alteration, such as an increase or decrease, in the amount, type or quality of antibiotic production. For example, an isolated protein with an amino acid sequence which is at least 80% identical in amino acid sequence to any of SEQ ID NO: 22, 24, 41, 42, or 43 is capable of regulating antibiotic production.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl Math.* 2:482, 1981; Needleman and Wunsch, *J. Mol. Biol* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.,* 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins (or nucleic acids) with even greater similarity to the reference sequences will show increasing percentage identities when assessed by this method, such as at least 50%, at least 60%, at least 70%, at least 80%, at least 85%, at least 90%, or at least 95% sequence identity.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity.

An alternative indication that two nucleic acid molecules are closely related is that the two molecules hybridize to each other under stringent conditions (see "Hybridization" above).

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Transfected: A process by which a nucleic acid molecule is introduced into cell, for instance by molecular biology techniques, resulting in a transfected (or transformed) cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Transposon: A mobile genetic element having nearly identical repeating sequences at either end, and containing at least a gene encoding a transposase (the enzyme needed to insert the transposon in the DNA sequence). Transposons can be integrated into different positions in the genome of a cell, or over an isolated plasmid, cosmid, or fosmid DNA template in vitro. Transposons may also contain genes other than those needed for insertion.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

Suitable methods and materials for the practice of the disclosed embodiments are described below. In addition, any appropriate method or technique well known to the ordinarily skilled artisan can be used in the performance of the disclosed embodiments. Some conventional methods and techniques applicable to the present disclosure are described, for example, in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Enduracidin Gene Cluster, ORFs, and Proteins Encoded Thereby

This disclosure provides the nucleic acid sequence of an enduracidin gene cluster located within a 116 kb genetic locus, the ORFs contained therein, and the proteins encoded thereby. This information enables, for example, the isolation of related nucleic acid molecules encoding homologs of the enduracidin gene cluster and the corresponding ORFs, such as in other *Streptomyces* sp. This disclosure further enables the production of variants of the enzymes (such as, EndA, EndB, EndC or EndD) or proteins (such as an ABC transporter) encoded by an enduracidin gene cluster, and nucleic acid molecules encoding such variants.

Figure 4:
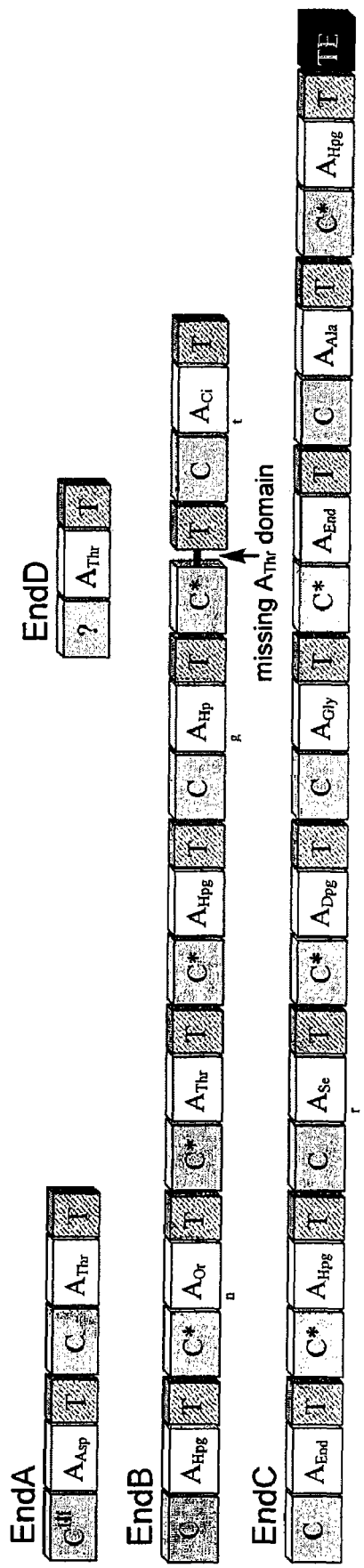
FIG. 4 is a schematic illustrating the module and domain organization of the enduracidin NRPSs. Proposed dual function condensation/epimerization domains are indicated with C*.

The enduracidin gene cluster included within SEQ ID NO: 49 (nucleotide residues 31147-114619) includes twenty-five ORFs referred to as ORF 22 to 46 respectively (SEQ ID NOs: 22-46, respectively). An additional twenty-three ORFs were identified that flank the 5' (ORFs 1-21) and 3' (ORF 47-48) end of the enduracidin gene cluster, respectively. ORFs 36, 37, 38 and 40 are four genes endA, endB, endC, and endD, which encode two-, seven-, eight- and one-module NRPSs, respectively (EndA, SEQ ID NO: 36; EndB, SEQ ID NO: 37; EndC, SEQ ID NO: 38; and EndD, SEQ ID NO: 40). Collectively, these four peptide synthetases (EndA, EndB, EndC, and EndD) assemble the 17-residue enduracidin peptide backbone. The organization of the modules and domains in these four proteins is shown in FIG. 4. Further detail regarding this organization is provided in Example 5.

In addition, five gene products (SEQ ID NOs: 35, 39, 44, 45 and 25) are believed to activate and modify a precursor fatty acid and transfer it to the amine of Asp$^1$ to form enduracidin A. This predicted activation, modification and attachment of the lipid tail of enduracidin A is provided in FIG. 7 and is further elucidated in Example 7. orf30 encodes a halogenase (SEQ ID NO: 30) in the enduracidin gene cluster and is predicted to carry out the chlorination of an NRPS bound-Hpg or on the nascent peptide to form 3,5-dichloro-L-4-hydroxyphenylglycine (Dpg). Nucleic acids that encode SEQ ID NOs: 31, 32, and 33 are predicted to encode components of ABC transporters and be involved in the export of the enduracidin peptide from the cell. SEQ ID NOs: 22, 24, 41, 42 or 43 are involved in the regulation of antibiotic production, and possibly self-resistance determinant expression. SEQ ID NO: 10 that is located within the 116 kb gene locus, but upstream of the disclosed enduracidin gene cluster is possibly involved in lipid tail formation.

TABLE 1

Summary of proteins encoded by ORFs identified in an enduracidin gene cluster and flanking regions.

| SEQ ID NO: | Gene | Size | Ramoplanin homologue (% identity) | Best match Accession number | Proposed function |
| --- | --- | --- | --- | --- | --- |
| 1 | | 409 | | BAC69955 | DXP synthase 2 (incomplete, C-terminal portion) |
| 2 | | 498 | | CAA19226 | Cationic amino acid transporter |
| 3 | | 133 | | CAA19227 | Unknown |
| 4 | | 373 | | CAA19231 | Unknown |
| 5 | | 360 | | CAA19232 | Transcriptional regulator |
| 6 | | 1290 | | CAD55196 | Glycosyltransferase |
| 7 | | 305 | | CAC16706 | Unknown |
| 8 | | 482 | | | Unknown |
| 9 | | 496 | | | Unknown |
| 10 | | 709 | | CAA19238 | Fatty acid oxidation complex alpha-subunit |
| 11 | | 405 | | CAA19239 | Acetyl-CoA acetyltransferase (thiolase) |
| 12 | | 345 | ORF33 (29%) | CAA20609 | Transcriptional regulator |

TABLE 1-continued

Summary of proteins encoded by ORFs identified in an enduracidin gene cluster and flanking regions.

| SEQ ID NO: | Gene | Size | Ramoplanin homologue (% identity) | Best match Accession number | Proposed function |
|---|---|---|---|---|---|
| 13 | | 793 | | CAA20608 | Beta-mannosidase |
| 14 | | 440 | | CAA20607 | Probable sugar transport system lipoprotein |
| 15 | | 258 | | CAA20606 | Sugar transport system permease protein |
| 16 | | 276 | | CAA20605 | Sugar transport system permease protein |
| 17 | | 430 | | BAC69942 | Ribonuclease D |
| 18 | | 220 | ORF21 (26%) | BAC69941 | Two-component response regulator |
| 19 | | 224 | | CAA19242 | Unknown |
| 20 | | 364 | | BAC69939 | Uroporphyrinogen decarboxylase |
| 21 | | 664 | | AAZ54144 | PAS protein phosphatase 2C-like |
| 22 | | 328 | ORF5 (43%) | BAC76461 | StrR-like regulatory protein |
| 23 | | 362 | ORF4 (51%) | CAD55177 | Prephenate dehydrogenase |
| 24 | | 311 | ORF5 (49%) | AAM80553 | Unknown (StaQ homolog) |
| 25 | | 356 | ORF30 (48%) | EAM81892 | 4Hydroxyphenylpyruvate dioxygenase (HmaS homolog) |
| 26 | endR | 279 | — | AAU34211 | Unknown (MppR homolog) |
| 27 | endQ | 419 | — | AAU34210 | PLP-dependent aminotransferase (MppQ homolog) |
| 28 | endP | 293 | — | AAU34209 | PLP-dependent aminotransferase (MppP homolog) |
| 29 | | 790 | ORF7 (66%) and ORF6 (69%) | EAM81890 and EAM81900 | FMN-dependent α-hydroxy acid dehydrogenase (HmaO homolog) and PLP-dependent class I and II Aminotransferase (HpgT homolog) |
| 30 | | 504 | ORF20 (62%) | CAG15020 | Halogenase |
| 31 | | 341 | ORF1 (50%) | EAP97899 | Transmembrane transport protein |
| 32 | | 307 | ORF2 (69%) and ORF23 (55%) | AAP03101 | ABC transporter |
| 33 | | 651 | ORF8 (72%) | EAM81899 | ABC transporter |
| 34 | | 275 | ORF9 (76%) | AAZ23080 | Type II thioesterase |
| 35 | | 90 | ORF11 (67%) | BAC71361 | Carrier protein (ACP/PCP) |
| 36 | endA | 2101 | RamoA | | NRPS |
| 37 | endB | 6943 | RamoB | | NRPS |
| 38 | endC | 8986 | RamoC | | NRPS |
| 39 | | 274 | ORF16 (79%) | BAC70911 | Acyl-CoA dehydrogenase/reductase |
| 40 | endD | 859 | ORF17 | | NRPS |
| 41 | | 223 | ORF21 (70%) | AAP03103 | Two-component response regulator |
| 42 | | 370 | ORF22 (54%) | AAP03102 | Two-component system sensor kinase |
| 43 | | 181 | ORF22 (43%) | AAP03102 | Two-component system sensor kinase |
| 44 | | 625 | ORF24 (62%) | BAC71362 | Acyl-CoA dehydrogenase |
| 45 | | 1177 | ORF26 (53%) | BAC71363 | Acyl-CoA ligase/dehydrogenase fusion protein |
| 46 | | 71 | | AAX31560 | MbtH-like protein |
| 47 | | 245 | | CAA19250 | Integral membrane protein |
| 48 | | 118 | | CAA19250 | Integral membrane protein |

With the provision herein of the sequences of the disclosed gene locus (SEQ ID NO: 49) and the ORFs contained therein (SEQ ID NOs: 1 to 48), in vitro nucleic acid amplification (such as PCR) may be utilized as a simple method for producing nucleic acid sequences encoding one or more of the enduracidin biosynthetic proteins listed in Table 1. The following provides representative techniques for preparing a protein-encoding nucleic acid molecule in this manner.

RNA or DNA is extracted from cells by any one of a variety of methods well known to those of ordinary skill in the art. Sambrook et al. (In *Molecular Cloning: A Laboratory Manual*, Cold Spring Harbor Laboratory Press, New York, 1989) and Ausubel et al. (In *Current Protocols in Molecular Biology*, Greene Publ. Assoc. and Wiley-Intersciences, 1992) provide representative descriptions of methods for RNA or DNA isolation. The enduracidin biosynthetic enzymes are expressed, at least, in the *Streptomyces fungicidicus*. Thus, in some examples, RNA or DNA may be extracted from *Streptomyces fungicidicus* cells. Extracted RNA is used, for example, as a template for performing reverse transcription (RT)-PCR amplification to produce cDNA. Representative methods and conditions for RT-PCR are described by Kawasaki et al. (In *PCR Protocols, A Guide to Methods and Applications*, Innis et al. (eds.) 21-27 Academic Press, Inc., San Diego, Calif., 1990).

The selection of amplification primers will be made according to the portion(s) of the DNA that is to be amplified. In one embodiment, primers may be chosen to amplify a segment of a DNA (e.g., a specific ORF or set of adjacent ORFs) or, in another embodiment, the entire DNA molecule. Variations in amplification conditions may be required to accommodate primers and amplicons of differing lengths and composition; such considerations are well known in the art and are discussed for instance in Innis et al. (*PCR Protocols, A Guide to Methods and Applications*, Academic Press, Inc., San Diego, Calif., 1990). By way of example, the nucleic acid molecules encoding selected enduracidin biosynthetic enzymes (such as, EndA, EndB, EndC or EndD) may be amplified using primers directed towards the 5'- and 3'-ends of the prototypical *Streptomyces fungicidicus* endA, endB, endC, and endD sequences (SEQ ID NOs: 36, 37, 38 or 40).

It will be appreciated that many different primers may be derived from the provided nucleic acid sequences. Re-sequencing of amplification products obtained by any amplification procedure is recommended to facilitate confirmation of the amplified sequence and to provide information on natural variation between an enduracidin and amplified sequence. Oligonucleotides derived from any of the enduracidin sequences may be used in sequencing, for instance, the corresponding enduracidin (or enduracidin-related) amplicon.

In addition, both conventional hybridization and PCR amplification procedures may be utilized to clone sequences encoding orthologs of the enduracidin gene cluster, or enduracidin ORFs (for example, one or more of SEQ ID NOs: 1-48). Common to both of these techniques is the hybridization of probes or primers that are derived from the enduracidin gene cluster with or without the upstream and downstream flanking regions or enduracidin ORFs nucleic acid sequences. Furthermore, the hybridization may occur in the context of Northern blots, Southern blots, or PCR.

Direct PCR amplification may be performed on DNA libraries prepared from the bacterial species in question, or RT-PCR may be performed using RNA extracted from the bacterial cells using standard methods. PCR primers will comprise at least 10 consecutive nucleotides of the enduracidin gene cluster with or without the upstream and downstream flanking regions or enduracidin ORFs nucleic acid sequences. One of skill in the art will appreciate that sequence differences between the enduracidin gene cluster or enduracidin ORFs nucleic acid sequences and the target nucleic acid to be amplified may result in lower amplification efficiencies. To compensate for this, longer PCR primers or lower annealing temperatures may be used during the amplification cycle. Whenever lower annealing temperatures are used, sequential rounds of amplification using nested primer pairs may be useful to enhance amplification specificity.

Orthologs of the disclosed enduracidin biosynthetic proteins are likely present in a number of other members of the *Streptomyces* genus, in other strains of the *Streptomyces fungicidicus* species, and in other enduracidin-producing organisms. With the provision of the nucleic acid sequence of the disclosed enduracidin gene cluster and its ORFs 22 to 46, as well as flanking ORFs 1-21 to 47-48, the cloning by standard methods of protein-encoding DNA (such as, ORFs) and gene clusters that encode enduracidin biosynthetic enzyme orthologs in these other organisms is now enabled. Orthologs of the disclosed enduracidin biosynthetic enzymes and proteins have a biological activity or function as disclosed herein, including for example NRPS, two-component system sensor kinase, halogenase, or ABC transporter function.

Orthologs will generally share at least 65% sequence identity with the nucleic acid sequences encoding the disclosed enduracidin biosynthetic proteins (for example, one or more of SEQ ID NOs: 1-48). In specific embodiments, orthologous enduracidin gene clusters or enduracidin ORFs may share at least 70%, at least 75%, at least 80% at least 85%, at least 90%, at least 91%, at least 93%, at least 95%, or at least 98% sequence identity with the disclosed *Streptomyces fungicidicus* nucleotide or amino acid sequences, as applicable.

For conventional hybridization techniques the hybridization probe is preferably conjugated with a detectable label such as a radioactive label, and the probe is preferably at least 10 nucleotides in length. As is well known in the art, increasing the length of hybridization probes tends to give enhanced specificity. A labeled probe derived from an enduracidin gene cluster or enduracidin ORFs nucleic acid sequence may be hybridized to a bacterial DNA library and the hybridization signal detected using methods known in the art. The hybridizing colony or plaque (depending on the type of library used) is purified and the cloned sequence contained in that colony or plaque isolated and characterized.

In specific examples, genomic library construction can be accomplished rapidly using a variety of cosmid or fosmid systems that are commercially available (Stratagene, Epicentre). Advantageously, these systems minimize instability of the cloned DNA. In such examples, genomic library screening is followed by cosmid or fosmid isolation, grouping into families of overlapping clones and analysis to establish cluster identity. Cosmid end sequencing can be used to obtain preliminary information regarding the relevance of a particular clone based on expected pathway characteristics predicted from the natural product structure and its presumed biosynthetic origin.

Orthologs of an enduracidin gene cluster (+/− upstream or downstream flanking regions) or enduracidin ORFs nucleic acid sequences alternatively may be obtained by immuno-screening of an expression library. With the provision herein of the disclosed 116 kb gene locus (SEQ ID NO: 49), the corresponding proteins can be expressed and purified in a heterologous expression system (e.g., *E. coli*) and used to raise antibodies (monoclonal or polyclonal) specific for the enduracidin biosynthetic enzymes or proteins, such as EndA, EndB, EndC, EndD or ABC transporters. Antibodies also may be raised against synthetic peptides derived from the enduracidin amino acid sequences presented herein (SEQ ID NOs: 22-46 for the gene cluster, and SEQ ID NOs: 1-21 and 47-48 for the flanking regions). Methods of raising antibodies are well known in the art and are described generally in Harlow and Lane, *Antibodies, A Laboratory Manual*, Cold Springs Harbor, 1988. Such antibodies can be used to screen an expression library produced from bacteria. For example, this screening will identify the enduracidin orthologs. The selected DNAs can be confirmed by sequencing and enzyme activity assays.

Oligonucleotides derived from an enduracidin gene cluster (SEQ ID NOs: 22 to 46) or nucleic acid sequences encoding ORFs 1-48 (SEQ ID NOs: 1-48), or fragments of these nucleic acid sequences, are encompassed within the scope of the present disclosure. Such oligonucleotides may be used, for example, as probes or primers. In one embodiment, oligonucleotides may comprise a sequence of at least 10 consecutive nucleotides of an enduracidin gene cluster (+/− upstream and downstream flanking regions) or an enduracidin ORF nucleic acid sequence. If these oligonucleotides are used with an in vitro amplification procedure (such as PCR), lengthening the oligonucleotides may enhance amplification specificity. Thus, in other embodiments, oligonucleotide primers comprising at least 15, 20, 25, 30, 35, 40, 45, 50, or more consecutive nucleotides of these sequences may be used. In another example, a primer comprising 30 consecutive nucleotides of a nucleic acid molecule encoding an enduracidin biosynthetic enzyme (such as, SEQ ID NOs: 36, 37, 38 or 40) or protein (such as, SEQ ID NOs: 33 or 42) will anneal to a target sequence, such as an enduracidin gene cluster (+/− upstream and downstream flanking regions) or an enduracidin homolog present in a DNA library from another *Streptomyces* species (or other enduracidin-producing species), with a higher specificity than a corresponding primer of only 15 nucleotides. In order to obtain greater specificity, probes and primers can be selected that comprise at least 17, 20, 23, 25, 30, 35, 40, 45, 50 or more consecutive nucleotides of enduracidin gene cluster (+/− upstream and downstream flanking regions) or an enduracidin ORF nucleotide sequences. In particular examples, probes or primers can be at least 100, 250, 500, 600 or 1000 consecutive nucleic acids of a disclosed enduracidin gene cluster (+/− upstream and downstream flanking regions) or an enduracidin ORF sequence.

Oligonucleotides (such as, primers or probes) may be obtained from any region of a disclosed enduracidin gene cluster (+/− upstream and downstream flanking regions) or an enduracidin ORF nucleic acid sequence. By way of example, an enduracidin gene cluster (+/− upstream and downstream flanking regions) or an enduracidin ORF sequences may be apportioned into about halves, thirds or quarters based on sequence length, and the isolated nucleic acid molecules (e.g., oligonucleotides) may be derived from the first or second halves of the molecules, from any of the three thirds, or from any of the four quarters. The nucleic acid sequence of interest also could be divided into smaller regions, e.g., about eighths, sixteenths, twentieths, fiftieths and so forth, with similar effect. Alternatively, it may be divided into regions that encode for conserved domains. For example, an EndA nucleic acid molecule could be divided into regions corresponding to the various EndA modules (SEQ ID NO: 36; Table 2, Table 3 and Example 5, below).

IV. Enduracidin Biosynthetic Enzyme and Protein Variants

With the provision herein of the enduracidin biosynthetic proteins and corresponding nucleic acid sequences, the creation of variants of these sequences is now enabled. Variant enduracidin biosynthetic enzymes include proteins that differ in amino acid sequence from the disclosed prototype enzymes and still retain the biological activity/function of the prototype proteins as listed in Table 1. Variant enzymes may also be stripped of their activity/function producing biosynthetic precursors to, or novel analogs of, the enduracidin antibiotics.

NRPSs are modular enzymes wherein each module consists of several catalytic domains that carry out the activation, optional modifications, and incorporation of a specific amino acid residue into a peptide chain. Usually, the enzyme organization is such that the modules occur in the primary sequence in the same order that the amino acids are assembled into the peptide product (colinearity principle). There are three components to the minimum extending module. The adenylation (A) domain recognizes a specific amino acid and uses ATP to activate the carboxyl as the adenylate. This facilitates attachment of the carboxyl to the thiol of a 4'-phosphopantetheine (p-pant) cofactor attached to the peptidyl carrier (PCP, or thiolation (T)) domain. The third domain is the condensation (C) domain that catalyzes formation of peptide bonds between amino acids or peptides attached to PCP domains or adjacent modules, thereby promoting directional peptide chain elongation. The order of these domains in a normal module is C-A-T. An NRPS may contain a single or many (2-10+) modules. Subsequent modifications and the remainder of the assembly process occur via covalent thioester intermediates. The linear peptide precursor is typically released from the NRPS complex by a thioesterase domain (Te) that can yield linear or cyclic peptides. For example, a EndA variant catalyzes the condensation of two peptides (including amino acids) (such as N-lipo-L-Asp$^1$ and L-Thr$^2$) that is transferred to EndB, a EndB and/or EndD variant catalyzes the peptidyl chain elongation from amino acid residue L-Thr$^2$ to L-Cit$^9$, a EndC variant catalyzes the peptidyl chain extension from amino acid residues D-End10 to L-Hpg17, and terminates with a thioesterase domain that promotes the cyclization and release of the peptide. Variants can be specific for one or more of the modules responsible for NRPS such SEQ ID NO: 36, 37, 38, 40 and 64-102.

In one embodiment, variant enduracidin biosynthetic proteins include proteins that differ in amino acid sequence from the disclosed enduracidin biosynthetic protein sequences (e.g., SEQ ID NOs: 1-48 and 64-102) but that share at least 65% amino acid sequence identity with such enzyme sequences. In other embodiments, other variants will share at least 70%, at least 75%, at least 80%, at least 85%, at least 90%, at least 95%, or at least 98% amino acid sequence identity. Manipulation of the disclosed enduracidin gene cluster (+/− upstream and downstream flanking regions) and enduracidin ORF nucleotide sequences using standard procedures (e.g., site-directed mutagenesis or PCR), can be used to produce such variants. The simplest modifications involve the substitution of one or more amino acids for amino acids having similar biochemical properties. These so-called conservative substitutions are likely to have minimal impact on the activity of the resultant protein.

In some embodiments, the function of an enduracidin biosynthetic protein variant can be maintained if amino acid substitutions are introduced in regions outside of the conserved domains of the protein, where amino acid substitutions are less likely to affect protein function.

In another embodiment, more substantial changes in enduracidin biosynthetic enzyme function or other protein features may be obtained by selecting amino acid substitutions that are less conservative than conservative substitutions. In one specific, non-limiting, embodiment, such changes include changing residues that differ more significantly in their effect on maintaining polypeptide backbone structure (e.g., sheet or helical conformation) near the substitution, charge or hydrophobicity of the molecule at the target site, or bulk of a specific side chain. The following specific, non-limiting, examples are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histidyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant enduracidin biosynthetic enzyme or protein encoding sequences may be produced by standard DNA mutagenesis techniques. In one specific, non-limiting, embodiment, M13 primer mutagenesis is performed. Details of these techniques are provided in Sambrook et al. (In *Molecular Cloning: A Laboratory Manual*, Cold Spring Harbor Laboratory Press, New York, 1989), Ch. 15. By the use of such techniques, variants may be created that differ from the disclosed enduracidin biosynthetic enzyme or protein sequences. DNA molecules and nucleotide sequences that are derivatives of those specifically disclosed herein, and which differ from those disclosed by the deletion, addition, or substitution of nucleotides while still encoding a protein having the biological activity of the prototype enzyme.

In some embodiments the disruption of portions of the gene cluster may be achieved by use of the transposon-based method disclosed herein, which randomly inserts mutations into the gene cluster. These random mutations may be screened by restriction analysis in conjunction with DNA sequencing to select variants of the gene cluster with mutations in the sequences for specific enzymes involved in enduracidin synthesis. Variants expressing one or more mutations may be selected. For example, mutations in portions of the gene cluster encoding for dehydrogenase enzymes or halogenase enzymes may be selected from the random mutations resulting from mutations of the gene cluster.

In one embodiment, variants may differ from the disclosed sequences by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed enduracidin biosynthetic enzyme and protein amino acid sequences (e.g., SEQ ID NOs: 1-48). For example, because of the degeneracy of the genetic code, four nucleotide codon triplets—(GCT, GCG, GCC and GCA)—code for alanine. The coding sequence of any specific alanine residue within an enduracidin biosynthetic enzyme (such as, EndA, EndB, EndC or EndD), therefore, could be changed to any of these alternative codons without affecting the amino acid composition or characteristics of the encoded protein. Based upon the degeneracy of the genetic code, variant DNA molecules may be derived from the nucleic acid sequences disclosed herein using standard DNA mutagenesis techniques, as described above, or by synthesis of DNA sequences. Thus, this disclosure also encompasses nucleic acid sequences that encode an enduracidin biosynthetic enzyme (such as, EndA, EndB, EndC or EndD) or protein (such as an ABC transporter), but which vary from the disclosed nucleic acid sequences by virtue of the degeneracy of the genetic code.

In one embodiment, variants of an enduracidin biosynthetic enzyme or protein may also be defined in terms of its sequence identity with the prototype enduracidin biosynthetic enzymes or variants. Nucleic acid sequences that encode such proteins/fragments readily may be determined simply by applying the genetic code to the amino acid sequence of an enduracidin biosynthetic enzyme, protein or fragment thereof, and such nucleic acid molecules may readily be produced by assembling oligonucleotides corresponding to portions of the sequence.

Nucleic acid molecules that are derived from an enduracidin gene cluster (+/− upstream and downstream flanking regions) and enduracidin ORF nucleic acid sequences include molecules that hybridize under low stringency, high stringency, or very high stringency conditions to the disclosed prototypical enduracidin gene cluster (+/− upstream and downstream flanking regions) and enduracidin ORFs and fragments thereof.

Nucleic acid molecules encoding one or more enduracidin biosynthetic enzyme or protein (including the amino acid sequences set forth in SEQ ID NOs: 1-48, and nucleic acids encoding these sequences), and orthologs and homologs of these sequences, may be incorporated into transformation or expression vectors.

V. Biosynthetic Production of Enduracidin

Biosynthetic methods for creating enduracidin are useful for efficient production of the antibiotic and can be similarly employed for the production of enduracidin and analogs thereof. For example, Kosan Biosciences, Inc. has used biosynthetic methods to produce erthyromycin antibiotics and the epothilone antitumor agents. In another example, Walsh and Marahiel laboratories have successfully attached synthetic polypeptides as well as hybrid polyketides-polypeptides to PEGA resin beads to effect macrocyclization reactions from cloned and soluble thioesterases (TEs), such as that from the tyrocidine A pathway (Kohli et al., *Proc. Natl. Acad. Sci. USA,* 99: 1247-1252, 2002; and Kohli et al., *Nature,* 418:658-661, 2002). Thus, cloning and expression of the enduracidin biosynthetic gene cluster or ORFs therefrom in a heterologous host, such as *E. coli* or *S. lividans,* can be used to increase production of enduracidin, enduracidin precursor(s), enduracidin intermediate(s), or an enzyme or protein included within the gene cluster. In addition, genetic recombination and domain-exchange constructs permit the creation of enduracidin structures that would be difficult to make using traditional synthetic methodologies.

In an embodiment, a recombinant expression system is selected from prokaryotic hosts. Bacterial cells are available from numerous sources including public sources to those skilled in the art, such as the American Type Culture Collection (ATCC; Manassas, Va.). Commercial sources of cells used for recombinant protein expression also provide instructions for usage of such cells.

One representative heterologous host system for expression of an enduracidin gene cluster is *Streptomyces* sp. In specific examples, *Streptomyces* spp. have been used as artificial hosts to express natural product biosynthetic gene clusters of very large sizes (see, e.g., Stutzman-Engwall and Hutchinson *Proc. Natl. Acad. Sci. USA* 86: 3135-3139, 1989; Motamedi and Hutchinson *Proc. Natl. Acad. Sci. USA* 84: 4445-4449, 1987; Grim et al. *Gene* 151: 1-10 1994; Kao et al. *Science* 265: 509-512, 1994: and Hopwood et al. *Meth. Enzymol.* 153: 116-166, 1987). *Streptomyces* spp. are useful heterologous host systems because they are easily grown, plasmids and cosmids for the expression and/or integration of biosynthetic gene clusters are well characterized, and they house many of the modifying and auxiliary enzymes required to produce functional pathways (Donadio et al *J. Biotechnol.* 99:187-198, 2002).

Another representative heterologous host system for expression of an enduracidin gene cluster (or one or more of its OFRs) is *E. coli. E. coli* has successfully been used for the functional production of NRPS and PKS enzyme systems (Kealey et al. *Proc. Natl. Acad. Sci. USA* 95(2):505-509, 1998; Pfeifer *App. Environ. Microbiol.* 69(11): 6698-6702, 2003). *E. coli* is an attractive artificial expression system because it is fast growing and easy to genetically manipulate. Recent advances in *E. coli* based expression systems have greatly aided efforts to simultaneously express multiple genes in a single host organism. Multiple ORFs from a complex biosynthetic system can now be expressed simultaneously in *E. coli.* To ensure adequate and coordinate production of multiple biosynthetic enzymes from a single pathway, each ORF is placed under control of a single type of promoter, such as the inducible T7 promoter. Novagen (San Diego, Calif.) has introduced the Duet™ vectors, which are designed with compatible replicons and drug resistance genes for effective propagation and maintenance of four plasmids in a single cell. This allows for the coexpression of up to eight different proteins. The activity of NRPS enzymes may require the correct post-translational modification of the corresponding peptidyl carrier protein. Typically this is accomplished by the co-expression of an appropriate phosphopantetheinyl transferase (PPtase) gene, for example sfp from *Bacillus subtilus* (Quadri et al. *Biochem.* 37(6):1585-1595, 1998).

The choice of the expression system will depend however on the features desired for the expressed polypeptides. Any transducible cloning vector can be used as a cloning vector for the nucleic acid constructs presently disclosed. If large clusters are to be expressed, it is preferable that phagemids, cosmids, fosmids, P1s, YACs, BACs, PACs, HACs or similar cloning vectors are used for cloning the nucleotide sequences into the host cell. These vectors are advantageous due to their ability to insert and stably propagate larger fragments of DNA compared to M13 phage and lambda phage, respectively.

In an embodiment, one or more of the disclosed ORFs and/or variant thereof can be inserted into one or more expression vectors, using methods known to those of skill in the art. Vectors are used to introduce enduracidin biosynthesis genes or a gene cluster into host cells. Prokaryotic host cells or other host cells with rigid cell walls may be transformed using any method known in the art, including, for example, calcium phosphate precipitation, or electroporation. Representative prokaryote transformation techniques are described in Dower (*Genetic Engineering, Principles and Methods* 12: 275-296, Plenum Publishing Corp., 1990) and Hanahan et al. (*Meth. Enzymol.* 204: 63, 1991). Vectors include one or more control sequences operably linked to the desired ORF. However, the choice of an expression cassette may depend upon the host system selected and features desired for the expressed polypeptide or natural product. Typically, the expression cassette includes a promoter that is functional in the selected host system and can be constitutive or inducible. In an embodiment, the expression cassette includes a promoter, ribosome binding site, a start codon (ATG) if necessary, and optionally a region encoding a leader peptide in addition to the desired DNA molecule and stop codon. In addition, a 3' terminal region (translation and/or transcription terminator) can be included within the cassette. The ORF constituted in the DNA molecule may be solely controlled by the promoter so that transcription and translation occur in the host cell. Promoters encoding regions are well known and available to those of skill in the art. Examples of promoters can include control sequences derived from enduracidin and/or NRPS gene clusters, bacterial promoters (such as those derived from sugar metabolizing enzymes, such as galactose, lactose and maltose), promoter sequences derived from biosynthetic enzymes such as tryptophan, the beta-lactamase promoter system, bacteriophage lambda PL and TF and viral promoters.

The presence of additional regulatory sequences within the expression cassette may be desirable to allow for regulation of expression of the one or more ORFs relative to the growth of the host cell. These regulatory sequences are well known in the art. Examples of regulatory sequences include sequences that turn gene expression on or off in response to chemical or physical stimulus as well as enhancer sequences. In addition, to the regulatory sequences, selectable markers can be included to assist in selection of transformed cells. For example, genes that confer antibiotic resistance or sensitivity to the plasmid may be used as selectable markers.

It is contemplated that various enduracidin ORFs and/or gene cluster or proteins of interest can be cloned into one or more recombinant vectors as individual cassettes, with separate control elements, or under the control of a single control element (e.g., a promoter). In an embodiment, the ORFs include two or more restriction sites to allow for the easy deletion and insertion of other open reading frames so that hybrid synthetic pathways can be generated. The design and use of such restriction sites is well known in the art and can be carried out by using techniques described above such as PCR or site-directed mutagenesis. Proteins expressed by the transformed cells can be recovered according to standard methods well known to those of skill in the art. For example, proteins can be expressed with a convenient tag to facilitate isolation. Further, the resulting polypeptide can be purified by affinity chromatography by using a ligand (such as a compound related to enduracidin) that binds to the polypeptide.

It is further contemplated that various enduracidin ORFs, gene cluster or enduracidin proteins of interest may be produced by utilizing fermentation conditions as previously described for the production of enduracidin (Higashide et al. *J. Antibiot.* 21: 126-137, 1968). After production, the compounds can be purified and/or analyzed by methods well known to one of skill in the art including HPLC analysis as described in Example 1. Methods of producing enduracidin and harvesting this compound from growth medium can be found in U.S. Pat. No. 4,465,771, which is hereby incorporated by reference in its entirety.

VI. Enduracidin Analogs

This disclosure includes analogs of enduracidin produced by manipulation of the gene cluster responsible for biosynthesis of enduracidin. Embodiments of the analogs include compounds wherein elements of the enduracidin structure are incompletely synthesized. For example, such analogs may comprise compounds where the lipid side chain attached to the starter Asp unit is fully reduced, and/or the hydroxyphenylglycine residue has not been halogenated.

In one embodiment, impairment of orf45 disrupted the normal dehydrogenation of the lipid side chain that is attached to the starter Asp unit, resulting in production of tetrahydroenduracidin A and tetrahydroenduracidin B. See FIG. 10.

Figure 11:
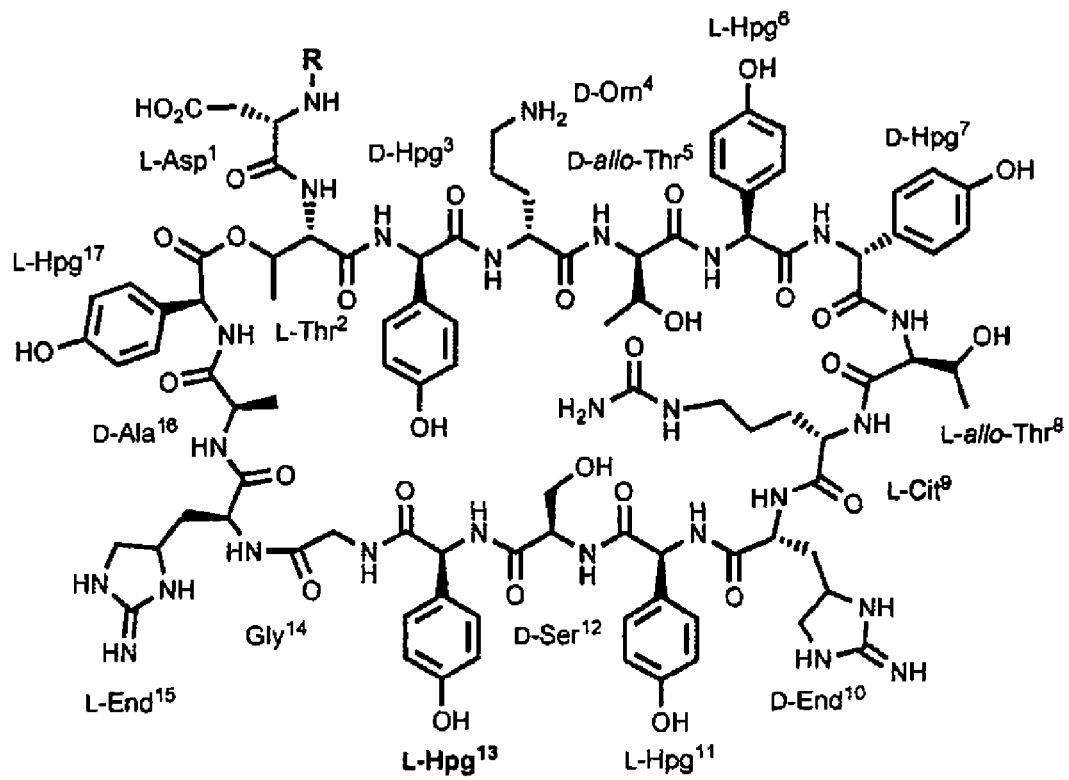
FIG. 11 illustrates the chemical structure of deschloroenduracidins A and B.
Figure 11:
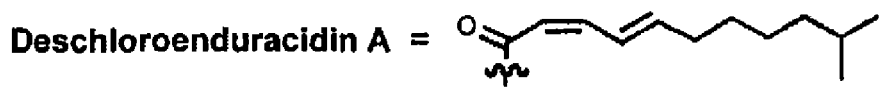
Figure 11:
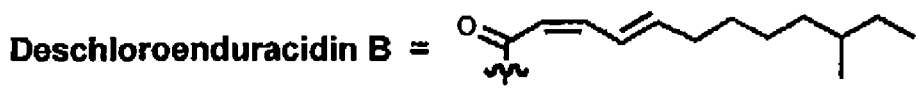

In another embodiment, impairment of orf30 disrupted the normal halogenation of a hydroxyphenylglycine residue, yielding deschloroenduracidin A and deschloroenduracidin B. See FIG. 11.

Figure 12:
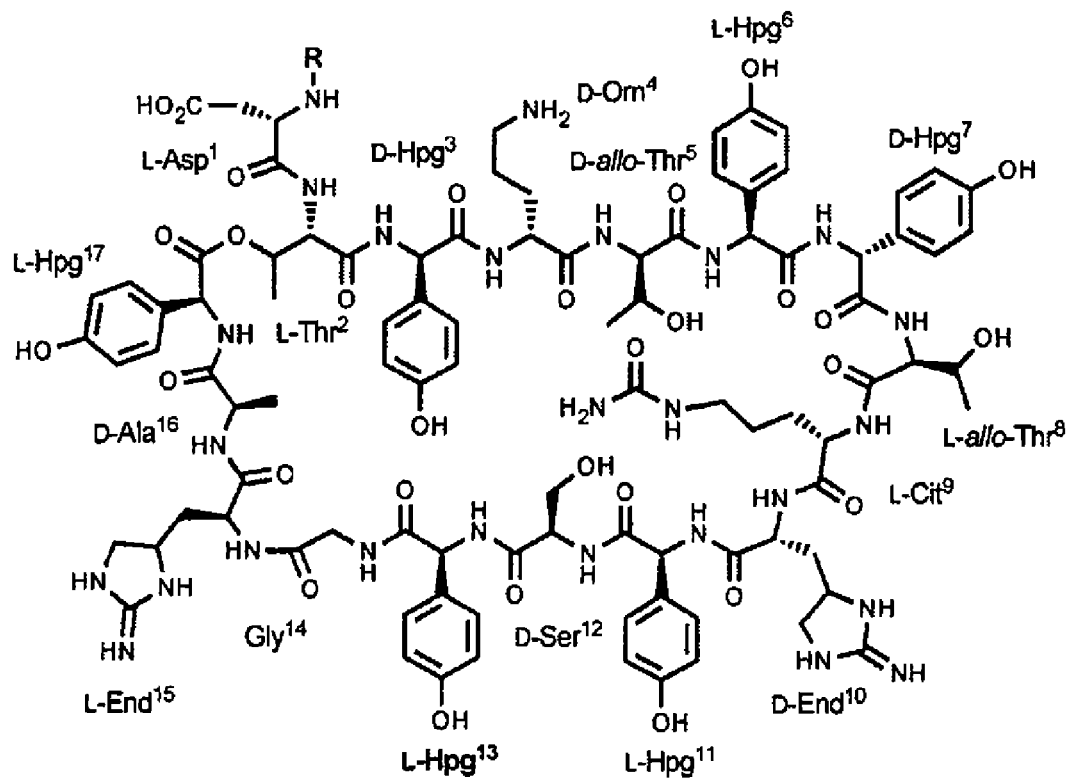
FIG. 12 illustrates the chemical structure of deschlorotetrahydroenduracidins A and B.
Figure 12:
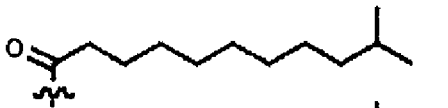
Figure 12:
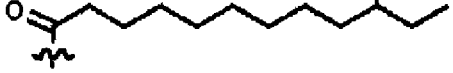

In another embodiment, impairment of both orf45 and orf30 disrupts the normal dehydrogenation of the lipid side chain attached to the starter Asp unit and the normal halogenation of a hydroxyphenylglycine residue, resulting in deschlorotetrahydroenduracidin A and deschlorotetrahydroenduracidin B. See FIG. 12.

VII. Pharmaceutical Compositions

This disclosure includes pharmaceutical compositions comprising at least one enduracidin formulation for use in human or veterinary medicine. Embodiments of pharmaceutical compositions include a pharmaceutically acceptable carrier and at least one active ingredient. Useful pharmaceutically acceptable carriers and excipients are known in the art. Active ingredients may comprise, for example, at least one enduracidin compound or analog thereof such as enduracidin A, enduracidin B, tetrahydroenduracidin A, tetrahydroenduracidin B, deschloroenduracidin A, deschloroenduracidin B, deschlorotetrahydroenduracidin A, and deschlorotetrahydroenduracidin B as described herein. In addition, other medicinal or pharmaceutical agents, for example, with similar, related or complementary effects on the affliction being treated, may be included as active ingredients in pharmaceutical compositions.

The pharmaceutical compositions comprising enduracidin may be formulated in a variety of ways depending, for example, on the mode of administration and/or on the location and type of disease to be treated. For example, such pharmaceutical compositions may be formulated as pharmaceutically acceptable salts. As another example, parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as cremophor, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The dosage form of the pharmaceutical composition will be determined by the mode of administration chosen. For example, in addition to injectable fluids, topical and oral formulations may be employed. Topical preparations may include eye drops, ointments, sprays and the like. Oral formulations may be liquid (e.g., syrups, solutions or suspensions), or solid (e.g., powders, pills, tablets, or capsules). For solid compositions, conventional non-toxic solid carriers may include pharmaceutical grades of mannitol, lactose, starch, or magnesium stearate. Actual methods of preparing such dosage forms are known, or will be apparent, to those skilled in the art.

Certain embodiments of the pharmaceutical compositions comprising enduracidin as described herein may be formulated in unit dosage form suitable for individual administration of precise dosages. The amount of a therapeutic compound administered will depend on the subject being treated, the severity of the affliction, and the manner of administration, and is known to those skilled in the art. Within these bounds, the formulation to be administered will contain a quantity of the enduracidin disclosed herein in an amount effective to achieve the desired effect in the subject being treated (e.g., eliminating Gram-positive pathogens).

VIII. Therapeutic Uses

The present disclosure contemplates treatments for infection of a subject by a Gram-positive bacteria, including VRE and MRSA. Such treatments include administering enduracidin A or B or analogs thereof (such as tetrahydroenduracidin A, tetrahydroenduracidin B, deschloroenduracidin A, deschloroenduracidin B, deschlorotetrahydroenduracidin A, and deschlorotetrahydroenduracidin B), or a combination of enduracidin and one or more other pharmaceutical agents (also referred to herein as "drug" or "drugs"), to the subject in a pharmaceutically acceptable carrier and in an amount effective to treat a Gram-positive bacteria. Subjects can be selected using more specific criteria, such as a definitive diagnosis of a condition based on, for example, a biological specimen that has been provided to be tested for a bacterial infection.

The vehicle in which the drug is delivered may include, for example, the pharmaceutical compositions described above. Routes of administration include but are not limited to oral and parenteral routes, such as intravenous (iv), intraperitoneal (ip), rectal, topical, ophthalmic, nasal, and transdermal.

Therapeutically effective doses of enduracidin can be determined by one of skill in the art. An example of a dosage range is 0.1 to 200 mg/kg body weight orally in single or divided doses. Another example of a dosage range is 1.0 to 100 mg/kg body weight orally in single or divided doses. For oral administration, the compositions are, for example, provided in the form of a tablet containing 0.1 or 1.0 to 1000 mg of the active ingredient, particularly 1, 5, 10, 15, 20, 25, 50, 100, 200, 400, 500, 600, and 1000 mg of the active ingredient for the symptomatic adjustment of the dosage to the subject being treated.

The specific dose level and frequency of dosage for any particular subject may be varied and will depend upon a variety of factors, including the activity of the specific enduracidin compound, the metabolic stability and length of action of that compound, the age, body weight, general health, sex and diet of the subject, mode and time of administration, rate of excretion, drug combination, and severity of the condition of the subject undergoing therapy.

The following examples are provided to illustrate certain particular features and/or embodiments. These examples should not be construed to limit the invention to the particular features or embodiments described.

EXAMPLES

Example 1

Methods for Isolation and Characterization of an Enduracidin Gene Cluster

This example provides representative methods for isolation and characterization of an enduracidin gene cluster.

Bacterial strains, plasmids, fosmids and culture conditions. *Streptomyces fungicidicus* ATCC21013 and *Escherichia coli* S17-1 (ATCC47055) were purchased from ATCC (Manassas, Va.). *E. coli* strains DH5α (Life Technologies, Inc.), EPI300 (Epicentre), and XL10-Gold (Stratagene) were routinely used as hosts for *E. coli* plasmids, fosmids and *E. coli*-*Streptomyces* shuttle vectors. The plasmid pSET152 (Bierman et al., *Gene* 116, 43-49, 1992) was obtained from Prof. K. F. Chater (Norwich, England), the pGEM-T easy cloning vector was from Promega, and the pCC1FOS system was purchased from Epicentre. Media and culture conditions for *S. fungicidicus* were previously described (Higashide et al, *J. Antibiot.* 21: 126-137, 1968). All *E. coli* procedures were performed according to standard protocols (Sambrook & Russell, *Molecular Cloning A Laboratory Manual* $3^{rd}$ edn. 2001). Standards of enduracidins A and B were purchased from Sigma-Aldrich.

DNA isolation and manipulations. Isolation of chromosomal DNA from *S. fungicidicus* and agarose gel electrophoresis were performed according to Kieser et al (*Practical Streptomyces Genetics*, Crowes, Norwich, England 2000) and QIAprep Spin Miniprep kits (Qiagen) were used to prepare plasmids and fosmids from *E. coli* strains. Restriction endonucleases, DNA ligase, DNA polymerase and alkaline phosphatase were purchased from various sources and used according to the manufacturers' recommendations. DNA fragments were purified using QIAquick Gel Extraction kits (Qiagen).

Generation of NRPS and prephenate dehydrogenase gene probes. PCR primers were designed to amplify internal fragments of NRPS genes, corresponding to the region between conserved motifs A3 and T (Marahiel et al, *Chem. Rev.* 97: 2651-2674, 1997). Primer design took into consideration *Streptomyces* codon bias (Wright & Bibb, *Gene* 113: 55-65, 1992). The degenerate primers were PSA3f; 5'-ATCTACAC-STCSGGCACSACSGGCAAGCCSAAGGG-3' (SEQ ID NO: 50) and PSTr; 5'-AWIGAGKSICCICCSRRSIMGAA-GAA-3' (S=G+C; W=A+T; K=T+G; R=G+A; M=A+C; I=inosine; SEQ ID NO: 51). PCR template was *S. fungicidicus* genomic DNA digested with HindIII, BamHI or BglII. PCR mixtures (final volume of 100 μl) contained 2.5 μg of digested chromosomal DNA, 100 μmol of each primer, 0.25 mM dNTPs, Taq DNA polymerase reaction buffer without $MgCl_2$ (Promega), 1.5 mM $MgCl_2$, 5% DMSO, and 1 μl polymix (added at 80° C.) from Expand Long Template PCR System (Roche). PCR was performed as follows: 1 cycle for 3 min at 95° C. and 1 min at 80° C., 30 cycles for 1 min at 95° C., 1 min at 55° C. and 2 min at 72° C. The reaction was terminated with one extension cycle at 72° C. for 10 min. PCR products of the correct size (1.2 kb) were gel-purified and cloned into the pGEM-T easy vector. DNA sequence analysis of randomly selected clones revealed five unique plasmids: pGEMTE-sfPS5, pGEMTE-sfPS9, pGEMTE-sfPS11, pGEMTE-sfPS15 and pGEMTE-sfPS18 (Table 1 below).

To amplify a prephenate dehydrogenase (PDH) gene probe, degenerate oligonucleotide primers (Pdhf: 5'-GGSACCGGSCTSATCGGBACSTCS-3', SEQ ID NO: 52; and Pdhr: 5'-GTGSGAGACGAGSGCCACSGCSCG-GTCGTG-3'; S=G+C, B=G+C+T, SEQ ID NO: 53) were designed based on the alignment of PDH proteins from *Actinoplanes* sp. ATCC33076 (AX417445), *S. coelicolor* A3(2) (NP733544), and *S. avermitilis* MA-4680 (NP827697). The PCR conditions were the same as described above. An amplicon of the expected size (0.5 kb) was purified and cloned into the pGEM-T easy vector to obtain plasmid pGEMTE-sfPdh. DNA sequence analysis confirmed the insert (538 bps) codes for the N-terminal portion of a putative PDH.

Inactivation of enduracidin NRPS genes. The NRPS substrate specificity sequences extracted from the insert of pGEMTE-sfPS11, pGEMTE-sfPS15 and pGEMTE-sfPS18 predicted that they activate Thr, Hpg and Asp, respectively, and are consistent with involvement in enduracidin formation (Challis et al, *Chem. Biol.* 7: 211-224, 2000; Rausch et al, *Nucleic Acids Res.* 33: 5799-5808, 2005; Stachelhaus et al, *Chem. Biol.* 6: 493-505, 1999). These plasmid inserts were used to construct gene disruption plasmids in vector pXY300, an *E. coli*/Streptomyces temperature-sensitive conjugal vector (Yin et al, *Gene* 312: 215-224, 2003). A 1 kb fragment from plasmid pSET152 carrying the aac(3)IV gene conferring apramycin resistance ($Am^R$) was amplified by PCR using primers that introduced BamHI/HindIII restriction sites at both ends (apraRf: 5'-CACGGATCCAAGCTTGGTTCAT-GTGCA-3' and apraRr: 5'-ATCGGATCCAAGCTTACGT-GTTGC-3'; BamHI/HindIII sites are in bold, SEQ ID NOs: 54 and 55, respectively). The gene disruption plasmids were constructed as follows: the $Am^R$ fragment was ligated with the unique BglII site in the insert of pGEMTE-sfPS11 to yield the plasmid pGEMTE-sfPS1-$Am^R$. The insert of pGEMTE-sfPS1-$Am^R$ was excised with EcoRI and ligated with similarly restricted pXY300 to obtain the final construct pXY300-sfPS11-$Am^R$. Site-directed mutagenesis was used to introduce BglII restriction sites near the middle of the pGEMTE-sfPS15 and pGEMTE-sfPS18 inserts. Two sets of primers were synthesized (sfPS15BglIIf: 5'-TCTACGTC-CTGGACAGATCTCTGAACCCGGTG-3' and sfPS15BglIIr: 5'-CACCGGGTTCAGAGATCTGTCCAG-GACGTAGA-3'; sfPS18BglIIf: 5'-TCAACCCCGTAC-CCGTCAGATCTCTGGGGGAGCT-3' and sfPS18BglIIr: 5'-AGCTCCCCCAGAGATCTGACGGG-TACGGGGTTGA-3'; BglII sites are in bold; SEQ ID NOS: 56, 57, 58, and 59, respectively), and the desired BglII sites were created using the QuikChange® Site-Directed Mutagenesis kit (Stratagene) following the manufacturer's protocol. The $Am^R$ fragment was ligated into the newly created BglII sites to produce plasmids pGEMTE-sfPS15-$Am^R$ and pGEMTE-sfPS18-$Am^R$. The inserts of these two plasmids were excised by EcoRI digestion and ligated with the similarly restricted pXY300 to give the final constructs pXY300-sfPS15-$Am^R$ and pXY300-sfPS18-$Am^R$.

The gene disruption plasmids were individually introduced into *E. coli* S17-1 by transformation, and then conjugation with *S. fungicidicus* was carried out according to the literature (Kieser et al, *Practical Streptomyces Genetics*, John Innes Foundation, Crowes Printers, Norwich, England (eds) 2000). Briefly, freshly harvested *S. fungicidicus* spores were pregerminated and *E. coli* S17-1 cells were grown overnight at 37° C. in Terrific broth (Sambrook & Russell, *Molecular Cloning A Laboratory Manual* $3^{rd}$ edn. 2001). Serial dilutions of the germinated spore suspension were made and 100 μl of each dilution was mixed with an equal volume of *E. coli* S17-1 harboring the pXY300-based disruption plasmids. The solutions were plated onto ISP4 agar plates with addition of 10 mM $MgCl_2$ and incubated for 22 hrs at either 30 or 37° C. Each plate was overlayed with 3 ml of soft nutrient agar containing sodium nalidixate and apramycin (Am) (0.5 mg/ml each) and further incubated at 30° C. for about one week. Isolated exconjugants that survived antibiotic selection were purified by streaking onto ISP4 agar plates supplemented with sodium nalidixate and Am (50 μg/ml each).

To conduct the gene disruption experiments, exconjugants were first cultured in TSB liquid medium containing Am (5 μg/ml) at 30° C. for 24 hrs at which time the mycelia were harvested, homogenized and used to inoculate TSB and YEME liquid media supplemented with Am (5 μg/ml). After 3 to 6 days incubation at 40° C., the mycelia were homogenized and plated onto ISP4 agar plates containing Am (50 μg/ml) and incubated at 30° C. for one week. Genomic DNA was isolated from randomly selected individual surviving colonies and analyzed by Southern blot to confirm that single or double crossover disruption had occurred.

Construction of *S. fungicidicus* genomic libraries. Genomic DNA was prepared from *S. fungicidicus* ATCC21013 wild type and disruptant strains according to Kieser et al (Kieser et al, *Practical Streptomyces Genetics*, John Innes Foundation, Crowes Printers, Norwich, England (eds) 2000)). Three genomic libraries were constructed using the CopyControl™ Fosmid Library Production kit and EPI300™ *E. coli* plating strain (Epicentre) following the manufacturer's specifications. Briefly, chromosomal DNA was end-repaired and fractionated on a 1% low melting point agarose gel. The band at approximately 40 kb was excised and recovered from the agarose gel. After gelase digestion, the DNA was precipitated with sodium acetate and ethanol. Purified genomic DNA was ligated with linearized, dephosphorylated pCC1FOS™ vector at room temperature for 2 hrs. The ligation mixture was packaged using MaxPlax™ Lambda Packaging Extract (Epicentre) followed by transfection into *E. coli* EPI300™ cells.

The first fosmid library was constructed using *S. fungicidicus* wild type genomic DNA. A partial genome scan was performed by end sequencing the inserts of 389 randomly selected clones using the universal T7 promoter primer. Eleven clones were identified as harboring a portion of an enduracidin or other NRPS gene cluster. Both ends of these inserts were sequenced.

The second fosmid library was constructed using pooled genomic DNA from *S. fungicidicus* strains with disrupted enduracidin NRPS genes. This library included approximately 60,000 colonies and was plated on LB agar medium containing Am (100 mg/ml). Only 91 clones survived antibiotic selection. The fosmids were purified and the inserts end-sequenced in order to find DNA segments that spanned gaps between positive fosmids in the first library.

A third fosmid library was constructed using wild-type genomic DNA and was divided into two portions of approximately 5500-6000 colonies. Each portion was screened by in situ hybridization. The first portion of the library was screened using a 5.8 kb BamHI fragment from the left end of the pXYF24 insert and a fragment of a Thr A domain amplified by PCR. Forty positive colonies were obtained and 24 of these were randomly selected for end sequencing. This allowed the extending inserts in fosmids pXYF103 and pXYF305 to be identified. The second portion of this library was screened using a 2.6 kb internal BamHI fragment from the pXYF305 insert. Thirty one positive colonies were identified and 16 were end sequenced, identifying fosmid pXYF607 that further extended the contiguous cloned region of DNA.

HPLC analysis of enduracidin production. Fermentation conditions for the production of enduracidin from wild-type S. fungicidicus ATCC21013 and the disruptant strains SfPS18D17 and SfPS18D29 were as previously described (Higashide et al. J. Antibiot. 21: 126-137, 1968). For HPLC analysis, 60 g of freshly harvested mycelia was washed with 120 ml deionized water, resuspended in 120 ml methanol and sonicated with a microprobe tip for 1 min at 15 watts. The mixture was shaken at 230 RPM at 18° C. for 3 hrs, then centrifuged at 2000 g for 20 min. The supernatant was collected and evaporated to near dryness at 35° C. under reduced pressure, and the precipitate resuspended in 10 ml of 90% methanol. The solution was adjusted to pH 4.3 with 1 M HCl, and centrifuged at 2000 g for 20 min. The supernatant was filtered through a 0.45 μm syringe filter prior to analysis. HPLC was performed using a Gemini $C_{18}$ column (4.6×150 mm, 5 μm, Phenomenex) with isocratic elution in 30% acetonitrile and 70% 50 mM $NaH_2PO_4$, pH 4.5 at a flow rate of 1.0 ml/min. The UV region from 200-300 nm was scanned with a photodiode array detector, or 267 nm was monitored with a variable wavelength detector.

Southern hybridization. S. fungicidicus genomic DNA was cleaved with restriction endonucleases, electrophoresed in 0.8% agarose gels and transferred onto Hybond-N nylon membranes (Roche). The manufacturer's protocol for colony lifts for in situ hybridization was followed. DNA probes were prepared using a digoxigenin-labeled system and hybridization was revealed using a digoxigenin-DNA detection kit (Roche).

DNA Sequencing and analysis. Routine DNA sequencing of plasmids and PCR products, primer walking sequencing, and fosmid insert end sequencing were performed at the Oregon State University Center for Genome Research and Biocomputing (CGRB) using the Amplitaq T dye-terminator sequencing system (Perkin Elmer) and Applied Biosystems automated DNA sequencers (models 373 and 377). Fosmid DNA used for sequencing was prepared from 5 ml induced LB culture with QIAprep Spin Miniprep kit (Qiagen). Sequencing of the entire fosmid inserts at ten to twenty fold coverage was performed by Macrogen (Seoul, South Korea). The nucleotide sequences were determined for both strands. Sequence analysis was carried out using the Vector NTI (Invitrogen) software package. Nucleotide and amino acid sequence similarity comparisons were carried out in public databases using the BLAST program (Altschul et al. J. Mol. Biol. 215: 403-410, 1990).

GenBank accession number. The nucleotide sequence for the region of the S. fungicidicus genome harboring the enduracidin biosynthetic gene cluster has been deposited in GenBank (Accession number DQ403252; SEQ ID NO: 49).

Example 2

Isolation and Characterization of an Enduracidin Gene Cluster

This example describes the cloning of the enduracidin biosynthesis gene cluster.

NRPSs have highly conserved core motifs located in the A (adenylation) and PCP domains that permit the use of degenerate PCR primers to specifically amplify fragments of the NRPS genes (Marahiel et al., Chem. Rev. 97: 2651-2674, 1997). Using S. fungicidicus ATCC21013 genomic DNA as template and a set of degenerate oligonucleotide primers targeted for regions coding for the A3 and PCP motifs, PCR yielding amplicons of the expected size (approx. 1.2 kb) that were cloned and sequenced. Five unique peptide synthetase (PS) probes/sequences were identified and designated sfPS5, sfPS9, sfPS11, sfPS15 and sfPS18. The standard in silico methods to predict A domain substrate specificity indicated each of the cloned PS probes was expected to activate an amino acid found in enduracidin (Challis et al. Chem. Biol. 7: 211-224, 2000; Rausch et al. Nucleic Acids Res. 33: 5799-5808, 2005; and Stachelhaus et al. Chem. Biol. 6: 493-505, 1999).

Enduracidin contains the 10 nonproteinogenic amino acid residues including D- and L-enduracididine (End), D- and L-4-hydroxyphenylglycine (Hpg), 3,5-dichloro-L-4-hydroxyphenylglycine (Dpg), L-citrulline (Cit) and D-ornithine (Orn) (FIG. 1). The genes directing Hpg biosynthesis in the chloroeremomycin pathway have been identified and their products characterized (Choroba et al. J. Am. Chem. Soc. 122: 5389-5390, 2000; Hubbard et al. Chem. Biol. 7: 931-942, 2000; and van Wageningen et al. Chem. Biol. 5: 155-162, 1998). However, these genes have not been previously identified in S. fungicidicus. Homologs of one of the genes, encoding prephenate dehydrogenase, are present in several other NRPS biosynthesis gene clusters (Chiu et al. Proc. Natl. Acad. Sci. U.S.A. 98: 8548-8553, 2001; Hojati et al. Chem. Biol. 9: 1175-1187, 2002; Li et al. Chem. Biol. 11: 107-119, 2004; Pootoolal et al. Proc. Natl. Acad. Sci. U.S.A. 99: 8962-8967, 2002; and Sosio et al. Chem. Biol. 10: 541-549, 2003). To aid in rapidly identifying an enduracidin gene cluster, a specific PDH gene probe was amplified. Degenerate primers were designed from conserved regions identified in prephenate dehydrogenases from other NRPS gene clusters and used to amplify a 0.5 kb PCR product from S. fungicidicus genomic DNA. The PCR product was cloned into pGEM-T easy vector to yield pGEMTE-sfPhd-Nt. Sequence analysis confirmed it encoded the N-terminal portion of a putative PDH.

Example 3

Inactivation of the siPS11-, sfPS15- and sfPS18-Containing NRPS Genes

This example demonstrates that the genes amplified in Example 2 are involved in enduracidin biosynthesis.

Figure 2A:
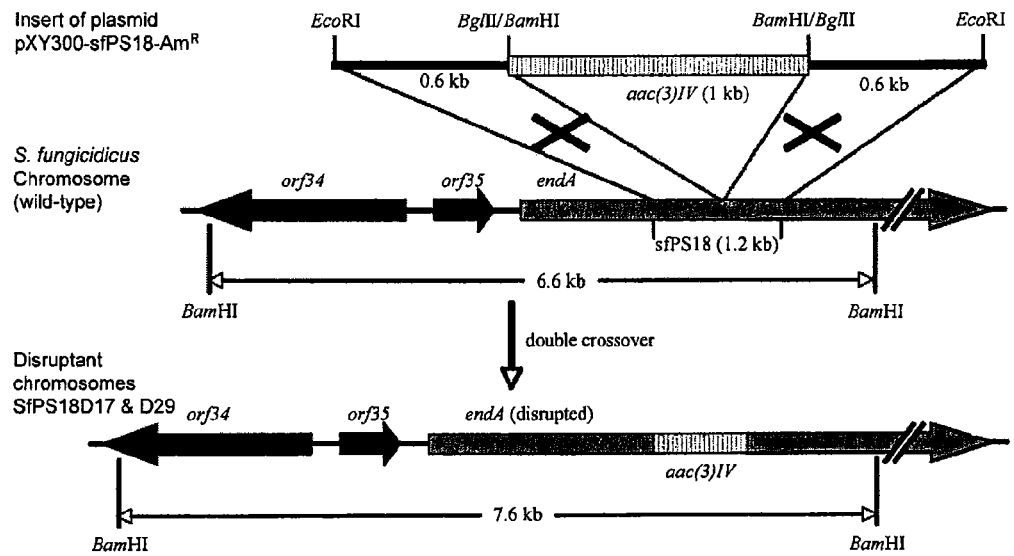
FIG. 2A is a schematic illustrating the insertion of the apramycin resistance marker aac(3)IV into the region of sfPS18 encoding the A domain of EndA via double crossover homologous recombination.
Figure 2B:
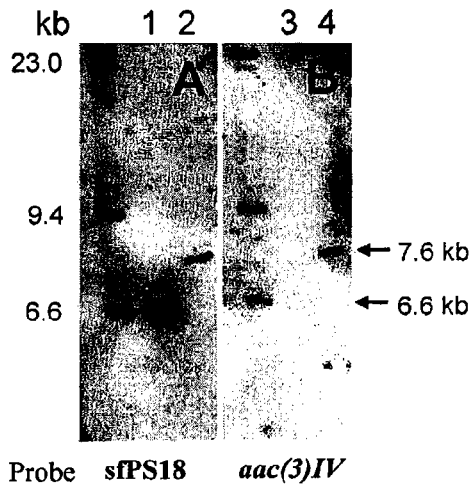
FIG. 2B is a digital image of a gel of wild-type *S. fungicidicus* (Lanes 1 and 3) and disruptant (SfPS18D29) genomic DNA digested with BamHI. Blot A was probed with DIG-labeled sfPS18 and blot B was probed with DIG-labeled aac(3)IV.
Figure 2C:
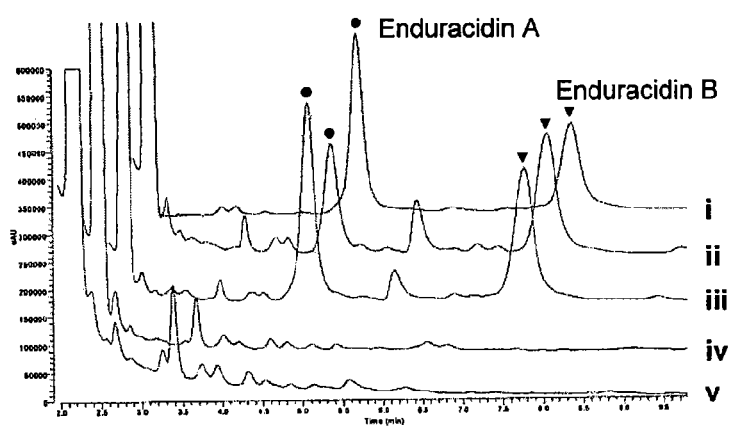
FIG. 2C is a tracing illustrating enduracidin production by *S. fungicidicus* wild-type and mutant strains.

To provide direct evidence that the genes corresponding to the PCR-amplified probes in Example 2 are involved in enduracidin biosynthesis, probes corresponding to Thr (sfPS11), Hpg (sfPS15) and Asp (sfPS18) activating A domains were used for gene disruption by single or double-crossover homologous recombination. Gene disruption constructs were made by introducing the apramycin resistance marker into sfpS11, sfpS15 and sfPS18, carried in the pGEM-T vector. These aac(3)IV-containing inserts were then transferred into the Streptomyces-E. coli temperature-sensitive conjugal shuttle vector pXY300(Yin et al, Gene 312: 215-224, 2003). The three gene disruption constructs, pXY300-sfPS11-$Am^R$, pXY300-sfPS15-$Am^R$, pXY300-sfPS18-$Am^R$, were separately introduced into S. fungicidicus by intergeneric conjugation (Kieser et al. Practical Streptomyces Genetics 2000). Independent double-crossover disruptants obtained with pXY300-sfPS18-$Am^R$ (FIG. 2A) were confirmed by Southern blot analysis of the chromosomal DNA (FIG. 2B) and later by sequencing the insert of disrupted fosmid pXYFD16. The loss of enduracidin production from the double-crossover mutant strains SfPS18D17 and SfPS18D29 was confirmed by HPLC (See FIG. 2C). FIG. 2C i including Enduracidin A and B standards; FIG. 2C ii, methanolic extract of wild-type mycelia; FIG. 2C iii, co-injection of wild-type extract and standards; and FIG. 2C iv and v, methanolic extract of S. fungicidicus disruptant strains SfPS18D17 and SfPS18D29.

Southern blot analysis revealed that constructs pXY300-sfPS11-Am$^R$ and pXY300-sfPS15-Am$^R$ produced untargeted disruptants (SfPS11D9, SfPS15D12 and SfPS15D31) through partial homologous recombination. sfPS11 exhibited 96% identity over 879 nucleotides with the DNA sequence coding for the Ser 2-activating A domain from the end cluster. Likewise, six Hpg/Dpg-activating A domains in the end cluster, including module 17 corresponding to sfPS15, share 78-90% identity over 879 nucleotides. Inactivation of the enduracidin Ser$^{12}$-activating A domain via single crossover partial homologous recombination was also confirmed by sequencing the insert of the disrupted fosmid pXYFD18. HPLC analysis indicated that these disruptants also lost the ability to produce enduracidin.

Example 4

Cloning and Sequencing the Enduracidin Biosynthetic Gene Cluster

This example describes the cloning and sequencing of the enduracidin biosynthetic gene cluster.

A first fosmid genomic library was constructed from S. fungicidicus wild-type chromosomal DNA. A partial genome scan to be conducted to identify fosmid inserts with ends homologous to genes expected for enduracidin biosynthesis. Eleven clones were identified with NRPS genes or sequence similar to genes in the ramoplanin cluster. Three fosmids, pXYF24, pXYF148 and pXYF200, were selected for further analysis. Restriction and Southern blot analysis indicated that pXYF24 overlaps pXYF148 but neither of them overlaps pXYF200. One end of pXYF200 encodes an Hpg activating A domain and an incomplete thioesterase domain, suggesting this segment should be near the end of the clustered NRPS genes.

Figure 3A:
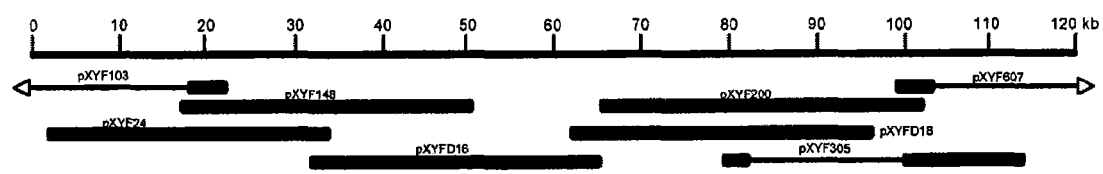
FIG. 3A is a schematic showing overlapping fosmid inserts cloned from the *S. fungicidicus* genome that harbors the enduracidin biosynthetic gene cluster. Thick lines represent the 116 kb region that was fully sequenced (SEQ ID NO: 49). Arrows indicate the insert extends beyond the 120 kb scale shown.

A second library was constructed using mixed genomic DNA prepared from the five strains with inactivated enduracidin NRPS genes. The aim was to use a positive selection strategy to find fosmids that would connect pXYF148 to pXYF200 and also extend the region located downstream of the thioesterase end of pXYF200. Because the aac(3)IV gene was inserted into the enduracidin cluster in these strains, clones in this library that survive antibiotic selection harbor a fragment of the targeted cluster. A total of 91 apramycin-resistant clones were identified. Restriction fragment length analysis and additional sequence from primer walking and subcloning, identified two disrupted fosmids, pXYFD16 and pXYFD18, that connected pXYF148 with pXYF200. With these fosmids, an overlapping fosmid insert map covering approximately 100 kb was constructed as shown in FIG. 3A.

Fosmids extending the contiguous segment of the chromosome beyond the ends of pXYF24 and pXYF200 were not identified in either the original wild-type or the disruptant library. Therefore, a second S. fungicidicus wild-type genomic library was constructed and screened. The new library was divided into two portions and each was screened by in situ hybridization. The first portion was screened using a fragment from the left end of the pXYF24 insert and a NRPS A domain predicted to activate Thr. This allowed fosmid pXYF103 to be identified, which overlaps with and extends 15 kb beyond the left end of pXYF24, and fosmid pXYF305 that overlaps with and extends 14 kb beyond the right end of pXYF200 as illustrated in FIG. 3A.

The second portion of this library was screened using an internal BamHI fragment from the pXYF305 insert. Fosmid pXYF607 was identified that overlaps with and extends 15 kb beyond the right end of pXYF305. In all, eight overlapping fosmid inserts were identified that span approximately 148 kb of contiguous DNA on the S. fungicidicus chromosome. The inserts from fosmids pXYF24, pXYF148, pXYFD16, pXYFD18 and pXYF200 were completely sequenced and that of pXYF305 was partially sequenced, covering a 116 kb region that harbors the entire enduracidin (end) biosynthetic gene cluster (see FIG. 3A).

Example 5

Analysis of the Enduracidin (End) Biosynthetic Gene Cluster

This example provides an overall analysis of the enduracidin biosynthetic gene cluster.

Figure 3B:
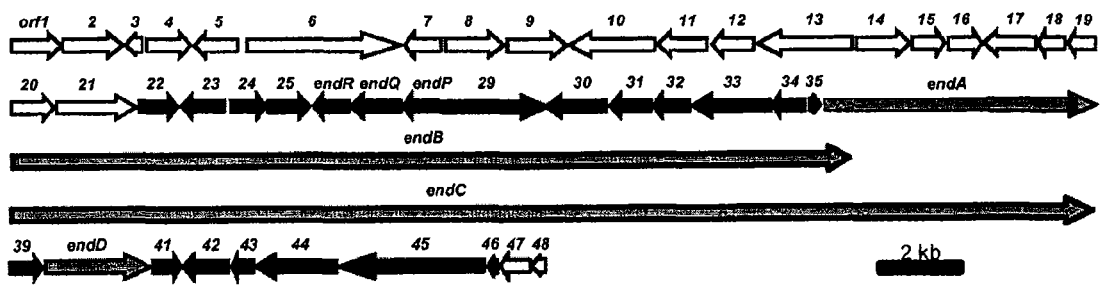
FIG. 3B is a schematic showing the organization of the sequenced end cluster (filled arrows) and flanking regions (white arrows). Lightly shaded arrows represent the non-ribosomal peptide synthetase (NRPS) genes.

The end gene cluster resides on an 84 kb segment of the S. fungicidicus chromosome and includes 25 ORFs (encoding SEQ ID NOs: 22 to 46). The predicted function for each ORF was assigned by comparing the translated product with known proteins in public databases as provided in Table 1. All of the references in Table 1 are each incorporated by reference in their entirety. Table 1 provides a summary of ORFs identified in an enduracidin gene cluster and flanking regions. The organization of the end cluster is shown in FIG. 3B. Size indicates the number of amino acids in the translated product. Homologues found in the related ramoplanin biosynthetic gene cluster are presented in Table 1 separately from the best matching protein identified by BLAST analysis.

Genes identified include those required for the formation of the lipid and nonproteinogenic amino acid precursors, assembly of the peptide backbone, export and regulation of enduracidin biosynthesis. Twenty-one ORFs exhibit significant similarity with counterparts in the ramoplanin cluster as illustrated in Table 1. The probable boundaries of the end cluster were established by comparison of the sequence with the ramoplanin gene cluster and from the deduced functions of the end and flanking gene products.

Four peptide synthetases, designated EndA, EndB, EndC and EndD, assemble the 17 residue enduracidin peptide backbone. The organization of the modules and domains in these four proteins is shown in FIG. 4 and, in general, follows the NRPS colinearity principle (Marahiel et al. Chem. Rev. 97: 2651-2674 1997). However, an A domain from module 8 in EndB that should incorporate L-allo-Thr$^8$ and EndD, which is a single module NRPS with a unique N-terminal region and an A domain predicted to activate Thr are absent. The other modules and domains exhibit typical NRPS features and the predicted substrate for the A domain of each module correlated with the residue expected based on the colinearity rule are presented in Table 2 below. An exemplary NRPS adenylation domain for an EndA module includes a substrate recognition sequence of $DX_1X_2X_3VGX_4V$ (SEQ ID NO: 64), whereby $X_1$ can be an L or F, $X_2$ can be a T or W, $X_3$ can be a K or S, $X_4$ can be an H or M, such as EndA-m1 or -m2 (SEQ ID NOs: 65 and 66). Exemplary NRPS adenylation domain for an EndB module includes a substrate recognition sequence of SEQ ID NOs: 67-72, for an EndC module SEQ ID NOs 73-80, and for an EndD module SEQ ID NO: 81.

TABLE 2

Derived substrate signature sequences for NRPS adenylation domains identified in the enduracidin cluster.

| SEQ ID NO: | Module | Substrate recognition sequence | Corresponding amino acid in enduracidin | Predicted amino acid |
|---|---|---|---|---|
| 64 | EndA | DXXXVGXV | | |
| 65 | EndA-m1 | DLTKVGHV | lipo-L-Asp | Asp |
| 66 | EndA-m2 | DFWSVGMV | L-Thr | Thr |
| 67 | EndB-m1 | DAYHLGLL | D-Hpg | Hpg |
| 68 | EndB-m2 | DMETDGSV | D-Orn | Orn |
| 69 | EndB-m3 | DFWSVGMV | D-allo-Thr | Thr |
| 70 | EndB-m4 | DAYHLGLL | L-Hpg | Hpg |
| 71 | EndB-m5 | DAYHLGLL | D-Hpg | Hpg |
|  | EndB-m6 | No A domain | L-allo-Thr | |
| 72 | EndB-m7 | DMEADGAV | L-Cit | Orn/Lys |
| 73 | EndC-m1 | DAETDGSV | D-End | Lys |
| 74 | EndC-m2 | DAYHLGML | L-Hpg | Hpg |
| 75 | EndC-m3 | DVWSVAMV | D-Ser | Thr |
| 76 | EndC-m4 | DAYHLGLL | L-Dpg | Hpg |
| 77 | EndC-m5 | DILQLGLV | Gly | Gly |
| 78 | EndC-m6 | DAETDGSV | L-End | Lys |
| 79 | EndC-m7 | DIFQLALV | D-Ala | Ala |
| 80 | EndC-m8 | DAYHLGLL | L-Hpg | Hpg |
| 81 | EndD | DFWSVGMV | L-allo-Thr | Thr |

The NRPS substrate binding pocket databases (*Nucleic Acids Res*. July 1; 32 (Web Server issue): W405-W413, 2004) do not contain signature sequences for citrulline (L-Cit, module 9) or enduracididine (D- and L-End, modules 10 and 15, respectively). The same A domain substrate recognition sequence, DFWSVGMV (SEQ ID NO: 66), is found in modules incorporating L-Thr[2] (EndA-m2), D-allo-Thr[5] (EndB-m3), and L-allo-Thr[8] (EndD). EndA-m2 and EndB-m3 are both predicted to recognize L-Thr as substrate and, accordingly, the regions between core motifs A4 and A5 that define much of the substrate binding pockets of the A domains are identical at the amino acid level. The A domain of EndD is predicted to recognize the rare L-allo diastereomer of Thr. The same eight substrate specifying residues are shared with EndA-m2 and EndB-m3. However, the A4 to A5 region of EndD shares only 59% identity with that of EndA-m2 and EndB-m3 and is three residues longer, allowing for differences that could discriminate between L-Thr and L-allo-Thr. Also, the location of EndC-m3 corresponds to the incorporation of D-Ser[12] but the substrate recognition sequence (DVWSVAMV; SEQ ID NO: 75) most closely resembles Thr incorporating A domains and shows moderate similarity to Ser A domains from the *Pseudomonas fluorescens* Pf-5 pyoverdin synthetase (Paulsen et al. *Nat. Biotechnol.* 23: 873-878, 2005). The corresponding amino acid in ramoplanin is D-allo-Thr and the deduced substrate specificity sequence for the ramoplanin module 12 A domain is DFWSVGMV (SEQ ID NO: 81). The presence of a Phe in the second position of the substrate specificity sequence may be a factor for Thr recognition and Phe is found at this position in all three enduracidin synthetase Thr A domains (Table 2) (Challis et al. *Chem. Biol.* 7: 211-224, 2000). Inspection of the endC and ramoC sequence encoding this residue reveals a GTC in endC and a TTC in ramoC. The mutation changes the Val codon GUC to the Phe codon UUC (or vice versa) and accounts for the switch in substrate specificity from Ser to Thr by the respective peptide synthetases. Finally, the A domain in the 3,5-dichloro-L-4-hydroxyphenylglycine (Dpg) module shares the same substrate specificity sequence (DAYHLGLL; SEQ ID NO: 70 or 71) as four of the Hpg A domains, suggesting that chlorination of Hpg to yield the Dpg residue occurs on a NRPS-bound species or the nascent peptide, rather than at the free amino acid stage.

Enduracidin assembly presumably begins with EndA (SEQ ID NO: 36), predicted to be a 2101 amino acid (224 kDa) two module NRPS with an N-terminal condensation domain (EndA-C1) similar to those found in other lipopeptide loading modules proposed to accept a lipid substrate from an acyl carrier protein (Duitman et al. *Proc. Natl. Acad. Sci. U.S.A.* 96: 13294-13299, 1999). These have been referred to as $C^{III}$ domains and examples are found in the ramoplanin, CDA, and daptomycin systems (Miao et al. *Microbiology* 151: 1507-1523, 2005; Miao et al. *J. Ind. Microbiol. Biotechnol.* 33: 129-140, 2006). EndA-C2 then couples N-lipo-L-Asp[1] and L-Thr[2] to form a dipeptide that is transferred to EndB (6943 aa, 741 kDa). EndB (SEQ ID NO: 37) is comprised of seven modules, but as noted above, the identified sequence is missing an A domain from module 8 (EndB-m6). EndD (SEQ ID NO: 40) is a single module NRPS (859 aa, 91 kDa) with an A domain predicted to activate Thr and a PCP domain. Preceding the A domain is an N-terminal region of approximately 280 aa that shares weak homology with NRPS C domains. Presumably, EndD activates and tethers L-allo-Thr to the PCP domain and the N-terminal domain directs the protein-protein interaction for the transfer of L-allo-Thr to module 8 (EndB-m6). Similar proposals are suggested for syringomycin and ramoplanin biosynthesis (Guenzi et al. *J. Biol. Chem.* 273: 32857-32863, 1998; McCafferty et al. *Biopolymers* 66: 261-284, 2002). EndB, with possible participation of EndD, then catalyzes the peptidyl chain elongation from amino acid residue L-Thr[2] to L-Cit[9]. Experimental confirmation of the function of the N-terminal portion of EndD and proof of in trans loading of EndB is underway. EndC (SEQ ID NO: 38) is the final NRPS (8986 aa, 955 kDa) and includes eight modules and catalyzes the peptidyl chain extension from amino acid residues D-End[10] to L-Hpg[17], and terminates with a thioesterase (TE) domain that promotes the cyclization and release of the peptide.

There are 18 thiolation or peptidyl carrier protein (T or PCP) domains in the four enduracidin synthetases identified herein (SEQ ID NOs: 36, 37, 38 and 40). Conceptually 17 PCP domains are sufficient for enduracidin assembly. The extra PCP domain occurs because of the proposed transfer of L-allo-Thr from EndD (SEQ ID NO: 40) to EndB-m6 (module 8 included within SEQ ID NO: 37). One possibility for substrate transfer between these NRPSs is that the EndB-m6 PCP is redundant or non-functional and the C domain of EndB-m7 directly condenses the L-allo-Thr on EndD with the L-Cit residue bound to the EndB-m7 PCP. The C domain of EndB-m6 could couple the resulting dipeptide on EndB-m7 with the peptidyl species attached to EndB-m5, allowing normal peptide assembly to continue. Alternatively, EndD could transfer the tethered L-allo-Thr directly to the PCP of EndB-m6, but a PCP to PCP transfer may require the action of a separate acyltransferase (Vaillancourt et al. *Nature* 436: 1191-1194, 2005). The PCP domain core motif found in both EndD (SEQ ID NO: 102) and EndB-m6 (SEQ ID NO: 91) is LGGNSL. The occurrence of an Asn residue preceding the Ser to which the 4'-phophopantetheine arm is attached is rarely observed. For PCP domains that accept L amino acids, T(L) domains, the core motif is LGGDSI, whereas for PCP domains that are associated with epimerization (E) domains and accept D amino acids, T(D) domains, the consensus core motif is XGGHSL (contained within SEQ ID NO: 93) (Linne et al. *Biochemistry* 40: 15824-15834, 2001). The corresponding PCP domains in the ramoplanin synthetases also have an Asn residue in the core motif Table 3 correlates the PCP domains in the enduracidin synthetases with the respective modules and corresponding substrate amino acids. An exemplary PCP domain for an EndA module includes a substrate recognition sequence of DDDFFALGGHSLXATR (SEQ ID NO: 82), whereby X can be a P or L, such as EndA-m1 or -m2 (SEQ ID NOs: 83 and 84). Exemplary PCP domains for an EndB module includes a substrate recognition sequence of $X_1DX_2FFALGGX_3SLX_4X_5X_6X_7$ (SEQ ID NO:85), whereby $X_1$ can be an E or D, $X_2$ a D or H, $X_3$ an H or N, $X_4$ an L or V, $X_5$ an A or V, $X_6$ a V, M or T, and an $X_7$ an R or S (such as SEQ ID NOs: 86-92). Exemplary PCP domains for an EndC module are provided in SEQ ID NOs: 93-101 and an EndD module in SEQ ID NO: 102. For example, a PCP domain in an EndC module can include the motif of $X_1DDFFX_2X_3GGHSLLX_4X_5X_6$ (SEQ ID NO:93) in which $X_1$ can be an E or D, $X_2$ an A or T, $X_3$ and L or K, $X_4$ an A or V, $X_5$ a V or T and $X_6$ an S, R or V, such as in SEQ ID NOs: 94-101.

TABLE 3

Comparison of conserved core motifs in the peptidyl carrier (PCP) domains of enduracidin synthetases.

| SEQ ID NO: | Module | PCP-domain Core motif region | Corresponding amino acid |
|---|---|---|---|
| 82 | EndA | DDDFFALGGHSLXATR | |
| 83 | EndA-m1 | DDDFFALGGHSLPATR | Lipo-L-Asp |
| 84 | EndA-m2 | DDDFFALGGHSLLATR | L-Thr |
| 85 | EndB | XDXFFALGGXSLXXXX | |
| 86 | EndB-m1 | EDDFFALGGHSLLAVS | D-Hpg |
| 87 | EndB-m2 | DDDFFALGGHSLLVVS | D-Orn |
| 88 | EndB-m3 | DDDFFALGGHSLLAVS | D-allo-Thr |
| 89 | EndB-m4 | DDDFFLLGGHSLLAMR | L-Hpg |
| 90 | EndB-m5 | EDDFFALGGHSLLAVS | D-Hpg |
| 91 | EndB-m6 | DDDFFALGGNSLVATR | L-allo-Thr |
| 92 | EndB-m7 | DDHFFALGGHSLLATR | L-Cit |
| 93 | EndC | XDDFFXXGGHSLLXXX | |
| 94 | EndC-m1 | EDDFFALGGHSLLAVS | D-End |
| 95 | EndC-m2 | DDDFFTLGGHSLLVTR | L-Hpg |
| 96 | EndC-m3 | DDDFFALGGHSLLAVS | D-Ser |
| 97 | EndC-m4 | DDDFFAKGGHSLLATV | L-Dpg |
| 98 | EndC-m5 | DDDFFALGGHSLLAVS | Gly |
| 99 | EndC-m6 | DDDFFALGGHSLLATR | L-End |
| 100 | EndC-m7 | DDDFFALGGHSLLAVS | D-Ala |
| 101 | EndC-m8 | DDDFFALGGHSLLAVR | L-Hpg |
| 102 | EndD | SDSFWELGGNSLLAVR | L-allo-Thr |

With the exception of EndB-m6 and EndD discussed above, all enduracidin synthetase PCP domains in the identified gene cluster are of the T(L) type. This is consistent with the lack of E domains in the enduracidin synthetases but does not correlate with occurrence of seven D amino acids in the peptide product. Analysis of the translated products of NRPS genes from the actinomycete *Nocardia farcinica* IFM10152 reveals the core motifs of the PCP domains primarily contain Asn instead of Asp or H is (Ishikawa et al., *Proc. Natl. Acad. Sci. U.S.A.* 101: 14925-14930, 2004).

Enduracidin contains seven D amino acids but the megasynthetase contains no epimerization (E) domains and there were no racemase or epimerase genes detected in the sequenced region of the *S. fungicidicus* chromosome. This unusual situation has previously been observed in *Pseudomonas* peptide synthetases assembling the lipopeptides syringomycin (Guenzi et al. *J. Biol. Chem.* 273: 32857-32863, 1998), syringopeptin (Scholz-Schroeder et al. *Mol Plant Microbe. Interact.* 16: 271-280, 2003), and arthrofactin (Roongsawang et al. *Chem. Biol.* 10: 869-880, 2003). Ramoplanin synthetase is an actinomycete NPRS that shares this feature (McCafferty et al. *Biopolymers* 66: 261-284, 2002). The epimerization function required for the biosynthesis of syringomycin may be provided in trans by external amino acid racemase(s) (Guenzi et al. *J. Biol. Chem.* 273: 32857-32863, 1998). Biochemical analysis of recombinant A domains from these systems demonstrated that they preferentially activate L amino acids even when the excised A domain correlates with the position of a D amino acid in the peptide product (Guenzi et al. *J. Biol. Chem.* 273: 32857-32863, 1998; Recktenwald et al. *Microbiology* 148: 1105-1118, 2002; Roongsawang et al. *Chem. Biol.* 10: 869-880, 2003; and Trauger & Walsh *Proc. Natl. Acad. Sci. U.S.A.* 97: 3112-3117, 2000). This discrepancy was very recently resolved when Balibar et al. demonstrated that the D amino acids in arthrofactin are generated on the surface of the NRPS by dual function C/E domains (*Chem. Biol* 12: 1189-1200, 2005).

Figure 5:
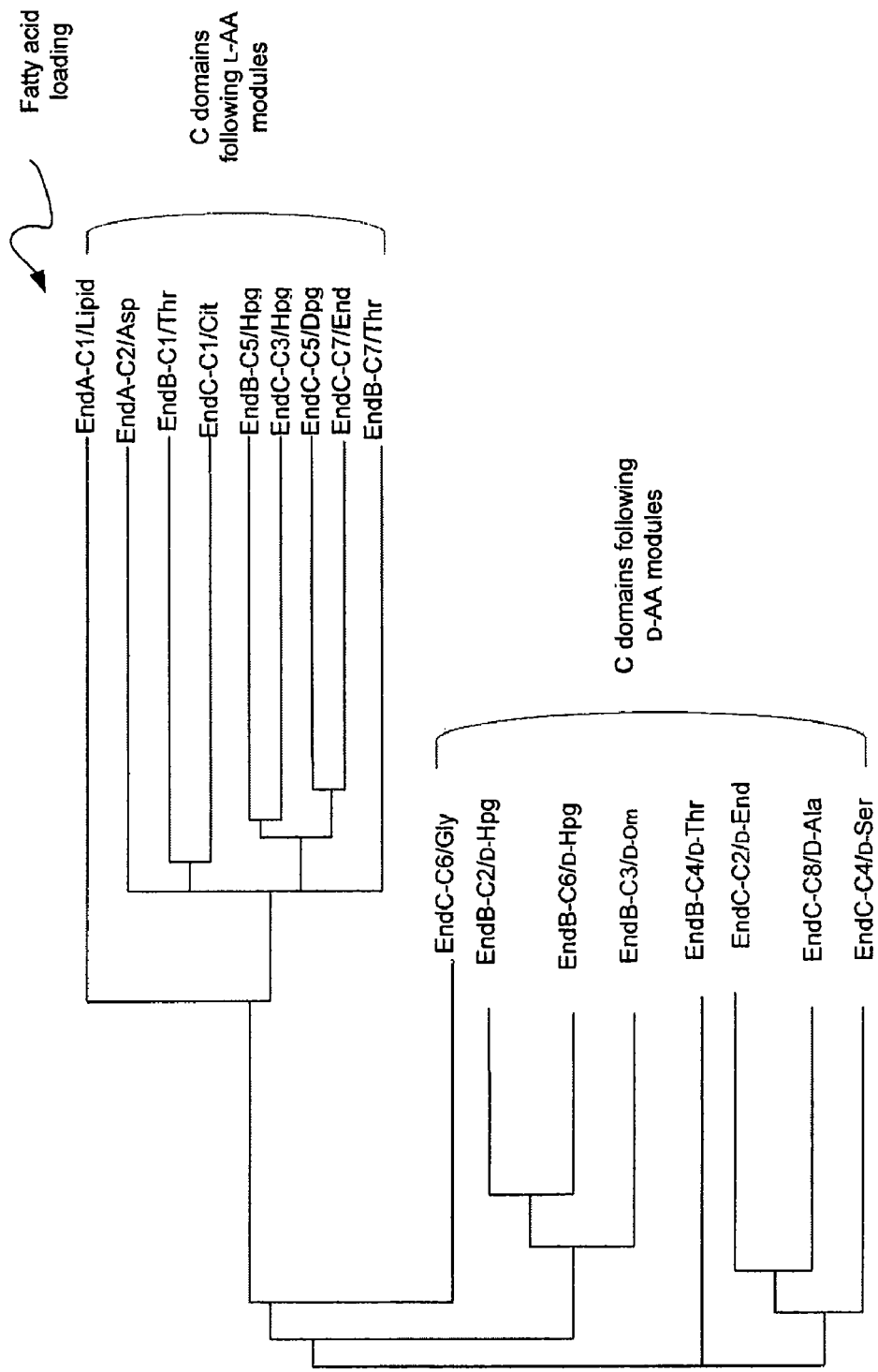
FIG. 5 is a phylogram of enduracidin synthetase condensation domains.

The formation of D amino acid residues in enduracidin likely involves the same mechanism demonstrated for arthrofactin. The C domains in both peptide assembly lines that are immediately downstream of modules corresponding to D amino acids share 50-60% overall amino acid identities and are clearly distinct from the more typical C domains following L amino acid modules (FIG. 5). The studies by Balibar et al. also revealed that epimerization of the donor peptidyl-5-enzyme species only occurred when the adjacent downstream acceptor aminoacyl-5-enzyme species was present (*Chem. Biol.* 12: 1189-1200, 2005). This is relevant to the in trans loading of EndB-m6 discussed above because this module possesses a C/E domain that should epimerize the Hpg residue on EndB-m5. The necessity of having the downstream PCP module loaded for epimerization to occur may support a loading mechanism wherein the L-allo-Thr tethered to EndD is directly transferred to the PCP of EndB-m6.

Example 6

Biosynthesis of Nonproteinogenic Amino Acids

This example provides a method of synthesizing nonproteinogenic amino acids.

The biosynthesis of Hpg has been elucidated by biochemical analysis of recombinant enzymes from the chloroeremomycin pathway (Choroba et al., *J. Am. Chem. Soc.* 122: 5389-5390, 2000; Hubbard et al., *Chem. Biol.* 7: 931-942, 2000; van Wageningen et al., *Chem. Biol.* 5: 115-162, 1998). The process requires four gene products: PDH, 4-hydroxymandelic acid synthase (HmaS), 4-hydroxymandelic acid oxidase (HmaO), and 4-hydroxyphenylglycine aminotransferase (HpgT). Orf23 (SEQ ID NO: 23) and Orf25 (SEQ ID NO: 25) are homologs of PDH and HmaS, respectively, and orf29 apparently encodes a HpgT/HmaO fusion protein (SEQ ID NO:29). In addition to orf23, *S. fungicidicus* possesses another PDH gene located outside of the end cluster that is presumably involved in normal aromatic amino acid biosynthesis. A portion of this second PDH gene was amplified by PCR and comparison of the available translated sequence (168 aa) with Orf23 (SEQ ID NO: 23) showed this region shared 61% identity. Inactivation of the second PDH gene had no effect on enduracidin production.

The unusual organization of the hmaO and hpgT homologs in a single orf in the end cluster was reconfirmed by double strand sequencing of multiple fosmid templates. HmaO and HpgT catalyze sequential reactions in the generation of Hpg and the fusion protein may lead to more efficient production of Hpg inasmuch as it contributes to six of the 17 amino acid residues in enduracidin. In the chloroeremomycin (van Wageningen et al, *Chem. Biol* 5: 115-162, 1998), balhimycin (Recktenwald et al. *Microbiology* 148: 1105-1118, 2002) and teicoplanin (Li et al. *Chem. Biol.* 11: 107-119, 2004) clusters, hmaS and hmaO are organized in a two-gene operon and in the CDA cluster, hmaO and hpgT form an operon (Hojati et al. *Chem. Biol.* 9: 1175-1187, 2002). Although the genes coding for HpgT and HmaO are adjacent in the ramoplanin cluster, there is no operon organization observed among the HpgT, HmaO and HmaS encoding genes (McCafferty et al. *Biopolymers* 66: 261-284, 2002).

Figure 6:
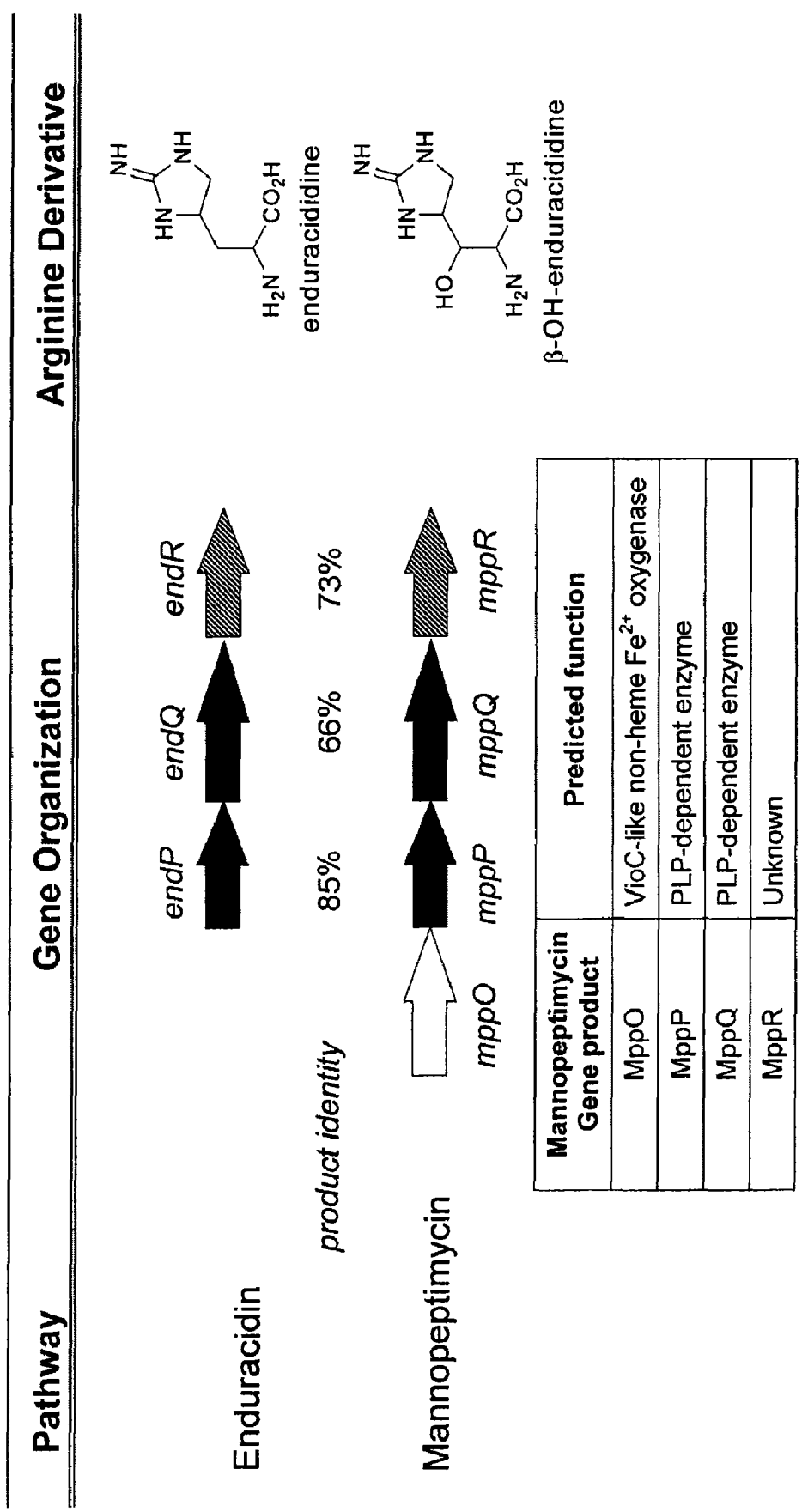
FIG. 6 is schematic showing the relationship and organization of the mppPQR and endPQR operons.

The rare D- and L-enduracididine (End) residues are known to originate from L-Arg (Hatano et al. *Agric. Biol. Chem.* 48: 1503-1508, 1984). The mannopeptimycins, isolated from a strain of *S. hygroscopicus*, contain D- and L-β-hydroxyenduracididine (β-OHEnd) residues and are other peptide antibiotics that contain this unusual amino acid (He et al. *J. Am. Chem. Soc.* 124: 9729-9736, 2002). As illustrated in FIG. 6, both the mannopeptimycin (mpp, Accession No. AY735112) and end clusters contain a three gene operon, mppPQR and endPQR, respectively, that share very high identity. Given that End and β-OHEnd are the only nonproteinogenic amino acids common to mannopeptimycin and enduracidin, the products of these three genes are proposed to direct End biosynthesis. The gene immediately upstream of the mppPQR operon, mppO, has a translated product that is homologous to VioC, a non-heme iron, α-ketoglutarate dependent oxygenase that catalyzes the formation of 2S-hydroxy-L-Arg from L-Arg (Yin & Zabriskie *Chem. Biochem.* 5: 1274-1277, 2004). VioC and the pyridoxal phosphate-dependent enzyme VioD can act in tandem to form the 2S,3R-capreomycidine residue found in the peptide antibiotic viomycin (Ju et al. *Chem. Biochem.* 5: 583-586, 2004; Yin et al. *Chem. Biochem.* 5: 1278-1281, 2004). Through gene disruption experiments and biochemical characterization of recombinant MppO, this enzyme has been demonstrated to hydroxylate the β-position of L-End and does not generate a precursor for cyclization of the Arg side chain (Haltli et al. *Chem. Biol.* 12: 1163-1168, 2005). The fact that MppO is not involved in L-End formation is consistent with absence of a mppO homolog in the end cluster.

Routes to enduracididine production can be proposed that are analogous to the formation of capreomycidine by VioD, and rely on the putative PLP-dependent enzymes EndP and/or EndQ to catalyze elimination/replacement reactions beginning with either α-hydroxy or γ-hydroxyarginine. Two additional nonproteinogenic amino acids in enduracidin are ornithine and citrulline. Genes directing the synthesis of these compounds were not expected in the cluster, inasmuch as these amino acids are normally found in the bacterial cell as intermediates in arginine metabolism.

Example 7

Formation and Attachment of the Fatty Acid Tail to Form Enduracidin A

This example describes the four gene products that are believed to be involved in the formation and attachment of the fatty acid tail to form enduracidin A.

Figure 7:
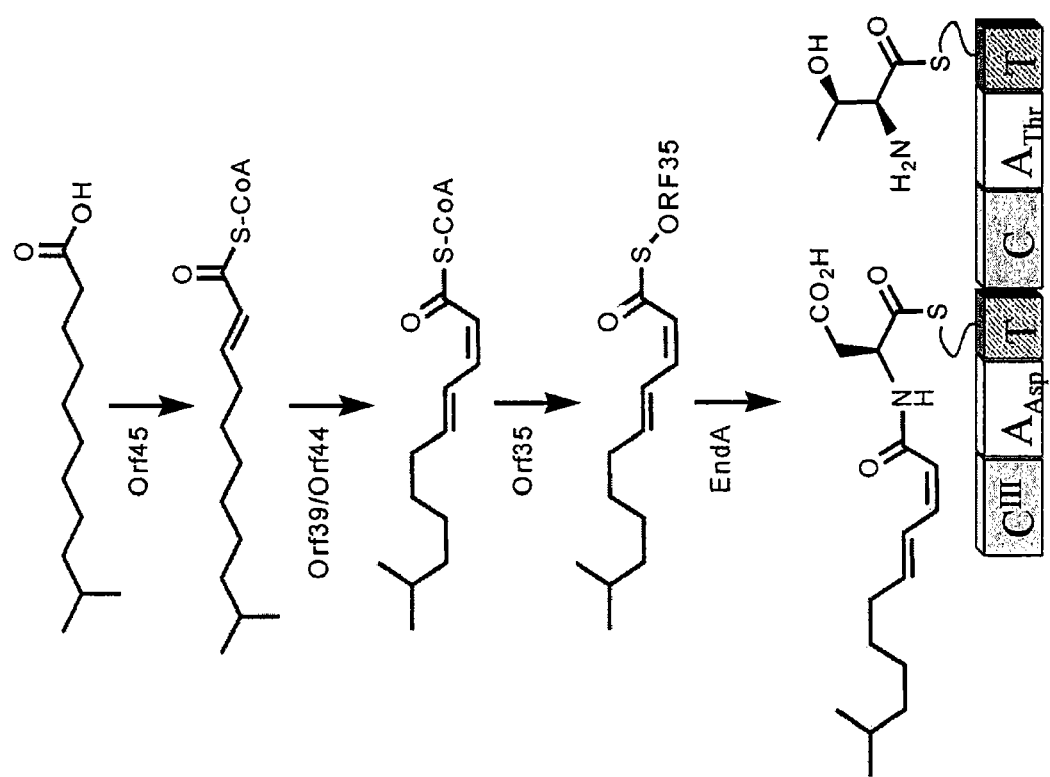
FIG. 7 is a flow chart illustrating a proposed activation, modification and attachment of the lipid tail of enduracidin A.

Enduracidins A and B differ only in the fatty acid side chain attached to the starter Asp unit (Iwasaki et al. *Proc. Natl. Acad. Sci. U.S.A.* 101: 14925-14930, 1973). As illustrated in FIG. 7, four gene products, Orf5 (SEQ ID NO: 35), Orf9 (SEQ ID NO: 39), Orf44 (SEQ ID NO: 44) and Orf45 (SEQ ID NO: 45), are predicted to activate and modify a precursor fatty acid and transfer it to the amine of $Asp^1$ on EndA. Counterparts of these proteins are found in the ramoplanin pathway, which incorporates a shorter, but similar, 2Z,4E unsaturated lipid (cf. FIG. 1 and Table 1). However, Orf45 from the end pathway appears to be a fusion protein consisting of an acyl-CoA ligase and an acyl-CoA dehydrogenase. In the ramoplanin cluster orf26 encodes an acyl-CoA ligase and orf24 and orf25 encode homologous acyl-CoA dehydrogenases (McCafferty et al. *Biopolymers* 66: 261-284, 2002).

The dehydrogenase function of Orf45 is believed to introduce the first double bond in the fatty acid and then Orf9 and/or Orf44 participate in the second dehydrogenation and double bond isomerization. Recently, an acyl-CoA dehydrogenase in the friulimicin pathway was shown to be involved in the formation of the Δcis3 double bond in the lipid side chain of that lipopeptide (Heinzelmann et al. *Microbiology* 151: 1963-1974, 2005). Transfer of the modified fatty acid to the carrier protein Orf35 facilitates acylation of the Asp residue on EndA. It is also possible that Orf5 accepts an intermediate species that is further modified as the carrier protein-bound substrate rather than as a coenzyme A adduct.

Example 8

Chlorination of 4-hydroxyphenylglycine to Form 3,5-dichloro-L-4-hydroxyphenylglycine This example describes the mechanism by which 3,5-dichloro-L-4-hydroxyphenylglycine (Dpg) is formed.

The deduced product of orf30 (SEQ ID NO: 30) shows at least 69% amino acid identity to several halogenases associated with various glycopeptide biosynthesis pathways and is predicted to carry out the chlorination of $Hpg^{13}$ to form Dpg (Li et al. *Chem. Biol.* 11: 107-119, 2004; Pootoolal et al. *Proc. Natl. Acad. Sci. U.S.A.* 99: 8962-8967, 2002; Recktenwald et al. *Microbiology* 148: 1105-1118, 2002; and van Wageningen et al. *Chem. Biol.* 5: 155-162, 1998). orf30 encodes the only halogenase in the end cluster, suggesting that both chlorine atoms in the Dpg residue are introduced by a single enzyme. Similarly, complestatin contains two Dpg residues and the gene cluster only contains a single halogenase gene, comH (Chiu et al. *Proc. Natl. Acad. Sci. U.S.A.* 98: 8548-8553, 2001). In balhimycin biosynthesis, one halogenase introduces two chlorine atoms at different positions of the glycopeptide antibiotic (Puk et al. *Chem. Biol* 9: 225-235, 2002). PltA, a $FADH_2$-dependent halogenase involved in pyoluteorin biosynthesis, has been shown to catalyze the dichlorination of a carrier protein-bound pyrrole species (Dorrestein et al. *Proc. Natl. Acad. Sci. U.S.A.* 102: 13843-13848, 2005). These $FADH_2$-dependent halogenases required a NADH-dependent flavin reductase for cofactor recycling and two component systems have been characterized that generate 7-chlorotryptophan during rebeccamycin and pyrrolnitrin biosynthesis (Keller et al. *Angew. Chem. Int. Ed. Engl.* 39: 2300-2302, 2000; and Yeh et al. *Proc. Natl. Acad. Sci. U.S.A.* 102: 3960-3965, 2005). A flavin reductase gene has not been identified near the enduracidin biosynthetic genes.

The timing of chlorination has been demonstrated to occur after peptide assembly. In-frame deletion of the halogenase gene orf30 results in a mutant that produces deschloroenduracidins. This is consistent with bionformatic analysis indicating that the substrate specificity sequence for the A domain of module 13 (EndC-m4), that corresponds to Dpg, is identical to the substrate specificity sequences deduced for four A domains predicted to activate Hpg (see Table 2). Therefore, it would seem unlikely that free L-Hpg is chlorinated by Orf30 and the resulting Dpg is directly incorporated by the NRPS. Given the lack of additional A domain/carrier protein genes and the fact that EndC-m4 appears to be a functional module, halogenation is predicted to occur on a NRPS-bound Hpg or on the nascent peptide.

Example 9

Genes for Self-Resistance, Regulation and Export in an Enduracidin Gene Cluster

This example describes genes that may provide self-resistance, regulation and export of enduracidin in an enduracidin gene cluster.

The mechanism(s) employed by the enduracidin and ramoplanin producers to protect intracellular Lipid I and Lipid II from being complexed by these peptide antibiotics is not fully characterized. Self-resistance mechanisms for cell wall-active glycopeptide antibiotics like vancomycin typically involve alteration of the terminal residue of the pentapeptide moiety of Lipid II (Marshall et al. *Antimicrob. Agents Chemother.* 42: 2215-2220, 1998; and Li et al., *Chem. Biol.* 11: 107-119, 2004)). A partial scan of the *S. fungicidicus* genome identified vancomycin-type resistance genes, but this mechanism is unlikely to be related to enduracidin self-resistance, because the peptides recognize different regions of Lipid II and enduracidin is active against vancomycin resistant bacteria. In other lipopeptide biosynthetic gene clusters, such as those for daptomycin, CDA and ramoplanin, the identity of the genes conferring antibiotic immunity also remains unknown.

Export of the peptide from the cell likely involves Orf31, Orf32, and Orf33, predicted to encode components of ABC transporters similar to those in other antibiotic biosynthetic gene clusters. Regulation of antibiotic production, and possibly self-resistance determinant expression, is believed to involve orf22, orf24, orf41, orf42 and orf43. Orf41 is similar to the LuxR family of DNA-binding proteins that are activated by bacterial autoinducer molecules (Demain *Int. Microbiol.* 1: 259-264, 1998). orf42 and orf43 encode elements of two-component sensor kinase systems such as those activating expression of vancomycin resistance genes and orf22 and orf24 also exhibit similarity to known regulatory genes in other secondary metabolite clusters. All of these putative regulatory genes have orthologs in the ramoplanin cluster (see Table 1 above).

Example 10

Boundaries and Remaining Genes Identified in the Enduracidin Biosynthetic Gene Cluster This example describes the boundaries and possible roles for the genes that flank the enduracidin biosynthetic gene cluster.

The probable boundaries of the end cluster were assigned based on the deduced functions of the end gene products and flanking gene products and by comparison with the ramoplanin gene cluster. With the possible exception of orf10 being involved in the lipid tail formation, the ORFs in the sequenced region upstream of orf22 are not predicted to have functions involved in enduracidin formation. Likewise, the region located downstream of orf46 has no ramoplanin counterparts or genes with a function likely to be involved in enduracidin biosynthesis. Therefore, the boundaries of an enduracidin gene cluster are believed to be defined by orf22 and orf46. It is however possible that genes in the flanking regions that encode products of unknown function are involved in antibiotic regulation or resistance.

Example 11

Generation of a Gene Cluster-Wide Disruption Library

This example describes the process for obtaining a library of enduracidin gene clusters that have disruptive mutations in desired open reading frames.

Design and Construction of the Transposon Cassette Tn5AT

The transposon cassette Tn5AT was constructed with an oriT element, required for RP4-based intergeneric conjugation between *E. coli* and *Streptomyces*, and the aac(3)IV gene conferring apramycin resistance to allow antibiotic selection in both *E. coli* and *Streptomyces*. The aac(3)IV gene and oriT element are flanked by the hyperactive 19-bp Mosaic Ends (ME) that are specifically recognized by Tn5 transposase (FIG. 8). The cassette was prepared by restricting plasmid pMOD™-2<MCS> (Epicentre) with XbaI and ligating this product with a 1295 bp XbaI fragment excised from plasmid pIJ773 (provided by Prof K. Chater, Norwich, England) that harbors aac(3)IV and oriT. The resulting plasmids were designated pXYTn5AT1 and pXYTn5AT2, which differ only in the orientation of their inserts. The 1476 bp Tn5AT cassette is obtained from either pXYTn5AT1 or pXYTn5AT2 by PvuII digestion. Thus, fosmid and plasmid libraries generated by random in vitro transposon mutagenesis can be transformed into *E. coli* and selected on apramycin containing media. After screening for mutagenized fosmids of interest, the fosmids can be introduced to *Streptomyces* spp. by intergeneric conjugation. Only clones that have undergone homologous recombination to incorporate the disrupted gene into the chromosome survive apramycin selection.

Generating and Screening Gene Cluster Mutations

To generate an enduracidin gene cluster-wide disruption library, fosmids pXYF24, pXYF148, pXYF305 and pXYF607 (as described in Example 1) were used as templates for in vitro Tn5AT mutagenesis. These fosmids harbor the majority of the non-NRPS genes in the cluster and the flanking region. Mutagenesis was performed with Tn5AT and commercial Tn5 transposase (Epicentre) following the supplier's instructions. The mutagenesis reaction mixture was transformed into *E. coli* strain EPI300™-T1$^R$ (Epicentre) by electroporation. Transformants carrying mutagenized fosmids were selected by resistance to both apramycin and chloramphenicol (100 and 25 µg/mL, respectively). Twenty four single colonies were randomly selected from each of the four mutagenized fosmid libraries and grown in LB liquid culture with apramycin (100 µg/mL) for fosmid isolation and analysis. Out of 96 fosmids screened, restriction fragment analysis (FIG. 9) identified 19 unique gene disruptions that were further analyzed by DNA sequencing to locate the disruption site. The sequencing revealed the relevant open reading frame, the number of amino acids modified and the insert position (determined by direct sequencing). Some mutations occurred outside the sequenced region (marked ND). See Table 4. This protocol was also used to create mutant libraries from two plasmids carrying fragments of the enduracidin gene cluster.

TABLE 4

Summary of the inactivated genes obtained in vitro by single insertion of the transposon cassette Tn5AT into the individual fosmid or plasmid inserts.

| Fosmid/plasmid | Seq. ID | Amino Acids | Insert position (from Tn5AT position) | Predicted function |
|---|---|---|---|---|
| pXYF24D2 | 12 | 345 | 18149 | Transcriptional regulator |
| pXYF24D3 | 18 | 220 | 26386 | Two-component system regulator |
| pXYF24D4 | 6 | 1290 | 8700 | Glycosyltransferase |
| pXYF24D10 | 9 | 496 | 13231 | Unknown |
| pXYF24D14 | 10 | 709 | 14990 | Fatty acid oxidation complex alpha-subunit |
| pXYF24D21 | 13 | 793 | 19556 | Beta-mannosidase |
| pXYF24D16 | 17 | 430 | 24686 | Ribonuclease D |
| pXYF24D23 | 2 | 498 | 2479 | Cationic amino acid transporter |
| pXYF148D3 | 29 | 790 | 41407 | HmaO/HpgT fusion protein |
| pXYF148D13 | 34 | 275 | 47908 | Type II thioesterase |
| pXYF148D14 | 28 (endP) | 293 | 37996 | MppP homolog |
| pXYF305D3, D6 and D15 | 45 | 1177 | 113216, 111335 and 113903 | Acyl-CoA ligase/dehydrogenase fusion protein |
| pXYF305D8 | 42 | 370 | 108156 | Two-component system sensor kinase |
| pXYF305D14 | 39 | 274 | 103546 | Acyl-CoA dehydrogenase/reductase |
| pXYF607D2 | ND | ND | (442) | Integral membrane protein |
| pXYF607D7 and D21 | 44 | 625 | 110582 and 109247 | Acyl-CoA dehydrogenase |
| pXYF607D11 | ND | ND | (715) | Flavoprotein oxidoreductase |
| pXYF607D16 | ND | ND | (551) | Iron-sulfur binding oxidoreductase |
| pXYF607D18 | Intergenic region | | 114583 | Between orf46 and orf47 |
| pXYF607D22 | ND | ND | (636) | Hydrolase |
| pXYHaloD5 | 30 | 504 | 42913 | Halogenase |
| pXYPQR-D2P | 28 (endP) | 293 | 38474 | MppP homolog |
| pXYPQR-D3R | 26 (endR) | 279 | 36210 | MppR homolog |

The transposon cassette Tn5AT contains a single HindIII site. This is particularly useful when screening for single versus multiple disruption events over the fosmid insert. The HindIII site is rare in *Streptomyces* DNA and none of the fosmid inserts used as templates for the mutagenesis has a HindIII site and only one HindIII site is present in the fosmid vector polylinker. Restriction analysis of the mutagenized fosmid DNA using HindIII readily distinguishes a single insertion of Tn5AT (2 bands) from multiple ones (FIG. 9A). Moreover, the estimated sizes of the HindIII bands can help approximate the location of the disruption site, and the gene effected, if the sequence of the fosmid insert is available.

Example 12

Production of Tetrahydroenduaracidins A and B by Inactivation of Acyl CoA Ligase/Dehydrogenase Gene Orf45

This example describes isolation of tetrahydroenduaracidins A and B (analogs of enduracidin) from organisms with selected mutated gene clusters.

Mutagenized fosmids pXYF305D6 and pXYF305D15 made according to Example 11, carrying disrupted orf45, were introduced to *E. coli* S17-1 cells and the resulting strains used for conjugal transformation of germinated *S. fungicidicus* spores. Disruptants were selected on conjugative ISP4 agar plates supplemented with 10 mM MgSO$_4$, incubated for 22 hours at 37° C., then covered with 3 mL soft agar containing apramycin and nalidixic acid (1.5 mg/mL each). The surviving colonies were further purified by streaking on ISP2 agar plates with apramycin (50 μg/mL). The mutant strain Sf305D6 was confirmed by Southern analysis to have orf45 disrupted.

Figure 10:
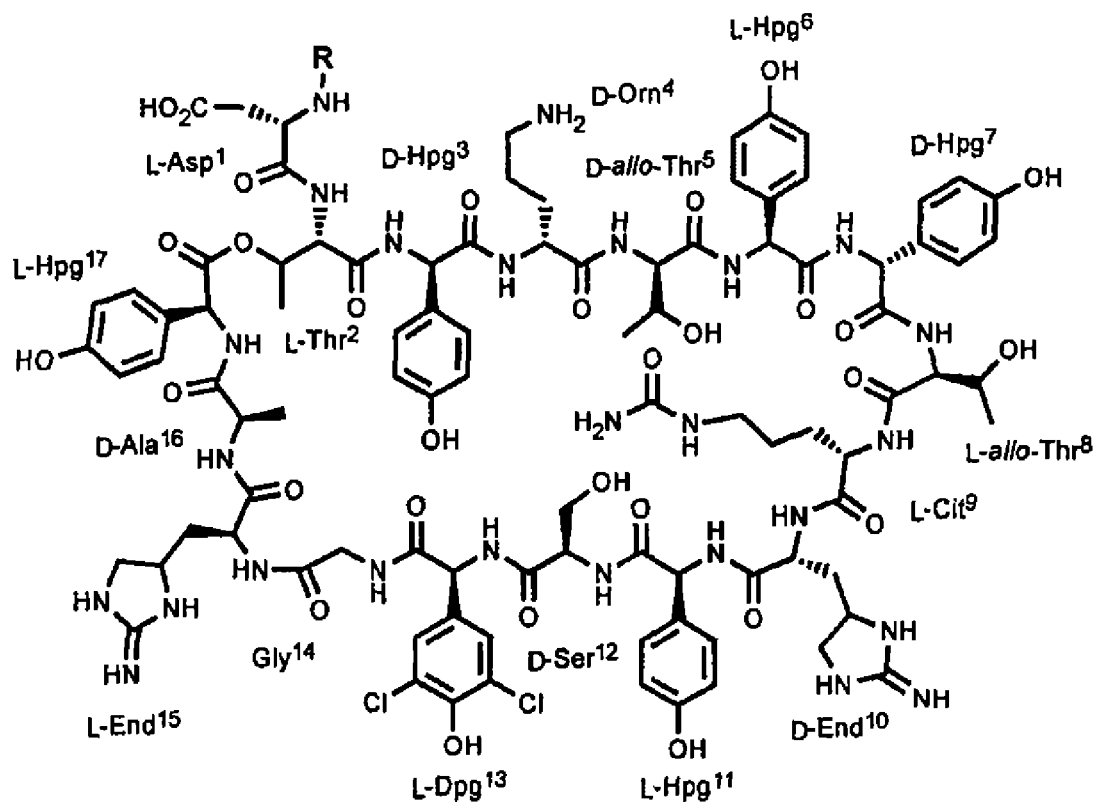
FIG. 10 illustrates the chemical structure of tetrahydroenduracidins A and B.
Figure 10:
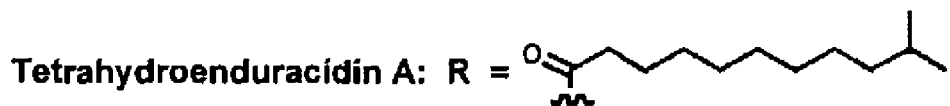
Figure 10:
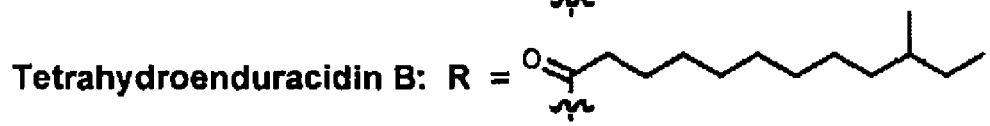
Figure 13A:
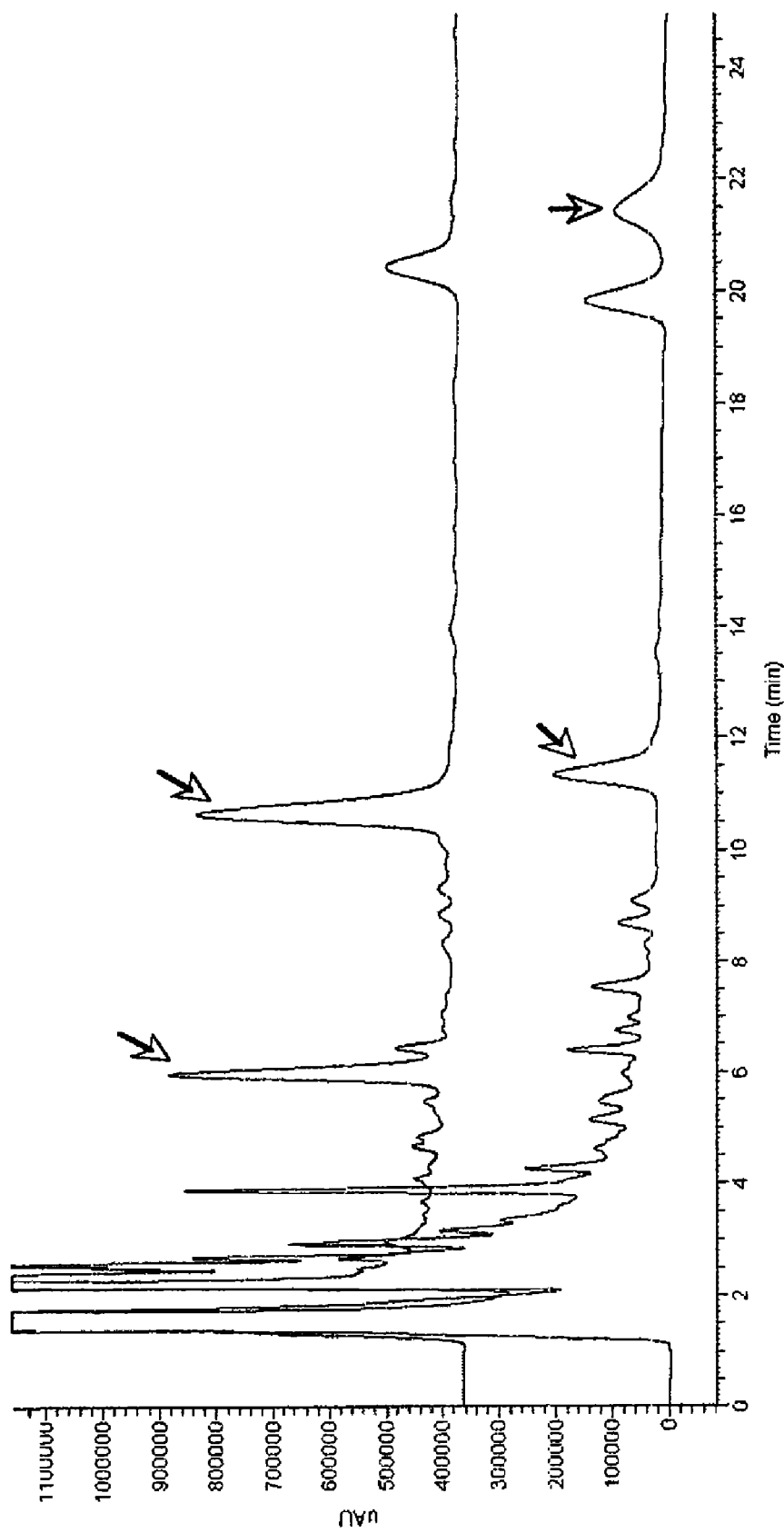
FIGS. 13A-13C illustrate the chemical properties of tetrahydroenduracidin A and tetrahydroenduracidin B.
Figure 13B:
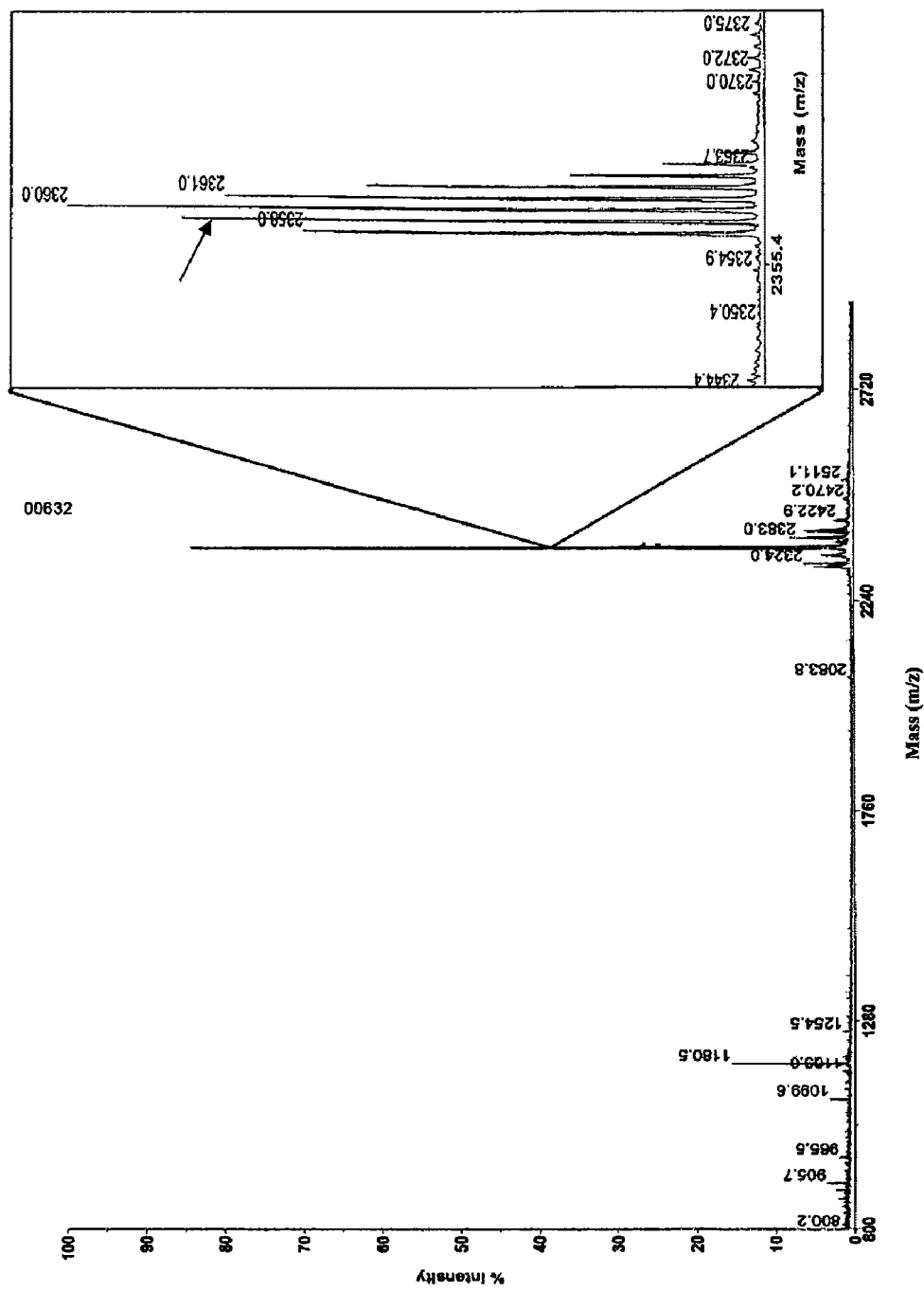
Figure 13C:
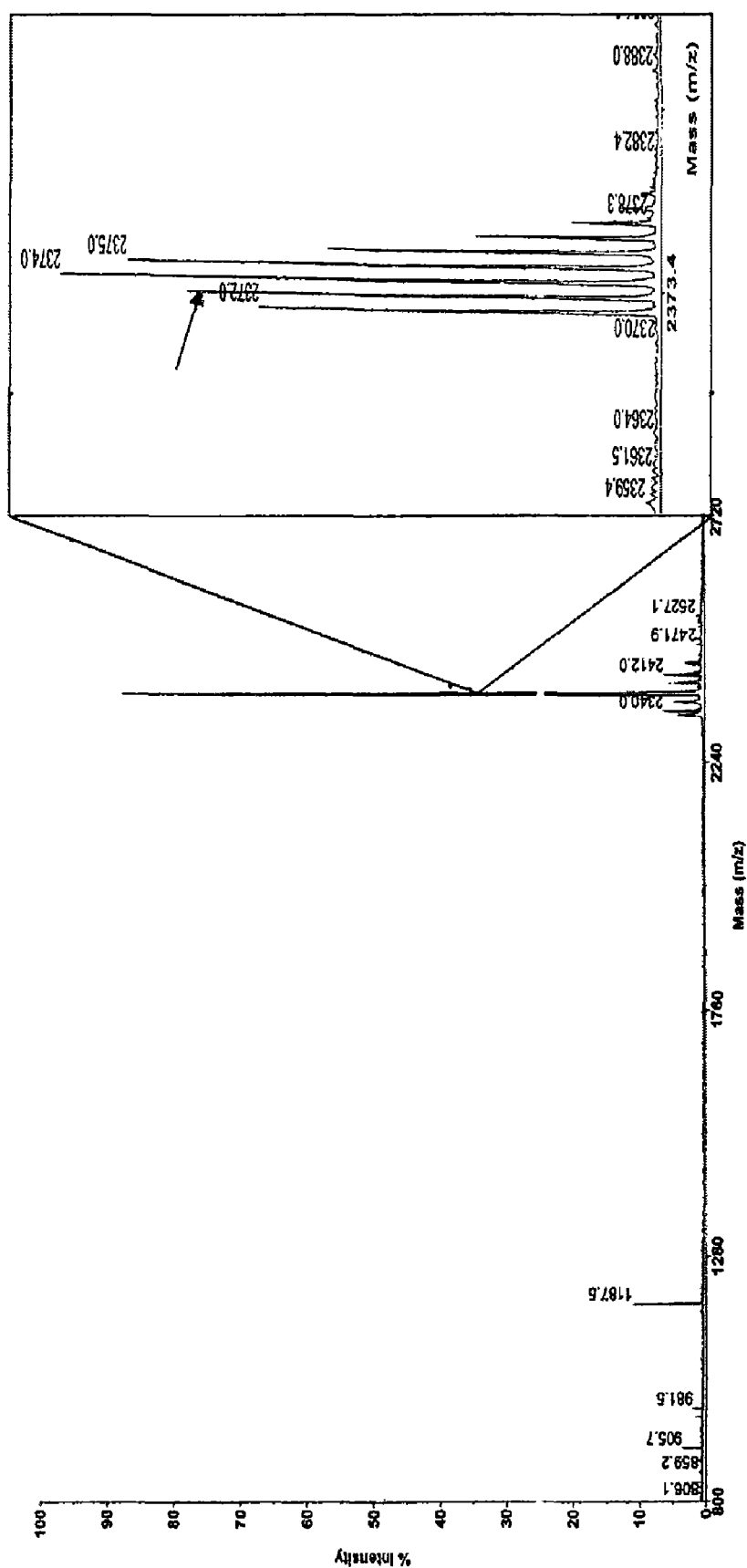
Figure 14A:
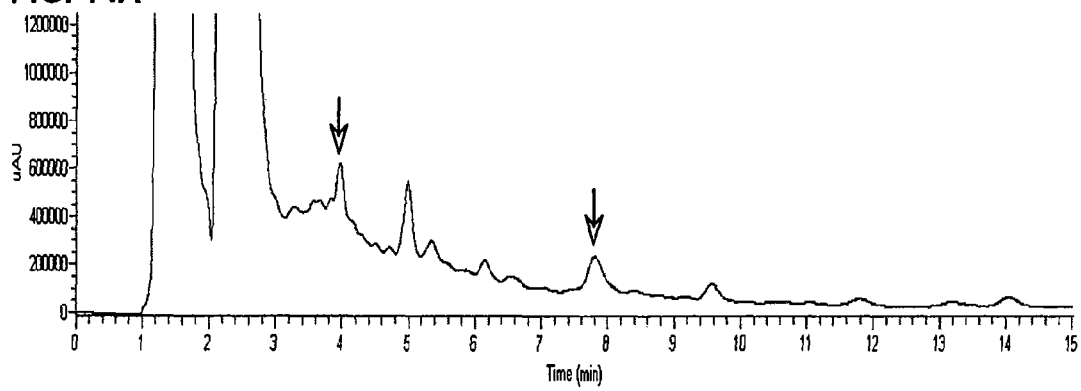
FIGS. 14A-14C illustrate the chemical properties of deschlorohydroenduracidin A and deschlorohydroenduracidin B.
Figure 14B:
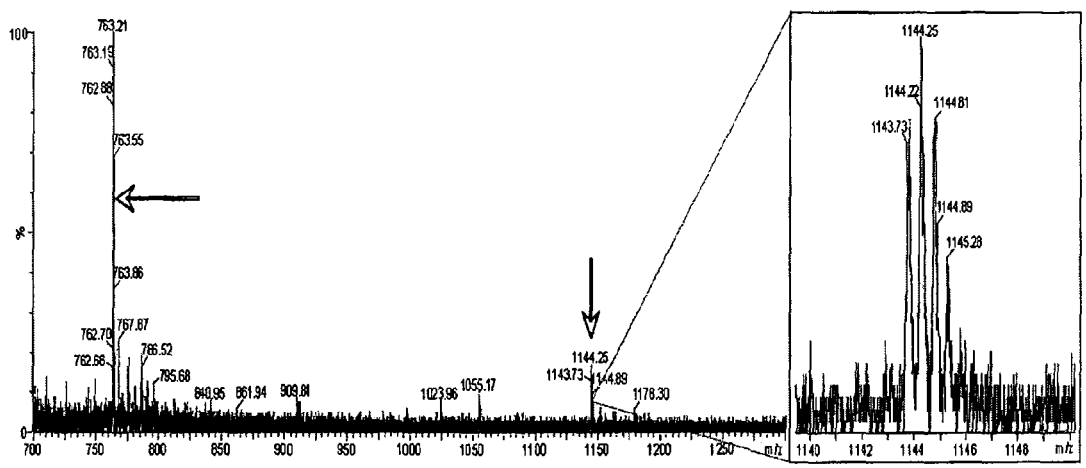
Figure 14C:
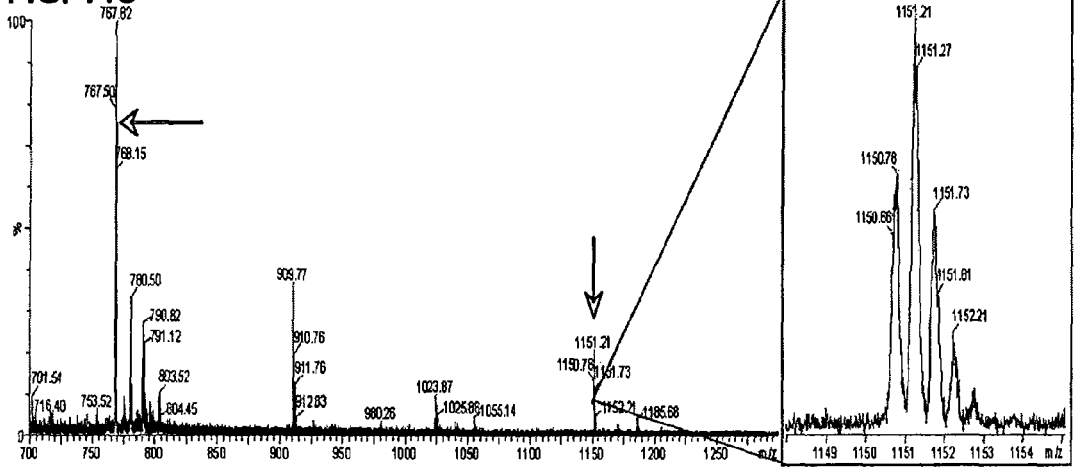

*S. fungicidicus* mutant strain Sf305D6 was grown under enduracidin producing conditions and the fermentation products analyzed by LC-MS. The mycelia extract of the orf45-disrupted mutant showed no enduracidins but did contain two new compounds, tetrahydroenduracidins A and B (FIG. 10). The compounds were isolated by HPLC (panel A, FIG. 13) and analyzed by MALDI-TOF mass spectrometry, which revealed the compounds had the expected masses for enduracidins A and B analogs possessing fully reduced fatty acid side chains (monoisotopic [M+H]+=2359.0 and 2373.0, respectively). See FIGS. 13B and 13C.

Example 13

Production of Deschloroenduracidins A and B by In-Frame Deletion of the Halogenase Gene Orf30

This example describes isolation of deschloroenduracidins A and B (analogs of enduracidin) from organisms with selected mutated gene clusters.

Construction of Plasmid pXY300-orf30-infd

Plasmid pXY300-orf30-infd was constructed by cloning two fragments that flank the target chromosomal sequence which will be deleted into the *E. coli*-Streptomyces shuttle conjugal temperature sensitive vector pXY300 containing the tsr resistance gene for selection in *Streptomyces*. An "upstream" 1.3 kb and a "downstream" 1.6 kb flanking sequences, designated orf30Δ1 and orf30Δ2, respectively, were generated by PCR using fosmid pXYF148 as the template; primers orf30infdF1 (5'-GTCAAGCTTGAG-GAACTCGTGCTCG—SEQ ID NO: 60; a HindIII site incorporated) and orf30infdR1 (5'-CTGAGATCTACTCATTCGGCCTC—SEQ ID NO: 61; a BglII site introduced) were used to amplify orf30Δ1; primers orf30infdF2 (5' GCGAGATCTGGAGAGTACGCCG-GCGA—SEQ ID NO: 62; a BglII site incorporated) and orf30infdR2 (5'-CTGACGGACGCGAATTCCCTTGC-SEQ ID NO: 63; a EcoRI site introduced) were used to amplify orf30Δ2. These two PCR fragments were appropriately restricted and simultaneously ligated with vector pXY300, prepared by digestion with EcoRI and HindIII, to yield plasmid pXY300-orf30-infd.

Generation of In-Frame Deletion Mutant Strain (Sforf30infd)

The delivery plasmid pXY300-orf30-infd used to delete orf30 from the chromosome was conjugally introduced into the wild type *S. fungicidicus*. The double crossover gene replacement procedures were as described previously in the preceding examples as well as procedures known to one of skill in the art. Thiostrepton-resistant exconjugants were isolated and passed through the high temperature (40° C.) selection. Independent markerless double-crossover mutants showing thiostrepton-sensitive phenotype were obtained and further confirmed by colony PCR.

Characterization of Peptides from an orf30 Deletion Mutant.

*S. fungicidicus* mutant strain Sforf30infd3 was grown under enduracidin producing conditions. Initial HPLC analysis of the fermentation products revealed the absence of enduracidins A and B and the presence of two new chromatographic peaks (FIG. 14A). These peaks partially purified and analyzed by ESI-MS which confirmed they were deschloroenduracidin A ([M+2H]2+=1144.28, FIG. 14B) and deschloroenduracidin B ([M+2H]2+=1151.21, FIG. 14C). The observed pseudomolecular ions correspond to the doubly charged deschloroenduracidin A and B species, and correlate to the parent molecular weights of 2285.0 and 2299.0, respectively.

Example 14

Determination of Activity of Disclosed Enduracidin Analogs

This example describes a representative method useful for determining activity of enduracidin analogs, such as tetrahydroenduracidin A, tetrahydroenduracidin B, deschloroenduracidin A, and deschloroenduracidin B.

Biological activity(s) of enduracidin analogs, including those specifically disclosed herein, can be determined by methods known to those of skill in the art, and including methods provided above.

For example, the minimal inhibitory concentration (MICs) of the enduracidin analog antibiotic can be determined by a microdilution method broth procedure. Sequential twofold dilutions of the compounds can be performed in 100 microliters of Luria-Bertani (LB) broth in sterile 96-well microtiter plates. Overnight cultures of bacteria can be diluted 100 times in LB broth and subgrown for several hours and 10 microliters of diluted cultures are transferred into the antibiotic-containing microtiter plates to bring final inoculums to $10^5$ CFU/mL. Cultures are incubated overnight at 35° C. and microtiter plates checked from below with a reflective viewer for bacterial growth. MICs are defined as the lowest concentrations of the compound at which the tested microorganism did not demonstrate visible growth.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An isolated gene cluster, comprising:
 a nucleic acid sequence having at least 95% sequence identity to the nucleotide sequence of position 31147 to position 114619 of SEQ ID NO: 49 and which encodes a functional enduracidin synthetase for synthesis of an enduracidin, an enduracidin analog or a precursor thereof.

2. The isolated gene cluster of claim 1, further comprising the nucleotide sequence of position 1 to position 31146 of SEQ ID NO: 49.

3. The isolated gene cluster of claim 1, further comprising the nucleotide sequence of position 14174 to position 16303 of SEQ ID NO: 49.

4. The isolated gene cluster of claim 1, wherein the gene cluster has the nucleotide sequence of position 31147 to position 114619 of SEQ ID NO: 49.

5. A method for producing an enduracidin analog, comprising:
 inserting a transposon cassette comprising at least a selection marker into the isolated enduracidin gene cluster of claim 1 to produce mutations;
 transforming the resultant mutated gene clusters into an organism suitable for screening, wherein screening comprises DNA analysis;
 selecting a mutant organism, having a variant enduracidin gene cluster; and producing an enduracidin or enduracidin analog.

6. The method according to claim 5, wherein the transposon cassette comprises 19 bp Mosaic End sequences at the beginning and end of the cassette, an oriT element, and the aac(3)IV gene.

7. The method according to claim 5, wherein the organism suitable for screening is *E. coli*.

8. The method according to claim 5, wherein the DNA analysis comprises restriction enzyme analysis and DNA sequencing.

9. The method according to claim 5, wherein the mutant organism suitable for enduracidin or enduracidin analog production is *S. fungicidicus*.

* * * * *